(12) United States Patent
Pauli et al.

(10) Patent No.: US 11,739,374 B2
(45) Date of Patent: *Aug. 29, 2023

(54) METHODS AND COMPOSITIONS FOR PATHOGEN DETECTION IN PLANTS

(71) Applicant: Front Range Biosciences, Inc., Boulder, CO (US)

(72) Inventors: Christopher Stephen Pauli, Boulder, CO (US); Reginald Gaudino, San Marcos, CA (US); Anthony Torres, Oakland, CA (US); Christopher Stephen Zalewski, Seaside, CA (US)

(73) Assignee: FRONT RANGE BIOSCIENCES, INC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,648

(22) Filed: Oct. 13, 2021

(65) Prior Publication Data

US 2022/0042088 A1    Feb. 10, 2022

Related U.S. Application Data

(63) Continuation of application No. 17/334,400, filed on May 28, 2021.

(60) Provisional application No. 63/032,155, filed on May 29, 2020.

(51) Int. Cl.
*C12Q 1/6853* (2018.01)
*C12Q 1/70* (2006.01)

(52) U.S. Cl.
CPC .............. *C12Q 1/6853* (2013.01); *C12Q 1/70* (2013.01)

(58) Field of Classification Search
CPC .............................. C12Q 1/6853; C12Q 1/70
See application file for complete search history.

(56) References Cited

U.S. PATENT DOCUMENTS

| | | | |
|---|---|---|---|
| 4,469,863 A | 9/1984 | Ts'o et al. |
| 5,536,821 A | 7/1996 | Agrawal et al. |
| 5,541,306 A | 7/1996 | Agrawal et al. |
| 5,614,622 A | 3/1997 | Iyer et al. |
| 5,637,683 A | 6/1997 | Usher et al. |
| 5,637,684 A | 6/1997 | Cook et al. |
| 5,700,922 A | 12/1997 | Cook |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,773,601 A | 6/1998 | Agrawal |
| 5,886,165 A | 3/1999 | Kandimalla et al. |
| 5,929,226 A | 7/1999 | Padmapriya et al. |
| 5,955,599 A | 9/1999 | Iyer et al. |
| 5,962,674 A | 10/1999 | Iyer et al. |
| 5,977,296 A | 11/1999 | Nielsen et al. |
| 6,117,992 A | 9/2000 | Iyer et al. |
| 6,133,436 A | 10/2000 | Koster et al. |
| 6,140,482 A | 10/2000 | Iyer et al. |
| 10,501,814 B2 | 12/2019 | Hogan et al. |
| 10,513,745 B2 | 12/2019 | Hogan et al. |
| 10,612,075 B2 | 4/2020 | Hogan et al. |
| 10,640,835 B2 | 5/2020 | Hogan et al. |
| 2003/0074691 A1 | 4/2003 | Roth et al. |
| 2005/0287592 A1 | 12/2005 | Kless |
| 2009/0165153 A1 | 6/2009 | Wang et al. |
| 2010/0203500 A1 | 8/2010 | Okada et al. |
| 2011/0195418 A1 | 8/2011 | Matsushita |
| 2013/0012399 A1 | 1/2013 | Myers et al. |
| 2014/0096282 A1 | 4/2014 | Wintermantel et al. |
| 2018/0251822 A1 | 9/2018 | Hogan et al. |
| 2019/0032045 A1 | 1/2019 | Hogan et al. |
| 2019/0032046 A1 | 1/2019 | Hogan et al. |
| 2020/0283845 A1 | 9/2020 | Hogan et al. |
| 2021/0381039 A1 | 12/2021 | Pauli et al. |

FOREIGN PATENT DOCUMENTS

| | | | |
|---|---|---|---|
| CA | 2188900 A1 | 4/1997 |
| CN | 102719562 A | 10/2012 |
| CN | 102382903 B | 8/2013 |
| CN | 104498634 B | 8/2016 |
| EP | 2 090 652 A1 | 8/2009 |
| KR | 10-2019-0050135 A | 5/2019 |

(Continued)

OTHER PUBLICATIONS

Strausbaugh et al., Plant Disease 2017; 101: 1373-1382 (Year: 2017).*

(Continued)

*Primary Examiner* — Angela M. Bertagna
(74) *Attorney, Agent, or Firm* — Loza & Loza, LLP

(57) ABSTRACT

The technology relates in part to methods and compositions for detecting one or more pathogens in plants. In some aspects, the technology relates to methods and compositions for detecting hops latent viroid in plants. In some aspects, the technology relates to methods and compositions for detecting hops latent viroid in *cannabis* plants. In some aspects, the technology relates to methods and compositions for classifying a hops latent viroid genotype. In certain aspects, the technology relates to methods and compositions for determining the presence, absence and/or amount of one or more pathogens in plants, either independently or simultaneously. In aspects, the pathogen is a virus. In some aspects, the virus is selected from among one or more of hops latent viroid, beet curly top virus and alfalfa mosaic virus.

19 Claims, 110 Drawing Sheets

Specification includes a Sequence Listing.

(56) References Cited

FOREIGN PATENT DOCUMENTS

| | | |
|---|---|---|
| WO | 91/08307 A1 | 6/1991 |
| WO | 00/56746 A2 | 9/2000 |
| WO | 00/75372 A1 | 12/2000 |
| WO | 01/14398 A1 | 3/2001 |
| WO | 2007/056463 A2 | 5/2007 |
| WO | 2020/198452 A1 | 10/2020 |

OTHER PUBLICATIONS

VanGuilder et al. BioTechniques 2008; 44: 619-626 (Year: 2008).*
Di Serio et al. Archives of Virology 2014; 159: 3467-3478 (Year: 2014).*
Zeigler et al. Journal für Kulturpflanzen 2014; 66: 248-254 (Year: 2014).*
Gen Bank Accession No. MK803280 for Beet Curly Top Virus isolate BCTV-Can, complete genome, Oct. 27, 2019 [online], [retrieved on Jul. 8, 2022], retrieved from the Internet: <URL: www.ncbi.nlm.nih.gov/nuccore/MK803280.1?report=GenBank>. (Year: 2019).*
Weller et al. Applied and Environmental Microbiology 2000; 66: 2853-2858 (Year: 2000).*
To et al. Journal of Medical Microbiology & Diagnosis 2015; 4: 3 (Year: 2015).*
GENBANK Accession No. AJ290404.1, Mar. 18, 2002, 1 page.
GENBANK Accession No. AJ290405.1, Mar. 18, 2002, 1 page.
GENBANK Accession No. AJ290406.1, Mar. 18, 2002, 1 page.
GENBANK Accession No. AJ290407.1, Mar. 18, 2002, 1 page.
GENBANK Accession No. AJ290408.1, Mar. 18, 2002, 1 page.
GenBank Accession No. AJ290409.1, Mar. 18, 2002, 1 page.
GENBANK Accession No. AJ290410.1, Mar. 18, 2002, 1 page.
GENBANK Accession No. AJ290411.1, Mar. 18, 2002, 1 page.
GENBANK Accession No. AJ290412.1, Mar. 18, 2002, 1 page.
GENBANK Accession No. EF613181.1, Apr. 2, 2008, 1 page.
GENBANK Accession No. EF613183.1, Apr. 2, 2008, 1 page.
GENBANK Accession No. EF613185.1, Apr. 2, 2008, 1 page.
GENBANK Accession No. EF613188.1, Apr. 2, 2008, 1 page.
GENBANK Accession No. EF613192.1, Apr. 2, 2008, 1 page.
GENBANK Accession No. KT600317.1, Feb. 7, 2016, 1 page.
GENBANK Accession No. KT600318.1, Feb. 7, 2016, 1 page.
GENBANK Accession No. KX867057.1, Jul. 13, 2017, 1 page.
GENBANK Accession No. MK791751.1, Nov. 10, 2019, 1 page.
GENBANK Accession No. NC_002025.1, Aug. 13, 2018, 1 page.
GENBANK Accession No. NC_003611.1, Aug. 13, 2018, 1 page.
GENBANK Accession No. NP_041195.1, Aug. 13, 2018, 1 page.
GENBANK Accession No. X07397.1, Feb. 7, 2016, 1 page.
GenBank Assembly Accession: GCA_900626175.1, Feb. 14, 2019, 2 pages.
AL&L Crop Solutions, "Hemp and Hop Diseases", Retrieved on Jul. 13, 2021, https://allcropsolutions.com/disease-testing/hemp-and-hop-diseases/, 11 pages.
Almasi et al., "Comparison and Evaluation of Three Diagnostic Methods for Detection of Beet Curly Top Virus in Sugar Beet Using Different Visualizing Systems", Applied Biochemistry and Biotechnology, https://pubmed.ncbi.nlm.nih.gov/24894659/, Aug. 2014, 173(7):1836-1848.
Al-Saleh et al., "Biological and Molecular Variability of Alfalfa mosaic virus Affecting Alfalfa Crop in Riyadh Region", The Plant Pathology Journal, https://www.ncbi.nlm.nih.gov/pmc/articles/PMC4174816/, 2013, 29(4):410-417.
Bakro et al., "An Overview of Pathogen and Insect Threats to Fibre and Oilseed Hemp (*Cannabis sativa* L.) and Methods for Their Biocontrol", Integrated Control in Oilseed Crops IOBC-WPRS Bulletin, https://bib.irb.hr/datoteka/955682.iobc-wprs_bulletin_2018_136.pdf#page=21, 2018, 136:9-20.
Beaucage et al., "Deoxynucleoside Phosphoramidites—A New Class of Key Intermediates for Deoxypolynucleotide Synthesis", Tetrahedron Letters, 1981, 22(20):1859-1862.
Bektas et al., "Occurrence of Hop Latent Viroid in Cannabis sativa with Symptoms of Cannabis Stunting Disease in California", Plant Disease, APS Publications; https://apsjournals.apsnet.org/doi/full/10.1094/PDIS-03-19-0459-PDN, Aug. 21, 2019, 103(10):3 pages.
Caruthers Marvinh. , "Gene Synthesis Machines: DNA Chemistry and Its Use", Science, Oct. 18, 1985, 230:281-285.
Chen et al., "Characterization of Curtoviruses Associated with Curly Top Disease of Tomato in California and Monitoring for These Viruses in Beet Leafhoppers", Plant Disease, APS Publications; https://apsjournals.apsnet.org/doi/pdf/10.1094/PDIS-94-1-0099, Jan. 2010, 94(1):99-108.
Claeboe et al., "3'-Modified Oligonucleotides by Reverse DNA Synthesis", Nucleic Acids Research, 2003, 31(19):5685-5691.
Eastwell et al., "Occurrence of Viroids in Commercial Hop (*Humulus lupulus* L.) Production Areas of Washington State", Plant Health Progress https://apsjournals.apsnet.org/doi/abs/10.1094/PHP-2007-1127-01-RS, Nov. 27, 2007, 8(1):8 pages.
Fischbach et al., "Shining a Light on LAMP Assays—a Comparison of LAMP Visualization Methods Including the Novel Use of Berberine", Biotechniques, Apr. 2015, 58(4):189-194.
Giladi et al., "First Report of Beet Curly Top Virus Infecting Cannabis sativa in Western Colorado", Plant Disease, APS Publications, https://doi.org/10.1094/PDIS-08-19-1656-PDN, Jan. 9, 2020, 104(3):3 pages.
Gilbertson Robert L. , "Beet Curly Top Virus and Other Viruses of Concern", Department of Plant Pathology, University of California Davis, https://ucanr.edu/sites/Vegetable_Crops/files/227742.pdf, Apr. 9, 2020, 47 pages.
Gucek et al., "One-Step Multiplex RT-PCR for Simultaneous Detection of Four Viroids from Hop (*Humulus lupulus* L.)", European Journal of Plant Pathology, Feb. 13, 2019, 154(2):273-286.
Hadad et al., "Lettuce Chlorosis Virus Disease: A New Threat to Cannabis Production", Viruses, https://doi.org/10.3390/v11090802, Aug. 29, 2019, 11:802:15 pages.
Hur et al., "Identification of a Promoter Motif Involved in Curtovirus Sense-Gene Expression in Transgenic *Arabidopsis*", Molecules and Cells; https://www.researchgate.net/publication/5255816_Identification_of_a_promoter_motif_involved in Curtovirus sense-gene_expression_in_transgenic_*Arabidopsis*, Jul. 3, 2008, 26:131-139.
Luna et al., "Characterization of Curtovirus V2 Protein, a Functional Homolog of Begomovirus V2", Frontiers in Plant Science, https://www.frontiersin.org/articles/10.3389/fpls.2020.00835/full, Jun. 19, 2020, 11(835):14 pages.
Matousek et al., "The Variability of Hop Latent Viroid as Induced upon Heat Treatment", Virology, Aug. 2, 2001, 287:349-358.
Mckernan et al., "Cannabis Microbiome Sequencing Reveals Several Mycotoxic Fungi Native to Dispensary Grade Cannabis Flowers", F1000Research, Dec. 10, 2015, 4:1422:25 pages.
Mckernan et al., "Quantitative PCR for Cannabis Flower Containing SARs-CoV-2", bioRxiv, Jun. 11, 2020, 20 pages.
Mcpartland et al., "Hemp Diseases and Pests: Management and Biological Control: An Advanced Treatise", CABI, 2000, 276 pages.
Mcpartland J. M., "A review of Cannabis diseases", Journal of the International Hemp Association, Retrieved Feb. 5, 2020, http://druglibrary.org/olsen/hemp/iha/iha03111.html, 1996, 3(1):7 pages.
Meijer et al., "The Inheritance of Chemical Phenotype in *Cannabis sativa* L. (V): Regulation of the Propyl-/Pentyl Cannabinoid Ratio, Completion of a Genetic Model", Euphytica; https://www.researchgate.net/publication/303357650_The_inheritance_of_chemical_phenotype_in_Cannabis_sativa_L_V_regulation_of_the_propyl-pentyl_cannabinoid_ratio_completion_of_a_genetic_model, May 18, 2016, 210(2):291-307.
Nachappa et al., "Beet Leafhopper and Beet Curly Top Virus", CSU Press Release; https://webdoc.agsci.colostate.edu/hempinsects/PDFs/Curly%20Top%20Beet%20Leafhopper%202020.pdf, 2019, 5 pages.
Nakahara et al., "A Simple, Rapid Method of Nucleic Acid Extraction Without Tissue Homogenization for Detecting Viroids by Hybridization and RT-PCR", Journal of Virological Methods, 1999, 77:47-58.
Needham-Vandevanter et al., "Characterization of an Adduct Between CC-1065 and a Defined Oligodeoxynucleotide Duplex", Nucleic Acids Research, 1984, 12(15):6159-6168.

(56) References Cited

OTHER PUBLICATIONS

Pearson et al., "High-Performance Anion-Exchange Chromatography of Oligonucleotides", Journal of Chromatography, 1983, 255:137-149.

Righetti et al., "Not the One, but the Only One: About Cannabis Cryptic Virus in Plants Showing 'Hemp Streak' Disease Symptoms", European Journal of Plant Pathology, https://doi.org/10.1007/s10658-017-1301-y, Jul. 22, 2017, 150:575-588.

Rondon et al., "Characterization of Beet curly top virus Strains Circulating in Beet Leafhoppers (*Hemiptera: Cicadellidae*) in Northeastern Oregon", Plant Disease, APS Publications; https://apsjournals.apsnet.org/doi/pdf/10.1094/PDIS-10-15-1189-RE, Aug. 2016, 100(8):1586-1590.

Sambrook et al., "Molecular Cloning: A Laboratory Manual", Cold Spring Harbor Laboratory Press, 2001, 3(10):52 pages.

Sevik M.A, "Virus-Induced Diseases in Hemp (*Cannabis sativa* L.) Plants", Türkiye Tarimsal Araştirmalar Dergisi, https://www.cabdirect.org/cabdirect/abstract/20203197681, 2020, 7(1):111-119.

Staha et al., "The Scientific Reason for "Dud" Plants—Hop Latent Viroid (HLVd) Discovery in Cannabis", Phylos; https://phylos.bio/blog/hop-latent-viroid-discovery-in-cannabis, Nov. 6, 2019, 4 pages.

Strauss William M. , "Current Protocols in Molecular Biology", John Wiley & Sons, N.Y., 1993, 6.3.1-6.3.6.

Vincent et al., "Helicase-Dependent Isothermal DNA Amplification", EMBO Reports, 2004, 5(8):795-800.

Waring Scot, "Pathogen Detection in Cannabis: A Very Brief Overview of Issues, Science, Technology, Priorities, and Practices", elucidation, Essex, Vermont, https://www.uvm.edu/sites/default/files/Northwest-Crops-and-Soils-Program/2020%20HempConf%20Presentations/ScotWaring_20200220-WARING_2020-UVM-Industrial-Hemp-Conf-Delivered.pdf, Feb. 20, 2020, 18 pages.

Warren et al., "Occurrence of Hop Latent Viroid Causing Disease in Cannabis sativa in California", Plant Disease, APS Publications; https://doi.org/10.1094/PDIS-03-19-0530-PDN, Aug. 21, 2019, 103(10):3 pages.

Wintermantel et al., "Mapping of Curly Top Incidence and Determination of Genetic Variation Among Viruses Responsible for Curly Top in California", https://bsdf-assbt.org/wp-content/uploads/2017/04/PassbtVol34Agp220to221MappingofCurlyTopIncidenceandDeterminationofGeneticVariationAmongVirusesReponsibelforCurlyTopinCalifornia.pdf, Apr. 2017, 220-221.

Xu et al., "Identification, Characterization, and Molecular Detection of Alfalfa mosaic virus in Potato", Phytopathology, 2006, 96(11):1237-1242.

Ziegler et al., "Complete Sequence of a Cryptic Virus from Hemp (*Cannabis sativa*)", Archives of Virology, https://doi.org/10.1007/s00705-011-1168-8, Feb. 2012, 157(2):383-385.

International Search Report and Written Opinion dated Jan. 18, 2022 in PCT Patent Application No. PCT/US2021/34961, filed on May 28, 2021, 23 pages.

\* cited by examiner

| Sample ID | HPLVd A-G p1 | HPLVd F-D p3 |
|---|---|---|
| Gel CZ1 | + | + |
| GG#4 5.1 | - | - |
| BBM#4 5.1 | - | - |
| BS 2.1 | + | + |
| GSC 5.3 | - | - |
| Gel CZ4 | + | + |
| Gel CZ3 | + | + |
| Gel CZ2 | + | + |

Implementing Ung AmpErase to eliminate late amplifiers

FIG. 5 (Cont.)

| Sample | Amp Status | HPLVd A-G p1 | HPLVd B-G p5 |
|---|---|---|---|
| BS2.3 | No Amp | - | - |
| GG#4 5.3 | Amp | - | - |
| NTC | No Amp | - | - |
| Gel CZ1 | Amp | + | + |
| PP1 | Amp | + | + |
| RH5.2 | Amp | - | - |
| RH5.3 | Amp | - | - |
| SQR2 | Amp | + | + |
| SQR3 | Amp | - | - |
| Ven4.2 | No Amp | - | - |
| Ven4.3 | No Amp | - | - |

FIG. 6 (Cont.)

| Sample | Amp Status | A-G p1 Result | B-G p5 Result |
|---|---|---|---|
| 9.5 Old FTA Card | No Amp | - | - |
| BK13419 gDNA | No Amp | - | - |
| BK48007 gDNA | No Amp | - | - |
| Crag 107-8 Old FTA Card | No Amp | - | - |
| Crag 108-4 Old FTA Card | No Amp | - | - |
| Durban Poison gDNA | No Amp | - | - |
| G17 gDNA | No Amp | - | - |
| G3 gDNA | No Amp | - | - |
| Gel 5.1 cDNA | Amp | + | + |
| Gel 5.1 Fresh FTA Card | Amp | + | + |
| Gel 5.1 Fresh Leaf | Amp | + | + |
| NTC | No Amp | - | - |
| OCBG gDNA | No Amp | - | - |

FIG. 7 (Cont.)

Figure adapted from: Royal Society of Chemistry

FIG 11A - Results Table

| Well Position | Sample | Target | Reporter | Amp Status | Cq | Primer/Probe | Result |
|---|---|---|---|---|---|---|---|
| B1 | 1ng Cannabis cDNA ; HPLVd Positive + AMV Spike 1 | AMV | CY5 | Amp | 28.36648242 | AMV B-C / pB | AMV Positive |
| B1 | 1ng Cannabis cDNA ; HPLVd Positive + AMV Spike 1 | HPLVd | FAM | Amp | 21.57162588 | HPLVd B-D / p1 | HPLVd Positive |
| B1 | 1ng Cannabis cDNA ; HPLVd Positive + AMV Spike 1 | 26S | VIC | Amp | 13.63945163 | 26S/p1 | Reaction Positive |
| B2 | 1ng Cannabis cDNA ; HPLVd Positive + AMV Spike 2 | AMV | CY5 | Amp | 27.87037565 | AMV B-C / pB | AMV Positive |
| B2 | 1ng Cannabis cDNA ; HPLVd Positive + AMV Spike 2 | HPLVd | FAM | Amp | 21.66018725 | HPLVd B-D / p1 | HPLVd Positive |
| B2 | 1ng Cannabis cDNA ; HPLVd Positive + AMV Spike 2 | 26S | VIC | Amp | 12.98723099 | 26S/p1 | Reaction Positive |
| B3 | 1ng Cannabis cDNA ; HPLVd Positive + AMV Spike 3 | AMV | CY5 | Amp | 27.26593054 | AMV B-C / pB | AMV Positive |
| B3 | 1ng Cannabis cDNA ; HPLVd Positive + AMV Spike 3 | HPLVd | FAM | Amp | 21.85357922 | HPLVd B-D / p1 | HPLVd Positive |
| B3 | 1ng Cannabis cDNA ; HPLVd Positive + AMV Spike 3 | 26S | VIC | Amp | 13.40280495 | 26S/p1 | Reaction Positive |
| B4 | 1ng Cannabis cDNA ; HPLVd Positive + AMV Spike 4 | AMV | CY5 | Amp | 27.91785835 | AMV B-C / pB | AMV Positive |
| B4 | 1ng Cannabis cDNA ; HPLVd Positive + AMV Spike 4 | HPLVd | FAM | Amp | 21.84462647 | HPLVd B-D / p1 | HPLVd Positive |
| B4 | 1ng Cannabis cDNA ; HPLVd Positive + AMV Spike 4 | 26S | VIC | Amp | 14.30028244 | 26S/p1 | Reaction Positive |
| B5 | 1ng Cannabis cDNA ; HPLVd Positive + AMV Spike 5 | AMV | CY5 | Amp | 27.97667203 | AMV B-C / pB | AMV Positive |
| B5 | 1ng Cannabis cDNA ; HPLVd Positive + AMV Spike 5 | HPLVd | FAM | Amp | 21.82169459 | HPLVd B-D / p1 | HPLVd Positive |
| B5 | 1ng Cannabis cDNA ; HPLVd Positive + AMV Spike 5 | 26S | VIC | Amp | 13.21587267 | 26S/p1 | Reaction Positive |
| B6 | 1ng Cannabis cDNA ; HPLVd Positive + AMV Spike 6 | AMV | CY5 | Amp | 27.83488369 | AMV B-C / pB | AMV Positive |
| B6 | 1ng Cannabis cDNA ; HPLVd Positive + AMV Spike 6 | HPLVd | FAM | Amp | 21.86924275 | HPLVd B-D / p1 | HPLVd Positive |
| B6 | 1ng Cannabis cDNA ; HPLVd Positive + AMV Spike 6 | 26S | VIC | Amp | 13.30674302 | 26S/p1 | Reaction Positive |

FIG 11A contd

| Well | Sample | Target | Dye | Amp | Ct | Target detail | Result |
|---|---|---|---|---|---|---|---|
| B7 | 1ng Cannabis cDNA ; HPLVd Positive + AMV Spike 7 | AMV | CY5 | Amp | 27.42382259 | AMV B-C / pB | AMV Positive |
| B7 | 1ng Cannabis cDNA ; HPLVd Positive + AMV Spike 7 | HPLVd | FAM | Amp | 21.81139239 | HPLVd B-D / p1 | HPLVd Positive |
| B7 | 1ng Cannabis cDNA ; HPLVd Positive + AMV Spike 7 | 26S | VIC | Amp | 13.21746633 | 26S/p1 | Reaction Positive |
| B8 | 1ng Cannabis cDNA ; HPLVd Positive + AMV Spike 8 | AMV | CY5 | Amp | 27.47255438 | AMV B-C / pB | AMV Positive |
| B8 | 1ng Cannabis cDNA ; HPLVd Positive + AMV Spike 8 | HPLVd | FAM | Amp | 21.80945314 | HPLVd B-D / p1 | HPLVd Positive |
| B8 | 1ng Cannabis cDNA ; HPLVd Positive + AMV Spike 8 | 26S | VIC | Amp | 13.85869634 | 26S/p1 | Reaction Positive |
| B9 | 1ng Cannabis cDNA ; HPLVd Positive + AMV Spike 9 | AMV | CY5 | Amp | 27.88302212 | AMV B-C / pB | AMV Positive |
| B9 | 1ng Cannabis cDNA ; HPLVd Positive + AMV Spike 9 | HPLVd | FAM | Amp | 21.97318816 | HPLVd B-D / p1 | HPLVd Positive |
| B9 | 1ng Cannabis cDNA ; HPLVd Positive + AMV Spike 9 | 26S | VIC | Amp | 14.17017557 | 26S/p1 | Reaction Positive |
| B10 | 1ng Cannabis cDNA ; HPLVd Positive + AMV Spike 10 | AMV | CY5 | Amp | 28.07322275 | AMV B-C / pB | AMV Positive |
| B10 | 1ng Cannabis cDNA ; HPLVd Positive + AMV Spike 10 | HPLVd | FAM | Amp | 21.99180343 | HPLVd B-D / p1 | HPLVd Positive |
| B10 | 1ng Cannabis cDNA ; HPLVd Positive + AMV Spike 10 | 26S | VIC | Amp | 13.593352 | 26S/p1 | Reaction Positive |
| B11 | 1ng Cannabis cDNA ; HPLVd Negative | AMV | CY5 | No Amp | Undetermined | AMV B-C / pB | AMV Negative |
| B11 | 1ng Cannabis cDNA ; HPLVd Negative | HPLVd | FAM | No Amp | Undetermined | HPLVd B-D / p1 | HPLVd Negative |
| B11 | 1ng Cannabis cDNA ; HPLVd Negative | 26S | VIC | Amp | 11.55385945 | 26S/p1 | Reaction Positive |
| B12 | NTC | AMV | CY5 | No Amp | Undetermined | AMV B-C / pB | AMV Negative |
| B12 | NTC | HPLVd | FAM | No Amp | Undetermined | HPLVd B-D / p1 | HPLVd Negative |
| B12 | NTC | 26S | VIC | No Amp | Undetermined | 26S/p1 | Reaction Negative |
| C1 | 0.1ng Cannabis cDNA ; HPLVd Positive + AMV Spike 1 | AMV | CY5 | Amp | 29.89016872 | AMV B-C / pB | AMV Positive |

FIG 11A contd

| | Description | Target | Dye | Amp | Ct | Assay | Result |
|---|---|---|---|---|---|---|---|
| C1 | 0.1ng Cannabis cDNA ; HPLVd Positive + AMV Spike 1 | HPLVd | FAM | Amp | 25.51488986 | HPLVd B-D / p1 | HPLVd Positive |
| C1 | 0.1ng Cannabis cDNA ; HPLVd Positive + AMV Spike 1 | 26S | VIC | Amp | 17.99080198 | 26S/p1 | Reaction Positive |
| C2 | 0.1ng Cannabis cDNA ; HPLVd Positive + AMV Spike 2 | AMV | CY5 | Amp | 30.094227 | AMV B-C / pB | AMV Positive |
| C2 | 0.1ng Cannabis cDNA ; HPLVd Positive + AMV Spike 2 | HPLVd | FAM | Amp | 25.49804281 | HPLVd B-D / p1 | HPLVd Positive |
| C2 | 0.1ng Cannabis cDNA ; HPLVd Positive + AMV Spike 2 | 26S | VIC | Amp | 18.19333216 | 26S/p1 | Reaction Positive |
| C3 | 0.1ng Cannabis cDNA ; HPLVd Positive + AMV Spike 3 | AMV | CY5 | Amp | 30.06478662 | AMV B-C / pB | AMV Positive |
| C3 | 0.1ng Cannabis cDNA ; HPLVd Positive + AMV Spike 3 | HPLVd | FAM | Amp | 25.49063136 | HPLVd B-D / p1 | HPLVd Positive |
| C3 | 0.1ng Cannabis cDNA ; HPLVd Positive + AMV Spike 3 | 26S | VIC | Amp | 18.07032187 | 26S/p1 | Reaction Positive |
| C4 | 0.1ng Cannabis cDNA ; HPLVd Positive + AMV Spike 4 | AMV | CY5 | Amp | 29.83321909 | AMV B-C / pB | AMV Positive |
| C4 | 0.1ng Cannabis cDNA ; HPLVd Positive + AMV Spike 4 | HPLVd | FAM | Amp | 25.62642663 | HPLVd B-D / p1 | HPLVd Positive |
| C4 | 0.1ng Cannabis cDNA ; HPLVd Positive + AMV Spike 4 | 26S | VIC | Amp | 18.13237199 | 26S/p1 | Reaction Positive |
| C5 | 0.1ng Cannabis cDNA ; HPLVd Positive + AMV Spike 5 | AMV | CY5 | Amp | 30.0656365 | AMV B-C / pB | AMV Positive |
| C5 | 0.1ng Cannabis cDNA ; HPLVd Positive + AMV Spike 5 | HPLVd | FAM | Amp | 25.60599567 | HPLVd B-D / p1 | HPLVd Positive |
| C5 | 0.1ng Cannabis cDNA ; HPLVd Positive + AMV Spike 5 | 26S | VIC | Amp | 18.08870587 | 26S/p1 | Reaction Positive |
| C6 | 0.1ng Cannabis cDNA ; HPLVd Positive + AMV Spike 6 | AMV | CY5 | Amp | 29.83247951 | AMV B-C / pB | AMV Positive |
| C6 | 0.1ng Cannabis cDNA ; HPLVd Positive + AMV Spike 6 | HPLVd | FAM | Amp | 25.4685032 | HPLVd B-D / p1 | HPLVd Positive |
| C6 | 0.1ng Cannabis cDNA ; HPLVd Positive + AMV Spike 6 | 26S | VIC | Amp | 17.78558323 | 26S/p1 | Reaction Positive |
| C7 | 0.1ng Cannabis cDNA ; HPLVd Positive + AMV Spike 7 | AMV | CY5 | Amp | 29.4487718 | AMV B-C / pB | AMV Positive |
| C7 | 0.1ng Cannabis cDNA ; HPLVd Positive + AMV Spike 7 | HPLVd | FAM | Amp | 25.37136896 | HPLVd B-D / p1 | HPLVd Positive |

FIG 11A contd

| Well | Sample | Target | Dye | Amp | CT | Assay | Reaction |
|---|---|---|---|---|---|---|---|
| C7 | 0.1ng Cannabis cDNA ; HPLVd Positive + AMV Spike 7 | 26S | VIC | Amp | 17.48771957 | 26S/p1 | Reaction Positive |
| C8 | 0.1ng Cannabis cDNA ; HPLVd Positive + AMV Spike 8 | AMV | CY5 | Amp | 30.2515059 | AMV B-C / pB | AMV Positive |
| C8 | 0.1ng Cannabis cDNA ; HPLVd Positive + AMV Spike 8 | HPLVd | FAM | Amp | 25.68287279 | HPLVd B-D / p1 | HPLVd Positive |
| C8 | 0.1ng Cannabis cDNA ; HPLVd Positive + AMV Spike 8 | 26S | VIC | Amp | 17.97909124 | 26S/p1 | Reaction Positive |
| C9 | 0.1ng Cannabis cDNA ; HPLVd Positive + AMV Spike 9 | AMV | CY5 | Amp | 29.65545326 | AMV B-C / pB | AMV Positive |
| C9 | 0.1ng Cannabis cDNA ; HPLVd Positive + AMV Spike 9 | HPLVd | FAM | Amp | 25.28577802 | HPLVd B-D / p1 | HPLVd Positive |
| C9 | 0.1ng Cannabis cDNA ; HPLVd Positive + AMV Spike 9 | 26S | VIC | Amp | 17.77287759 | 26S/p1 | Reaction Positive |
| C10 | 0.1ng Cannabis cDNA ; HPLVd Positive + AMV Spike 10 | AMV | CY5 | Amp | 29.40858811 | AMV B-C / pB | AMV Positive |
| C10 | 0.1ng Cannabis cDNA ; HPLVd Positive + AMV Spike 10 | HPLVd | FAM | Amp | 25.32589014 | HPLVd B-D / p1 | HPLVd Positive |
| C10 | 0.1ng Cannabis cDNA ; HPLVd Positive + AMV Spike 10 | 26S | VIC | Amp | 17.48513 | 26S/p1 | Reaction Positive |
| C11 | 0.1ng Cannabis cDNA ; HPLVd Negative | AMV | CY5 | No Amp | Undetermined | AMV B-C / pB | AMV Negative |
| C11 | 0.1ng Cannabis cDNA ; HPLVd Negative | HPLVd | FAM | No Amp | Undetermined | HPLVd B-D / p1 | HPLVd Negative |
| C11 | 0.1ng Cannabis cDNA ; HPLVd Negative | 26S | VIC | Amp | 16.00968321 | 26S/p1 | Reaction Positive |
| C12 | NTC | AMV | CY5 | No Amp | Undetermined | AMV B-C / pB | AMV Negative |
| C12 | NTC | HPLVd | FAM | No Amp | Undetermined | HPLVd B-D / p1 | HPLVd Negative |
| C12 | NTC | 26S | VIC | No Amp | Undetermined | 26S/p1 | Reaction Negative |
| D1 | 1ng Cannabis cDNA ; HPLVd Positive + AMV Spike 1 | AMV | CY5 | Amp | 27.38896726 | AMV B-C / pB | AMV Positive |
| D1 | 1ng Cannabis cDNA ; HPLVd Positive + AMV Spike 1 | HPLVd | FAM | Amp | 20.87010681 | HPLVd B-E / p1 | HPLVd Positive |
| D1 | 1ng Cannabis cDNA ; HPLVd Positive + AMV Spike 1 | 26S | VIC | Amp | 12.77286054 | 26S/p1 | Reaction Positive |

FIG 11A contd

| | | | | | | |
|---|---|---|---|---|---|---|
| D2 | 1ng Cannabis cDNA ; HPLVd Positive + AMV Spike 2 | AMV | CY5 | Amp | 28.21075242 | AMV B-C / pB | AMV Positive |
| D2 | 1ng Cannabis cDNA ; HPLVd Positive + AMV Spike 2 | HPLVd | FAM | Amp | 21.02141858 | HPLVd B-E / p1 | HPLVd Positive |
| D2 | 1ng Cannabis cDNA ; HPLVd Positive + AMV Spike 2 | 26S | VIC | Amp | 13.43717333 | 26S/p1 | Reaction Positive |
| D3 | 1ng Cannabis cDNA ; HPLVd Positive + AMV Spike 3 | AMV | CY5 | Amp | 28.5401024 | AMV B-C / pB | AMV Positive |
| D3 | 1ng Cannabis cDNA ; HPLVd Positive + AMV Spike 3 | HPLVd | FAM | Amp | 21.17503559 | HPLVd B-E / p1 | HPLVd Positive |
| D3 | 1ng Cannabis cDNA ; HPLVd Positive + AMV Spike 3 | 26S | VIC | Amp | 14.12221114 | 26S/p1 | Reaction Positive |
| D4 | 1ng Cannabis cDNA ; HPLVd Positive + AMV Spike 4 | AMV | CY5 | Amp | 27.97993998 | AMV B-C / pB | AMV Positive |
| D4 | 1ng Cannabis cDNA ; HPLVd Positive + AMV Spike 4 | HPLVd | FAM | Amp | 21.18904244 | HPLVd B-E / p1 | HPLVd Positive |
| D4 | 1ng Cannabis cDNA ; HPLVd Positive + AMV Spike 4 | 26S | VIC | Amp | 13.70030622 | 26S/p1 | Reaction Positive |
| D5 | 1ng Cannabis cDNA ; HPLVd Positive + AMV Spike 5 | AMV | CY5 | Amp | 27.96234817 | AMV B-C / pB | AMV Positive |
| D5 | 1ng Cannabis cDNA ; HPLVd Positive + AMV Spike 5 | HPLVd | FAM | Amp | 21.122592 | HPLVd B-E / p1 | HPLVd Positive |
| D5 | 1ng Cannabis cDNA ; HPLVd Positive + AMV Spike 5 | 26S | VIC | Amp | 13.62492083 | 26S/p1 | Reaction Positive |
| D6 | 1ng Cannabis cDNA ; HPLVd Positive + AMV Spike 6 | AMV | CY5 | Amp | 31.68851541 | AMV B-C / pB | AMV Positive |
| D6 | 1ng Cannabis cDNA ; HPLVd Positive + AMV Spike 6 | HPLVd | FAM | Amp | 21.2858125 | HPLVd B-E / p1 | HPLVd Positive |
| D6 | 1ng Cannabis cDNA ; HPLVd Positive + AMV Spike 6 | 26S | VIC | Amp | 14.06068513 | 26S/p1 | Reaction Positive |
| D7 | 1ng Cannabis cDNA ; HPLVd Positive + AMV Spike 7 | AMV | CY5 | Amp | 27.15275237 | AMV B-C / pB | AMV Positive |
| D7 | 1ng Cannabis cDNA ; HPLVd Positive + AMV Spike 7 | HPLVd | FAM | Amp | 20.92552658 | HPLVd B-E / p1 | HPLVd Positive |
| D7 | 1ng Cannabis cDNA ; HPLVd Positive + AMV Spike 7 | 26S | VIC | Amp | 13.34944357 | 26S/p1 | Reaction Positive |
| D8 | 1ng Cannabis cDNA ; HPLVd Positive + AMV Spike 8 | AMV | CY5 | Amp | 27.70183457 | AMV B-C / pB | AMV Positive |

FIG 11A contd

| Well | Sample | Target | Reporter | Amp Status | Ct | Assay | Result |
|---|---|---|---|---|---|---|---|
| D8 | 1ng Cannabis cDNA ; HPLVd Positive + AMV Spike 8 | HPLVd | FAM | Amp | 20.98261223 | HPLVd B-E / p1 | HPLVd Positive |
| D8 | 1ng Cannabis cDNA ; HPLVd Positive + AMV Spike 8 | 26S | VIC | Amp | 13.23285853 | 26S/p1 | Reaction Positive |
| D9 | 1ng Cannabis cDNA ; HPLVd Positive + AMV Spike 9 | AMV | CY5 | Amp | 27.72216649 | AMV B-C / pB | AMV Positive |
| D9 | 1ng Cannabis cDNA ; HPLVd Positive + AMV Spike 9 | HPLVd | FAM | Amp | 20.84313143 | HPLVd B-E / p1 | HPLVd Positive |
| D9 | 1ng Cannabis cDNA ; HPLVd Positive + AMV Spike 9 | 26S | VIC | Amp | 13.51671826 | 26S/p1 | Reaction Positive |
| D10 | 1ng Cannabis cDNA ; HPLVd Positive + AMV Spike 10 | AMV | CY5 | Amp | 27.81355629 | AMV B-C / pB | AMV Positive |
| D10 | 1ng Cannabis cDNA ; HPLVd Positive + AMV Spike 10 | HPLVd | FAM | Amp | 20.91774427 | HPLVd B-E / p1 | HPLVd Positive |
| D10 | 1ng Cannabis cDNA ; HPLVd Positive + AMV Spike 10 | 26S | VIC | Amp | 13.07902559 | 26S/p1 | Reaction Positive |
| D11 | 1ng Cannabis cDNA ; HPLVd Negative | AMV | CY5 | No Amp | Undetermined | AMV B-C / pB | AMV Negative |
| D11 | 1ng Cannabis cDNA ; HPLVd Negative | HPLVd | FAM | No Amp | Undetermined | HPLVd B-E / p1 | HPLVd Negative |
| D11 | 1ng Cannabis cDNA ; HPLVd Negative | 26S | VIC | Amp | 11.66240809 | 26S/p1 | Reaction Positive |
| D12 | NTC | AMV | CY5 | No Amp | Undetermined | AMV B-C / pB | AMV Negative |
| D12 | NTC | HPLVd | FAM | No Amp | Undetermined | HPLVd B-E / p1 | HPLVd Negative |
| D12 | NTC | 26S | VIC | No Amp | Undetermined | 26S/p1 | Reaction Negative |
| E1 | 0.1ng Cannabis cDNA ; HPLVd Positive + AMV Spike 1 | AMV | CY5 | Amp | 29.50257653 | AMV B-C / pB | AMV Positive |
| E1 | 0.1ng Cannabis cDNA ; HPLVd Positive + AMV Spike 1 | HPLVd | FAM | Amp | 24.41417863 | HPLVd B-E / p1 | HPLVd Positive |
| E1 | 0.1ng Cannabis cDNA ; HPLVd Positive + AMV Spike 1 | 26S | VIC | Amp | 17.74787147 | 26S/p1 | Reaction Positive |
| E2 | 0.1ng Cannabis cDNA ; HPLVd Positive + AMV Spike 2 | AMV | CY5 | Amp | 30.40745719 | AMV B-C / pB | AMV Positive |
| E2 | 0.1ng Cannabis cDNA ; HPLVd Positive + AMV Spike 2 | HPLVd | FAM | Amp | 24.4809272 | HPLVd B-E / p1 | HPLVd Positive |

FIG 11A contd

| | Sample | Target1 | Dye1 | Result1 | Ct | Target2 | Reaction |
|---|---|---|---|---|---|---|---|
| E2 | 0.1ng Cannabis cDNA ; HPLVd Positive + AMV Spike 2 | 26S | VIC | Amp | 17.53948328 | 26S/p1 | Reaction Positive |
| E3 | 0.1ng Cannabis cDNA ; HPLVd Positive + AMV Spike 3 | AMV | CY5 | Amp | 30.35396254 | AMV B-C / pB | AMV Positive |
| E3 | 0.1ng Cannabis cDNA ; HPLVd Positive + AMV Spike 3 | HPLVd | FAM | Amp | 24.50422249 | HPLVd B-E / p1 | HPLVd Positive |
| E3 | 0.1ng Cannabis cDNA ; HPLVd Positive + AMV Spike 3 | 26S | VIC | Amp | 17.89277425 | 26S/p1 | Reaction Positive |
| E4 | 0.1ng Cannabis cDNA ; HPLVd Positive + AMV Spike 4 | AMV | CY5 | Amp | 30.3429172 | AMV B-C / pB | AMV Positive |
| E4 | 0.1ng Cannabis cDNA ; HPLVd Positive + AMV Spike 4 | HPLVd | FAM | Amp | 24.78084426 | HPLVd B-E / p1 | HPLVd Positive |
| E4 | 0.1ng Cannabis cDNA ; HPLVd Positive + AMV Spike 4 | 26S | VIC | Amp | 17.80254202 | 26S/p1 | Reaction Positive |
| E5 | 0.1ng Cannabis cDNA ; HPLVd Positive + AMV Spike 5 | AMV | CY5 | Amp | 30.30341367 | AMV B-C / pB | AMV Positive |
| E5 | 0.1ng Cannabis cDNA ; HPLVd Positive + AMV Spike 5 | HPLVd | FAM | Amp | 24.57202771 | HPLVd B-E / p1 | HPLVd Positive |
| E5 | 0.1ng Cannabis cDNA ; HPLVd Positive + AMV Spike 5 | 26S | VIC | Amp | 17.93860887 | 26S/p1 | Reaction Positive |
| E6 | 0.1ng Cannabis cDNA ; HPLVd Positive + AMV Spike 6 | AMV | CY5 | Amp | 29.9107165 | AMV B-C / pB | AMV Positive |
| E6 | 0.1ng Cannabis cDNA ; HPLVd Positive + AMV Spike 6 | HPLVd | FAM | Amp | 24.49627295 | HPLVd B-E / p1 | HPLVd Positive |
| E6 | 0.1ng Cannabis cDNA ; HPLVd Positive + AMV Spike 6 | 26S | VIC | Amp | 17.64626026 | 26S/p1 | Reaction Positive |
| E7 | 0.1ng Cannabis cDNA ; HPLVd Positive + AMV Spike 7 | AMV | CY5 | Amp | 29.78889143 | AMV B-C / pB | AMV Positive |
| E7 | 0.1ng Cannabis cDNA ; HPLVd Positive + AMV Spike 7 | HPLVd | FAM | Amp | 24.51304712 | HPLVd B-E / p1 | HPLVd Positive |
| E7 | 0.1ng Cannabis cDNA ; HPLVd Positive + AMV Spike 7 | 26S | VIC | Amp | 17.45836068 | 26S/p1 | Reaction Positive |
| E8 | 0.1ng Cannabis cDNA ; HPLVd Positive + AMV Spike 8 | AMV | CY5 | Amp | 29.58664972 | AMV B-C / pB | AMV Positive |
| E8 | 0.1ng Cannabis cDNA ; HPLVd Positive + AMV Spike 8 | HPLVd | FAM | Amp | 24.45543696 | HPLVd B-E / p1 | HPLVd Positive |
| E8 | 0.1ng Cannabis cDNA ; HPLVd Positive + AMV Spike 8 | 26S | VIC | Amp | 17.63284314 | 26S/p1 | Reaction Positive |

FIG 11A contd

| | | | | | | |
|---|---|---|---|---|---|---|
| E9 | 0.1ng Cannabis cDNA ; HPLVd Positive + AMV Spike 9 | AMV | CY5 | Amp | 30.16389078 | AMV B-C / pB | AMV Positive |
| E9 | 0.1ng Cannabis cDNA ; HPLVd Positive + AMV Spike 9 | HPLVd | FAM | Amp | 24.59932195 | HPLVd B-E / p1 | HPLVd Positive |
| E9 | 0.1ng Cannabis cDNA ; HPLVd Positive + AMV Spike 9 | 26S | VIC | Amp | 17.69356049 | 26S/p1 | Reaction Positive |
| E10 | 0.1ng Cannabis cDNA ; HPLVd Positive + AMV Spike 10 | AMV | CY5 | Amp | 29.78044067 | AMV B-C / pB | AMV Positive |
| E10 | 0.1ng Cannabis cDNA ; HPLVd Positive + AMV Spike 10 | HPLVd | FAM | Amp | 24.44175957 | HPLVd B-E / p1 | HPLVd Positive |
| E10 | 0.1ng Cannabis cDNA ; HPLVd Positive + AMV Spike 10 | 26S | VIC | Amp | 17.65380714 | 26S/p1 | Reaction Positive |
| E11 | 0.1ng Cannabis cDNA ; HPLVd Negative | AMV | CY5 | No Amp | Undetermined | AMV B-C / pB | AMV Negative |
| E11 | 0.1ng Cannabis cDNA ; HPLVd Negative | HPLVd | FAM | No Amp | Undetermined | HPLVd B-E / p1 | HPLVd Negative |
| E11 | 0.1ng Cannabis cDNA ; HPLVd Negative | 26S | VIC | Amp | 15.60774986 | 26S/p1 | Reaction Positive |
| E12 | NTC | AMV | CY5 | No Amp | Undetermined | AMV B-C / pB | AMV Negative |
| E12 | NTC | HPLVd | FAM | No Amp | Undetermined | HPLVd B-E / p1 | HPLVd Negative |
| E12 | NTC | 26S | VIC | No Amp | Undetermined | 26S/p1 | Reaction Negative |
| F1 | 1ng Cannabis cDNA ; HPLVd Positive + AMV Spike 1 | AMV | CY5 | Amp | 27.90550913 | AMV B-C / pB | AMV Positive |
| F1 | 1ng Cannabis cDNA ; HPLVd Positive + AMV Spike 1 | HPLVd | FAM | Amp | 20.61667937 | HPLVd B-F / p1 | HPLVd Positive |
| F1 | 1ng Cannabis cDNA ; HPLVd Positive + AMV Spike 1 | 26S | VIC | Amp | 12.82214519 | 26S/p1 | Reaction Positive |
| F2 | 1ng Cannabis cDNA ; HPLVd Positive + AMV Spike 2 | AMV | CY5 | Amp | 27.971787 | AMV B-C / pB | AMV Positive |
| F2 | 1ng Cannabis cDNA ; HPLVd Positive + AMV Spike 2 | HPLVd | FAM | Amp | 20.75154728 | HPLVd B-F / p1 | HPLVd Positive |
| F2 | 1ng Cannabis cDNA ; HPLVd Positive + AMV Spike 2 | 26S | VIC | Amp | 13.08008079 | 26S/p1 | Reaction Positive |
| F3 | 1ng Cannabis cDNA ; HPLVd Positive + AMV Spike 3 | AMV | CY5 | Amp | 27.70403924 | AMV B-C / pB | AMV Positive |

FIG 11A contd

| | Sample | Target | Dye | Task | Cq | Probe | Result |
|---|---|---|---|---|---|---|---|
| F3 | 1ng Cannabis cDNA ; HPLVd Positive + AMV Spike 3 | HPLVd | FAM | Amp | 20.86847899 | HPLVd B-F / p1 | HPLVd Positive |
| F3 | 1ng Cannabis cDNA ; HPLVd Positive + AMV Spike 3 | 26S | VIC | Amp | 13.17334942 | 26S/p1 | Reaction Positive |
| F4 | 1ng Cannabis cDNA ; HPLVd Positive + AMV Spike 4 | AMV | CY5 | Amp | 27.52644436 | AMV B-C / pB | AMV Positive |
| F4 | 1ng Cannabis cDNA ; HPLVd Positive + AMV Spike 4 | HPLVd | FAM | Amp | 21.01918698 | HPLVd B-F / p1 | HPLVd Positive |
| F4 | 1ng Cannabis cDNA ; HPLVd Positive + AMV Spike 4 | 26S | VIC | Amp | 14.27891599 | 26S/p1 | Reaction Positive |
| F5 | 1ng Cannabis cDNA ; HPLVd Positive + AMV Spike 5 | AMV | CY5 | Amp | 27.6467174 | AMV B-C / pB | AMV Positive |
| F5 | 1ng Cannabis cDNA ; HPLVd Positive + AMV Spike 5 | HPLVd | FAM | Amp | 20.85144609 | HPLVd B-F / p1 | HPLVd Positive |
| F5 | 1ng Cannabis cDNA ; HPLVd Positive + AMV Spike 5 | 26S | VIC | Amp | 13.09223671 | 26S/p1 | Reaction Positive |
| F6 | 1ng Cannabis cDNA ; HPLVd Positive + AMV Spike 6 | AMV | CY5 | Amp | 27.25548146 | AMV B-C / pB | AMV Positive |
| F6 | 1ng Cannabis cDNA ; HPLVd Positive + AMV Spike 6 | HPLVd | FAM | Amp | 20.84453994 | HPLVd B-F / p1 | HPLVd Positive |
| F6 | 1ng Cannabis cDNA ; HPLVd Positive + AMV Spike 6 | 26S | VIC | Amp | 13.13770557 | 26S/p1 | Reaction Positive |
| F7 | 1ng Cannabis cDNA ; HPLVd Positive + AMV Spike 7 | AMV | CY5 | Amp | 27.37878523 | AMV B-C / pB | AMV Positive |
| F7 | 1ng Cannabis cDNA ; HPLVd Positive + AMV Spike 7 | HPLVd | FAM | Amp | 20.84497317 | HPLVd B-F / p1 | HPLVd Positive |
| F7 | 1ng Cannabis cDNA ; HPLVd Positive + AMV Spike 7 | 26S | VIC | Amp | 13.01029802 | 26S/p1 | Reaction Positive |
| F8 | 1ng Cannabis cDNA ; HPLVd Positive + AMV Spike 8 | AMV | CY5 | Amp | 27.22175566 | AMV B-C / pB | AMV Positive |
| F8 | 1ng Cannabis cDNA ; HPLVd Positive + AMV Spike 8 | HPLVd | FAM | Amp | 20.78480702 | HPLVd B-F / p1 | HPLVd Positive |
| F8 | 1ng Cannabis cDNA ; HPLVd Positive + AMV Spike 8 | 26S | VIC | Amp | 12.97720179 | 26S/p1 | Reaction Positive |
| F9 | 1ng Cannabis cDNA ; HPLVd Positive + AMV Spike 9 | AMV | CY5 | Amp | 27.47393132 | AMV B-C / pB | AMV Positive |
| F9 | 1ng Cannabis cDNA ; HPLVd Positive + AMV Spike 9 | HPLVd | FAM | Amp | 20.72275035 | HPLVd B-F / p1 | HPLVd Positive |

FIG 11A contd

| | Description | Target | Dye | Amp | Ct | Target | Reaction |
|---|---|---|---|---|---|---|---|
| F9 | 1ng Cannabis cDNA ; HPLVd Positive + AMV Spike 9 | 26S | VIC | Amp | 12.97290449 | 26S/p1 | Reaction Positive |
| F10 | 1ng Cannabis cDNA ; HPLVd Positive + AMV Spike 10 | AMV | CY5 | Amp | 27.83922336 | AMV B-C / pB | AMV Positive |
| F10 | 1ng Cannabis cDNA ; HPLVd Positive + AMV Spike 10 | HPLVd | FAM | Amp | 20.83717376 | HPLVd B-F / p1 | HPLVd Positive |
| F10 | 1ng Cannabis cDNA ; HPLVd Positive + AMV Spike 10 | 26S | VIC | Amp | 12.86546511 | 26S/p1 | Reaction Positive |
| F11 | 1ng Cannabis cDNA ; HPLVd Negative | AMV | CY5 | No Amp | Undetermined | AMV B-C / pB | AMV Negative |
| F11 | 1ng Cannabis cDNA ; HPLVd Negative | HPLVd | FAM | No Amp | Undetermined | HPLVd B-F / p1 | HPLVd Negative |
| F11 | 1ng Cannabis cDNA ; HPLVd Negative | 26S | VIC | Amp | 11.33156307 | 26S/p1 | Reaction Positive |
| F12 | NTC | AMV | CY5 | No Amp | Undetermined | AMV B-C / pB | AMV Negative |
| F12 | NTC | HPLVd | FAM | No Amp | Undetermined | HPLVd B-F / p1 | HPLVd Negative |
| F12 | NTC | 26S | VIC | No Amp | Undetermined | 26S/p1 | Reaction Negative |
| G1 | 0.1ng Cannabis cDNA ; HPLVd Positive + AMV Spike 1 | AMV | CY5 | Amp | 30.08929042 | AMV B-C / pB | AMV Positive |
| G1 | 0.1ng Cannabis cDNA ; HPLVd Positive + AMV Spike 1 | HPLVd | FAM | Amp | 24.2010285 | HPLVd B-F / p1 | HPLVd Positive |
| G1 | 0.1ng Cannabis cDNA ; HPLVd Positive + AMV Spike 1 | 26S | VIC | Amp | 17.45465045 | 26S/p1 | Reaction Positive |
| G2 | 0.1ng Cannabis cDNA ; HPLVd Positive + AMV Spike 2 | AMV | CY5 | Amp | 29.52751501 | AMV B-C / pB | AMV Positive |
| G2 | 0.1ng Cannabis cDNA ; HPLVd Positive + AMV Spike 2 | HPLVd | FAM | Amp | 24.24199847 | HPLVd B-F / p1 | HPLVd Positive |
| G2 | 0.1ng Cannabis cDNA ; HPLVd Positive + AMV Spike 2 | 26S | VIC | Amp | 17.34175838 | 26S/p1 | Reaction Positive |
| G3 | 0.1ng Cannabis cDNA ; HPLVd Positive + AMV Spike 3 | AMV | CY5 | Amp | 29.86837647 | AMV B-C / pB | AMV Positive |
| G3 | 0.1ng Cannabis cDNA ; HPLVd Positive + AMV Spike 3 | HPLVd | FAM | Amp | 24.37137941 | HPLVd B-F / p1 | HPLVd Positive |
| G3 | 0.1ng Cannabis cDNA ; HPLVd Positive + AMV Spike 3 | 26S | VIC | Amp | 17.69604999 | 26S/p1 | Reaction Positive |

FIG 11A contd

| | | | | | | |
|---|---|---|---|---|---|---|
| G4 | 0.1ng Cannabis cDNA ; HPLVd Positive + AMV Spike 4 | AMV | CY5 | Amp | 29.64897778 | AMV B-C / pB | AMV Positive |
| G4 | 0.1ng Cannabis cDNA ; HPLVd Positive + AMV Spike 4 | HPLVd | FAM | Amp | 24.45356344 | HPLVd B-F / p1 | HPLVd Positive |
| G4 | 0.1ng Cannabis cDNA ; HPLVd Positive + AMV Spike 4 | 26S | VIC | Amp | 17.55956815 | 26S/p1 | Reaction Positive |
| G5 | 0.1ng Cannabis cDNA ; HPLVd Positive + AMV Spike 5 | AMV | CY5 | Amp | 29.9168771 | AMV B-C / pB | AMV Positive |
| G5 | 0.1ng Cannabis cDNA ; HPLVd Positive + AMV Spike 5 | HPLVd | FAM | Amp | 24.3186539 | HPLVd B-F / p1 | HPLVd Positive |
| G5 | 0.1ng Cannabis cDNA ; HPLVd Positive + AMV Spike 5 | 26S | VIC | Amp | 17.50039799 | 26S/p1 | Reaction Positive |
| G6 | 0.1ng Cannabis cDNA ; HPLVd Positive + AMV Spike 6 | AMV | CY5 | Amp | 26.31881659 | AMV B-C / pB | AMV Positive |
| G6 | 0.1ng Cannabis cDNA ; HPLVd Positive + AMV Spike 6 | HPLVd | FAM | Amp | 24.16290843 | HPLVd B-F / p1 | HPLVd Positive |
| G6 | 0.1ng Cannabis cDNA ; HPLVd Positive + AMV Spike 6 | 26S | VIC | Amp | 17.58936543 | 26S/p1 | Reaction Positive |
| G7 | 0.1ng Cannabis cDNA ; HPLVd Positive + AMV Spike 7 | AMV | CY5 | Amp | 29.69527808 | AMV B-C / pB | AMV Positive |
| G7 | 0.1ng Cannabis cDNA ; HPLVd Positive + AMV Spike 7 | HPLVd | FAM | Amp | 24.1011536 | HPLVd B-F / p1 | HPLVd Positive |
| G7 | 0.1ng Cannabis cDNA ; HPLVd Positive + AMV Spike 7 | 26S | VIC | Amp | 17.16203795 | 26S/p1 | Reaction Positive |
| G8 | 0.1ng Cannabis cDNA ; HPLVd Positive + AMV Spike 8 | AMV | CY5 | Amp | 29.70350424 | AMV B-C / pB | AMV Positive |
| G8 | 0.1ng Cannabis cDNA ; HPLVd Positive + AMV Spike 8 | HPLVd | FAM | Amp | 24.36588212 | HPLVd B-F / p1 | HPLVd Positive |
| G8 | 0.1ng Cannabis cDNA ; HPLVd Positive + AMV Spike 8 | 26S | VIC | Amp | 17.44652068 | 26S/p1 | Reaction Positive |
| G9 | 0.1ng Cannabis cDNA ; HPLVd Positive + AMV Spike 9 | AMV | CY5 | Amp | 29.51356355 | AMV B-C / pB | AMV Positive |
| G9 | 0.1ng Cannabis cDNA ; HPLVd Positive + AMV Spike 9 | HPLVd | FAM | Amp | 24.4736456 | HPLVd B-F / p1 | HPLVd Positive |
| G9 | 0.1ng Cannabis cDNA ; HPLVd Positive + AMV Spike 9 | 26S | VIC | Amp | 17.92328255 | 26S/p1 | Reaction Positive |
| G10 | 0.1ng Cannabis cDNA ; HPLVd Positive + AMV Spike 10 | AMV | CY5 | Amp | 29.90099144 | AMV B-C / pB | AMV Positive |

FIG 11A contd

| Well | Description | Target | Dye | Amp | Ct | Primer/Probe | Reaction Result |
|---|---|---|---|---|---|---|---|
| G10 | 0.1ng Cannabis cDNA ; HPLVd Positive + AMV Spike 10 | HPLVd | FAM | Amp | 24.41443948 | HPLVd B-F / p1 | HPLVd Positive |
| G10 | 0.1ng Cannabis cDNA ; HPLVd Positive + AMV Spike 10 | 26S | VIC | Amp | 17.70755717 | 26S/p1 | Reaction Positive |
| G11 | 0.1ng Cannabis cDNA ; HPLVd Negative | AMV | CY5 | No Amp | Undetermined | AMV B-C / pB | AMV Negative |
| G11 | 0.1ng Cannabis cDNA ; HPLVd Negative | HPLVd | FAM | No Amp | Undetermined | HPLVd B-F / p1 | HPLVd Negative |
| G11 | 0.1ng Cannabis cDNA ; HPLVd Negative | 26S | VIC | Amp | 15.59008463 | 26S/p1 | Reaction Positive |
| G12 | NTC | AMV | CY5 | No Amp | Undetermined | AMV B-C / pB | AMV Negative |
| G12 | NTC | HPLVd | FAM | No Amp | Undetermined | HPLVd B-F / p1 | HPLVd Negative |
| G12 | NTC | 26S | VIC | No Amp | Undetermined | 26S/p1 | Reaction Negative |
| B1 | 1ng Cannabis cDNA ; HPLVd Positive + AMV Spike 1 | AMV | CY5 | Amp | 28.61770191 | AMV B-C / pB | AMV Positive |
| B1 | 1ng Cannabis cDNA ; HPLVd Positive + AMV Spike 1 | HPLVd | FAM | Amp | 22.17614434 | HPLVd B-D / p2 | HPLVd Positive |
| B1 | 1ng Cannabis cDNA ; HPLVd Positive + AMV Spike 1 | 26S | VIC | Amp | 17.61971506 | 26S/p1 | Reaction Positive |
| B2 | 1ng Cannabis cDNA ; HPLVd Positive + AMV Spike 2 | AMV | CY5 | Amp | 28.96338542 | AMV B-C / pB | AMV Positive |
| B2 | 1ng Cannabis cDNA ; HPLVd Positive + AMV Spike 2 | HPLVd | FAM | Amp | 22.39862746 | HPLVd B-D / p2 | HPLVd Positive |
| B2 | 1ng Cannabis cDNA ; HPLVd Positive + AMV Spike 2 | 26S | VIC | Amp | 19.98653903 | 26S/p1 | Reaction Positive |
| B3 | 1ng Cannabis cDNA ; HPLVd Positive + AMV Spike 3 | AMV | CY5 | Amp | 28.96161037 | AMV B-C / pB | AMV Positive |
| B3 | 1ng Cannabis cDNA ; HPLVd Positive + AMV Spike 3 | HPLVd | FAM | Amp | 22.32537851 | HPLVd B-D / p2 | HPLVd Positive |
| B3 | 1ng Cannabis cDNA ; HPLVd Positive + AMV Spike 3 | 26S | VIC | Amp | 17.94198107 | 26S/p1 | Reaction Positive |
| B4 | 1ng Cannabis cDNA ; HPLVd Positive + AMV Spike 4 | AMV | CY5 | Amp | 28.87167568 | AMV B-C / pB | AMV Positive |
| B4 | 1ng Cannabis cDNA ; HPLVd Positive + AMV Spike 4 | HPLVd | FAM | Amp | 22.42321085 | HPLVd B-D / p2 | HPLVd Positive |

FIG 11A contd

| | Description | Target | Dye | | Ct | Probe | Reaction |
|---|---|---|---|---|---|---|---|
| B4 | 1ng Cannabis cDNA ; HPLVd Positive + AMV Spike 4 | 26S | VIC | Amp | 18.02422351 | 26S/p1 | Reaction Positive |
| B5 | 1ng Cannabis cDNA ; HPLVd Positive + AMV Spike 5 | AMV | CY5 | Amp | 28.6122433 | AMV B-C / pB | AMV Positive |
| B5 | 1ng Cannabis cDNA ; HPLVd Positive + AMV Spike 5 | HPLVd | FAM | Amp | 22.33801195 | HPLVd B-D / p2 | HPLVd Positive |
| B5 | 1ng Cannabis cDNA ; HPLVd Positive + AMV Spike 5 | 26S | VIC | Amp | 18.275946 | 26S/p1 | Reaction Positive |
| B6 | 1ng Cannabis cDNA ; HPLVd Positive + AMV Spike 6 | AMV | CY5 | Amp | 28.694715 | AMV B-C / pB | AMV Positive |
| B6 | 1ng Cannabis cDNA ; HPLVd Positive + AMV Spike 6 | HPLVd | FAM | Amp | 22.39418111 | HPLVd B-D / p2 | HPLVd Positive |
| B6 | 1ng Cannabis cDNA ; HPLVd Positive + AMV Spike 6 | 26S | VIC | Amp | 18.3245685 | 26S/p1 | Reaction Positive |
| B7 | 1ng Cannabis cDNA ; HPLVd Positive + AMV Spike 7 | AMV | CY5 | Amp | 28.66128853 | AMV B-C / pB | AMV Positive |
| B7 | 1ng Cannabis cDNA ; HPLVd Positive + AMV Spike 7 | HPLVd | FAM | Amp | 22.4257288 | HPLVd B-D / p2 | HPLVd Positive |
| B7 | 1ng Cannabis cDNA ; HPLVd Positive + AMV Spike 7 | 26S | VIC | Amp | 18.01483414 | 26S/p1 | Reaction Positive |
| B8 | 1ng Cannabis cDNA ; HPLVd Positive + AMV Spike 8 | AMV | CY5 | Amp | 28.65646611 | AMV B-C / pB | AMV Positive |
| B8 | 1ng Cannabis cDNA ; HPLVd Positive + AMV Spike 8 | HPLVd | FAM | Amp | 22.37327576 | HPLVd B-D / p2 | HPLVd Positive |
| B8 | 1ng Cannabis cDNA ; HPLVd Positive + AMV Spike 8 | 26S | VIC | Amp | 17.88953121 | 26S/p1 | Reaction Positive |
| B9 | 1ng Cannabis cDNA ; HPLVd Positive + AMV Spike 9 | AMV | CY5 | Amp | 28.79799333 | AMV B-C / pB | AMV Positive |
| B9 | 1ng Cannabis cDNA ; HPLVd Positive + AMV Spike 9 | HPLVd | FAM | Amp | 22.41418287 | HPLVd B-D / p2 | HPLVd Positive |
| B9 | 1ng Cannabis cDNA ; HPLVd Positive + AMV Spike 9 | 26S | VIC | Amp | 18.18971326 | 26S/p1 | Reaction Positive |
| B10 | 1ng Cannabis cDNA ; HPLVd Positive + AMV Spike 10 | AMV | CY5 | Amp | 29.00145787 | AMV B-C / pB | AMV Positive |
| B10 | 1ng Cannabis cDNA ; HPLVd Positive + AMV Spike 10 | HPLVd | FAM | Amp | 22.57196983 | HPLVd B-D / p2 | HPLVd Positive |
| B10 | 1ng Cannabis cDNA ; HPLVd Positive + AMV Spike 10 | 26S | VIC | Amp | 18.6084229 | 26S/p1 | Reaction Positive |

FIG 11A contd

| | Sample | | Target | Channel | Amp | Ct | Assay | Result |
|---|---|---|---|---|---|---|---|---|
| B11 | 1ng Cannabis cDNA ; HPLVd Negative | | AMV | CY5 | No Amp | Undetermined | AMV B-C / pB | AMV Negative |
| B11 | 1ng Cannabis cDNA ; HPLVd Negative | | HPLVd | FAM | No Amp | Undetermined | HPLVd B-D / p2 | HPLVd Negative |
| B11 | 1ng Cannabis cDNA ; HPLVd Negative | | 26S | VIC | Amp | 15.75161558 | 26S/p1 | Reaction Positive |
| B12 | NTC | | AMV | CY5 | No Amp | Undetermined | AMV B-C / pB | AMV Negative |
| B12 | NTC | | HPLVd | FAM | No Amp | Undetermined | HPLVd B-D / p2 | HPLVd Negative |
| B12 | NTC | | 26S | VIC | No Amp | Undetermined | 26S/p1 | Reaction Negative |
| C1 | 0.1ng Cannabis cDNA ; HPLVd Positive + AMV Spike 1 | | AMV | CY5 | Amp | 32.09304916 | AMV B-C / pB | AMV Positive |
| C1 | 0.1ng Cannabis cDNA ; HPLVd Positive + AMV Spike 1 | | HPLVd | FAM | Amp | 26.24329716 | HPLVd B-D / p2 | HPLVd Positive |
| C1 | 0.1ng Cannabis cDNA ; HPLVd Positive + AMV Spike 1 | | 26S | VIC | Amp | 23.59837993 | 26S/p1 | Reaction Positive |
| C2 | 0.1ng Cannabis cDNA ; HPLVd Positive + AMV Spike 2 | | AMV | CY5 | Amp | 31.83490638 | AMV B-C / pB | AMV Positive |
| C2 | 0.1ng Cannabis cDNA ; HPLVd Positive + AMV Spike 2 | | HPLVd | FAM | Amp | 26.3787008 | HPLVd B-D / p2 | HPLVd Positive |
| C2 | 0.1ng Cannabis cDNA ; HPLVd Positive + AMV Spike 2 | | 26S | VIC | Inconclusive | Undetermined | 26S/p1 | 26S Failure |
| C3 | 0.1ng Cannabis cDNA ; HPLVd Positive + AMV Spike 3 | | AMV | CY5 | Amp | 31.58455969 | AMV B-C / pB | AMV Positive |
| C3 | 0.1ng Cannabis cDNA ; HPLVd Positive + AMV Spike 3 | | HPLVd | FAM | Amp | 26.44030687 | HPLVd B-D / p2 | HPLVd Positive |
| C3 | 0.1ng Cannabis cDNA ; HPLVd Positive + AMV Spike 3 | | 26S | VIC | Amp | 22.33932847 | 26S/p1 | Reaction Positive |
| C4 | 0.1ng Cannabis cDNA ; HPLVd Positive + AMV Spike 4 | | AMV | CY5 | Amp | 32.43209735 | AMV B-C / pB | AMV Positive |
| C4 | 0.1ng Cannabis cDNA ; HPLVd Positive + AMV Spike 4 | | HPLVd | FAM | Amp | 26.5551404 | HPLVd B-D / p2 | HPLVd Positive |
| C4 | 0.1ng Cannabis cDNA ; HPLVd Positive + AMV Spike 4 | | 26S | VIC | Amp | 23.43756431 | 26S/p1 | Reaction Positive |
| C5 | 0.1ng Cannabis cDNA ; HPLVd Positive + AMV Spike 5 | | AMV | CY5 | Amp | 31.06589056 | AMV B-C / pB | AMV Positive |

FIG 11A contd

| | | | | | | | |
|---|---|---|---|---|---|---|---|
| C5 | 0.1ng Cannabis cDNA ; HPLVd Positive + AMV Spike 5 | HPLVd | FAM | Amp | 26.50726053 | HPLVd B-D / p2 | HPLVd Positive |
| C5 | 0.1ng Cannabis cDNA ; HPLVd Positive + AMV Spike 5 | 26S | VIC | Amp | 22.92433172 | 26S/p1 | Reaction Positive |
| C6 | 0.1ng Cannabis cDNA ; HPLVd Positive + AMV Spike 6 | AMV | CY5 | Amp | 31.49665563 | AMV B-C / pB | AMV Positive |
| C6 | 0.1ng Cannabis cDNA ; HPLVd Positive + AMV Spike 6 | HPLVd | FAM | Amp | 26.3653759 | HPLVd B-D / p2 | HPLVd Positive |
| C6 | 0.1ng Cannabis cDNA ; HPLVd Positive + AMV Spike 6 | 26S | VIC | Amp | 23.74908634 | 26S/p1 | Reaction Positive |
| C7 | 0.1ng Cannabis cDNA ; HPLVd Positive + AMV Spike 7 | AMV | CY5 | Amp | 31.58013958 | AMV B-C / pB | AMV Positive |
| C7 | 0.1ng Cannabis cDNA ; HPLVd Positive + AMV Spike 7 | HPLVd | FAM | Amp | 26.36037512 | HPLVd B-D / p2 | HPLVd Positive |
| C7 | 0.1ng Cannabis cDNA ; HPLVd Positive + AMV Spike 7 | 26S | VIC | Amp | 22.26323664 | 26S/p1 | Reaction Positive |
| C8 | 0.1ng Cannabis cDNA ; HPLVd Positive + AMV Spike 8 | AMV | CY5 | Amp | 31.1706207 | AMV B-C / pB | AMV Positive |
| C8 | 0.1ng Cannabis cDNA ; HPLVd Positive + AMV Spike 8 | HPLVd | FAM | Amp | 26.65831951 | HPLVd B-D / p2 | HPLVd Positive |
| C8 | 0.1ng Cannabis cDNA ; HPLVd Positive + AMV Spike 8 | 26S | VIC | Amp | 23.9173371 | 26S/p1 | Reaction Positive |
| C9 | 0.1ng Cannabis cDNA ; HPLVd Positive + AMV Spike 9 | AMV | CY5 | Amp | 31.12765316 | AMV B-C / pB | AMV Positive |
| C9 | 0.1ng Cannabis cDNA ; HPLVd Positive + AMV Spike 9 | HPLVd | FAM | Amp | 26.28674069 | HPLVd B-D / p2 | HPLVd Positive |
| C9 | 0.1ng Cannabis cDNA ; HPLVd Positive + AMV Spike 9 | 26S | VIC | Amp | 23.41753354 | 26S/p1 | Reaction Positive |
| C10 | 0.1ng Cannabis cDNA ; HPLVd Positive + AMV Spike 10 | AMV | CY5 | Amp | 31.71103946 | AMV B-C / pB | AMV Positive |
| C10 | 0.1ng Cannabis cDNA ; HPLVd Positive + AMV Spike 10 | HPLVd | FAM | Amp | 26.27975998 | HPLVd B-D / p2 | HPLVd Positive |
| C10 | 0.1ng Cannabis cDNA ; HPLVd Positive + AMV Spike 10 | 26S | VIC | Amp | 22.93059905 | 26S/p1 | Reaction Positive |
| C11 | 0.1ng Cannabis cDNA ; HPLVd Negative | AMV | CY5 | No Amp | Undetermined | AMV B-C / pB | AMV Negative |
| C11 | 0.1ng Cannabis cDNA ; HPLVd Negative | HPLVd | FAM | No Amp | Undetermined | HPLVd B-D / p2 | HPLVd Negative |

FIG 11A contd

| | | | | | | | |
|---|---|---|---|---|---|---|---|
| C11 | 0.1ng Cannabis cDNA ; HPLVd Negative | 26S | VIC | Amp | 20.09941193 | 26S/p1 | Reaction Positive |
| C12 | NTC | AMV | CY5 | No Amp | Undetermined | AMV B-C / pB | AMV Negative |
| C12 | NTC | HPLVd | FAM | No Amp | Undetermined | HPLVd B-D / p2 | HPLVd Negative |
| C12 | NTC | 26S | VIC | No Amp | Undetermined | 26S/p1 | Reaction Negative |
| D1 | 1ng Cannabis cDNA ; HPLVd Positive + AMV Spike 1 | AMV | CY5 | Amp | 28.59159193 | AMV B-C / pB | AMV Positive |
| D1 | 1ng Cannabis cDNA ; HPLVd Positive + AMV Spike 1 | HPLVd | FAM | Amp | 21.4116826 | HPLVd B-E / p2 | HPLVd Positive |
| D1 | 1ng Cannabis cDNA ; HPLVd Positive + AMV Spike 1 | 26S | VIC | Amp | 16.21570279 | 26S/p1 | Reaction Positive |
| D2 | 1ng Cannabis cDNA ; HPLVd Positive + AMV Spike 2 | AMV | CY5 | Amp | 29.21027894 | AMV B-C / pB | AMV Positive |
| D2 | 1ng Cannabis cDNA ; HPLVd Positive + AMV Spike 2 | HPLVd | FAM | Amp | 21.78502326 | HPLVd B-E / p2 | HPLVd Positive |
| D2 | 1ng Cannabis cDNA ; HPLVd Positive + AMV Spike 2 | 26S | VIC | Amp | 16.36722324 | 26S/p1 | Reaction Positive |
| D3 | 1ng Cannabis cDNA ; HPLVd Positive + AMV Spike 3 | AMV | CY5 | Amp | 28.53487803 | AMV B-C / pB | AMV Positive |
| D3 | 1ng Cannabis cDNA ; HPLVd Positive + AMV Spike 3 | HPLVd | FAM | Amp | 21.77865859 | HPLVd B-E / p2 | HPLVd Positive |
| D3 | 1ng Cannabis cDNA ; HPLVd Positive + AMV Spike 3 | 26S | VIC | Amp | 17.34615226 | 26S/p1 | Reaction Positive |
| D4 | 1ng Cannabis cDNA ; HPLVd Positive + AMV Spike 4 | AMV | CY5 | Amp | 29.10144069 | AMV B-C / pB | AMV Positive |
| D4 | 1ng Cannabis cDNA ; HPLVd Positive + AMV Spike 4 | HPLVd | FAM | Amp | 21.70490253 | HPLVd B-E / p2 | HPLVd Positive |
| D4 | 1ng Cannabis cDNA ; HPLVd Positive + AMV Spike 4 | 26S | VIC | Amp | 17.02184107 | 26S/p1 | Reaction Positive |
| D5 | 1ng Cannabis cDNA ; HPLVd Positive + AMV Spike 5 | AMV | CY5 | Amp | 29.08592236 | AMV B-C / pB | AMV Positive |
| D5 | 1ng Cannabis cDNA ; HPLVd Positive + AMV Spike 5 | HPLVd | FAM | Amp | 21.71592396 | HPLVd B-E / p2 | HPLVd Positive |
| D5 | 1ng Cannabis cDNA ; HPLVd Positive + AMV Spike 5 | 26S | VIC | Amp | 16.46678957 | 26S/p1 | Reaction Positive |

FIG 11A contd

| Well | Sample | Target | Dye | Amp | Ct | Assay | Result |
|---|---|---|---|---|---|---|---|
| D6 | 1ng Cannabis cDNA ; HPLVd Positive + AMV Spike 6 | AMV | CY5 | Amp | 28.94747233 | AMV B-C / pB | AMV Positive |
| D6 | 1ng Cannabis cDNA ; HPLVd Positive + AMV Spike 6 | HPLVd | FAM | Amp | 21.71911373 | HPLVd B-E / p2 | HPLVd Positive |
| D6 | 1ng Cannabis cDNA ; HPLVd Positive + AMV Spike 6 | 26S | VIC | Amp | 16.17593618 | 26S/p1 | Reaction Positive |
| D7 | 1ng Cannabis cDNA ; HPLVd Positive + AMV Spike 7 | AMV | CY5 | Amp | 28.2105437 | AMV B-C / pB | AMV Positive |
| D7 | 1ng Cannabis cDNA ; HPLVd Positive + AMV Spike 7 | HPLVd | FAM | Amp | 21.52071409 | HPLVd B-E / p2 | HPLVd Positive |
| D7 | 1ng Cannabis cDNA ; HPLVd Positive + AMV Spike 7 | 26S | VIC | Amp | 16.16798073 | 26S/p1 | Reaction Positive |
| D8 | 1ng Cannabis cDNA ; HPLVd Positive + AMV Spike 8 | AMV | CY5 | Amp | 28.36049154 | AMV B-C / pB | AMV Positive |
| D8 | 1ng Cannabis cDNA ; HPLVd Positive + AMV Spike 8 | HPLVd | FAM | Amp | 21.51370011 | HPLVd B-E / p2 | HPLVd Positive |
| D8 | 1ng Cannabis cDNA ; HPLVd Positive + AMV Spike 8 | 26S | VIC | Amp | 16.28958546 | 26S/p1 | Reaction Positive |
| D9 | 1ng Cannabis cDNA ; HPLVd Positive + AMV Spike 9 | AMV | CY5 | Amp | 28.60453007 | AMV B-C / pB | AMV Positive |
| D9 | 1ng Cannabis cDNA ; HPLVd Positive + AMV Spike 9 | HPLVd | FAM | Amp | 21.55382931 | HPLVd B-E / p2 | HPLVd Positive |
| D9 | 1ng Cannabis cDNA ; HPLVd Positive + AMV Spike 9 | 26S | VIC | Amp | 16.14054814 | 26S/p1 | Reaction Positive |
| D10 | 1ng Cannabis cDNA ; HPLVd Positive + AMV Spike 10 | AMV | CY5 | Amp | 28.7912164 | AMV B-C / pB | AMV Positive |
| D10 | 1ng Cannabis cDNA ; HPLVd Positive + AMV Spike 10 | HPLVd | FAM | Amp | 21.58126505 | HPLVd B-E / p2 | HPLVd Positive |
| D10 | 1ng Cannabis cDNA ; HPLVd Positive + AMV Spike 10 | 26S | VIC | Amp | 16.83015959 | 26S/p1 | Reaction Positive |
| D11 | 1ng Cannabis cDNA ; HPLVd Negative | AMV | CY5 | No Amp | Undetermined | AMV B-C / pB | AMV Negative |
| D11 | 1ng Cannabis cDNA ; HPLVd Negative | HPLVd | FAM | No Amp | Undetermined | HPLVd B-E / p2 | HPLVd Negative |
| D11 | 1ng Cannabis cDNA ; HPLVd Negative | 26S | VIC | Amp | 14.49235109 | 26S/p1 | Reaction Positive |
| D12 | NTC | AMV | CY5 | No Amp | Undetermined | AMV B-C / pB | AMV Negative |

FIG 11A contd

| | Sample | Target | Dye | Amp Status | Ct | Assay | Result |
|---|---|---|---|---|---|---|---|
| D12 | NTC | | | | | | HPLVd Negative |
| D12 | NTC | 26S | VIC | No Amp | Undetermined | 26S/p1 | Reaction Negative |
| E1 | 0.1ng Cannabis cDNA ; HPLVd Positive + AMV Spike 1 | AMV | CY5 | Amp | 31.24408847 | AMV B-C / pB | AMV Positive |
| E1 | 0.1ng Cannabis cDNA ; HPLVd Positive + AMV Spike 1 | HPLVd | FAM | Amp | 25.28562263 | HPLVd B-E / p2 | HPLVd Positive |
| E1 | 0.1ng Cannabis cDNA ; HPLVd Positive + AMV Spike 1 | 26S | VIC | Amp | 22.87900207 | 26S/p1 | Reaction Positive |
| E2 | 0.1ng Cannabis cDNA ; HPLVd Positive + AMV Spike 2 | AMV | CY5 | Amp | 31.66989464 | AMV B-C / pB | AMV Positive |
| E2 | 0.1ng Cannabis cDNA ; HPLVd Positive + AMV Spike 2 | HPLVd | FAM | Amp | 25.38328415 | HPLVd B-E / p2 | HPLVd Positive |
| E2 | 0.1ng Cannabis cDNA ; HPLVd Positive + AMV Spike 2 | 26S | VIC | Amp | 22.77675052 | 26S/p1 | Reaction Positive |
| E3 | 0.1ng Cannabis cDNA ; HPLVd Positive + AMV Spike 3 | AMV | CY5 | Amp | 31.45614084 | AMV B-C / pB | AMV Positive |
| E3 | 0.1ng Cannabis cDNA ; HPLVd Positive + AMV Spike 3 | HPLVd | FAM | Amp | 25.64720674 | HPLVd B-E / p2 | HPLVd Positive |
| E3 | 0.1ng Cannabis cDNA ; HPLVd Positive + AMV Spike 3 | 26S | VIC | Amp | 24.051757 | 26S/p1 | Reaction Positive |
| E4 | 0.1ng Cannabis cDNA ; HPLVd Positive + AMV Spike 4 | AMV | CY5 | Amp | 32.05795403 | AMV B-C / pB | AMV Positive |
| E4 | 0.1ng Cannabis cDNA ; HPLVd Positive + AMV Spike 4 | HPLVd | FAM | Amp | 25.83776371 | HPLVd B-E / p2 | HPLVd Positive |
| E4 | 0.1ng Cannabis cDNA ; HPLVd Positive + AMV Spike 4 | 26S | VIC | Amp | 23.79480907 | 26S/p1 | Reaction Positive |
| E5 | 0.1ng Cannabis cDNA ; HPLVd Positive + AMV Spike 5 | AMV | CY5 | Amp | 31.86074975 | AMV B-C / pB | AMV Positive |
| E5 | 0.1ng Cannabis cDNA ; HPLVd Positive + AMV Spike 5 | HPLVd | FAM | Amp | 25.66752719 | HPLVd B-E / p2 | HPLVd Positive |
| E5 | 0.1ng Cannabis cDNA ; HPLVd Positive + AMV Spike 5 | 26S | VIC | Amp | 22.93901036 | 26S/p1 | Reaction Positive |
| E6 | 0.1ng Cannabis cDNA ; HPLVd Positive + AMV Spike 6 | AMV | CY5 | Amp | 31.19336098 | AMV B-C / pB | AMV Positive |
| E6 | 0.1ng Cannabis cDNA ; HPLVd Positive + AMV Spike 6 | HPLVd | FAM | Amp | 25.6510746 | HPLVd B-E / p2 | HPLVd Positive |

FIG 11A contd

| ID | Description | Target | Dye | Amp | Ct | Assay | Reaction |
|---|---|---|---|---|---|---|---|
| E6 | 0.1ng Cannabis cDNA ; HPLVd Positive + AMV Spike 6 | 26S | VIC | Amp | 23.13539114 | 26S/p1 | Reaction Positive |
| E7 | 0.1ng Cannabis cDNA ; HPLVd Positive + AMV Spike 7 | AMV | CY5 | Amp | 31.41910753 | AMV B-C / pB | AMV Positive |
| E7 | 0.1ng Cannabis cDNA ; HPLVd Positive + AMV Spike 7 | HPLVd | FAM | Amp | 25.54853554 | HPLVd B-E / p2 | HPLVd Positive |
| E7 | 0.1ng Cannabis cDNA ; HPLVd Positive + AMV Spike 7 | 26S | VIC | Amp | 23.07119956 | 26S/p1 | Reaction Positive |
| E8 | 0.1ng Cannabis cDNA ; HPLVd Positive + AMV Spike 8 | AMV | CY5 | Amp | 30.94348547 | AMV B-C / pB | AMV Positive |
| E8 | 0.1ng Cannabis cDNA ; HPLVd Positive + AMV Spike 8 | HPLVd | FAM | Amp | 25.55691876 | HPLVd B-E / p2 | HPLVd Positive |
| E8 | 0.1ng Cannabis cDNA ; HPLVd Positive + AMV Spike 8 | 26S | VIC | Amp | 22.79073401 | 26S/p1 | Reaction Positive |
| E9 | 0.1ng Cannabis cDNA ; HPLVd Positive + AMV Spike 9 | AMV | CY5 | Amp | 31.61538862 | AMV B-C / pB | AMV Positive |
| E9 | 0.1ng Cannabis cDNA ; HPLVd Positive + AMV Spike 9 | HPLVd | FAM | Amp | 25.4816046 | HPLVd B-E / p2 | HPLVd Positive |
| E9 | 0.1ng Cannabis cDNA ; HPLVd Positive + AMV Spike 9 | 26S | VIC | Amp | 22.88686426 | 26S/p1 | Reaction Positive |
| E10 | 0.1ng Cannabis cDNA ; HPLVd Positive + AMV Spike 10 | AMV | CY5 | Amp | 31.1438872 | AMV B-C / pB | AMV Positive |
| E10 | 0.1ng Cannabis cDNA ; HPLVd Positive + AMV Spike 10 | HPLVd | FAM | Amp | 25.45564637 | HPLVd B-E / p2 | HPLVd Positive |
| E10 | 0.1ng Cannabis cDNA ; HPLVd Positive + AMV Spike 10 | 26S | VIC | Amp | 22.73913883 | 26S/p1 | Reaction Positive |
| E11 | 0.1ng Cannabis cDNA ; HPLVd Negative | AMV | CY5 | No Amp | Undetermined | AMV B-C / pB | AMV Negative |
| E11 | 0.1ng Cannabis cDNA ; HPLVd Negative | HPLVd | FAM | No Amp | Undetermined | HPLVd B-E / p2 | HPLVd Negative |
| E11 | 0.1ng Cannabis cDNA ; HPLVd Negative | 26S | VIC | Amp | 19.8200877 | 26S/p1 | Reaction Positive |
| E12 | NTC | AMV | CY5 | No Amp | Undetermined | AMV B-C / pB | AMV Negative |
| E12 | NTC | HPLVd | FAM | No Amp | Undetermined | HPLVd B-E / p2 | HPLVd Negative |
| E12 | NTC | 26S | VIC | No Amp | Undetermined | 26S/p1 | Reaction Negative |

FIG 11A contd

| | | | | | | |
|---|---|---|---|---|---|---|
| F1 | 1ng Cannabis cDNA ; HPLVd Positive + AMV Spike 1 | AMV | CY5 | Amp | 28.67683991 | AMV B-C / pB | AMV Positive |
| F1 | 1ng Cannabis cDNA ; HPLVd Positive + AMV Spike 1 | HPLVd | FAM | Amp | 21.18561886 | HPLVd B-F / p2 | HPLVd Positive |
| F1 | 1ng Cannabis cDNA ; HPLVd Positive + AMV Spike 1 | 26S | VIC | Amp | 17.59000681 | 26S/p1 | Reaction Positive |
| F2 | 1ng Cannabis cDNA ; HPLVd Positive + AMV Spike 2 | AMV | CY5 | Amp | 28.97637426 | AMV B-C / pB | AMV Positive |
| F2 | 1ng Cannabis cDNA ; HPLVd Positive + AMV Spike 2 | HPLVd | FAM | Amp | 21.35188683 | HPLVd B-F / p2 | HPLVd Positive |
| F2 | 1ng Cannabis cDNA ; HPLVd Positive + AMV Spike 2 | 26S | VIC | Amp | 16.30529314 | 26S/p1 | Reaction Positive |
| F3 | 1ng Cannabis cDNA ; HPLVd Positive + AMV Spike 3 | AMV | CY5 | Amp | 28.91995103 | AMV B-C / pB | AMV Positive |
| F3 | 1ng Cannabis cDNA ; HPLVd Positive + AMV Spike 3 | HPLVd | FAM | Amp | 21.40247296 | HPLVd B-F / p2 | HPLVd Positive |
| F3 | 1ng Cannabis cDNA ; HPLVd Positive + AMV Spike 3 | 26S | VIC | Amp | 17.20111137 | 26S/p1 | Reaction Positive |
| F4 | 1ng Cannabis cDNA ; HPLVd Positive + AMV Spike 4 | AMV | CY5 | Amp | 28.7263011 | AMV B-C / pB | AMV Positive |
| F4 | 1ng Cannabis cDNA ; HPLVd Positive + AMV Spike 4 | HPLVd | FAM | Amp | 21.62367519 | HPLVd B-F / p2 | HPLVd Positive |
| F4 | 1ng Cannabis cDNA ; HPLVd Positive + AMV Spike 4 | 26S | VIC | Amp | 18.40977633 | 26S/p1 | Reaction Positive |
| F5 | 1ng Cannabis cDNA ; HPLVd Positive + AMV Spike 5 | AMV | CY5 | Amp | 28.46843197 | AMV B-C / pB | AMV Positive |
| F5 | 1ng Cannabis cDNA ; HPLVd Positive + AMV Spike 5 | HPLVd | FAM | Amp | 21.45161527 | HPLVd B-F / p2 | HPLVd Positive |
| F5 | 1ng Cannabis cDNA ; HPLVd Positive + AMV Spike 5 | 26S | VIC | Amp | 17.54061504 | 26S/p1 | Reaction Positive |
| F6 | 1ng Cannabis cDNA ; HPLVd Positive + AMV Spike 6 | AMV | CY5 | Amp | 28.7263296 | AMV B-C / pB | AMV Positive |
| F6 | 1ng Cannabis cDNA ; HPLVd Positive + AMV Spike 6 | HPLVd | FAM | Amp | 21.42926449 | HPLVd B-F / p2 | HPLVd Positive |
| F6 | 1ng Cannabis cDNA ; HPLVd Positive + AMV Spike 6 | 26S | VIC | Amp | 16.93932157 | 26S/p1 | Reaction Positive |
| F7 | 1ng Cannabis cDNA ; HPLVd Positive + AMV Spike 7 | AMV | CY5 | Amp | 28.20529753 | AMV B-C / pB | AMV Positive |

FIG 11A contd

| | Sample | | Target | Dye | Amp | Cq | Target | Call |
|---|---|---|---|---|---|---|---|---|
| F7 | 1ng Cannabis cDNA ; HPLVd Positive + AMV Spike 7 | | HPLVd | FAM | Amp | 21.35567062 | HPLVd B-F / p2 | HPLVd Positive |
| F7 | 1ng Cannabis cDNA ; HPLVd Positive + AMV Spike 7 | | 26S | VIC | Amp | 16.80186833 | 26S/p1 | Reaction Positive |
| F8 | 1ng Cannabis cDNA ; HPLVd Positive + AMV Spike 8 | | AMV | CY5 | Amp | 28.37534362 | AMV B-C / pB | AMV Positive |
| F8 | 1ng Cannabis cDNA ; HPLVd Positive + AMV Spike 8 | | HPLVd | FAM | Amp | 21.31249627 | HPLVd B-F / p2 | HPLVd Positive |
| F8 | 1ng Cannabis cDNA ; HPLVd Positive + AMV Spike 8 | | 26S | VIC | Amp | 18.19056352 | 26S/p1 | Reaction Positive |
| F9 | 1ng Cannabis cDNA ; HPLVd Positive + AMV Spike 9 | | AMV | CY5 | Amp | 28.48409869 | AMV B-C / pB | AMV Positive |
| F9 | 1ng Cannabis cDNA ; HPLVd Positive + AMV Spike 9 | | HPLVd | FAM | Amp | 21.37662658 | HPLVd B-F / p2 | HPLVd Positive |
| F9 | 1ng Cannabis cDNA ; HPLVd Positive + AMV Spike 9 | | 26S | VIC | Amp | 17.02984498 | 26S/p1 | Reaction Positive |
| F10 | 1ng Cannabis cDNA ; HPLVd Positive + AMV Spike 10 | | AMV | CY5 | Amp | 28.62686266 | AMV B-C / pB | AMV Positive |
| F10 | 1ng Cannabis cDNA ; HPLVd Positive + AMV Spike 10 | | HPLVd | FAM | Amp | 21.38012423 | HPLVd B-F / p2 | HPLVd Positive |
| F10 | 1ng Cannabis cDNA ; HPLVd Positive + AMV Spike 10 | | 26S | VIC | Amp | 17.3403584 | 26S/p1 | Reaction Positive |
| F11 | 1ng Cannabis cDNA ; HPLVd Negative | | AMV | CY5 | No Amp | Undetermined | AMV B-C / pB | AMV Negative |
| F11 | 1ng Cannabis cDNA ; HPLVd Negative | | HPLVd | FAM | No Amp | Undetermined | HPLVd B-F / p2 | HPLVd Negative |
| F11 | 1ng Cannabis cDNA ; HPLVd Negative | | 26S | VIC | No Amp | Undetermined | 26S/p1 | Reaction Negative |
| F12 | NTC | | AMV | CY5 | No Amp | Undetermined | AMV B-C / pB | AMV Negative |
| F12 | NTC | | HPLVd | FAM | Amp | 15.35809413 | HPLVd B-F / p2 | HPLVd Positive |
| F12 | NTC | | 26S | VIC | Undetermined | 26S/p1 | Reaction Negative |
| G1 | 0.1ng Cannabis cDNA ; HPLVd Positive + AMV Spike 1 | | AMV | CY5 | Amp | 31.03646929 | AMV B-C / pB | AMV Positive |
| G1 | 0.1ng Cannabis cDNA ; HPLVd Positive + AMV Spike 1 | | HPLVd | FAM | Amp | 25.13653237 | HPLVd B-F / p2 | HPLVd Positive |

FIG 11A contd

| | Sample | Target | Dye | Amp | Ct | Probe | Reaction |
|---|---|---|---|---|---|---|---|
| G1 | 0.1ng Cannabis cDNA ; HPLVd Positive + AMV Spike 1 | 26S | VIC | Amp | 23.05733924 | 26S/p1 | Reaction Positive |
| G2 | 0.1ng Cannabis cDNA ; HPLVd Positive + AMV Spike 2 | AMV | CY5 | Amp | 30.90950347 | AMV B-C / pB | AMV Positive |
| G2 | 0.1ng Cannabis cDNA ; HPLVd Positive + AMV Spike 2 | HPLVd | FAM | Amp | 25.17973396 | HPLVd B-F / p2 | HPLVd Positive |
| G2 | 0.1ng Cannabis cDNA ; HPLVd Positive + AMV Spike 2 | 26S | VIC | Amp | 23.63204746 | 26S/p1 | Reaction Positive |
| G3 | 0.1ng Cannabis cDNA ; HPLVd Positive + AMV Spike 3 | AMV | CY5 | Amp | 31.50280353 | AMV B-C / pB | AMV Positive |
| G3 | 0.1ng Cannabis cDNA ; HPLVd Positive + AMV Spike 3 | HPLVd | FAM | Amp | 25.38033098 | HPLVd B-F / p2 | HPLVd Positive |
| G3 | 0.1ng Cannabis cDNA ; HPLVd Positive + AMV Spike 3 | 26S | VIC | Amp | 24.36472701 | 26S/p1 | Reaction Positive |
| G4 | 0.1ng Cannabis cDNA ; HPLVd Positive + AMV Spike 4 | AMV | CY5 | Amp | 30.52251139 | AMV B-C / pB | AMV Positive |
| G4 | 0.1ng Cannabis cDNA ; HPLVd Positive + AMV Spike 4 | HPLVd | FAM | Amp | 25.3582001 | HPLVd B-F / p2 | HPLVd Positive |
| G4 | 0.1ng Cannabis cDNA ; HPLVd Positive + AMV Spike 4 | 26S | VIC | Inconclusive | Undetermined | 26S/p1 | 26S Failure |
| G5 | 0.1ng Cannabis cDNA ; HPLVd Positive + AMV Spike 5 | AMV | CY5 | Amp | 31.02372763 | AMV B-C / pB | AMV Positive |
| G5 | 0.1ng Cannabis cDNA ; HPLVd Positive + AMV Spike 5 | HPLVd | FAM | Amp | 25.47025498 | HPLVd B-F / p2 | HPLVd Positive |
| G5 | 0.1ng Cannabis cDNA ; HPLVd Positive + AMV Spike 5 | 26S | VIC | Amp | 22.98148209 | 26S/p1 | Reaction Positive |
| G6 | 0.1ng Cannabis cDNA ; HPLVd Positive + AMV Spike 6 | AMV | CY5 | Amp | 31.27356505 | AMV B-C / pB | AMV Positive |
| G6 | 0.1ng Cannabis cDNA ; HPLVd Positive + AMV Spike 6 | HPLVd | FAM | Amp | 25.27190146 | HPLVd B-F / p2 | HPLVd Positive |
| G6 | 0.1ng Cannabis cDNA ; HPLVd Positive + AMV Spike 6 | 26S | VIC | Amp | 22.80553855 | 26S/p1 | Reaction Positive |
| G7 | 0.1ng Cannabis cDNA ; HPLVd Positive + AMV Spike 7 | AMV | CY5 | Amp | 31.15579845 | AMV B-C / pB | AMV Positive |
| G7 | 0.1ng Cannabis cDNA ; HPLVd Positive + AMV Spike 7 | HPLVd | FAM | Amp | 25.04022042 | HPLVd B-F / p2 | HPLVd Positive |
| G7 | 0.1ng Cannabis cDNA ; HPLVd Positive + AMV Spike 7 | 26S | VIC | Amp | 22.40786219 | 26S/p1 | Reaction Positive |

FIG 11A contd

| Well | Sample | Target | Dye | Amp | Ct | Assay | Result |
|---|---|---|---|---|---|---|---|
| G8 | 0.1ng Cannabis cDNA ; HPLVd Positive + AMV Spike 8 | AMV | CY5 | Amp | 31.65052871 | AMV B-C / pB | AMV Positive |
| G8 | 0.1ng Cannabis cDNA ; HPLVd Positive + AMV Spike 8 | HPLVd | FAM | Amp | 25.31591122 | HPLVd B-F / p2 | HPLVd Positive |
| G8 | 0.1ng Cannabis cDNA ; HPLVd Positive + AMV Spike 8 | 26S | VIC | Amp | 23.27349485 | 26S/p1 | Reaction Positive |
| G9 | 0.1ng Cannabis cDNA ; HPLVd Positive + AMV Spike 9 | AMV | CY5 | Amp | 32.04907429 | AMV B-C / pB | AMV Positive |
| G9 | 0.1ng Cannabis cDNA ; HPLVd Positive + AMV Spike 9 | HPLVd | FAM | Amp | 25.46135487 | HPLVd B-F / p2 | HPLVd Positive |
| G9 | 0.1ng Cannabis cDNA ; HPLVd Positive + AMV Spike 9 | 26S | VIC | Amp | 23.50738775 | 26S/p1 | Reaction Positive |
| G10 | 0.1ng Cannabis cDNA ; HPLVd Positive + AMV Spike 10 | AMV | CY5 | Amp | 31.80963458 | AMV B-C / pB | AMV Positive |
| G10 | 0.1ng Cannabis cDNA ; HPLVd Positive + AMV Spike 10 | HPLVd | FAM | Amp | 25.42265084 | HPLVd B-F / p2 | HPLVd Positive |
| G10 | 0.1ng Cannabis cDNA ; HPLVd Positive + AMV Spike 10 | 26S | VIC | Amp | 23.57969339 | 26S/p1 | Reaction Positive |
| G11 | 0.1ng Cannabis cDNA ; HPLVd Negative | AMV | CY5 | No Amp | Undetermined | AMV B-C / pB | AMV Negative |
| G11 | 0.1ng Cannabis cDNA ; HPLVd Negative | HPLVd | FAM | No Amp | Undetermined | HPLVd B-F / p2 | HPLVd Negative |
| G11 | 0.1ng Cannabis cDNA ; HPLVd Negative | 26S | VIC | Amp | 19.7853274 | 26S/p1 | Reaction Positive |
| G12 | NTC | AMV | CY5 | No Amp | Undetermined | AMV B-C / pB | AMV Negative |
| G12 | NTC | HPLVd | FAM | No Amp | Undetermined | HPLVd B-F / p2 | HPLVd Negative |
| G12 | NTC | 26S | VIC | No Amp | Undetermined | 26S/p1 | Reaction Negative |
| B1 | 1ng Cannabis cDNA ; HPLVd Positive + AMV Spike 1 | AMV | CY5 | Amp | 28.2069296 | AMV B-C / pB | AMV Positive |
| B1 | 1ng Cannabis cDNA ; HPLVd Positive + AMV Spike 1 | HPLVd | FAM | Amp | 21.9246094 | HPLVd B-D / p3 | HPLVd Positive |
| B1 | 1ng Cannabis cDNA ; HPLVd Positive + AMV Spike 1 | 26S | VIC | Amp | 18.06872029 | 26S/p1 | Reaction Positive |
| B2 | 1ng Cannabis cDNA ; HPLVd Positive + AMV Spike 2 | AMV | CY5 | Amp | 27.29069136 | AMV B-C / pB | AMV Positive |

FIG 11A contd

| | | | | | | |
|---|---|---|---|---|---|---|
| B2 | 1ng Cannabis cDNA ; HPLVd Positive + AMV Spike 2 | HPLVd | FAM | Amp | | HPLVd Positive |
| B2 | 1ng Cannabis cDNA ; HPLVd Positive + AMV Spike 2 | 26S | VIC | Amp | 21.83683261 | HPLVd B-D / p3 | Reaction Positive |
| B3 | 1ng Cannabis cDNA ; HPLVd Positive + AMV Spike 3 | AMV | CY5 | Amp | 18.18193074 | 26S/p1 | AMV Positive |
| B3 | 1ng Cannabis cDNA ; HPLVd Positive + AMV Spike 3 | HPLVd | FAM | Amp | 27.50683115 | AMV B-C / pB | HPLVd Positive |
| B3 | 1ng Cannabis cDNA ; HPLVd Positive + AMV Spike 3 | 26S | VIC | Amp | 22.16808614 | HPLVd B-D / p3 | Reaction Positive |
| B4 | 1ng Cannabis cDNA ; HPLVd Positive + AMV Spike 4 | AMV | CY5 | Amp | 18.52805544 | 26S/p1 | AMV Positive |
| B4 | 1ng Cannabis cDNA ; HPLVd Positive + AMV Spike 4 | HPLVd | FAM | Amp | 27.85115244 | AMV B-C / pB | HPLVd Positive |
| B4 | 1ng Cannabis cDNA ; HPLVd Positive + AMV Spike 4 | 26S | VIC | Amp | 22.07779976 | HPLVd B-D / p3 | Reaction Positive |
| B5 | 1ng Cannabis cDNA ; HPLVd Positive + AMV Spike 5 | AMV | CY5 | Amp | 17.72697236 | 26S/p1 | AMV Positive |
| B5 | 1ng Cannabis cDNA ; HPLVd Positive + AMV Spike 5 | HPLVd | FAM | Amp | 27.67793071 | AMV B-C / pB | HPLVd Positive |
| B5 | 1ng Cannabis cDNA ; HPLVd Positive + AMV Spike 5 | 26S | VIC | Amp | 22.06018754 | HPLVd B-D / p3 | Reaction Positive |
| B6 | 1ng Cannabis cDNA ; HPLVd Positive + AMV Spike 6 | AMV | CY5 | Amp | 18.05799614 | 26S/p1 | AMV Positive |
| B6 | 1ng Cannabis cDNA ; HPLVd Positive + AMV Spike 6 | HPLVd | FAM | Amp | 27.27383892 | AMV B-C / pB | HPLVd Positive |
| B6 | 1ng Cannabis cDNA ; HPLVd Positive + AMV Spike 6 | 26S | VIC | Amp | 22.14295236 | HPLVd B-D / p3 | Reaction Positive |
| B7 | 1ng Cannabis cDNA ; HPLVd Positive + AMV Spike 7 | AMV | CY5 | Amp | 18.51987013 | 26S/p1 | AMV Positive |
| B7 | 1ng Cannabis cDNA ; HPLVd Positive + AMV Spike 7 | HPLVd | FAM | Amp | 27.37445935 | AMV B-C / pB | HPLVd Positive |
| B7 | 1ng Cannabis cDNA ; HPLVd Positive + AMV Spike 7 | 26S | VIC | Amp | 22.01727767 | HPLVd B-D / p3 | Reaction Positive |
| B8 | 1ng Cannabis cDNA ; HPLVd Positive + AMV Spike 8 | AMV | CY5 | Amp | 18.82455557 | 26S/p1 | AMV Positive |
| B8 | 1ng Cannabis cDNA ; HPLVd Positive + AMV Spike 8 | HPLVd | FAM | Amp | 27.98634127 | AMV B-C / pB | HPLVd Positive |
| B8 | 1ng Cannabis cDNA ; HPLVd Positive + AMV Spike 8 | | | | 22.13880499 | HPLVd B-D / p3 | |

FIG 11A contd

| Well | Sample | Target | Dye | Amp | Ct | Assay | Reaction |
|---|---|---|---|---|---|---|---|
| B8 | 1ng Cannabis cDNA ; HPLVd Positive + AMV Spike 8 | 26S | VIC | Amp | 17.8306691 | 26S/p1 | Reaction Positive |
| B9 | 1ng Cannabis cDNA ; HPLVd Positive + AMV Spike 9 | AMV | CY5 | Amp | 27.97662884 | AMV B-C / pB | AMV Positive |
| B9 | 1ng Cannabis cDNA ; HPLVd Positive + AMV Spike 9 | HPLVd | FAM | Amp | 22.11395488 | HPLVd B-D / p3 | HPLVd Positive |
| B9 | 1ng Cannabis cDNA ; HPLVd Positive + AMV Spike 9 | 26S | VIC | Amp | 17.96514913 | 26S/p1 | Reaction Positive |
| B10 | 1ng Cannabis cDNA ; HPLVd Positive + AMV Spike 10 | AMV | CY5 | Amp | 27.8013749 | AMV B-C / pB | AMV Positive |
| B10 | 1ng Cannabis cDNA ; HPLVd Positive + AMV Spike 10 | HPLVd | FAM | Amp | 22.2822411 | HPLVd B-D / p3 | HPLVd Positive |
| B10 | 1ng Cannabis cDNA ; HPLVd Positive + AMV Spike 10 | 26S | VIC | Amp | 17.81206837 | 26S/p1 | Reaction Positive |
| B11 | 1ng Cannabis cDNA ; HPLVd Negative | AMV | CY5 | No Amp | Undetermined | AMV B-C / pB | AMV Negative |
| B11 | 1ng Cannabis cDNA ; HPLVd Negative | HPLVd | FAM | No Amp | Undetermined | HPLVd B-D / p3 | HPLVd Negative |
| B11 | 1ng Cannabis cDNA ; HPLVd Negative | 26S | VIC | Amp | 14.85535441 | 26S/p1 | Reaction Positive |
| B12 | NTC | AMV | CY5 | No Amp | Undetermined | AMV B-C / pB | AMV Negative |
| B12 | NTC | HPLVd | FAM | No Amp | Undetermined | HPLVd B-D / p3 | HPLVd Negative |
| B12 | NTC | 26S | VIC | No Amp | Undetermined | 26S/p1 | Reaction Negative |
| C1 | 0.1ng Cannabis cDNA ; HPLVd Positive + AMV Spike 1 | AMV | CY5 | Amp | 32.00691432 | AMV B-C / pB | AMV Positive |
| C1 | 0.1ng Cannabis cDNA ; HPLVd Positive + AMV Spike 1 | HPLVd | FAM | Amp | 26.09040840 | HPLVd B-D / p3 | HPLVd Positive |
| C1 | 0.1ng Cannabis cDNA ; HPLVd Positive + AMV Spike 1 | 26S | VIC | Amp | 25.05620878 | 26S/p1 | Reaction Positive |
| C2 | 0.1ng Cannabis cDNA ; HPLVd Positive + AMV Spike 2 | AMV | CY5 | Amp | 32.33441981 | AMV B-C / pB | AMV Positive |
| C2 | 0.1ng Cannabis cDNA ; HPLVd Positive + AMV Spike 2 | HPLVd | FAM | Amp | 26.16924606 | HPLVd B-D / p3 | HPLVd Positive |
| C2 | 0.1ng Cannabis cDNA ; HPLVd Positive + AMV Spike 2 | 26S | VIC | Amp | 25.357701929 | 26S/p1 | Reaction Positive |

FIG 11A contd

| | | | | | | |
|---|---|---|---|---|---|---|
| C3 | 0.1ng Cannabis cDNA ; HPLVd Positive + AMV Spike 3 | AMV | CY5 | Amp | 32.07578749 | AMV B-C / pB | AMV Positive |
| C3 | 0.1ng Cannabis cDNA ; HPLVd Positive + AMV Spike 3 | HPLVd | FAM | Amp | 26.13757256 | HPLVd B-D / p3 | HPLVd Positive |
| C3 | 0.1ng Cannabis cDNA ; HPLVd Positive + AMV Spike 3 | 26S | VIC | Amp | 25.37079654 | 26S/p1 | Reaction Positive |
| C4 | 0.1ng Cannabis cDNA ; HPLVd Positive + AMV Spike 4 | AMV | CY5 | Amp | 32.20510751 | AMV B-C / pB | AMV Positive |
| C4 | 0.1ng Cannabis cDNA ; HPLVd Positive + AMV Spike 4 | HPLVd | FAM | Amp | 26.24968562 | HPLVd B-D / p3 | HPLVd Positive |
| C4 | 0.1ng Cannabis cDNA ; HPLVd Positive + AMV Spike 4 | 26S | VIC | Amp | 25.39849763 | 26S/p1 | Reaction Positive |
| C5 | 0.1ng Cannabis cDNA ; HPLVd Positive + AMV Spike 5 | AMV | CY5 | Amp | 32.45008798 | AMV B-C / pB | AMV Positive |
| C5 | 0.1ng Cannabis cDNA ; HPLVd Positive + AMV Spike 5 | HPLVd | FAM | Amp | 26.19223135 | HPLVd B-D / p3 | HPLVd Positive |
| C5 | 0.1ng Cannabis cDNA ; HPLVd Positive + AMV Spike 5 | 26S | VIC | Amp | 25.74921401 | 26S/p1 | Reaction Positive |
| C6 | 0.1ng Cannabis cDNA ; HPLVd Positive + AMV Spike 6 | AMV | CY5 | Amp | 31.90926782 | AMV B-C / pB | AMV Positive |
| C6 | 0.1ng Cannabis cDNA ; HPLVd Positive + AMV Spike 6 | HPLVd | FAM | Amp | 26.22964917 | HPLVd B-D / p3 | HPLVd Positive |
| C6 | 0.1ng Cannabis cDNA ; HPLVd Positive + AMV Spike 6 | 26S | VIC | Amp | 25.1305946 | 26S/p1 | Reaction Positive |
| C7 | 0.1ng Cannabis cDNA ; HPLVd Positive + AMV Spike 7 | AMV | CY5 | Amp | 32.41163435 | AMV B-C / pB | AMV Positive |
| C7 | 0.1ng Cannabis cDNA ; HPLVd Positive + AMV Spike 7 | HPLVd | FAM | Amp | 26.129 49679 | HPLVd B-D / p3 | HPLVd Positive |
| C7 | 0.1ng Cannabis cDNA ; HPLVd Positive + AMV Spike 7 | 26S | VIC | Amp | 24.94024136 | 26S/p1 | Reaction Positive |
| C8 | 0.1ng Cannabis cDNA ; HPLVd Positive + AMV Spike 8 | AMV | CY5 | Amp | 32.69527992 | AMV B-C / pB | AMV Positive |
| C8 | 0.1ng Cannabis cDNA ; HPLVd Positive + AMV Spike 8 | HPLVd | FAM | Amp | 26.4044901 | HPLVd B-D / p3 | HPLVd Positive |
| C8 | 0.1ng Cannabis cDNA ; HPLVd Positive + AMV Spike 8 | 26S | VIC | Amp | 24.82276242 | 26S/p1 | Reaction Positive |
| C9 | 0.1ng Cannabis cDNA ; HPLVd Positive + AMV Spike 9 | AMV | CY5 | Amp | 32.19725323 | AMV B-C / pB | AMV Positive |

FIG 11A contd

| Well | Sample | Target | Dye | Amp | Ct | Assay | Result |
|---|---|---|---|---|---|---|---|
| C9 | 0.1ng Cannabis cDNA ; HPLVd Positive + AMV Spike 9 | HPLVd | FAM | Amp | 26.1677592 | HPLVd B-D / p3 | HPLVd Positive |
| C9 | 0.1ng Cannabis cDNA ; HPLVd Positive + AMV Spike 9 | 26S | VIC | Amp | 24.86845618 | 26S/p1 | Reaction Positive |
| C10 | 0.1ng Cannabis cDNA ; HPLVd Positive + AMV Spike 10 | AMV | CY5 | Amp | 31.56235459 | AMV B-C / pB | AMV Positive |
| C10 | 0.1ng Cannabis cDNA ; HPLVd Positive + AMV Spike 10 | HPLVd | FAM | Amp | 25.99591341 | HPLVd B-D / p3 | HPLVd Positive |
| C10 | 0.1ng Cannabis cDNA ; HPLVd Positive + AMV Spike 10 | 26S | VIC | Amp | 24.63166008 | 26S/p1 | Reaction Positive |
| C11 | 0.1ng Cannabis cDNA ; HPLVd Negative | AMV | CY5 | No Amp | Undetermined | AMV B-C / pB | AMV Negative |
| C11 | 0.1ng Cannabis cDNA ; HPLVd Negative | HPLVd | FAM | No Amp | Undetermined | HPLVd B-D / p3 | HPLVd Negative |
| C11 | 0.1ng Cannabis cDNA ; HPLVd Negative | 26S | VIC | Amp | 22.30171219 | 26S/p1 | Reaction Positive |
| C12 | NTC | AMV | CY5 | No Amp | Undetermined | AMV B-C / pB | AMV Negative |
| C12 | NTC | HPLVd | FAM | No Amp | Undetermined | HPLVd B-D / p3 | HPLVd Negative |
| C12 | NTC | 26S | VIC | No Amp | Undetermined | 26S/p1 | Reaction Negative |
| D1 | 1ng Cannabis cDNA ; HPLVd Positive + AMV Spike 1 | AMV | CY5 | Amp | 28.26348797 | AMV B-C / pB | AMV Positive |
| D1 | 1ng Cannabis cDNA ; HPLVd Positive + AMV Spike 1 | HPLVd | FAM | Amp | 21.25361943 | HPLVd B-E / p3 | HPLVd Positive |
| D1 | 1ng Cannabis cDNA ; HPLVd Positive + AMV Spike 1 | 26S | VIC | Amp | 17.32437252 | 26S/p1 | Reaction Positive |
| D2 | 1ng Cannabis cDNA ; HPLVd Positive + AMV Spike 2 | AMV | CY5 | Amp | 27.97962785 | AMV B-C / pB | AMV Positive |
| D2 | 1ng Cannabis cDNA ; HPLVd Positive + AMV Spike 2 | HPLVd | FAM | Amp | 21.35943419 | HPLVd B-E / p3 | HPLVd Positive |
| D2 | 1ng Cannabis cDNA ; HPLVd Positive + AMV Spike 2 | 26S | VIC | Amp | 17.06494854 | 26S/p1 | Reaction Positive |
| D3 | 1ng Cannabis cDNA ; HPLVd Positive + AMV Spike 3 | AMV | CY5 | Amp | 28.58766697 | AMV B-C / pB | AMV Positive |
| D3 | 1ng Cannabis cDNA ; HPLVd Positive + AMV Spike 3 | HPLVd | FAM | Amp | 21.57170988 | HPLVd B-E / p3 | HPLVd Positive |

FIG 11A contd

| | Sample | Target | Dye | Amp | Ct | Probe | Reaction |
|---|---|---|---|---|---|---|---|
| D3 | 1ng Cannabis cDNA ; HPLVd Positive + AMV Spike 3 | 26S | VIC | Amp | 18.3347564 | 26S/p1 | Reaction Positive |
| D4 | 1ng Cannabis cDNA ; HPLVd Positive + AMV Spike 4 | AMV | CY5 | Amp | 28.2596586 | AMV B-C / pB | AMV Positive |
| D4 | 1ng Cannabis cDNA ; HPLVd Positive + AMV Spike 4 | HPLVd | FAM | Amp | 21.56858992 | HPLVd B-E / p3 | HPLVd Positive |
| D4 | 1ng Cannabis cDNA ; HPLVd Positive + AMV Spike 4 | 26S | VIC | Amp | 18.46312551 | 26S/p1 | Reaction Positive |
| D5 | 1ng Cannabis cDNA ; HPLVd Positive + AMV Spike 5 | AMV | CY5 | Amp | 28.06844691 | AMV B-C / pB | AMV Positive |
| D5 | 1ng Cannabis cDNA ; HPLVd Positive + AMV Spike 5 | HPLVd | FAM | Amp | 21.54879676 | HPLVd B-E / p3 | HPLVd Positive |
| D5 | 1ng Cannabis cDNA ; HPLVd Positive + AMV Spike 5 | 26S | VIC | Amp | 17.99252141 | 26S/p1 | Reaction Positive |
| D6 | 1ng Cannabis cDNA ; HPLVd Positive + AMV Spike 6 | AMV | CY5 | Amp | 28.02683069 | AMV B-C / pB | AMV Positive |
| D6 | 1ng Cannabis cDNA ; HPLVd Positive + AMV Spike 6 | HPLVd | FAM | Amp | 21.54889554 | HPLVd B-E / p3 | HPLVd Positive |
| D6 | 1ng Cannabis cDNA ; HPLVd Positive + AMV Spike 6 | 26S | VIC | Amp | 18.12492489 | 26S/p1 | Reaction Positive |
| D7 | 1ng Cannabis cDNA ; HPLVd Positive + AMV Spike 7 | AMV | CY5 | Amp | 27.65366464 | AMV B-C / pB | AMV Positive |
| D7 | 1ng Cannabis cDNA ; HPLVd Positive + AMV Spike 7 | HPLVd | FAM | Amp | 21.35955524 | HPLVd B-E / p3 | HPLVd Positive |
| D7 | 1ng Cannabis cDNA ; HPLVd Positive + AMV Spike 7 | 26S | VIC | Amp | 17.0497434 | 26S/p1 | Reaction Positive |
| D8 | 1ng Cannabis cDNA ; HPLVd Positive + AMV Spike 8 | AMV | CY5 | Amp | 27.95051691 | AMV B-C / pB | AMV Positive |
| D8 | 1ng Cannabis cDNA ; HPLVd Positive + AMV Spike 8 | HPLVd | FAM | Amp | 21.3883084 | HPLVd B-E / p3 | HPLVd Positive |
| D8 | 1ng Cannabis cDNA ; HPLVd Positive + AMV Spike 8 | 26S | VIC | Amp | 17.78235522 | 26S/p1 | Reaction Positive |
| D9 | 1ng Cannabis cDNA ; HPLVd Positive + AMV Spike 9 | AMV | CY5 | Amp | 27.99640376 | AMV B-C / pB | AMV Positive |
| D9 | 1ng Cannabis cDNA ; HPLVd Positive + AMV Spike 9 | HPLVd | FAM | Amp | 21.24877966 | HPLVd B-E / p3 | HPLVd Positive |
| D9 | 1ng Cannabis cDNA ; HPLVd Positive + AMV Spike 9 | 26S | VIC | Amp | 17.84636458 | 26S/p1 | Reaction Positive |

FIG 11A contd

| ID | Description | Target | Dye | Amp | Ct | Assay | Result |
|---|---|---|---|---|---|---|---|
| D10 | 1ng Cannabis cDNA ; HPLVd Positive + AMV Spike 10 | AMV | CY5 | Amp | 28.03249555 | AMV B-C / pB | AMV Positive |
| D10 | 1ng Cannabis cDNA ; HPLVd Positive + AMV Spike 10 | HPLVd | FAM | Amp | 21.25197254 | HPLVd B-E / p3 | HPLVd Positive |
| D10 | 1ng Cannabis cDNA ; HPLVd Positive + AMV Spike 10 | 26S | VIC | Amp | 18.17849519 | 26S/p1 | Reaction Positive |
| D11 | 1ng Cannabis cDNA ; HPLVd Negative | AMV | CY5 | No Amp | Undetermined | AMV B-C / pB | AMV Negative |
| D11 | 1ng Cannabis cDNA ; HPLVd Negative | HPLVd | FAM | No Amp | Undetermined | HPLVd B-E / p3 | HPLVd Negative |
| D11 | 1ng Cannabis cDNA ; HPLVd Negative | 26S | VIC | Amp | 15.44647417 | 26S/p1 | Reaction Positive |
| D12 | NTC | AMV | CY5 | No Amp | Undetermined | AMV B-C / pB | AMV Negative |
| D12 | NTC | HPLVd | FAM | No Amp | Undetermined | HPLVd B-E / p3 | HPLVd Negative |
| D12 | NTC | 26S | VIC | No Amp | Undetermined | 26S/p1 | Reaction Negative |
| E1 | 0.1ng Cannabis cDNA ; HPLVd Positive + AMV Spike 1 | AMV | CY5 | Amp | 32.21854577 | AMV B-C / pB | AMV Positive |
| E1 | 0.1ng Cannabis cDNA ; HPLVd Positive + AMV Spike 1 | HPLVd | FAM | Amp | 25.05793088 | HPLVd B-E / p3 | HPLVd Positive |
| E1 | 0.1ng Cannabis cDNA ; HPLVd Positive + AMV Spike 1 | 26S | VIC | Amp | 24.30424211 | 26S/p1 | Reaction Positive |
| E2 | 0.1ng Cannabis cDNA ; HPLVd Positive + AMV Spike 2 | AMV | CY5 | Amp | 31.59403053 | AMV B-C / pB | AMV Positive |
| E2 | 0.1ng Cannabis cDNA ; HPLVd Positive + AMV Spike 2 | HPLVd | FAM | Amp | 25.00716659 | HPLVd B-E / p3 | HPLVd Positive |
| E2 | 0.1ng Cannabis cDNA ; HPLVd Positive + AMV Spike 2 | 26S | VIC | Amp | 23.3838002 | 26S/p1 | Reaction Positive |
| E3 | 0.1ng Cannabis cDNA ; HPLVd Positive + AMV Spike 3 | AMV | CY5 | Amp | 32.76787372 | AMV B-C / pB | AMV Positive |
| E3 | 0.1ng Cannabis cDNA ; HPLVd Positive + AMV Spike 3 | HPLVd | FAM | Amp | 25.27326725 | HPLVd B-E / p3 | HPLVd Positive |
| E3 | 0.1ng Cannabis cDNA ; HPLVd Positive + AMV Spike 3 | 26S | VIC | Amp | 25.11707803 | 26S/p1 | Reaction Positive |
| E4 | 0.1ng Cannabis cDNA ; HPLVd Positive + AMV Spike 4 | AMV | CY5 | Amp | 32.70762996 | AMV B-C / pB | AMV Positive |

FIG 11A contd

| | Sample | Target | Dye | Amp | Cq | Target/Primer | Result |
|---|---|---|---|---|---|---|---|
| E4 | 0.1ng Cannabis cDNA ; HPLVd Positive + AMV Spike 4 | HPLVd | FAM | Amp | 25.61368988 | HPLVd B-E / p3 | HPLVd Positive |
| E4 | 0.1ng Cannabis cDNA ; HPLVd Positive + AMV Spike 4 | 26S | VIC | Amp | 25.72403848 | 26S/p1 | Reaction Positive |
| E5 | 0.1ng Cannabis cDNA ; HPLVd Positive + AMV Spike 5 | AMV | CY5 | Amp | 32.17053715 | AMV B-C / pB | AMV Positive |
| E5 | 0.1ng Cannabis cDNA ; HPLVd Positive + AMV Spike 5 | HPLVd | FAM | Amp | 25.35187608 | HPLVd B-E / p3 | HPLVd Positive |
| E5 | 0.1ng Cannabis cDNA ; HPLVd Positive + AMV Spike 5 | 26S | VIC | Amp | 25.54975194 | 26S/p1 | Reaction Positive |
| E6 | 0.1ng Cannabis cDNA ; HPLVd Positive + AMV Spike 6 | AMV | CY5 | Amp | 31.39977939 | AMV B-C / pB | AMV Positive |
| E6 | 0.1ng Cannabis cDNA ; HPLVd Positive + AMV Spike 6 | HPLVd | FAM | Amp | 25.23067155 | HPLVd B-E / p3 | HPLVd Positive |
| E6 | 0.1ng Cannabis cDNA ; HPLVd Positive + AMV Spike 6 | 26S | VIC | Amp | 24.14669419 | 26S/p1 | Reaction Positive |
| E7 | 0.1ng Cannabis cDNA ; HPLVd Positive + AMV Spike 7 | AMV | CY5 | Amp | 18.92412865 | AMV B-C / pB | AMV Positive |
| E7 | 0.1ng Cannabis cDNA ; HPLVd Positive + AMV Spike 7 | HPLVd | FAM | Amp | 25.05968829 | HPLVd B-E / p3 | HPLVd Positive |
| E7 | 0.1ng Cannabis cDNA ; HPLVd Positive + AMV Spike 7 | 26S | VIC | Amp | 24.47610956 | 26S/p1 | Reaction Positive |
| E8 | 0.1ng Cannabis cDNA ; HPLVd Positive + AMV Spike 8 | AMV | CY5 | Amp | 31.90484779 | AMV B-C / pB | AMV Positive |
| E8 | 0.1ng Cannabis cDNA ; HPLVd Positive + AMV Spike 8 | HPLVd | FAM | Amp | 25.53388265 | HPLVd B-E / p3 | HPLVd Positive |
| E8 | 0.1ng Cannabis cDNA ; HPLVd Positive + AMV Spike 8 | 26S | VIC | Amp | 22.53846888 | 26S/p1 | Reaction Positive |
| E9 | 0.1ng Cannabis cDNA ; HPLVd Positive + AMV Spike 9 | AMV | CY5 | Amp | 32.10941133 | AMV B-C / pB | AMV Positive |
| E9 | 0.1ng Cannabis cDNA ; HPLVd Positive + AMV Spike 9 | HPLVd | FAM | Amp | 25.14927938 | HPLVd B-E / p3 | HPLVd Positive |
| E9 | 0.1ng Cannabis cDNA ; HPLVd Positive + AMV Spike 9 | 26S | VIC | Amp | 24.61308569 | 26S/p1 | Reaction Positive |
| E10 | 0.1ng Cannabis cDNA ; HPLVd Positive + AMV Spike 10 | AMV | CY5 | Amp | 32.13596331 | AMV B-C / pB | AMV Positive |
| E10 | 0.1ng Cannabis cDNA ; HPLVd Positive + AMV Spike 10 | HPLVd | FAM | Amp | 25.27674451 | HPLVd B-E / p3 | HPLVd Positive |

FIG 11A contd

| Well | Sample | | | | Ct | | Reaction |
|---|---|---|---|---|---|---|---|
| E10 | 0.1ng Cannabis cDNA ; HPLVd Positive + AMV Spike 10 | 26S | VIC | Amp | 24.30299088 | 26S/p1 | Reaction Positive |
| E11 | 0.1ng Cannabis cDNA ; HPLVd Negative | AMV | CY5 | No Amp | Undetermined | AMV B-C / pB | AMV Negative |
| E11 | 0.1ng Cannabis cDNA ; HPLVd Negative | HPLVd | FAM | No Amp | Undetermined | HPLVd B-E / p3 | HPLVd Negative |
| E11 | 0.1ng Cannabis cDNA ; HPLVd Negative | 26S | VIC | Amp | 21.13319088 | 26S/p1 | Reaction Positive |
| E12 | NTC | AMV | CY5 | No Amp | Undetermined | AMV B-C / pB | AMV Negative |
| E12 | NTC | HPLVd | FAM | No Amp | Undetermined | HPLVd B-E / p3 | HPLVd Negative |
| E12 | NTC | 26S | VIC | No Amp | Undetermined | 26S/p1 | Reaction Negative |
| F1 | 1ng Cannabis cDNA ; HPLVd Positive + AMV Spike 1 | AMV | CY5 | Amp | 27.63838811 | AMV B-C / pB | AMV Positive |
| F1 | 1ng Cannabis cDNA ; HPLVd Positive + AMV Spike 1 | HPLVd | FAM | Amp | 20.94787871 | HPLVd B-F / p3 | HPLVd Positive |
| F1 | 1ng Cannabis cDNA ; HPLVd Positive + AMV Spike 1 | 26S | VIC | Amp | 16.53722178 | 26S/p1 | Reaction Positive |
| F2 | 1ng Cannabis cDNA ; HPLVd Positive + AMV Spike 2 | AMV | CY5 | Amp | 27.68388682 | AMV B-C / pB | AMV Positive |
| F2 | 1ng Cannabis cDNA ; HPLVd Positive + AMV Spike 2 | HPLVd | FAM | Amp | 21.05303366 | HPLVd B-F / p3 | HPLVd Positive |
| F2 | 1ng Cannabis cDNA ; HPLVd Positive + AMV Spike 2 | 26S | VIC | Amp | 18.00700901 | 26S/p1 | Reaction Positive |
| F3 | 1ng Cannabis cDNA ; HPLVd Positive + AMV Spike 3 | AMV | CY5 | Amp | 27.03561497 | AMV B-C / pB | AMV Positive |
| F3 | 1ng Cannabis cDNA ; HPLVd Positive + AMV Spike 3 | HPLVd | FAM | Amp | 21.04273707 | HPLVd B-F / p3 | HPLVd Positive |
| F3 | 1ng Cannabis cDNA ; HPLVd Positive + AMV Spike 3 | 26S | VIC | Amp | 17.36204638 | 26S/p1 | Reaction Positive |
| F4 | 1ng Cannabis cDNA ; HPLVd Positive + AMV Spike 4 | AMV | CY5 | Amp | 27.88897295 | AMV B-C / pB | AMV Positive |
| F4 | 1ng Cannabis cDNA ; HPLVd Positive + AMV Spike 4 | HPLVd | FAM | Amp | 21.18450984 | HPLVd B-F / p3 | HPLVd Positive |
| F4 | 1ng Cannabis cDNA ; HPLVd Positive + AMV Spike 4 | 26S | VIC | Inconclusive | Undetermined | 26S/p1 | 26S Failure |
| F5 | 1ng Cannabis cDNA ; HPLVd Positive + AMV Spike 5 | AMV | CY5 | Amp | 27.94394772 | AMV B-C / pB | AMV Positive |

FIG 11A contd

| | | | | | | |
|---|---|---|---|---|---|---|
| F5 | 1ng Cannabis cDNA ; HPLVd Positive + AMV Spike 5 | HPLVd | FAM | Amp | 21.12409372 | HPLVd B-F / p3 | HPLVd Positive |
| F5 | 1ng Cannabis cDNA ; HPLVd Positive + AMV Spike 5 | 26S | VIC | Amp | 17.82265353 | 26S/p1 | Reaction Positive |
| F6 | 1ng Cannabis cDNA ; HPLVd Positive + AMV Spike 6 | AMV | CY5 | Amp | 27.75259943 | AMV B-C / pB | AMV Positive |
| F6 | 1ng Cannabis cDNA ; HPLVd Positive + AMV Spike 6 | HPLVd | FAM | Amp | 21.17831752 | HPLVd B-F / p3 | HPLVd Positive |
| F6 | 1ng Cannabis cDNA ; HPLVd Positive + AMV Spike 6 | 26S | VIC | Amp | 17.78263247 | 26S/p1 | Reaction Positive |
| F7 | 1ng Cannabis cDNA ; HPLVd Positive + AMV Spike 7 | AMV | CY5 | Amp | 27.76138913 | AMV B-C / pB | AMV Positive |
| F7 | 1ng Cannabis cDNA ; HPLVd Positive + AMV Spike 7 | HPLVd | FAM | Amp | 21.09696416 | HPLVd B-F / p3 | HPLVd Positive |
| F7 | 1ng Cannabis cDNA ; HPLVd Positive + AMV Spike 7 | 26S | VIC | Amp | 17.91458177 | 26S/p1 | Reaction Positive |
| F8 | 1ng Cannabis cDNA ; HPLVd Positive + AMV Spike 8 | AMV | CY5 | Amp | 27.42794197 | AMV B-C / pB | AMV Positive |
| F8 | 1ng Cannabis cDNA ; HPLVd Positive + AMV Spike 8 | HPLVd | FAM | Amp | 21.07534671 | HPLVd B-F / p3 | HPLVd Positive |
| F8 | 1ng Cannabis cDNA ; HPLVd Positive + AMV Spike 8 | 26S | VIC | Amp | 17.54689221 | 26S/p1 | Reaction Positive |
| F9 | 1ng Cannabis cDNA ; HPLVd Positive + AMV Spike 9 | AMV | CY5 | Amp | 27.31454262 | AMV B-C / pB | AMV Positive |
| F9 | 1ng Cannabis cDNA ; HPLVd Positive + AMV Spike 9 | HPLVd | FAM | Amp | 21.12716076 | HPLVd B-F / p3 | HPLVd Positive |
| F9 | 1ng Cannabis cDNA ; HPLVd Positive + AMV Spike 9 | 26S | VIC | Amp | 17.38863571 | 26S/p1 | Reaction Positive |
| F10 | 1ng Cannabis cDNA ; HPLVd Positive + AMV Spike 10 | AMV | CY5 | Amp | 27.314963 | AMV B-C / pB | AMV Positive |
| F10 | 1ng Cannabis cDNA ; HPLVd Positive + AMV Spike 10 | HPLVd | FAM | Amp | 21.10419321 | HPLVd B-F / p3 | HPLVd Positive |
| F10 | 1ng Cannabis cDNA ; HPLVd Positive + AMV Spike 10 | 26S | VIC | Amp | 16.96359189 | 26S/p1 | Reaction Positive |
| F11 | 1ng Cannabis cDNA ; HPLVd Negative | AMV | CY5 | No Amp | Undetermined | AMV B-C / pB | AMV Negative |
| F11 | 1ng Cannabis cDNA ; HPLVd Negative | HPLVd | FAM | No Amp | Undetermined | HPLVd B-F / p3 | HPLVd Negative |

FIG 11A contd

| | | | | | | | Reaction Positive |
|---|---|---|---|---|---|---|---|
| F11 | 1ng Cannabis cDNA ; HPLVd Negative | 26S | VIC | Amp | 14.2527181 | 26S/p1 | Reaction Positive |
| F12 | NTC | AMV | CY5 | No Amp | Undetermined | AMV B-C / pB | AMV Negative |
| F12 | NTC | HPLVd | FAM | No Amp | Undetermined | HPLVd B-F / p3 | HPLVd Negative |
| F12 | NTC | 26S | VIC | No Amp | Undetermined | 26S/p1 | Reaction Negative |
| G1 | 0.1ng Cannabis cDNA ; HPLVd Positive + AMV Spike 1 | AMV | CY5 | Amp | 31.86000201 | AMV B-C / pB | AMV Positive |
| G1 | 0.1ng Cannabis cDNA ; HPLVd Positive + AMV Spike 1 | HPLVd | FAM | Amp | 24.75424551 | HPLVd B-F / p3 | HPLVd Positive |
| G1 | 0.1ng Cannabis cDNA ; HPLVd Positive + AMV Spike 1 | 26S | VIC | Amp | 24.02024427 | 26S/p1 | Reaction Positive |
| G2 | 0.1ng Cannabis cDNA ; HPLVd Positive + AMV Spike 2 | AMV | CY5 | Amp | 31.91222441 | AMV B-C / pB | AMV Positive |
| G2 | 0.1ng Cannabis cDNA ; HPLVd Positive + AMV Spike 2 | HPLVd | FAM | Amp | 24.97709955 | HPLVd B-F / p3 | HPLVd Positive |
| G2 | 0.1ng Cannabis cDNA ; HPLVd Positive + AMV Spike 2 | 26S | VIC | Amp | 24.75045736 | 26S/p1 | Reaction Positive |
| G3 | 0.1ng Cannabis cDNA ; HPLVd Positive + AMV Spike 3 | AMV | CY5 | Amp | 32.05923001 | AMV B-C / pB | AMV Positive |
| G3 | 0.1ng Cannabis cDNA ; HPLVd Positive + AMV Spike 3 | HPLVd | FAM | Amp | 25.03556093 | HPLVd B-F / p3 | HPLVd Positive |
| G3 | 0.1ng Cannabis cDNA ; HPLVd Positive + AMV Spike 3 | 26S | VIC | Amp | 25.43251257 | 26S/p1 | Reaction Positive |
| G4 | 0.1ng Cannabis cDNA ; HPLVd Positive + AMV Spike 4 | AMV | CY5 | Amp | 31.78408523 | AMV B-C / pB | AMV Positive |
| G4 | 0.1ng Cannabis cDNA ; HPLVd Positive + AMV Spike 4 | HPLVd | FAM | Amp | 24.89909069 | HPLVd B-F / p3 | HPLVd Positive |
| G4 | 0.1ng Cannabis cDNA ; HPLVd Positive + AMV Spike 4 | 26S | VIC | Inconclusive | Undetermined | 26S/p1 | 26S Failure |
| G5 | 0.1ng Cannabis cDNA ; HPLVd Positive + AMV Spike 5 | AMV | CY5 | Amp | 32.58021741 | AMV B-C / pB | AMV Positive |
| G5 | 0.1ng Cannabis cDNA ; HPLVd Positive + AMV Spike 5 | HPLVd | FAM | Amp | 25.06809738 | HPLVd B-F / p3 | HPLVd Positive |
| G5 | 0.1ng Cannabis cDNA ; HPLVd Positive + AMV Spike 5 | 26S | VIC | Amp | 25.2617644 | 26S/p1 | Reaction Positive |

FIG 11A contd

| Well | Sample | Target | Dye | Amp | Ct | Assay | Result |
|---|---|---|---|---|---|---|---|
| G6 | 0.1ng Cannabis cDNA ; HPLVd Positive + AMV Spike 6 | AMV | CY5 | Amp | 32.36957551 | AMV B-C / pB | AMV Positive |
| G6 | 0.1ng Cannabis cDNA ; HPLVd Positive + AMV Spike 6 | HPLVd | FAM | Amp | 25.06096463 | HPLVd B-F / p3 | HPLVd Positive |
| G6 | 0.1ng Cannabis cDNA ; HPLVd Positive + AMV Spike 6 | 26S | VIC | Amp | 25.29770205 | 26S/p1 | Reaction Positive |
| G7 | 0.1ng Cannabis cDNA ; HPLVd Positive + AMV Spike 7 | AMV | CY5 | Amp | 31.82241276 | AMV B-C / pB | AMV Positive |
| G7 | 0.1ng Cannabis cDNA ; HPLVd Positive + AMV Spike 7 | HPLVd | FAM | Amp | 25.07513241 | HPLVd B-F / p3 | HPLVd Positive |
| G7 | 0.1ng Cannabis cDNA ; HPLVd Positive + AMV Spike 7 | 26S | VIC | Amp | 25.07824208 | 26S/p1 | Reaction Positive |
| G8 | 0.1ng Cannabis cDNA ; HPLVd Positive + AMV Spike 8 | AMV | CY5 | Amp | 32.06991519 | AMV B-C / pB | AMV Positive |
| G8 | 0.1ng Cannabis cDNA ; HPLVd Positive + AMV Spike 8 | HPLVd | FAM | Amp | 25.02272474 | HPLVd B-F / p3 | HPLVd Positive |
| G8 | 0.1ng Cannabis cDNA ; HPLVd Positive + AMV Spike 8 | 26S | VIC | Amp | 25.14364609 | 26S/p1 | Reaction Positive |
| G9 | 0.1ng Cannabis cDNA ; HPLVd Positive + AMV Spike 9 | AMV | CY5 | Amp | 31.32142178 | AMV B-C / pB | AMV Positive |
| G9 | 0.1ng Cannabis cDNA ; HPLVd Positive + AMV Spike 9 | HPLVd | FAM | Amp | 25.19672323 | HPLVd B-F / p3 | HPLVd Positive |
| G9 | 0.1ng Cannabis cDNA ; HPLVd Positive + AMV Spike 9 | 26S | VIC | Amp | 25.08966334 | 26S/p1 | Reaction Positive |
| G10 | 0.1ng Cannabis cDNA ; HPLVd Positive + AMV Spike 10 | AMV | CY5 | Amp | 31.84846458 | AMV B-C / pB | AMV Positive |
| G10 | 0.1ng Cannabis cDNA ; HPLVd Positive + AMV Spike 10 | HPLVd | FAM | Amp | 25.12003201 | HPLVd B-F / p3 | HPLVd Positive |
| G10 | 0.1ng Cannabis cDNA ; HPLVd Positive + AMV Spike 10 | 26S | VIC | Amp | 24.55378727 | 26S/p1 | Reaction Positive |
| G11 | 0.1ng Cannabis cDNA ; HPLVd Negative | AMV | CY5 | No Amp | Undetermined | AMV B-C / pB | AMV Negative |
| G11 | 0.1ng Cannabis cDNA ; HPLVd Negative | HPLVd | FAM | No Amp | Undetermined | HPLVd B-F / p3 | HPLVd Negative |
| G11 | 0.1ng Cannabis cDNA ; HPLVd Negative | 26S | VIC | Amp | 21.03955382 | 26S/p1 | Reaction Positive |
| G12 | NTC | AMV | CY5 | No Amp | Undetermined | AMV B-C / pB | AMV Negative |

FIG 11A contd

| | | HPLVd | FAM | No Amp | Undetermined | HPLVd B-F / p3 | HPLVd Negative Reaction Negative |
|---|---|---|---|---|---|---|---|
| G12 | NTC | 26S | VIC | No Amp | Undetermined | 26S/p1 | |
| B1 | 1ng Cannabis cDNA ; HPLVd Positive + AMV Spike 1 | AMV | CY5 | Amp | 27.22922883 | AMV B-C / pB | AMV Positive |
| B1 | 1ng Cannabis cDNA ; HPLVd Positive + AMV Spike 1 | HPLVd | FAM | Amp | 21.99866112 | HPLVd B-D / p4 | HPLVd Positive |
| B1 | 1ng Cannabis cDNA ; HPLVd Positive + AMV Spike 1 | 26S | VIC | Amp | 18.51733769 | 26S/p1 | Reaction Positive |
| B2 | 1ng Cannabis cDNA ; HPLVd Positive + AMV Spike 2 | AMV | CY5 | Amp | 26.91617851 | AMV B-C / pB | AMV Positive |
| B2 | 1ng Cannabis cDNA ; HPLVd Positive + AMV Spike 2 | HPLVd | FAM | Amp | 22.1169655 | HPLVd B-D / p4 | HPLVd Positive |
| B2 | 1ng Cannabis cDNA ; HPLVd Positive + AMV Spike 2 | 26S | VIC | Amp | 19.17519356 | 26S/p1 | Reaction Positive |
| B3 | 1ng Cannabis cDNA ; HPLVd Positive + AMV Spike 3 | AMV | CY5 | Amp | 27.05155252 | AMV B-C / pB | AMV Positive |
| B3 | 1ng Cannabis cDNA ; HPLVd Positive + AMV Spike 3 | HPLVd | FAM | Amp | 22.25331658 | HPLVd B-D / p4 | HPLVd Positive |
| B3 | 1ng Cannabis cDNA ; HPLVd Positive + AMV Spike 3 | 26S | VIC | Amp | 19.84215488 | 26S/p1 | Reaction Positive |
| B4 | 1ng Cannabis cDNA ; HPLVd Positive + AMV Spike 4 | AMV | CY5 | Amp | 27.11010166 | AMV B-C / pB | AMV Positive |
| B4 | 1ng Cannabis cDNA ; HPLVd Positive + AMV Spike 4 | HPLVd | FAM | Amp | 22.08499808 | HPLVd B-D / p4 | HPLVd Positive |
| B4 | 1ng Cannabis cDNA ; HPLVd Positive + AMV Spike 4 | 26S | VIC | Amp | 19.29281438 | 26S/p1 | Reaction Positive |
| B5 | 1ng Cannabis cDNA ; HPLVd Positive + AMV Spike 5 | AMV | CY5 | Amp | 27.90507064 | AMV B-C / pB | AMV Positive |
| B5 | 1ng Cannabis cDNA ; HPLVd Positive + AMV Spike 5 | HPLVd | FAM | Amp | 22.29837974 | HPLVd B-D / p4 | HPLVd Positive |
| B5 | 1ng Cannabis cDNA ; HPLVd Positive + AMV Spike 5 | 26S | VIC | Amp | 18.07565138 | 26S/p1 | Reaction Positive |
| B6 | 1ng Cannabis cDNA ; HPLVd Positive + AMV Spike 6 | AMV | CY5 | Amp | 26.77432783 | AMV B-C / pB | AMV Positive |
| B6 | 1ng Cannabis cDNA ; HPLVd Positive + AMV Spike 6 | HPLVd | FAM | Amp | 21.98776707 | HPLVd B-D / p4 | HPLVd Positive |

FIG 11A contd

| | | | | | | |
|---|---|---|---|---|---|---|
| B6 | 1ng Cannabis cDNA ; HPLVd Positive + AMV Spike 6 | 26S | VIC | Amp | 18.79022634 | 26S/p1 | Reaction Positive |
| B7 | 1ng Cannabis cDNA ; HPLVd Positive + AMV Spike 7 | AMV | CY5 | Amp | 26.02809667 | AMV B-C / pB | AMV Positive |
| B7 | 1ng Cannabis cDNA ; HPLVd Positive + AMV Spike 7 | HPLVd | FAM | Amp | 21.99801355 | HPLVd B-D / p4 | HPLVd Positive |
| B7 | 1ng Cannabis cDNA ; HPLVd Positive + AMV Spike 7 | 26S | VIC | Amp | 19.13886888 | 26S/p1 | Reaction Positive |
| B8 | 1ng Cannabis cDNA ; HPLVd Positive + AMV Spike 8 | AMV | CY5 | Amp | 26.40556316 | AMV B-C / pB | AMV Positive |
| B8 | 1ng Cannabis cDNA ; HPLVd Positive + AMV Spike 8 | HPLVd | FAM | Amp | 22.04924553 | HPLVd B-D / p4 | HPLVd Positive |
| B8 | 1ng Cannabis cDNA ; HPLVd Positive + AMV Spike 8 | 26S | VIC | Amp | 18.08838786 | 26S/p1 | Reaction Positive |
| B9 | 1ng Cannabis cDNA ; HPLVd Positive + AMV Spike 9 | AMV | CY5 | Amp | 26.97011609 | AMV B-C / pB | AMV Positive |
| B9 | 1ng Cannabis cDNA ; HPLVd Positive + AMV Spike 9 | HPLVd | FAM | Amp | 22.2553996 | HPLVd B-D / p4 | HPLVd Positive |
| B9 | 1ng Cannabis cDNA ; HPLVd Positive + AMV Spike 9 | 26S | VIC | Amp | 19.13771557 | 26S/p1 | Reaction Positive |
| B10 | 1ng Cannabis cDNA ; HPLVd Positive + AMV Spike 10 | AMV | CY5 | Amp | 26.63362196 | AMV B-C / pB | AMV Positive |
| B10 | 1ng Cannabis cDNA ; HPLVd Positive + AMV Spike 10 | HPLVd | FAM | Amp | 22.22602631 | HPLVd B-D / p4 | HPLVd Positive |
| B10 | 1ng Cannabis cDNA ; HPLVd Positive + AMV Spike 10 | 26S | VIC | Amp | 18.42991377 | 26S/p1 | Reaction Positive |
| B11 | 1ng Cannabis cDNA ; HPLVd Negative | AMV | CY5 | No Amp | Undetermined | AMV B-C / pB | AMV Negative |
| B11 | 1ng Cannabis cDNA ; HPLVd Negative | HPLVd | FAM | No Amp | Undetermined | HPLVd B-D / p4 | HPLVd Negative |
| B11 | 1ng Cannabis cDNA ; HPLVd Negative | 26S | VIC | Amp | 15.57218576 | 26S/p1 | Reaction Positive |
| B12 | NTC | AMV | CY5 | No Amp | Undetermined | AMV B-C / pB | AMV Negative |
| B12 | NTC | HPLVd | FAM | No Amp | Undetermined | HPLVd B-D / p4 | HPLVd Negative |
| B12 | NTC | 26S | VIC | No Amp | Undetermined | 26S/p1 | Reaction Negative |

FIG 11A contd

| | Sample | | Target | Dye | | Ct | Probe | Result |
|---|---|---|---|---|---|---|---|---|
| C1 | 0.1ng Cannabis cDNA ; HPLVd Positive + AMV Spike 1 | AMV | CY5 | Amp | 31.49036527 | AMV B-C / pB | AMV Positive |
| C1 | 0.1ng Cannabis cDNA ; HPLVd Positive + AMV Spike 1 | HPLVd | FAM | Amp | 26.19932186 | HPLVd B-D / p4 | HPLVd Positive |
| C1 | 0.1ng Cannabis cDNA ; HPLVd Positive + AMV Spike 1 | 26S | VIC | Amp | 25.36507598 | 26S/p1 | Reaction Positive |
| C2 | 0.1ng Cannabis cDNA ; HPLVd Positive + AMV Spike 2 | AMV | CY5 | Amp | 33.05545596 | AMV B-C / pB | AMV Positive |
| C2 | 0.1ng Cannabis cDNA ; HPLVd Positive + AMV Spike 2 | HPLVd | FAM | Amp | 26.16210191 | HPLVd B-D / p4 | HPLVd Positive |
| C2 | 0.1ng Cannabis cDNA ; HPLVd Positive + AMV Spike 2 | 26S | VIC | Amp | 27.11778039 | 26S/p1 | Reaction Positive |
| C3 | 0.1ng Cannabis cDNA ; HPLVd Positive + AMV Spike 3 | AMV | CY5 | Amp | 32.18850509 | AMV B-C / pB | AMV Positive |
| C3 | 0.1ng Cannabis cDNA ; HPLVd Positive + AMV Spike 3 | HPLVd | FAM | Amp | 26.17871108 | HPLVd B-D / p4 | HPLVd Positive |
| C3 | 0.1ng Cannabis cDNA ; HPLVd Positive + AMV Spike 3 | 26S | VIC | Amp | 25.58350954 | 26S/p1 | Reaction Positive |
| C4 | 0.1ng Cannabis cDNA ; HPLVd Positive + AMV Spike 4 | AMV | CY5 | Amp | 32.91886044 | AMV B-C / pB | AMV Positive |
| C4 | 0.1ng Cannabis cDNA ; HPLVd Positive + AMV Spike 4 | HPLVd | FAM | Amp | 26.2638151 | HPLVd B-D / p4 | HPLVd Positive |
| C4 | 0.1ng Cannabis cDNA ; HPLVd Positive + AMV Spike 4 | 26S | VIC | Amp | 25.59787604 | 26S/p1 | Reaction Positive |
| C5 | 0.1ng Cannabis cDNA ; HPLVd Positive + AMV Spike 5 | AMV | CY5 | Amp | 32.26828943 | AMV B-C / pB | AMV Positive |
| C5 | 0.1ng Cannabis cDNA ; HPLVd Positive + AMV Spike 5 | HPLVd | FAM | Amp | 26.26067773 | HPLVd B-D / p4 | HPLVd Positive |
| C5 | 0.1ng Cannabis cDNA ; HPLVd Positive + AMV Spike 5 | 26S | VIC | Amp | 25.57787349 | 26S/p1 | Reaction Positive |
| C6 | 0.1ng Cannabis cDNA ; HPLVd Positive + AMV Spike 6 | AMV | CY5 | Amp | 31.71069893 | AMV B-C / pB | AMV Positive |
| C6 | 0.1ng Cannabis cDNA ; HPLVd Positive + AMV Spike 6 | HPLVd | FAM | Amp | 26.36864836 | HPLVd B-D / p4 | HPLVd Positive |
| C6 | 0.1ng Cannabis cDNA ; HPLVd Positive + AMV Spike 6 | 26S | VIC | Amp | 25.05958814 | 26S/p1 | Reaction Positive |
| C7 | 0.1ng Cannabis cDNA ; HPLVd Positive + AMV Spike 7 | AMV | CY5 | Amp | 31.76369985 | AMV B-C / pB | AMV Positive |

FIG 11A contd

| | | | | | | |
|---|---|---|---|---|---|---|
| C7 | 0.1ng Cannabis cDNA ; HPLVd Positive + AMV Spike 7 | HPLVd | FAM | Amp | 26.06319963 | HPLVd B-D / p4 | HPLVd Positive |
| C7 | 0.1ng Cannabis cDNA ; HPLVd Positive + AMV Spike 7 | 26S | VIC | Amp | 23.9190516 | 26S/p1 | Reaction Positive |
| C8 | 0.1ng Cannabis cDNA ; HPLVd Positive + AMV Spike 8 | AMV | CY5 | Amp | 32.78238963 | AMV B-C / pB | AMV Positive |
| C8 | 0.1ng Cannabis cDNA ; HPLVd Positive + AMV Spike 8 | HPLVd | FAM | Amp | 26.32523648 | HPLVd B-D / p4 | HPLVd Positive |
| C8 | 0.1ng Cannabis cDNA ; HPLVd Positive + AMV Spike 8 | 26S | VIC | Amp | 26.1926552 | 26S/p1 | Reaction Positive |
| C9 | 0.1ng Cannabis cDNA ; HPLVd Positive + AMV Spike 9 | AMV | CY5 | Amp | 32.18005998 | AMV B-C / pB | AMV Positive |
| C9 | 0.1ng Cannabis cDNA ; HPLVd Positive + AMV Spike 9 | HPLVd | FAM | Amp | 26.24611295 | HPLVd B-D / p4 | HPLVd Positive |
| C9 | 0.1ng Cannabis cDNA ; HPLVd Positive + AMV Spike 9 | 26S | VIC | Amp | 25.13654021 | 26S/p1 | Reaction Positive |
| C10 | 0.1ng Cannabis cDNA ; HPLVd Positive + AMV Spike 10 | AMV | CY5 | Amp | 32.17707963 | AMV B-C / pB | AMV Positive |
| C10 | 0.1ng Cannabis cDNA ; HPLVd Positive + AMV Spike 10 | HPLVd | FAM | Amp | 26.06783114 | HPLVd B-D / p4 | HPLVd Positive |
| C10 | 0.1ng Cannabis cDNA ; HPLVd Positive + AMV Spike 10 | 26S | VIC | Amp | 25.00055804 | 26S/p1 | Reaction Positive |
| C11 | 0.1ng Cannabis cDNA ; HPLVd Negative | AMV | CY5 | No Amp | Undetermined | AMV B-C / pB | AMV Negative |
| C11 | 0.1ng Cannabis cDNA ; HPLVd Negative | HPLVd | FAM | No Amp | Undetermined | HPLVd B-D / p4 | HPLVd Negative |
| C11 | 0.1ng Cannabis cDNA ; HPLVd Negative | 26S | VIC | Amp | 22.05863961 | 26S/p1 | Reaction Positive |
| C12 | NTC | AMV | CY5 | No Amp | Undetermined | AMV B-C / pB | AMV Negative |
| C12 | NTC | HPLVd | FAM | No Amp | Undetermined | HPLVd B-D / p4 | HPLVd Negative |
| C12 | NTC | 26S | VIC | No Amp | Undetermined | 26S/p1 | Reaction Negative |
| D1 | 1ng Cannabis cDNA ; HPLVd Positive + AMV Spike 1 | AMV | CY5 | Amp | 24.94170619 | AMV B-C / pB | AMV Positive |
| D1 | 1ng Cannabis cDNA ; HPLVd Positive + AMV Spike 1 | HPLVd | FAM | Amp | 21.0548529 | HPLVd B-E / p4 | HPLVd Positive |

FIG 11A contd

| | Sample | Target | Dye | Amp | Ct | Primer/Probe | Reaction |
|---|---|---|---|---|---|---|---|
| D1 | 1ng Cannabis cDNA ; HPLVd Positive + AMV Spike 1 | 26S | VIC | Amp | 18.34743474 | 26S/p1 | Reaction Positive |
| D2 | 1ng Cannabis cDNA ; HPLVd Positive + AMV Spike 2 | AMV | CY5 | Amp | 27.17744056 | AMV B-C / pB | AMV Positive |
| D2 | 1ng Cannabis cDNA ; HPLVd Positive + AMV Spike 2 | HPLVd | FAM | Amp | 21.41346691 | HPLVd B-E / p4 | HPLVd Positive |
| D2 | 1ng Cannabis cDNA ; HPLVd Positive + AMV Spike 2 | 26S | VIC | Amp | 19.57712514 | 26S/p1 | Reaction Positive |
| D3 | 1ng Cannabis cDNA ; HPLVd Positive + AMV Spike 3 | AMV | CY5 | Amp | 27.29743238 | AMV B-C / pB | AMV Positive |
| D3 | 1ng Cannabis cDNA ; HPLVd Positive + AMV Spike 3 | HPLVd | FAM | Amp | 21.60704578 | HPLVd B-E / p4 | HPLVd Positive |
| D3 | 1ng Cannabis cDNA ; HPLVd Positive + AMV Spike 3 | 26S | VIC | Amp | 21.25965547 | 26S/p1 | Reaction Positive |
| D4 | 1ng Cannabis cDNA ; HPLVd Positive + AMV Spike 4 | AMV | CY5 | Amp | 27.31580137 | AMV B-C / pB | AMV Positive |
| D4 | 1ng Cannabis cDNA ; HPLVd Positive + AMV Spike 4 | HPLVd | FAM | Amp | 21.47492814 | HPLVd B-E / p4 | HPLVd Positive |
| D4 | 1ng Cannabis cDNA ; HPLVd Positive + AMV Spike 4 | 26S | VIC | Amp | 19.63403641 | 26S/p1 | Reaction Positive |
| D5 | 1ng Cannabis cDNA ; HPLVd Positive + AMV Spike 5 | AMV | CY5 | Amp | 27.36300355 | AMV B-C / pB | AMV Positive |
| D5 | 1ng Cannabis cDNA ; HPLVd Positive + AMV Spike 5 | HPLVd | FAM | Amp | 21.32873392 | HPLVd B-E / p4 | HPLVd Positive |
| D5 | 1ng Cannabis cDNA ; HPLVd Positive + AMV Spike 5 | 26S | VIC | Amp | 19.51464683 | 26S/p1 | Reaction Positive |
| D6 | 1ng Cannabis cDNA ; HPLVd Positive + AMV Spike 6 | AMV | CY5 | Amp | 27.27691649 | AMV B-C / pB | AMV Positive |
| D6 | 1ng Cannabis cDNA ; HPLVd Positive + AMV Spike 6 | HPLVd | FAM | Amp | 21.2748888 | HPLVd B-E / p4 | HPLVd Positive |
| D6 | 1ng Cannabis cDNA ; HPLVd Positive + AMV Spike 6 | 26S | VIC | Amp | 18.53867566 | 26S/p1 | Reaction Positive |
| D7 | 1ng Cannabis cDNA ; HPLVd Positive + AMV Spike 7 | AMV | CY5 | Amp | 26.51748493 | AMV B-C / pB | AMV Positive |
| D7 | 1ng Cannabis cDNA ; HPLVd Positive + AMV Spike 7 | HPLVd | FAM | Amp | 21.21581763 | HPLVd B-E / p4 | HPLVd Positive |
| D7 | 1ng Cannabis cDNA ; HPLVd Positive + AMV Spike 7 | 26S | VIC | Amp | 18.20435481 | 26S/p1 | Reaction Positive |

FIG 11A contd

| Row | Sample | Target | Dye | Amp | Ct | Assay | Result |
|---|---|---|---|---|---|---|---|
| D8 | 1ng Cannabis cDNA ; HPLVd Positive + AMV Spike 8 | AMV | CY5 | Amp | 26.8565168 | AMV B-C / pB | AMV Positive |
| D8 | 1ng Cannabis cDNA ; HPLVd Positive + AMV Spike 8 | HPLVd | FAM | Amp | 21.1855413 | HPLVd B-E / p4 | HPLVd Positive |
| D8 | 1ng Cannabis cDNA ; HPLVd Positive + AMV Spike 8 | 26S | VIC | Amp | 17.34080651 | 26S/p1 | Reaction Positive |
| D9 | 1ng Cannabis cDNA ; HPLVd Positive + AMV Spike 9 | AMV | CY5 | Amp | 27.12161258 | AMV B-C / pB | AMV Positive |
| D9 | 1ng Cannabis cDNA ; HPLVd Positive + AMV Spike 9 | HPLVd | FAM | Amp | 21.06455762 | HPLVd B-E / p4 | HPLVd Positive |
| D9 | 1ng Cannabis cDNA ; HPLVd Positive + AMV Spike 9 | 26S | VIC | Amp | 18.71806466 | 26S/p1 | Reaction Positive |
| D10 | 1ng Cannabis cDNA ; HPLVd Positive + AMV Spike 10 | AMV | CY5 | Amp | 26.8221929 | AMV B-C / pB | AMV Positive |
| D10 | 1ng Cannabis cDNA ; HPLVd Positive + AMV Spike 10 | HPLVd | FAM | Amp | 21.03192658 | HPLVd B-E / p4 | HPLVd Positive |
| D10 | 1ng Cannabis cDNA ; HPLVd Positive + AMV Spike 10 | 26S | VIC | Amp | 18.93183721 | 26S/p1 | Reaction Positive |
| D11 | 1ng Cannabis cDNA ; HPLVd Negative | AMV | CY5 | No Amp | Undetermined | AMV B-C / pB | AMV Negative |
| D11 | 1ng Cannabis cDNA ; HPLVd Negative | HPLVd | FAM | No Amp | Undetermined | HPLVd B-E / p4 | HPLVd Negative |
| D11 | 1ng Cannabis cDNA ; HPLVd Negative | 26S | VIC | Amp | 16.10623004 | 26S/p1 | Reaction Positive |
| D12 | NTC | AMV | CY5 | No Amp | Undetermined | AMV B-C / pB | AMV Negative |
| D12 | NTC | HPLVd | FAM | No Amp | Undetermined | HPLVd B-E / p4 | HPLVd Negative |
| D12 | NTC | 26S | VIC | No Amp | Undetermined | 26S/p1 | Reaction Negative |
| E1 | 0.1ng Cannabis cDNA ; HPLVd Positive + AMV Spike 1 | AMV | CY5 | Amp | 31.73534941 | AMV B-C / pB | AMV Positive |
| E1 | 0.1ng Cannabis cDNA ; HPLVd Positive + AMV Spike 1 | HPLVd | FAM | Amp | 25.24867888 | HPLVd B-E / p4 | HPLVd Positive |
| E1 | 0.1ng Cannabis cDNA ; HPLVd Positive + AMV Spike 1 | 26S | VIC | Amp | 24.4238936 | 26S/p1 | Reaction Positive |
| E2 | 0.1ng Cannabis cDNA ; HPLVd Positive + AMV Spike 2 | AMV | CY5 | Amp | 31.95534448 | AMV B-C / pB | AMV Positive |

FIG 11A contd

| | Sample | Target | Dye | | Ct | Primer/Probe | Result |
|---|---|---|---|---|---|---|---|
| E2 | 0.1ng Cannabis cDNA ; HPLVd Positive + AMV Spike 2 | HPLVd | FAM | Amp | 25.58524123 | HPLVd B-E / p4 | HPLVd Positive |
| E2 | 0.1ng Cannabis cDNA ; HPLVd Positive + AMV Spike 2 | 26S | VIC | Amp | 25.36573524 | 26S/p1 | Reaction Positive |
| E3 | 0.1ng Cannabis cDNA ; HPLVd Positive + AMV Spike 3 | AMV | CY5 | Amp | 33.18632862 | AMV B-C / pB | AMV Positive |
| E3 | 0.1ng Cannabis cDNA ; HPLVd Positive + AMV Spike 3 | HPLVd | FAM | Amp | 25.42226374 | HPLVd B-E / p4 | HPLVd Positive |
| E3 | 0.1ng Cannabis cDNA ; HPLVd Positive + AMV Spike 3 | 26S | VIC | Amp | 25.81966641 | 26S/p1 | Reaction Positive |
| E4 | 0.1ng Cannabis cDNA ; HPLVd Positive + AMV Spike 4 | AMV | CY5 | Amp | 32.66443097 | AMV B-C / pB | AMV Positive |
| E4 | 0.1ng Cannabis cDNA ; HPLVd Positive + AMV Spike 4 | HPLVd | FAM | Amp | 25.31050672 | HPLVd B-E / p4 | HPLVd Positive |
| E4 | 0.1ng Cannabis cDNA ; HPLVd Positive + AMV Spike 4 | 26S | VIC | Amp | 25.17621419 | 26S/p1 | Reaction Positive |
| E5 | 0.1ng Cannabis cDNA ; HPLVd Positive + AMV Spike 5 | AMV | CY5 | Amp | 32.07963131 | AMV B-C / pB | AMV Positive |
| E5 | 0.1ng Cannabis cDNA ; HPLVd Positive + AMV Spike 5 | HPLVd | FAM | Amp | 25.80161205 | HPLVd B-E / p4 | HPLVd Positive |
| E5 | 0.1ng Cannabis cDNA ; HPLVd Positive + AMV Spike 5 | 26S | VIC | Amp | 25.33326913 | 26S/p1 | Reaction Positive |
| E6 | 0.1ng Cannabis cDNA ; HPLVd Positive + AMV Spike 6 | AMV | CY5 | Amp | 31.3754801 | AMV B-C / pB | AMV Positive |
| E6 | 0.1ng Cannabis cDNA ; HPLVd Positive + AMV Spike 6 | HPLVd | FAM | Amp | 25.86875256 | HPLVd B-E / p4 | HPLVd Positive |
| E6 | 0.1ng Cannabis cDNA ; HPLVd Positive + AMV Spike 6 | 26S | VIC | Amp | 25.16924249 | 26S/p1 | Reaction Positive |
| E7 | 0.1ng Cannabis cDNA ; HPLVd Positive + AMV Spike 7 | AMV | CY5 | Amp | 31.50684514 | AMV B-C / pB | AMV Positive |
| E7 | 0.1ng Cannabis cDNA ; HPLVd Positive + AMV Spike 7 | HPLVd | FAM | Amp | 25.54845197 | HPLVd B-E / p4 | HPLVd Positive |
| E7 | 0.1ng Cannabis cDNA ; HPLVd Positive + AMV Spike 7 | 26S | VIC | Amp | 24.18253839 | 26S/p1 | Reaction Positive |
| E8 | 0.1ng Cannabis cDNA ; HPLVd Positive + AMV Spike 8 | AMV | CY5 | Amp | 33.7624132 | AMV B-C / pB | AMV Positive |
| E8 | 0.1ng Cannabis cDNA ; HPLVd Positive + AMV Spike 8 | HPLVd | FAM | Amp | 25.36945717 | HPLVd B-E / p4 | HPLVd Positive |

FIG 11A contd

| ID | Description | Target | Dye | Amp | Cq | Assay | Reaction |
|---|---|---|---|---|---|---|---|
| E8 | 0.1ng Cannabis cDNA ; HPLVd Positive + AMV Spike 8 | 26S | VIC | Amp | 25.30242783 | 26S/p1 | Reaction Positive |
| E9 | 0.1ng Cannabis cDNA ; HPLVd Positive + AMV Spike 9 | AMV | CY5 | Amp | 32.97822363 | AMV B-C / pB | AMV Positive |
| E9 | 0.1ng Cannabis cDNA ; HPLVd Positive + AMV Spike 9 | HPLVd | FAM | Amp | 25.00080983 | HPLVd B-E / p4 | HPLVd Positive |
| E9 | 0.1ng Cannabis cDNA ; HPLVd Positive + AMV Spike 9 | 26S | VIC | Amp | 24.58526696 | 26S/p1 | Reaction Positive |
| E10 | 0.1ng Cannabis cDNA ; HPLVd Positive + AMV Spike 10 | AMV | CY5 | Amp | 31.88021473 | AMV B-C / pB | AMV Positive |
| E10 | 0.1ng Cannabis cDNA ; HPLVd Positive + AMV Spike 10 | HPLVd | FAM | Amp | 24.8828238 | HPLVd B-E / p4 | HPLVd Positive |
| E10 | 0.1ng Cannabis cDNA ; HPLVd Positive + AMV Spike 10 | 26S | VIC | Amp | 25.09797975 | 26S/p1 | Reaction Positive |
| E11 | 0.1ng Cannabis cDNA ; HPLVd Negative | AMV | CY5 | No Amp | Undetermined | AMV B-C / pB | AMV Negative |
| E11 | 0.1ng Cannabis cDNA ; HPLVd Negative | HPLVd | FAM | No Amp | Undetermined | HPLVd B-E / p4 | HPLVd Negative |
| E11 | 0.1ng Cannabis cDNA ; HPLVd Negative | 26S | VIC | Amp | 21.86486818 | 26S/p1 | Reaction Positive |
| E12 | NTC | AMV | CY5 | No Amp | Undetermined | AMV B-C / pB | AMV Negative |
| E12 | NTC | HPLVd | FAM | No Amp | Undetermined | HPLVd B-E / p4 | HPLVd Negative |
| E12 | NTC | 26S | VIC | No Amp | Undetermined | 26S/p1 | Reaction Negative |
| F1 | 1ng Cannabis cDNA ; HPLVd Positive + AMV Spike 1 | AMV | CY5 | Amp | 26.8747868 | AMV B-C / pB | AMV Positive |
| F1 | 1ng Cannabis cDNA ; HPLVd Positive + AMV Spike 1 | HPLVd | FAM | Amp | 20.92327544 | HPLVd B-F / p4 | HPLVd Positive |
| F1 | 1ng Cannabis cDNA ; HPLVd Positive + AMV Spike 1 | 26S | VIC | Amp | 17.42854235 | 26S/p1 | Reaction Positive |
| F2 | 1ng Cannabis cDNA ; HPLVd Positive + AMV Spike 2 | AMV | CY5 | Amp | 27.1869855 | AMV B-C / pB | AMV Positive |
| F2 | 1ng Cannabis cDNA ; HPLVd Positive + AMV Spike 2 | HPLVd | FAM | Amp | 21.12995103 | HPLVd B-F / p4 | HPLVd Positive |
| F2 | 1ng Cannabis cDNA ; HPLVd Positive + AMV Spike 2 | 26S | VIC | Amp | 18.2384329 | 26S/p1 | Reaction Positive |

FIG 11A contd

| | Sample | Target | Dye | Amp | Ct | Assay | Result |
|---|---|---|---|---|---|---|---|
| F3 | 1ng Cannabis cDNA ; HPLVd Positive + AMV Spike 3 | AMV | CY5 | Amp | 26.84146268 | AMV B-C / pB | AMV Positive |
| F3 | 1ng Cannabis cDNA ; HPLVd Positive + AMV Spike 3 | HPLVd | FAM | Amp | 21.34665893 | HPLVd B-F / p4 | HPLVd Positive |
| F3 | 1ng Cannabis cDNA ; HPLVd Positive + AMV Spike 3 | 26S | VIC | Amp | 18.39597635 | 26S/p1 | Reaction Positive |
| F4 | 1ng Cannabis cDNA ; HPLVd Positive + AMV Spike 4 | AMV | CY5 | Amp | 26.34677565 | AMV B-C / pB | AMV Positive |
| F4 | 1ng Cannabis cDNA ; HPLVd Positive + AMV Spike 4 | HPLVd | FAM | Amp | 21.29693975 | HPLVd B-F / p4 | HPLVd Positive |
| F4 | 1ng Cannabis cDNA ; HPLVd Positive + AMV Spike 4 | 26S | VIC | Amp | 18.28253089 | 26S/p1 | Reaction Positive |
| F5 | 1ng Cannabis cDNA ; HPLVd Positive + AMV Spike 5 | AMV | CY5 | Amp | 26.96203625 | AMV B-C / pB | AMV Positive |
| F5 | 1ng Cannabis cDNA ; HPLVd Positive + AMV Spike 5 | HPLVd | FAM | Amp | 21.12109181 | HPLVd B-F / p4 | HPLVd Positive |
| F5 | 1ng Cannabis cDNA ; HPLVd Positive + AMV Spike 5 | 26S | VIC | Amp | 17.34699522 | 26S/p1 | Reaction Positive |
| F6 | 1ng Cannabis cDNA ; HPLVd Positive + AMV Spike 6 | AMV | CY5 | Amp | 26.53072032 | AMV B-C / pB | AMV Positive |
| F6 | 1ng Cannabis cDNA ; HPLVd Positive + AMV Spike 6 | HPLVd | FAM | Amp | 21.20058736 | HPLVd B-F / p4 | HPLVd Positive |
| F6 | 1ng Cannabis cDNA ; HPLVd Positive + AMV Spike 6 | 26S | VIC | Amp | 18.16948335 | 26S/p1 | Reaction Positive |
| F7 | 1ng Cannabis cDNA ; HPLVd Positive + AMV Spike 7 | AMV | CY5 | Amp | 26.86625517 | AMV B-C / pB | AMV Positive |
| F7 | 1ng Cannabis cDNA ; HPLVd Positive + AMV Spike 7 | HPLVd | FAM | Amp | 21.11250759 | HPLVd B-F / p4 | HPLVd Positive |
| F7 | 1ng Cannabis cDNA ; HPLVd Positive + AMV Spike 7 | 26S | VIC | Amp | 17.18034091 | 26S/p1 | Reaction Positive |
| F8 | 1ng Cannabis cDNA ; HPLVd Positive + AMV Spike 8 | AMV | CY5 | Amp | 26.54791878 | AMV B-C / pB | AMV Positive |
| F8 | 1ng Cannabis cDNA ; HPLVd Positive + AMV Spike 8 | HPLVd | FAM | Amp | 20.98311153 | HPLVd B-F / p4 | HPLVd Positive |
| F8 | 1ng Cannabis cDNA ; HPLVd Positive + AMV Spike 8 | 26S | VIC | Amp | 17.96640691 | 26S/p1 | Reaction Positive |
| F9 | 1ng Cannabis cDNA ; HPLVd Positive + AMV Spike 9 | AMV | CY5 | Amp | 27.14046876 | AMV B-C / pB | AMV Positive |

FIG 11A contd

| | Sample | Target | Dye | Amp | Ct | Assay | Result |
|---|---|---|---|---|---|---|---|
| F9 | 1ng Cannabis cDNA ; HPLVd Positive + AMV Spike 9 | HPLVd | FAM | Amp | 21.0669251 | HPLVd B-F / p4 | HPLVd Positive |
| F9 | 1ng Cannabis cDNA ; HPLVd Positive + AMV Spike 9 | 26S | VIC | Amp | 17.31749812 | 26S/p1 | Reaction Positive |
| F10 | 1ng Cannabis cDNA ; HPLVd Positive + AMV Spike 10 | AMV | CY5 | Amp | 26.72698689 | AMV B-C / pB | AMV Positive |
| F10 | 1ng Cannabis cDNA ; HPLVd Positive + AMV Spike 10 | HPLVd | FAM | Amp | 21.13638045 | HPLVd B-F / p4 | HPLVd Positive |
| F10 | 1ng Cannabis cDNA ; HPLVd Positive + AMV Spike 10 | 26S | VIC | Amp | 17.43813908 | 26S/p1 | Reaction Positive |
| F11 | 1ng Cannabis cDNA ; HPLVd Negative | AMV | CY5 | No Amp | Undetermined | AMV B-C / pB | AMV Negative |
| F11 | 1ng Cannabis cDNA ; HPLVd Negative | HPLVd | FAM | No Amp | Undetermined | HPLVd B-F / p4 | HPLVd Negative |
| F11 | 1ng Cannabis cDNA ; HPLVd Negative | 26S | VIC | Amp | 15.38190258 | 26S/p1 | Reaction Positive |
| F12 | NTC | AMV | CY5 | No Amp | Undetermined | AMV B-C / pB | AMV Negative |
| F12 | NTC | HPLVd | FAM | No Amp | Undetermined | HPLVd B-F / p4 | HPLVd Negative |
| F12 | NTC | 26S | VIC | No Amp | Undetermined | 26S/p1 | Reaction Negative |
| G1 | 0.1ng Cannabis cDNA ; HPLVd Positive + AMV Spike 1 | AMV | CY5 | Amp | 31.99590347 | AMV B-C / pB | AMV Positive |
| G1 | 0.1ng Cannabis cDNA ; HPLVd Positive + AMV Spike 1 | HPLVd | FAM | Amp | 25.07954372 | HPLVd B-F / p4 | HPLVd Positive |
| G1 | 0.1ng Cannabis cDNA ; HPLVd Positive + AMV Spike 1 | 26S | VIC | Amp | 26.11603265 | 26S/p1 | Reaction Positive |
| G2 | 0.1ng Cannabis cDNA ; HPLVd Positive + AMV Spike 2 | AMV | CY5 | Amp | 31.31558404 | AMV B-C / pB | AMV Positive |
| G2 | 0.1ng Cannabis cDNA ; HPLVd Positive + AMV Spike 2 | HPLVd | FAM | Amp | 24.8972761 | HPLVd B-F / p4 | HPLVd Positive |
| G2 | 0.1ng Cannabis cDNA ; HPLVd Positive + AMV Spike 2 | 26S | VIC | Amp | 25.81884166 | 26S/p1 | Reaction Positive |
| G3 | 0.1ng Cannabis cDNA ; HPLVd Positive + AMV Spike 3 | AMV | CY5 | Amp | 32.27019734 | AMV B-C / pB | AMV Positive |
| G3 | 0.1ng Cannabis cDNA ; HPLVd Positive + AMV Spike 3 | HPLVd | FAM | Amp | 25.1629738 | HPLVd B-F / p4 | HPLVd Positive |

FIG 11A contd

| | Sample | Target | Dye | Amp | Cq | Target2 | Reaction |
|---|---|---|---|---|---|---|---|
| G3 | 0.1ng Cannabis cDNA ; HPLVd Positive + AMV Spike 3 | 26S | VIC | Amp | 25.54318506 | 26S/p1 | Reaction Positive |
| G4 | 0.1ng Cannabis cDNA ; HPLVd Positive + AMV Spike 4 | AMV | CY5 | Amp | 32.01386931 | AMV B-C / pB | AMV Positive |
| G4 | 0.1ng Cannabis cDNA ; HPLVd Positive + AMV Spike 4 | HPLVd | FAM | Amp | 24.92355799 | HPLVd B-F / p4 | HPLVd Positive |
| G4 | 0.1ng Cannabis cDNA ; HPLVd Positive + AMV Spike 4 | 26S | VIC | Amp | 26.77652086 | 26S/p1 | Reaction Positive |
| G5 | 0.1ng Cannabis cDNA ; HPLVd Positive + AMV Spike 5 | AMV | CY5 | Amp | 31.19103975 | AMV B-C / pB | AMV Positive |
| G5 | 0.1ng Cannabis cDNA ; HPLVd Positive + AMV Spike 5 | HPLVd | FAM | Amp | 25.21703428 | HPLVd B-F / p4 | HPLVd Positive |
| G5 | 0.1ng Cannabis cDNA ; HPLVd Positive + AMV Spike 5 | 26S | VIC | Amp | 25.04879656 | 26S/p1 | Reaction Positive |
| G6 | 0.1ng Cannabis cDNA ; HPLVd Positive + AMV Spike 6 | AMV | CY5 | Amp | 32.04227814 | AMV B-C / pB | AMV Positive |
| G6 | 0.1ng Cannabis cDNA ; HPLVd Positive + AMV Spike 6 | HPLVd | FAM | Amp | 25.13569448 | HPLVd B-F / p4 | HPLVd Positive |
| G6 | 0.1ng Cannabis cDNA ; HPLVd Positive + AMV Spike 6 | 26S | VIC | Amp | 25.57670309 | 26S/p1 | Reaction Positive |
| G7 | 0.1ng Cannabis cDNA ; HPLVd Positive + AMV Spike 7 | AMV | CY5 | Amp | 31.34035578 | AMV B-C / pB | AMV Positive |
| G7 | 0.1ng Cannabis cDNA ; HPLVd Positive + AMV Spike 7 | HPLVd | FAM | Amp | 24.7945521 | HPLVd B-F / p4 | HPLVd Positive |
| G7 | 0.1ng Cannabis cDNA ; HPLVd Positive + AMV Spike 7 | 26S | VIC | Amp | 23.99885605 | 26S/p1 | Reaction Positive |
| G8 | 0.1ng Cannabis cDNA ; HPLVd Positive + AMV Spike 8 | AMV | CY5 | Amp | 31.97933529 | AMV B-C / pB | AMV Positive |
| G8 | 0.1ng Cannabis cDNA ; HPLVd Positive + AMV Spike 8 | HPLVd | FAM | Amp | 25.09812626 | HPLVd B-F / p4 | HPLVd Positive |
| G8 | 0.1ng Cannabis cDNA ; HPLVd Positive + AMV Spike 8 | 26S | VIC | Amp | 25.34718508 | 26S/p1 | Reaction Positive |
| G9 | 0.1ng Cannabis cDNA ; HPLVd Positive + AMV Spike 9 | AMV | CY5 | Amp | 31.45542797 | AMV B-C / pB | AMV Positive |
| G9 | 0.1ng Cannabis cDNA ; HPLVd Positive + AMV Spike 9 | HPLVd | FAM | Amp | 25.25087942 | HPLVd B-F / p4 | HPLVd Positive |
| G9 | 0.1ng Cannabis cDNA ; HPLVd Positive + AMV Spike 9 | 26S | VIC | Amp | 25.61622226 | 26S/p1 | Reaction Positive |

FIG 11A contd

| Well | Sample | Target | Reporter | Amp Status | Ct | Assay | Result |
|---|---|---|---|---|---|---|---|
| G10 | 0.1ng Cannabis cDNA ; HPLVd Positive + AMV Spike 10 | AMV | CY5 | Amp | 31.09081512 | AMV B-C / pB | AMV Positive |
| G10 | 0.1ng Cannabis cDNA ; HPLVd Positive + AMV Spike 10 | HPLVd | FAM | Amp | 25.03473224 | HPLVd B-F / p4 | HPLVd Positive |
| G10 | 0.1ng Cannabis cDNA ; HPLVd Positive + AMV Spike 10 | 26S | VIC | No Amp | Undetermined | 26S/p1 | Reaction Positive |
| G11 | 0.1ng Cannabis cDNA ; HPLVd Negative | AMV | CY5 | No Amp | Undetermined | AMV B-C / pB | AMV Negative |
| G11 | 0.1ng Cannabis cDNA ; HPLVd Negative | HPLVd | FAM | No Amp | Undetermined | HPLVd B-F / p4 | HPLVd Negative |
| G11 | 0.1ng Cannabis cDNA ; HPLVd Negative | 26S | VIC | Amp | 22.72841944 | 26S/p1 | Reaction Positive |
| G12 | NTC | AMV | CY5 | No Amp | Undetermined | AMV B-C / pB | AMV Negative |
| G12 | NTC | HPLVd | FAM | No Amp | Undetermined | HPLVd B-F / p4 | HPLVd Negative |
| G12 | NTC | 26S | VIC | No Amp | Undetermined | 26S/p1 | Reaction Negative |
| B1 | 1ng Cannabis cDNA ; HPLVd Positive + AMV Spike 1 | AMV | CY5 | Amp | 27.88021507 | AMV B-C / pB | AMV Positive |
| B1 | 1ng Cannabis cDNA ; HPLVd Positive + AMV Spike 1 | HPLVd | FAM | Amp | 21.51963761 | HPLVd B-D / p5 | HPLVd Positive |
| B1 | 1ng Cannabis cDNA ; HPLVd Positive + AMV Spike 1 | 26S | VIC | Amp | 14.88052166 | 26S/p1 | Reaction Positive |
| B2 | 1ng Cannabis cDNA ; HPLVd Positive + AMV Spike 2 | AMV | CY5 | Amp | 28.23354935 | AMV B-C / pB | AMV Positive |
| B2 | 1ng Cannabis cDNA ; HPLVd Positive + AMV Spike 2 | HPLVd | FAM | Amp | 21.5584996 | HPLVd B-D / p5 | HPLVd Positive |
| B2 | 1ng Cannabis cDNA ; HPLVd Positive + AMV Spike 2 | 26S | VIC | Amp | 16.24776489 | 26S/p1 | Reaction Positive |
| B3 | 1ng Cannabis cDNA ; HPLVd Positive + AMV Spike 3 | AMV | CY5 | Amp | 27.42678918 | AMV B-C / pB | AMV Positive |
| B3 | 1ng Cannabis cDNA ; HPLVd Positive + AMV Spike 3 | HPLVd | FAM | Amp | 21.61540319 | HPLVd B-D / p5 | HPLVd Positive |
| B3 | 1ng Cannabis cDNA ; HPLVd Positive + AMV Spike 3 | 26S | VIC | Amp | 16.999907075 | 26S/p1 | Reaction Positive |
| B4 | 1ng Cannabis cDNA ; HPLVd Positive + AMV Spike 4 | AMV | CY5 | Amp | 27.23090596 | AMV B-C / pB | AMV Positive |

FIG 11A contd

| | | | | | | |
|---|---|---|---|---|---|---|
| B4 | 1ng Cannabis cDNA ; HPLVd Positive + AMV Spike 4 | HPLVd | FAM | Amp | 21.69895804 | HPLVd B-D / p5 | HPLVd Positive |
| B4 | 1ng Cannabis cDNA ; HPLVd Positive + AMV Spike 4 | 26S | VIC | Amp | 16.71157949 | 26S/p1 | Reaction Positive |
| B5 | 1ng Cannabis cDNA ; HPLVd Positive + AMV Spike 5 | AMV | CY5 | Amp | 23.60869815 | AMV B-C / pB | AMV Positive |
| B5 | 1ng Cannabis cDNA ; HPLVd Positive + AMV Spike 5 | HPLVd | FAM | Amp | 21.65281914 | HPLVd B-D / p5 | HPLVd Positive |
| B5 | 1ng Cannabis cDNA ; HPLVd Positive + AMV Spike 5 | 26S | VIC | Amp | 16.76106433 | 26S/p1 | Reaction Positive |
| B6 | 1ng Cannabis cDNA ; HPLVd Positive + AMV Spike 6 | AMV | CY5 | Amp | 26.34865369 | AMV B-C / pB | AMV Positive |
| B6 | 1ng Cannabis cDNA ; HPLVd Positive + AMV Spike 6 | HPLVd | FAM | Amp | 21.57658724 | HPLVd B-D / p5 | HPLVd Positive |
| B6 | 1ng Cannabis cDNA ; HPLVd Positive + AMV Spike 6 | 26S | VIC | Amp | 17.13764469 | 26S/p1 | Reaction Positive |
| B7 | 1ng Cannabis cDNA ; HPLVd Positive + AMV Spike 7 | AMV | CY5 | Amp | 26.34980135 | AMV B-C / pB | AMV Positive |
| B7 | 1ng Cannabis cDNA ; HPLVd Positive + AMV Spike 7 | HPLVd | FAM | Amp | 21.55248365 | HPLVd B-D / p5 | HPLVd Positive |
| B7 | 1ng Cannabis cDNA ; HPLVd Positive + AMV Spike 7 | 26S | VIC | Amp | 15.58687775 | 26S/p1 | Reaction Positive |
| B8 | 1ng Cannabis cDNA ; HPLVd Positive + AMV Spike 8 | AMV | CY5 | Amp | 26.47320056 | AMV B-C / pB | AMV Positive |
| B8 | 1ng Cannabis cDNA ; HPLVd Positive + AMV Spike 8 | HPLVd | FAM | Amp | 21.62983937 | HPLVd B-D / p5 | HPLVd Positive |
| B8 | 1ng Cannabis cDNA ; HPLVd Positive + AMV Spike 8 | 26S | VIC | Amp | 16.33331943 | 26S/p1 | Reaction Positive |
| B9 | 1ng Cannabis cDNA ; HPLVd Positive + AMV Spike 9 | AMV | CY5 | Amp | 27.6537694 | AMV B-C / pB | AMV Positive |
| B9 | 1ng Cannabis cDNA ; HPLVd Positive + AMV Spike 9 | HPLVd | FAM | Amp | 21.82479449 | HPLVd B-D / p5 | HPLVd Positive |
| B9 | 1ng Cannabis cDNA ; HPLVd Positive + AMV Spike 9 | 26S | VIC | Amp | 16.38911968 | 26S/p1 | Reaction Positive |
| B10 | 1ng Cannabis cDNA ; HPLVd Positive + AMV Spike 10 | AMV | CY5 | Amp | 27.45910649 | AMV B-C / pB | AMV Positive |
| B10 | 1ng Cannabis cDNA ; HPLVd Positive + AMV Spike 10 | HPLVd | FAM | Amp | 21.88317058 | HPLVd B-D / p5 | HPLVd Positive |

FIG 11A contd

| Well | Sample | Target | Dye | Amp | Cq | Assay | Reaction |
|---|---|---|---|---|---|---|---|
| B10 | 1ng Cannabis cDNA ; HPLVd Positive + AMV Spike 10 | 26S | VIC | Amp | 17.78748294 | 26S/p1 | Reaction Positive |
| B11 | NTC | AMV | CY5 | No Amp | Undetermined | AMV B-C / pB | AMV Negative |
| B11 | NTC | HPLVd | FAM | No Amp | Undetermined | HPLVd B-D / p5 | HPLVd Negative |
| B11 | NTC | 26S | VIC | No Amp | Undetermined | 26S/p1 | Reaction Negative |
| B12 | 1ng Cannabis cDNA ; HPLVd Negative | AMV | CY5 | No Amp | Undetermined | AMV B-C / pB | AMV Negative |
| B12 | 1ng Cannabis cDNA ; HPLVd Negative | HPLVd | FAM | No Amp | Undetermined | HPLVd B-D / p5 | HPLVd Negative |
| B12 | 1ng Cannabis cDNA ; HPLVd Negative | 26S | VIC | Amp | 12.80836006 | 26S/p1 | Reaction Positive |
| C1 | 0.1ng Cannabis cDNA ; HPLVd Positive + AMV Spike 1 | AMV | CY5 | Amp | 33.98167934 | AMV B-C / pB | AMV Positive |
| C1 | 0.1ng Cannabis cDNA ; HPLVd Positive + AMV Spike 1 | HPLVd | FAM | Amp | 25.85694678 | HPLVd B-D / p5 | HPLVd Positive |
| C1 | 0.1ng Cannabis cDNA ; HPLVd Positive + AMV Spike 1 | 26S | VIC | Inconclusive | Undetermined | 26S/p1 | 26S Failure |
| C2 | 0.1ng Cannabis cDNA ; HPLVd Positive + AMV Spike 2 | AMV | CY5 | Amp | 33.03067181 | AMV B-C / pB | AMV Positive |
| C2 | 0.1ng Cannabis cDNA ; HPLVd Positive + AMV Spike 2 | HPLVd | FAM | Amp | 25.72926876 | HPLVd B-D / p5 | HPLVd Positive |
| C2 | 0.1ng Cannabis cDNA ; HPLVd Positive + AMV Spike 2 | 26S | VIC | Amp | 24.33176978 | 26S/p1 | Reaction Positive |
| C3 | 0.1ng Cannabis cDNA ; HPLVd Positive + AMV Spike 3 | AMV | CY5 | Amp | 32.29031264 | AMV B-C / pB | AMV Positive |
| C3 | 0.1ng Cannabis cDNA ; HPLVd Positive + AMV Spike 3 | HPLVd | FAM | Amp | 26.05390856 | HPLVd B-D / p5 | HPLVd Positive |
| C3 | 0.1ng Cannabis cDNA ; HPLVd Positive + AMV Spike 3 | 26S | VIC | Amp | 25.26818803 | 26S/p1 | Reaction Positive |
| C4 | 0.1ng Cannabis cDNA ; HPLVd Positive + AMV Spike 4 | AMV | CY5 | Amp | 34.2584776 | AMV B-C / pB | AMV Positive |
| C4 | 0.1ng Cannabis cDNA ; HPLVd Positive + AMV Spike 4 | HPLVd | FAM | Amp | 26.10207376 | HPLVd B-D / p5 | HPLVd Positive |
| C4 | 0.1ng Cannabis cDNA ; HPLVd Positive + AMV Spike 4 | 26S | VIC | Amp | 23.97389165 | 26S/p1 | Reaction Positive |

FIG 11A contd

| | Description | Target | Reporter | Amp | Ct | Assay | Result |
|---|---|---|---|---|---|---|---|
| C5 | 0.1ng Cannabis cDNA ; HPLVd Positive + AMV Spike 5 | AMV | CY5 | Amp | 32.76770477 | AMV B-C / pB | AMV Positive |
| C5 | 0.1ng Cannabis cDNA ; HPLVd Positive + AMV Spike 5 | HPLVd | FAM | Amp | 25.69214233 | HPLVd B-D / p5 | HPLVd Positive |
| C5 | 0.1ng Cannabis cDNA ; HPLVd Positive + AMV Spike 5 | 26S | VIC | Amp | 23.74560804 | 26S/p1 | Reaction Positive |
| C6 | 0.1ng Cannabis cDNA ; HPLVd Positive + AMV Spike 6 | AMV | CY5 | Amp | 32.76250843 | AMV B-C / pB | AMV Positive |
| C6 | 0.1ng Cannabis cDNA ; HPLVd Positive + AMV Spike 6 | HPLVd | FAM | Amp | 25.73762758 | HPLVd B-D / p5 | HPLVd Positive |
| C6 | 0.1ng Cannabis cDNA ; HPLVd Positive + AMV Spike 6 | 26S | VIC | Amp | 24.35086389 | 26S/p1 | Reaction Positive |
| C7 | 0.1ng Cannabis cDNA ; HPLVd Positive + AMV Spike 7 | AMV | CY5 | Amp | 33.08682568 | AMV B-C / pB | AMV Positive |
| C7 | 0.1ng Cannabis cDNA ; HPLVd Positive + AMV Spike 7 | HPLVd | FAM | Amp | 25.57566719 | HPLVd B-D / p5 | HPLVd Positive |
| C7 | 0.1ng Cannabis cDNA ; HPLVd Positive + AMV Spike 7 | 26S | VIC | Amp | 23.36043586 | 26S/p1 | Reaction Positive |
| C8 | 0.1ng Cannabis cDNA ; HPLVd Positive + AMV Spike 8 | AMV | CY5 | Amp | 32.79535851 | AMV B-C / pB | AMV Positive |
| C8 | 0.1ng Cannabis cDNA ; HPLVd Positive + AMV Spike 8 | HPLVd | FAM | Amp | 25.84678801 | HPLVd B-D / p5 | HPLVd Positive |
| C8 | 0.1ng Cannabis cDNA ; HPLVd Positive + AMV Spike 8 | 26S | VIC | Amp | 24.08064978 | 26S/p1 | Reaction Positive |
| C9 | 0.1ng Cannabis cDNA ; HPLVd Positive + AMV Spike 9 | AMV | CY5 | Amp | 33.24145031 | AMV B-C / pB | AMV Positive |
| C9 | 0.1ng Cannabis cDNA ; HPLVd Positive + AMV Spike 9 | HPLVd | FAM | Amp | 25.63470753 | HPLVd B-D / p5 | HPLVd Positive |
| C9 | 0.1ng Cannabis cDNA ; HPLVd Positive + AMV Spike 9 | 26S | VIC | Amp | 23.7735002 | 26S/p1 | Reaction Positive |
| C10 | 0.1ng Cannabis cDNA ; HPLVd Positive + AMV Spike 10 | AMV | CY5 | Amp | 32.88070655 | AMV B-C / pB | AMV Positive |
| C10 | 0.1ng Cannabis cDNA ; HPLVd Positive + AMV Spike 10 | HPLVd | FAM | Amp | 25.56472959 | HPLVd B-D / p5 | HPLVd Positive |
| C10 | 0.1ng Cannabis cDNA ; HPLVd Positive + AMV Spike 10 | 26S | VIC | Amp | 23.61578218 | 26S/p1 | Reaction Positive |
| C11 | NTC | AMV | CY5 | No Amp | Undetermined | AMV B-C / pB | AMV Negative |

FIG 11A contd

| | | | | | | | |
|---|---|---|---|---|---|---|---|
| C11 | NTC | HPLVd | FAM | No Amp | Undetermined | HPLVd B-D / p5 | HPLVd Negative |
| C11 | NTC | 26S | VIC | No Amp | Undetermined | 26S/p1 | Reaction Negative |
| C12 | 0.1ng Cannabis cDNA ; HPLVd Negative | AMV | CY5 | No Amp | Undetermined | AMV B-C / pB | AMV Negative |
| C12 | 0.1ng Cannabis cDNA ; HPLVd Negative | HPLVd | FAM | No Amp | Undetermined | HPLVd B-D / p5 | HPLVd Negative |
| C12 | 0.1ng Cannabis cDNA ; HPLVd Negative | 26S | VIC | Amp | 21.24717008 | 26S/p1 | Reaction Positive |
| D1 | 1ng Cannabis cDNA ; HPLVd Positive + AMV Spike 1 | AMV | CY5 | Amp | 27.75359881 | AMV B-C / pB | AMV Positive |
| D1 | 1ng Cannabis cDNA ; HPLVd Positive + AMV Spike 1 | HPLVd | FAM | Amp | 20.89873984 | HPLVd B-D / p5 | HPLVd Positive |
| D1 | 1ng Cannabis cDNA ; HPLVd Positive + AMV Spike 1 | 26S | VIC | Amp | 17.20815108 | 26S/p1 | Reaction Positive |
| D2 | 1ng Cannabis cDNA ; HPLVd Positive + AMV Spike 2 | AMV | CY5 | Amp | 27.43762384 | AMV B-C / pB | AMV Positive |
| D2 | 1ng Cannabis cDNA ; HPLVd Positive + AMV Spike 2 | HPLVd | FAM | Amp | 21.12882279 | HPLVd B-E / p5 | HPLVd Positive |
| D2 | 1ng Cannabis cDNA ; HPLVd Positive + AMV Spike 2 | 26S | VIC | Amp | 17.37841755 | 26S/p1 | Reaction Positive |
| D3 | 1ng Cannabis cDNA ; HPLVd Positive + AMV Spike 3 | AMV | CY5 | Amp | 28.12704754 | AMV B-C / pB | AMV Positive |
| D3 | 1ng Cannabis cDNA ; HPLVd Positive + AMV Spike 3 | HPLVd | FAM | Amp | 21.18039457 | HPLVd B-E / p5 | HPLVd Positive |
| D3 | 1ng Cannabis cDNA ; HPLVd Positive + AMV Spike 3 | 26S | VIC | Amp | 18.61932931 | 26S/p1 | Reaction Positive |
| D4 | 1ng Cannabis cDNA ; HPLVd Positive + AMV Spike 4 | AMV | CY5 | Amp | 27.60727619 | AMV B-C / pB | AMV Positive |
| D4 | 1ng Cannabis cDNA ; HPLVd Positive + AMV Spike 4 | HPLVd | FAM | Amp | 21.40960154 | HPLVd B-E / p5 | HPLVd Positive |
| D4 | 1ng Cannabis cDNA ; HPLVd Positive + AMV Spike 4 | 26S | VIC | Amp | 17.56585753 | 26S/p1 | Reaction Positive |
| D5 | 1ng Cannabis cDNA ; HPLVd Positive + AMV Spike 5 | AMV | CY5 | Amp | 26.67312961 | AMV B-C / pB | AMV Positive |
| D5 | 1ng Cannabis cDNA ; HPLVd Positive + AMV Spike 5 | HPLVd | FAM | Amp | 21.09179433 | HPLVd B-E / p5 | HPLVd Positive |

FIG 11A contd

| | | | | | | | |
|---|---|---|---|---|---|---|---|
| D5 | 1ng Cannabis cDNA ; HPLVd Positive + AMV Spike 5 | 26S | VIC | Amp | 16.28078711 | 26S/p1 | Reaction Positive |
| D6 | 1ng Cannabis cDNA ; HPLVd Positive + AMV Spike 6 | AMV | CY5 | Amp | 27.94080889 | AMV B-C / pB | AMV Positive |
| D6 | 1ng Cannabis cDNA ; HPLVd Positive + AMV Spike 6 | HPLVd | FAM | Amp | 21.08387733 | HPLVd B-E / p5 | HPLVd Positive |
| D6 | 1ng Cannabis cDNA ; HPLVd Positive + AMV Spike 6 | 26S | VIC | Amp | 17.57004984 | 26S/p1 | Reaction Positive |
| D7 | 1ng Cannabis cDNA ; HPLVd Positive + AMV Spike 7 | AMV | CY5 | Amp | 27.70846791 | AMV B-C / pB | AMV Positive |
| D7 | 1ng Cannabis cDNA ; HPLVd Positive + AMV Spike 7 | HPLVd | FAM | Amp | 20.99063945 | HPLVd B-E / p5 | HPLVd Positive |
| D7 | 1ng Cannabis cDNA ; HPLVd Positive + AMV Spike 7 | 26S | VIC | Amp | 16.395455698 | 26S/p1 | Reaction Positive |
| D8 | 1ng Cannabis cDNA ; HPLVd Positive + AMV Spike 8 | AMV | CY5 | Amp | 27.3461805 | AMV B-C / pB | AMV Positive |
| D8 | 1ng Cannabis cDNA ; HPLVd Positive + AMV Spike 8 | HPLVd | FAM | Amp | 21.01123301 | HPLVd B-E / p5 | HPLVd Positive |
| D8 | 1ng Cannabis cDNA ; HPLVd Positive + AMV Spike 8 | 26S | VIC | Amp | 16.27460557 | 26S/p1 | Reaction Positive |
| D9 | 1ng Cannabis cDNA ; HPLVd Positive + AMV Spike 9 | AMV | CY5 | Amp | 27.23084885 | AMV B-C / pB | AMV Positive |
| D9 | 1ng Cannabis cDNA ; HPLVd Positive + AMV Spike 9 | HPLVd | FAM | Amp | 20.97202461 | HPLVd B-E / p5 | HPLVd Positive |
| D9 | 1ng Cannabis cDNA ; HPLVd Positive + AMV Spike 9 | 26S | VIC | Amp | 16.58335175 | 26S/p1 | Reaction Positive |
| D10 | 1ng Cannabis cDNA ; HPLVd Positive + AMV Spike 10 | AMV | CY5 | Amp | 27.92175793 | AMV B-C / pB | AMV Positive |
| D10 | 1ng Cannabis cDNA ; HPLVd Positive + AMV Spike 10 | HPLVd | FAM | Amp | 21.0610103 | HPLVd B-E / p5 | HPLVd Positive |
| D10 | 1ng Cannabis cDNA ; HPLVd Positive + AMV Spike 10 | 26S | VIC | Amp | 17.23840704 | 26S/p1 | Reaction Positive |
| D11 | NTC | AMV | CY5 | No Amp | Undetermined | AMV B-C / pB | AMV Negative |
| D11 | NTC | HPLVd | FAM | No Amp | Undetermined | HPLVd B-E / p5 | HPLVd Negative |
| D11 | NTC | 26S | VIC | No Amp | Undetermined | 26S/p1 | Reaction Negative |

FIG 11A contd

| | Sample | | | | | | |
|---|---|---|---|---|---|---|---|
| D12 | 1ng Cannabis cDNA ; HPLVd Negative | AMV | CY5 | No Amp | Undetermined | AMV B-C / pB | AMV Negative |
| D12 | 1ng Cannabis cDNA ; HPLVd Negative | HPLVd | FAM | No Amp | Undetermined | HPLVd B-E / p5 | HPLVd Negative |
| D12 | 1ng Cannabis cDNA ; HPLVd Negative | 26S | VIC | Amp | 14.07135593 | 26S/p1 | Reaction Positive |
| E1 | 0.1ng Cannabis cDNA ; HPLVd Positive + AMV Spike 1 | AMV | CY5 | Amp | 33.22941758 | AMV B-C / pB | AMV Positive |
| E1 | 0.1ng Cannabis cDNA ; HPLVd Positive + AMV Spike 1 | HPLVd | FAM | Amp | 24.68052602 | HPLVd B-E / p5 | HPLVd Positive |
| E1 | 0.1ng Cannabis cDNA ; HPLVd Positive + AMV Spike 1 | 26S | VIC | Amp | 24.31273442 | 26S/p1 | Reaction Positive |
| E2 | 0.1ng Cannabis cDNA ; HPLVd Positive + AMV Spike 2 | AMV | CY5 | Amp | 32.68171088 | AMV B-C / pB | AMV Positive |
| E2 | 0.1ng Cannabis cDNA ; HPLVd Positive + AMV Spike 2 | HPLVd | FAM | Amp | 24.78841441 | HPLVd B-E / p5 | HPLVd Positive |
| E2 | 0.1ng Cannabis cDNA ; HPLVd Positive + AMV Spike 2 | 26S | VIC | Amp | 24.66767186 | 26S/p1 | Reaction Positive |
| E3 | 0.1ng Cannabis cDNA ; HPLVd Positive + AMV Spike 3 | AMV | CY5 | Amp | 33.14289827 | AMV B-C / pB | AMV Positive |
| E3 | 0.1ng Cannabis cDNA ; HPLVd Positive + AMV Spike 3 | HPLVd | FAM | Amp | 25.15697722 | HPLVd B-E / p5 | HPLVd Positive |
| E3 | 0.1ng Cannabis cDNA ; HPLVd Positive + AMV Spike 3 | 26S | VIC | Amp | 24.1007006 | 26S/p1 | Reaction Positive |
| E4 | 0.1ng Cannabis cDNA ; HPLVd Positive + AMV Spike 4 | AMV | CY5 | Amp | 32.5947781 | AMV B-C / pB | AMV Positive |
| E4 | 0.1ng Cannabis cDNA ; HPLVd Positive + AMV Spike 4 | HPLVd | FAM | Amp | 25.18662904 | HPLVd B-E / p5 | HPLVd Positive |
| E4 | 0.1ng Cannabis cDNA ; HPLVd Positive + AMV Spike 4 | 26S | VIC | Amp | 23.88774488 | 26S/p1 | Reaction Positive |
| E5 | 0.1ng Cannabis cDNA ; HPLVd Positive + AMV Spike 5 | AMV | CY5 | Amp | 33.20441501 | AMV B-C / pB | AMV Positive |
| E5 | 0.1ng Cannabis cDNA ; HPLVd Positive + AMV Spike 5 | HPLVd | FAM | Amp | 25.01044343 | HPLVd B-E / p5 | HPLVd Positive |
| E5 | 0.1ng Cannabis cDNA ; HPLVd Positive + AMV Spike 5 | 26S | VIC | Amp | 24.39238704 | 26S/p1 | Reaction Positive |
| E6 | 0.1ng Cannabis cDNA ; HPLVd Positive + AMV Spike 6 | AMV | CY5 | Amp | 33.3243723 | AMV B-C / pB | AMV Positive |

FIG 11A contd

| | Sample | Target | Dye | Amp | Ct | Assay | Result |
|---|---|---|---|---|---|---|---|
| E6 | 0.1ng Cannabis cDNA ; HPLVd Positive + AMV Spike 6 | HPLVd | FAM | Amp | 25.05153998 | HPLVd B-E / p5 | HPLVd Positive |
| E6 | 0.1ng Cannabis cDNA ; HPLVd Positive + AMV Spike 6 | 26S | VIC | Amp | 24.14288311 | 26S/p1 | Reaction Positive |
| E7 | 0.1ng Cannabis cDNA ; HPLVd Positive + AMV Spike 7 | AMV | CY5 | Amp | 32.11858292 | AMV B-C / pB | AMV Positive |
| E7 | 0.1ng Cannabis cDNA ; HPLVd Positive + AMV Spike 7 | HPLVd | FAM | Amp | 24.88674373 | HPLVd B-E / p5 | HPLVd Positive |
| E7 | 0.1ng Cannabis cDNA ; HPLVd Positive + AMV Spike 7 | 26S | VIC | Amp | 23.81803732 | 26S/p1 | Reaction Positive |
| E8 | 0.1ng Cannabis cDNA ; HPLVd Positive + AMV Spike 8 | AMV | CY5 | Amp | 34.73188123 | AMV B-C / pB | AMV Positive |
| E8 | 0.1ng Cannabis cDNA ; HPLVd Positive + AMV Spike 8 | HPLVd | FAM | Amp | 24.889901373 | HPLVd B-E / p5 | HPLVd Positive |
| E8 | 0.1ng Cannabis cDNA ; HPLVd Positive + AMV Spike 8 | 26S | VIC | Amp | 25.84627167 | 26S/p1 | Reaction Positive |
| E9 | 0.1ng Cannabis cDNA ; HPLVd Positive + AMV Spike 9 | AMV | CY5 | Amp | 33.81558261 | AMV B-C / pB | AMV Positive |
| E9 | 0.1ng Cannabis cDNA ; HPLVd Positive + AMV Spike 9 | HPLVd | FAM | Amp | 24.98959502 | HPLVd B-E / p5 | HPLVd Positive |
| E9 | 0.1ng Cannabis cDNA ; HPLVd Positive + AMV Spike 9 | 26S | VIC | Amp | 24.76812555 | 26S/p1 | Reaction Positive |
| E10 | 0.1ng Cannabis cDNA ; HPLVd Positive + AMV Spike 10 | AMV | CY5 | Amp | 32.45673297 | AMV B-C / pB | AMV Positive |
| E10 | 0.1ng Cannabis cDNA ; HPLVd Positive + AMV Spike 10 | HPLVd | FAM | Amp | 24.92731971 | HPLVd B-E / p5 | HPLVd Positive |
| E10 | 0.1ng Cannabis cDNA ; HPLVd Positive + AMV Spike 10 | 26S | VIC | Amp | 23.90124042 | 26S/p1 | Reaction Positive |
| E11 | NTC | AMV | CY5 | No Amp | Undetermined | AMV B-C / pB | AMV Negative |
| E11 | NTC | HPLVd | FAM | No Amp | Undetermined | HPLVd B-E / p5 | HPLVd Negative |
| E11 | NTC | 26S | VIC | No Amp | Undetermined | 26S/p1 | Reaction Negative |
| E12 | 0.1ng Cannabis cDNA ; HPLVd Negative | AMV | CY5 | No Amp | Undetermined | AMV B-C / pB | AMV Negative |
| E12 | 0.1ng Cannabis cDNA ; HPLVd Negative | HPLVd | FAM | No Amp | Undetermined | HPLVd B-E / p5 | HPLVd Negative |

FIG 11A contd

| | | | | | | |
|---|---|---|---|---|---|---|
| E12 | 0.1ng Cannabis cDNA ; HPLVd Negative | 26S | VIC | Amp | 20.91945314 | 26S/p1 | Reaction Positive |
| F1 | 1ng Cannabis cDNA ; HPLVd Positive + AMV Spike 1 | AMV | CY5 | Amp | 26.62095097 | AMV B-C / pB | AMV Positive |
| F1 | 1ng Cannabis cDNA ; HPLVd Positive + AMV Spike 1 | HPLVd | FAM | Amp | 20.64433882 | HPLVd B-F / p5 | HPLVd Positive |
| F1 | 1ng Cannabis cDNA ; HPLVd Positive + AMV Spike 1 | 26S | VIC | Amp | 15.67273591 | 26S/p1 | Reaction Positive |
| F2 | 1ng Cannabis cDNA ; HPLVd Positive + AMV Spike 2 | AMV | CY5 | Amp | 28.01113131 | AMV B-C / pB | AMV Positive |
| F2 | 1ng Cannabis cDNA ; HPLVd Positive + AMV Spike 2 | HPLVd | FAM | Amp | 20.82233145 | HPLVd B-F / p5 | HPLVd Positive |
| F2 | 1ng Cannabis cDNA ; HPLVd Positive + AMV Spike 2 | 26S | VIC | Amp | 16.96477787 | 26S/p1 | Reaction Positive |
| F3 | 1ng Cannabis cDNA ; HPLVd Positive + AMV Spike 3 | AMV | CY5 | Amp | 27.90830386 | AMV B-C / pB | AMV Positive |
| F3 | 1ng Cannabis cDNA ; HPLVd Positive + AMV Spike 3 | HPLVd | FAM | Amp | 20.86808115 | HPLVd B-F / p5 | HPLVd Positive |
| F3 | 1ng Cannabis cDNA ; HPLVd Positive + AMV Spike 3 | 26S | VIC | Amp | 16.77256316 | 26S/p1 | Reaction Positive |
| F4 | 1ng Cannabis cDNA ; HPLVd Positive + AMV Spike 4 | AMV | CY5 | Amp | 27.78592432 | AMV B-C / pB | AMV Positive |
| F4 | 1ng Cannabis cDNA ; HPLVd Positive + AMV Spike 4 | HPLVd | FAM | Amp | 20.96885654 | HPLVd B-F / p5 | HPLVd Positive |
| F4 | 1ng Cannabis cDNA ; HPLVd Positive + AMV Spike 4 | 26S | VIC | Amp | 17.32537922 | 26S/p1 | Reaction Positive |
| F5 | 1ng Cannabis cDNA ; HPLVd Positive + AMV Spike 5 | AMV | CY5 | Amp | 26.91037648 | AMV B-C / pB | AMV Positive |
| F5 | 1ng Cannabis cDNA ; HPLVd Positive + AMV Spike 5 | HPLVd | FAM | Amp | 20.86893792 | HPLVd B-F / p5 | HPLVd Positive |
| F5 | 1ng Cannabis cDNA ; HPLVd Positive + AMV Spike 5 | 26S | VIC | Amp | 17.18785952 | 26S/p1 | Reaction Positive |
| F6 | 1ng Cannabis cDNA ; HPLVd Positive + AMV Spike 6 | AMV | CY5 | Amp | 27.51650493 | AMV B-C / pB | AMV Positive |
| F6 | 1ng Cannabis cDNA ; HPLVd Positive + AMV Spike 6 | HPLVd | FAM | Amp | 20.80955281 | HPLVd B-F / p5 | HPLVd Positive |
| F6 | 1ng Cannabis cDNA ; HPLVd Positive + AMV Spike 6 | 26S | VIC | Amp | 18.1060309 | 26S/p1 | Reaction Positive |

FIG 11A contd

| Well | Sample | Target | Dye | Amp | Ct | Assay | Result |
|---|---|---|---|---|---|---|---|
| F7 | 1ng Cannabis cDNA ; HPLVd Positive + AMV Spike 7 | AMV | CY5 | Amp | 27.4533682 | AMV B-C / pB | AMV Positive |
| F7 | 1ng Cannabis cDNA ; HPLVd Positive + AMV Spike 7 | HPLVd | FAM | Amp | 20.75376717 | HPLVd B-F / p5 | HPLVd Positive |
| F7 | 1ng Cannabis cDNA ; HPLVd Positive + AMV Spike 7 | 26S | VIC | Amp | 16.62863073 | 26S/p1 | Reaction Positive |
| F8 | 1ng Cannabis cDNA ; HPLVd Positive + AMV Spike 8 | AMV | CY5 | Amp | 25.51273509 | AMV B-C / pB | AMV Positive |
| F8 | 1ng Cannabis cDNA ; HPLVd Positive + AMV Spike 8 | HPLVd | FAM | Amp | 20.78943493 | HPLVd B-F / p5 | HPLVd Positive |
| F8 | 1ng Cannabis cDNA ; HPLVd Positive + AMV Spike 8 | 26S | VIC | Amp | 16.52770719 | 26S/p1 | Reaction Positive |
| F9 | 1ng Cannabis cDNA ; HPLVd Positive + AMV Spike 9 | AMV | CY5 | Amp | 25.94025612 | AMV B-C / pB | AMV Positive |
| F9 | 1ng Cannabis cDNA ; HPLVd Positive + AMV Spike 9 | HPLVd | FAM | Amp | 20.81543699 | HPLVd B-F / p5 | HPLVd Positive |
| F9 | 1ng Cannabis cDNA ; HPLVd Positive + AMV Spike 9 | 26S | VIC | Amp | 17.1529024 | 26S/p1 | Reaction Positive |
| F10 | 1ng Cannabis cDNA ; HPLVd Positive + AMV Spike 10 | AMV | CY5 | Amp | 27.49968202 | AMV B-C / pB | AMV Positive |
| F10 | 1ng Cannabis cDNA ; HPLVd Positive + AMV Spike 10 | HPLVd | FAM | Amp | 20.82789995 | HPLVd B-F / p5 | HPLVd Positive |
| F10 | 1ng Cannabis cDNA ; HPLVd Positive + AMV Spike 10 | 26S | VIC | Amp | 17.50657744 | 26S/p1 | Reaction Positive |
| F11 | NTC | AMV | CY5 | No Amp | Undetermined | AMV B-C / pB | AMV Negative |
| F11 | NTC | HPLVd | FAM | No Amp | Undetermined | HPLVd B-F / p5 | HPLVd Negative |
| F11 | NTC | 26S | VIC | No Amp | Undetermined | 26S/p1 | Reaction Negative |
| F12 | 1ng Cannabis cDNA ; HPLVd Negative | AMV | CY5 | No Amp | Undetermined | AMV B-C / pB | AMV Negative |
| F12 | 1ng Cannabis cDNA ; HPLVd Negative | HPLVd | FAM | No Amp | Undetermined | HPLVd B-F / p5 | HPLVd Negative |
| F12 | 1ng Cannabis cDNA ; HPLVd Negative | 26S | VIC | Amp | 14.37583772 | 26S/p1 | Reaction Positive |
| G1 | 0.1ng Cannabis cDNA ; HPLVd Positive + AMV Spike 1 | AMV | CY5 | Amp | 33.07564384 | AMV B-C / pB | AMV Positive |

FIG 11A contd

| | Sample | Target | Dye | Amp | Ct | Assay | Result |
|---|---|---|---|---|---|---|---|
| G1 | 0.1ng Cannabis cDNA ; HPLVd Positive + AMV Spike 1 | HPLVd | FAM | Amp | 24.59909754 | HPLVd B-F / p5 | HPLVd Positive |
| G1 | 0.1ng Cannabis cDNA ; HPLVd Positive + AMV Spike 1 | 26S | VIC | Amp | 24.35863691 | 26S/p1 | Reaction Positive |
| G2 | 0.1ng Cannabis cDNA ; HPLVd Positive + AMV Spike 2 | AMV | CY5 | Amp | 32.23192583 | AMV B-C / pB | AMV Positive |
| G2 | 0.1ng Cannabis cDNA ; HPLVd Positive + AMV Spike 2 | HPLVd | FAM | Amp | 24.50909524 | HPLVd B-F / p5 | HPLVd Positive |
| G2 | 0.1ng Cannabis cDNA ; HPLVd Positive + AMV Spike 2 | 26S | VIC | Amp | 24.86917146 | 26S/p1 | Reaction Positive |
| G3 | 0.1ng Cannabis cDNA ; HPLVd Positive + AMV Spike 3 | AMV | CY5 | Amp | 32.36770111 | AMV B-C / pB | AMV Positive |
| G3 | 0.1ng Cannabis cDNA ; HPLVd Positive + AMV Spike 3 | HPLVd | FAM | Amp | 24.81424596 | HPLVd B-F / p5 | HPLVd Positive |
| G3 | 0.1ng Cannabis cDNA ; HPLVd Positive + AMV Spike 3 | 26S | VIC | Amp | 23.94727956 | 26S/p1 | Reaction Positive |
| G4 | 0.1ng Cannabis cDNA ; HPLVd Positive + AMV Spike 4 | AMV | CY5 | Amp | 32.76337541 | AMV B-C / pB | AMV Positive |
| G4 | 0.1ng Cannabis cDNA ; HPLVd Positive + AMV Spike 4 | HPLVd | FAM | Amp | 24.79890378 | HPLVd B-F / p5 | HPLVd Positive |
| G4 | 0.1ng Cannabis cDNA ; HPLVd Positive + AMV Spike 4 | 26S | VIC | Amp | 25.06068564 | 26S/p1 | Reaction Positive |
| G5 | 0.1ng Cannabis cDNA ; HPLVd Positive + AMV Spike 5 | AMV | CY5 | Amp | 32.99657199 | AMV B-C / pB | AMV Positive |
| G5 | 0.1ng Cannabis cDNA ; HPLVd Positive + AMV Spike 5 | HPLVd | FAM | Amp | 24.73046518 | HPLVd B-F / p5 | HPLVd Positive |
| G5 | 0.1ng Cannabis cDNA ; HPLVd Positive + AMV Spike 5 | 26S | VIC | Amp | 22.91920717 | 26S/p1 | Reaction Positive |
| G6 | 0.1ng Cannabis cDNA ; HPLVd Positive + AMV Spike 6 | AMV | CY5 | Amp | 32.50389954 | AMV B-C / pB | AMV Positive |
| G6 | 0.1ng Cannabis cDNA ; HPLVd Positive + AMV Spike 6 | HPLVd | FAM | Amp | 24.740985 | HPLVd B-F / p5 | HPLVd Positive |
| G6 | 0.1ng Cannabis cDNA ; HPLVd Positive + AMV Spike 6 | 26S | VIC | Amp | 23.50708919 | 26S/p1 | Reaction Positive |
| G7 | 0.1ng Cannabis cDNA ; HPLVd Positive + AMV Spike 7 | AMV | CY5 | Amp | 32.07147613 | AMV B-C / pB | AMV Positive |
| G7 | 0.1ng Cannabis cDNA ; HPLVd Positive + AMV Spike 7 | HPLVd | FAM | Amp | 24.29133307 | HPLVd B-F / p5 | HPLVd Positive |

FIG 11A contd

| | Description | Target | Dye | Amp | Ct | Assay | Reaction |
|---|---|---|---|---|---|---|---|
| G7 | 0.1ng Cannabis cDNA ; HPLVd Positive + AMV Spike 7 | 26S | VIC | Amp | 22.06125328 | 26S/p1 | Reaction Positive |
| G8 | 0.1ng Cannabis cDNA ; HPLVd Positive + AMV Spike 8 | AMV | CY5 | Amp | 32.96543818 | AMV B-C / pB | AMV Positive |
| G8 | 0.1ng Cannabis cDNA ; HPLVd Positive + AMV Spike 8 | HPLVd | FAM | Amp | 24.72291718 | HPLVd B-F / p5 | HPLVd Positive |
| G8 | 0.1ng Cannabis cDNA ; HPLVd Positive + AMV Spike 8 | 26S | VIC | Amp | 23.77574085 | 26S/p1 | Reaction Positive |
| G9 | 0.1ng Cannabis cDNA ; HPLVd Positive + AMV Spike 9 | AMV | CY5 | Amp | 33.99879089 | AMV B-C / pB | AMV Positive |
| G9 | 0.1ng Cannabis cDNA ; HPLVd Positive + AMV Spike 9 | HPLVd | FAM | Amp | 24.80183738 | HPLVd B-F / p5 | HPLVd Positive |
| G9 | 0.1ng Cannabis cDNA ; HPLVd Positive + AMV Spike 9 | 26S | VIC | Amp | 24.0193184 | 26S/p1 | Reaction Positive |
| G10 | 0.1ng Cannabis cDNA ; HPLVd Positive + AMV Spike 10 | AMV | CY5 | Amp | 32.89423194 | AMV B-C / pB | AMV Positive |
| G10 | 0.1ng Cannabis cDNA ; HPLVd Positive + AMV Spike 10 | HPLVd | FAM | Amp | 24.72567632 | HPLVd B-F / p5 | HPLVd Positive |
| G10 | 0.1ng Cannabis cDNA ; HPLVd Positive + AMV Spike 10 | 26S | VIC | Amp | 23.87373911 | 26S/p1 | Reaction Positive |
| G11 | NTC | AMV | CY5 | No Amp | Undetermined | AMV B-C / pB | AMV Negative |
| G11 | NTC | HPLVd | FAM | No Amp | Undetermined | HPLVd B-F / p5 | HPLVd Negative |
| G11 | NTC | 26S | VIC | No Amp | Undetermined | 26S/p1 | Reaction Negative |
| G12 | 0.1ng Cannabis cDNA ; HPLVd Negative | AMV | CY5 | No Amp | Undetermined | AMV B-C / pB | AMV Negative |
| G12 | 0.1ng Cannabis cDNA ; HPLVd Negative | HPLVd | FAM | No Amp | Undetermined | HPLVd B-F / p5 | HPLVd Negative |
| G12 | 0.1ng Cannabis cDNA ; HPLVd Negative | 26S | VIC | Amp | 19.98634621 | 26S/p1 | Reaction Positive |

B-D p1

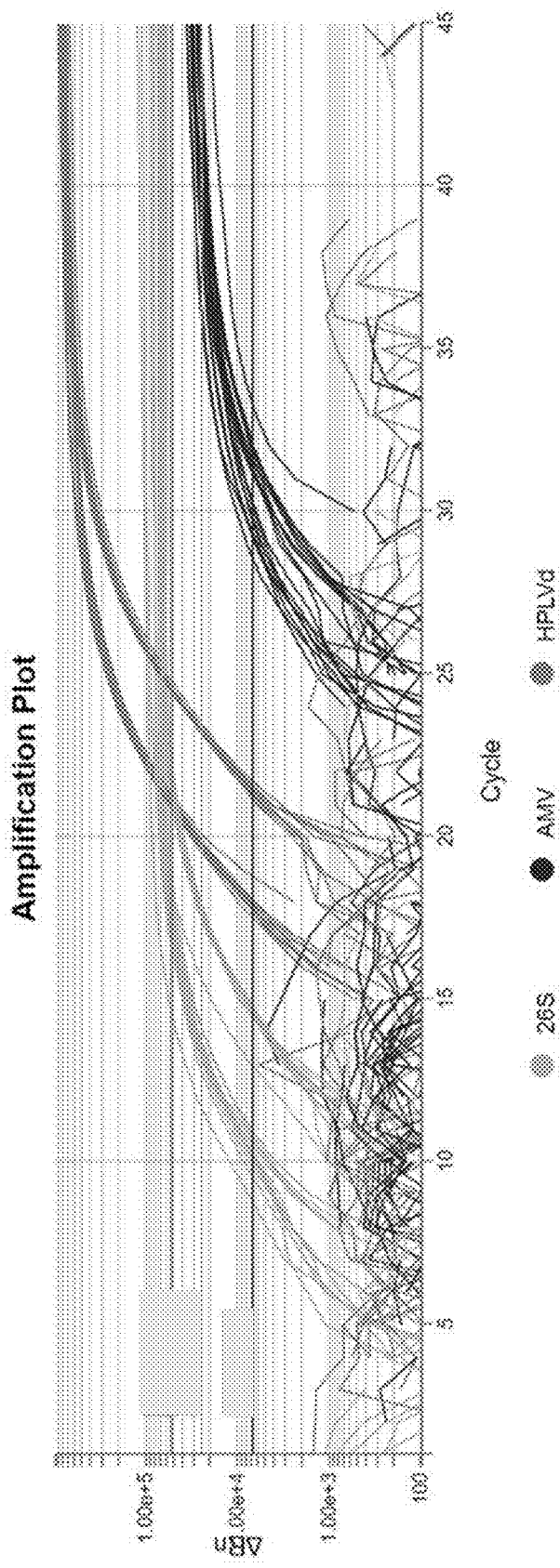
FIG 11B contd
B-E p1

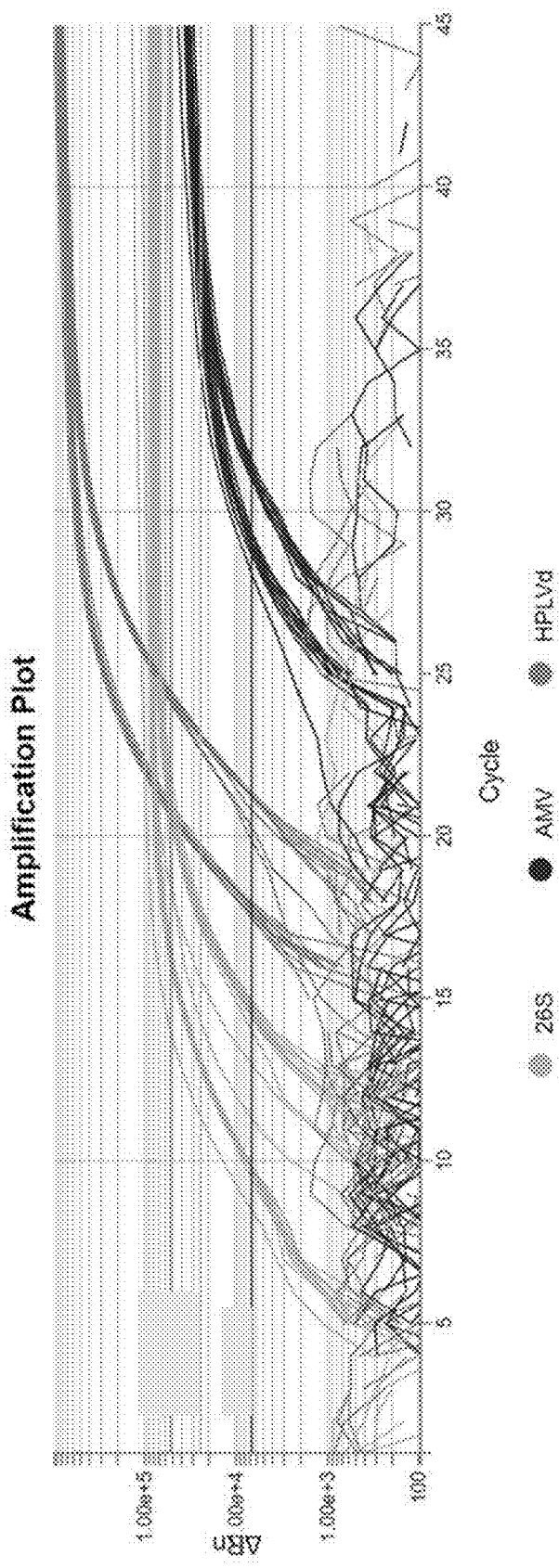
FIG 11B contd
B-F p1

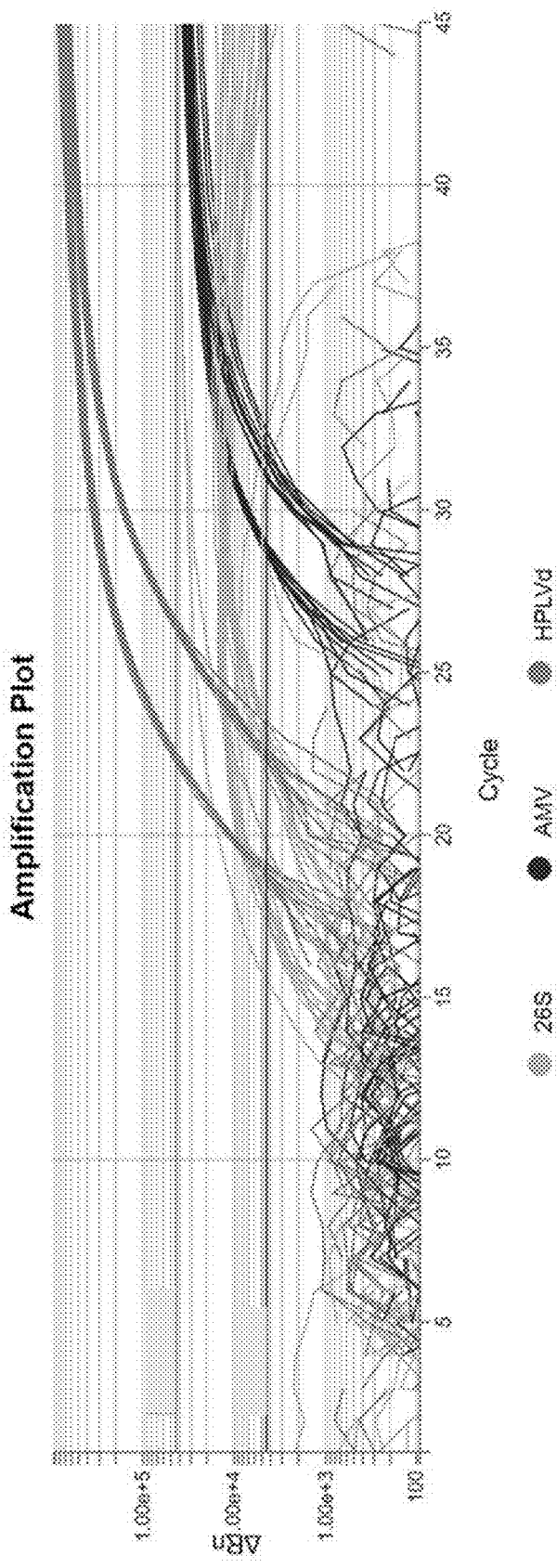
FIG 11B contd
B-D p2

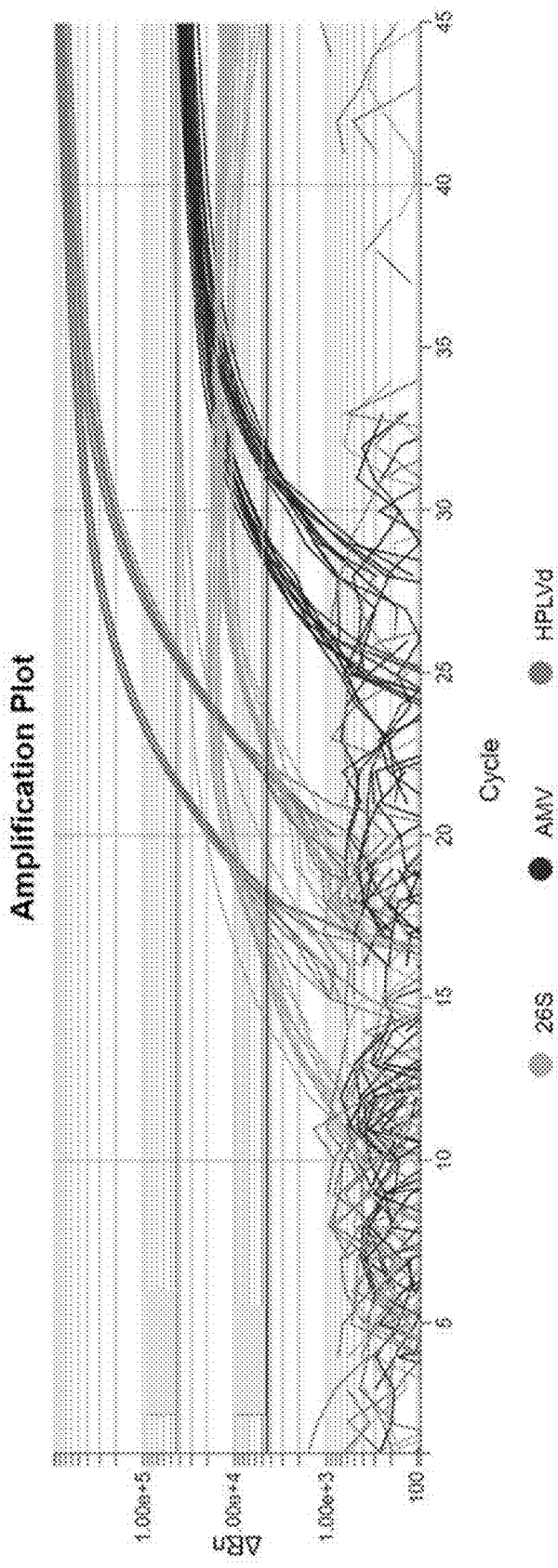
FIG 11B contd
B-E p2

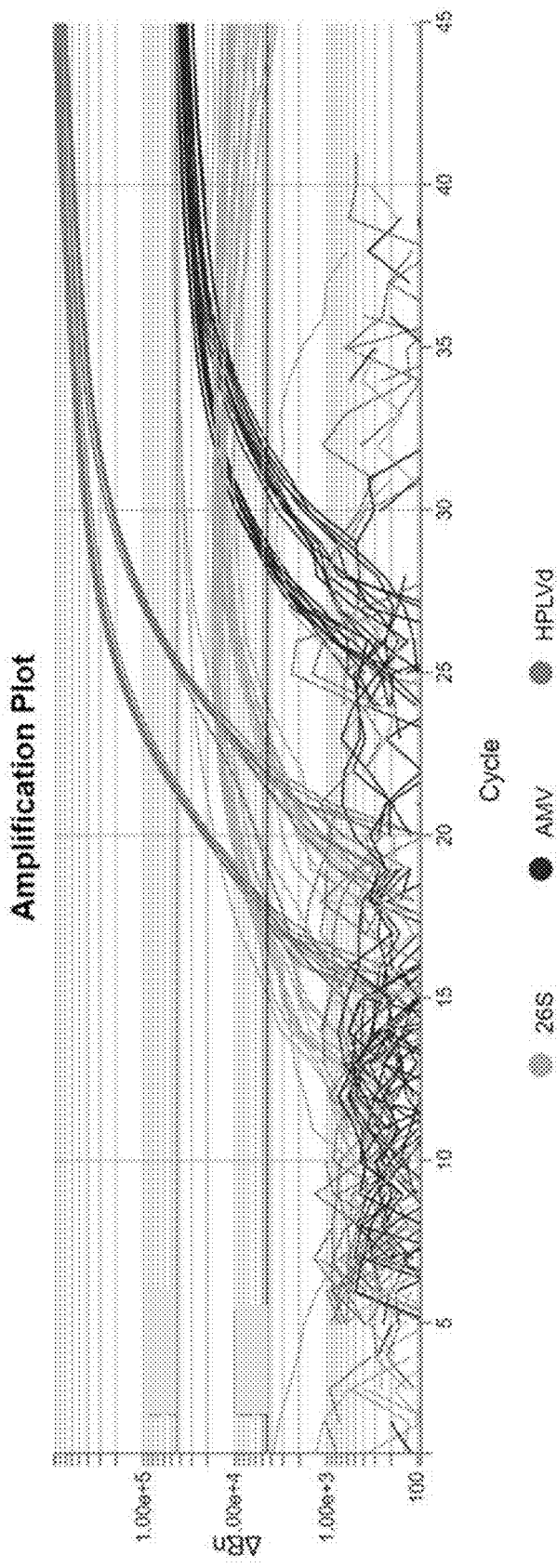
FIG 11B contd
B-F p2

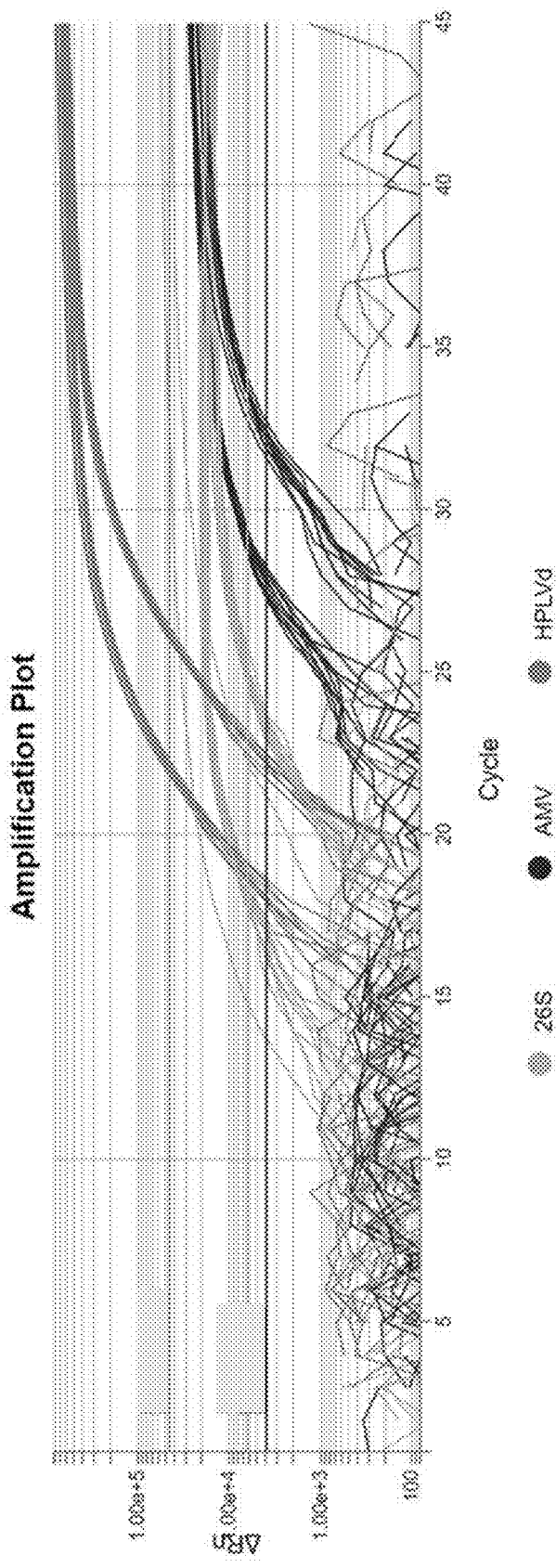
FIG 11B contd
B-D p3

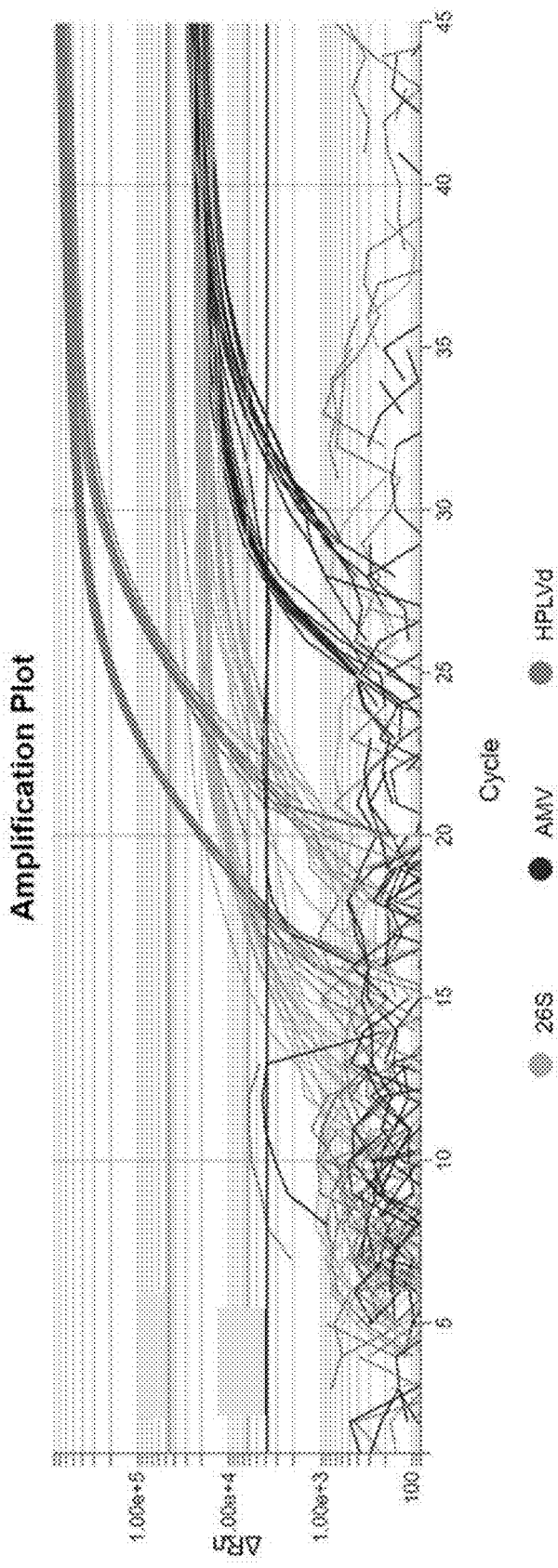
FIG 11B contd
B-E p3

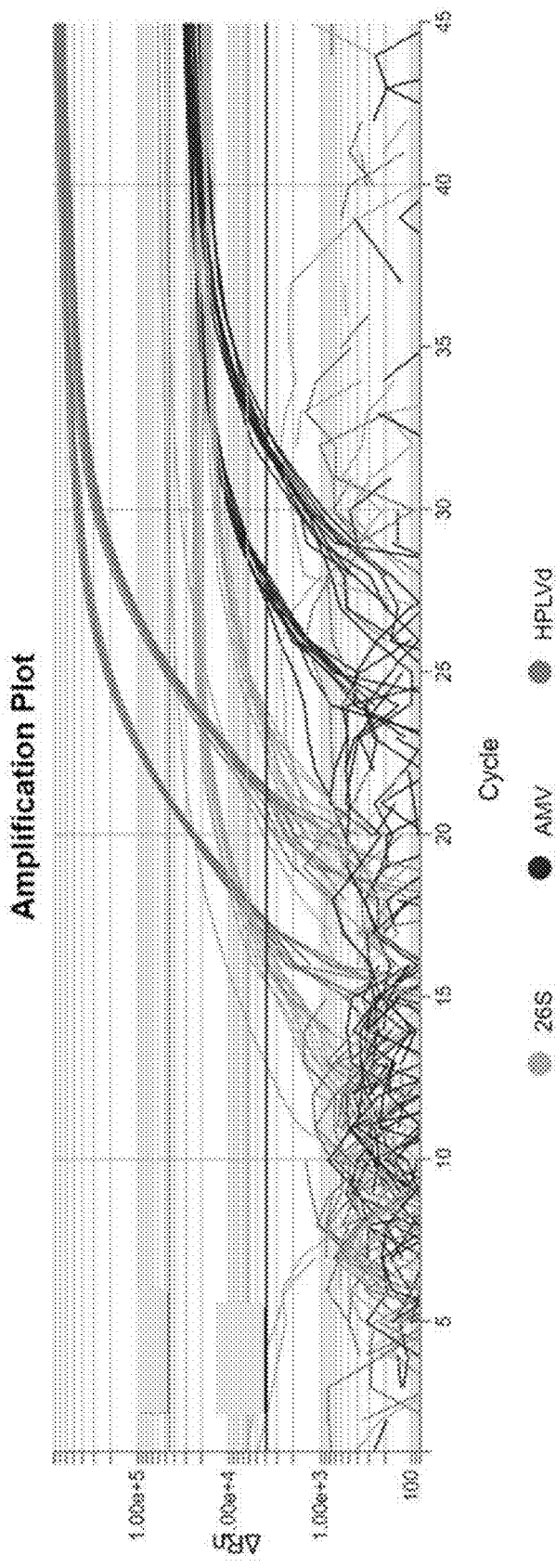
FIG 11B contd
B-F p3

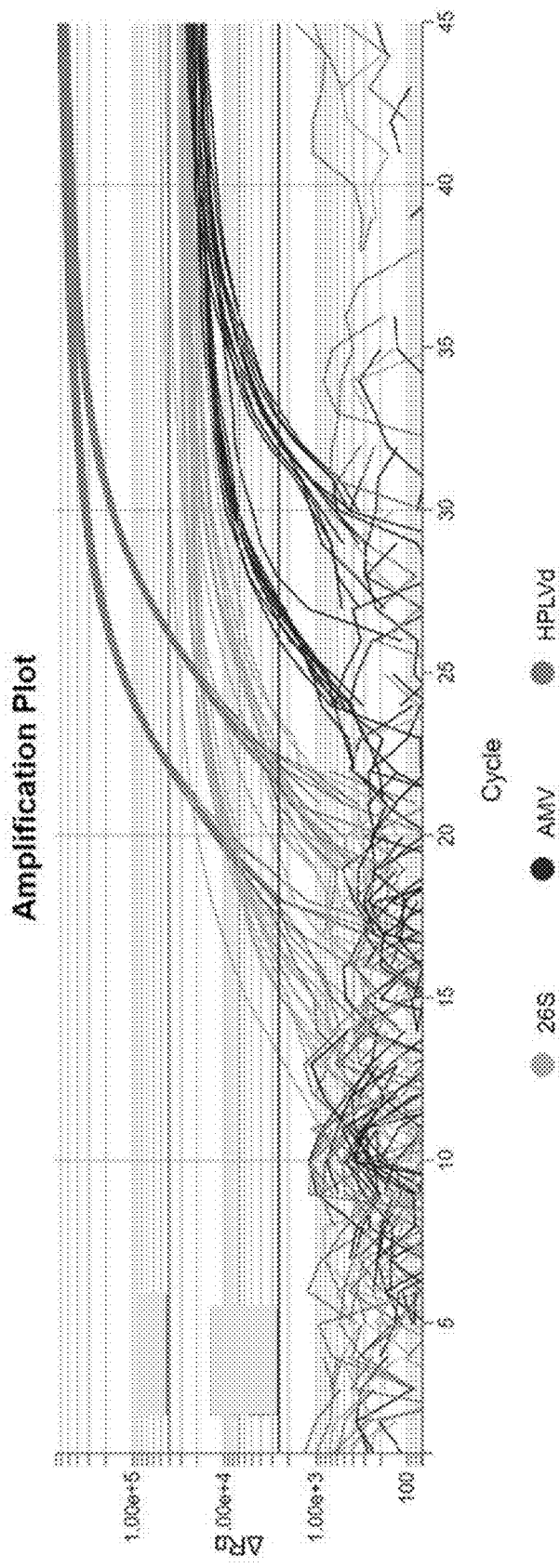
FIG 11B contd B-D p4

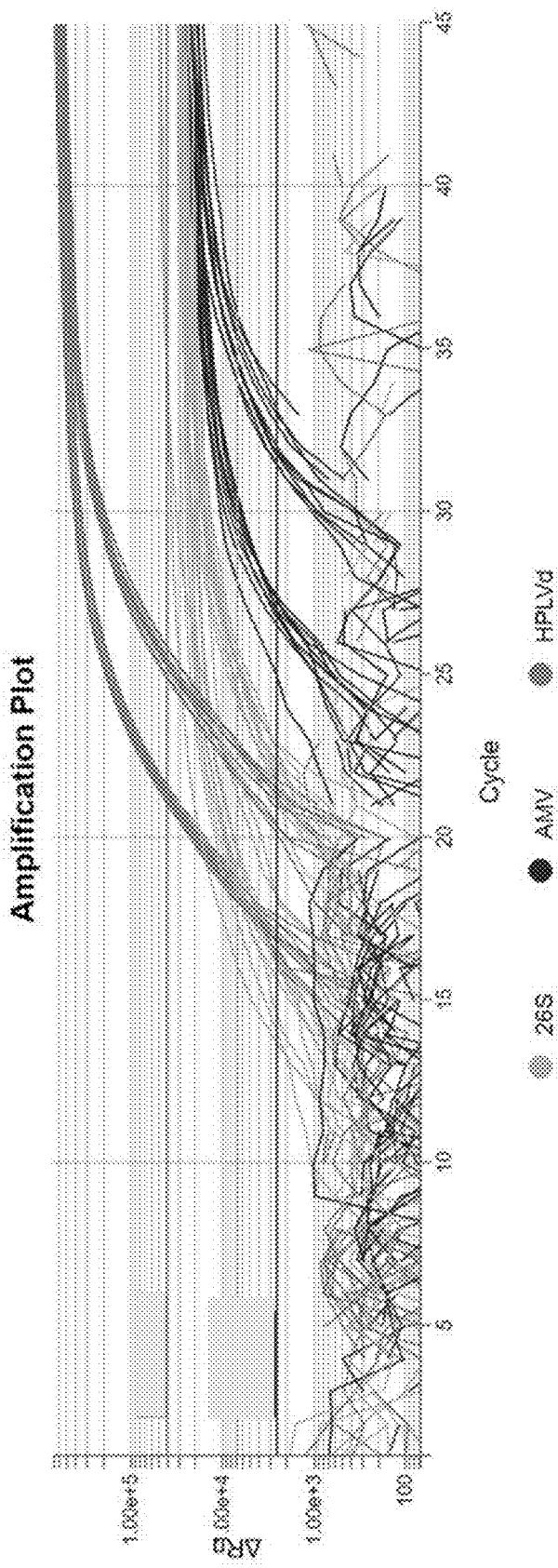
FIG 11B contd
B-E p4

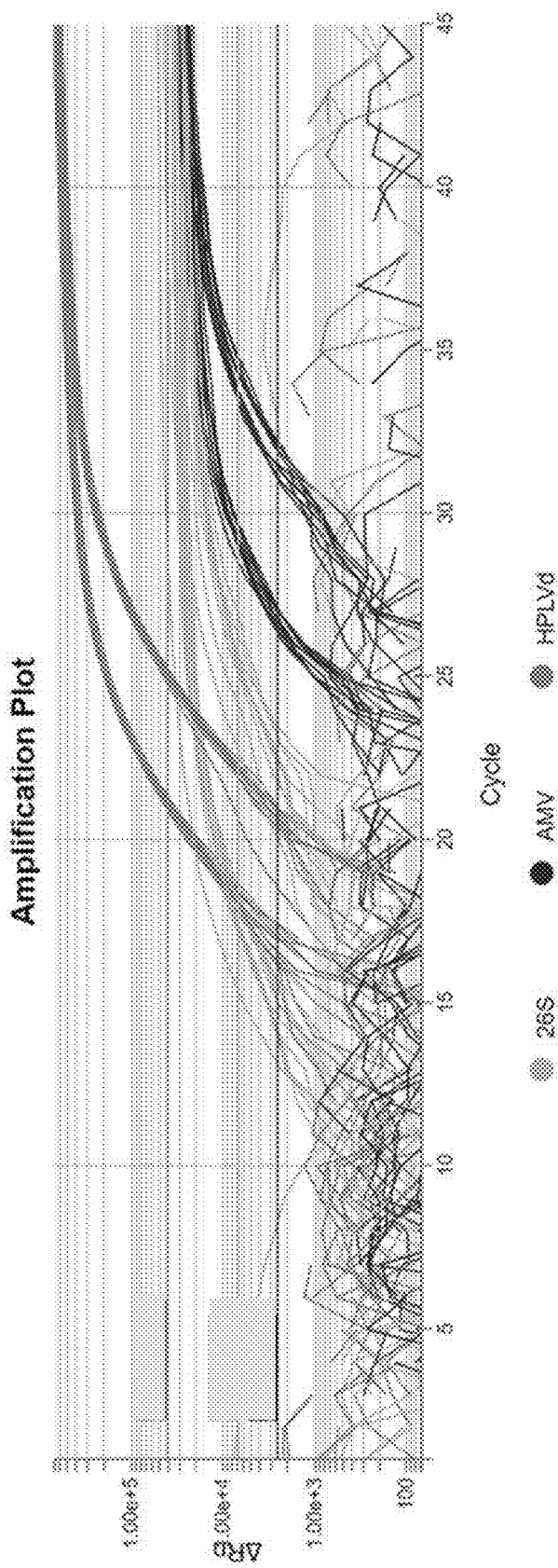
FIG 11B contd
B-F p4

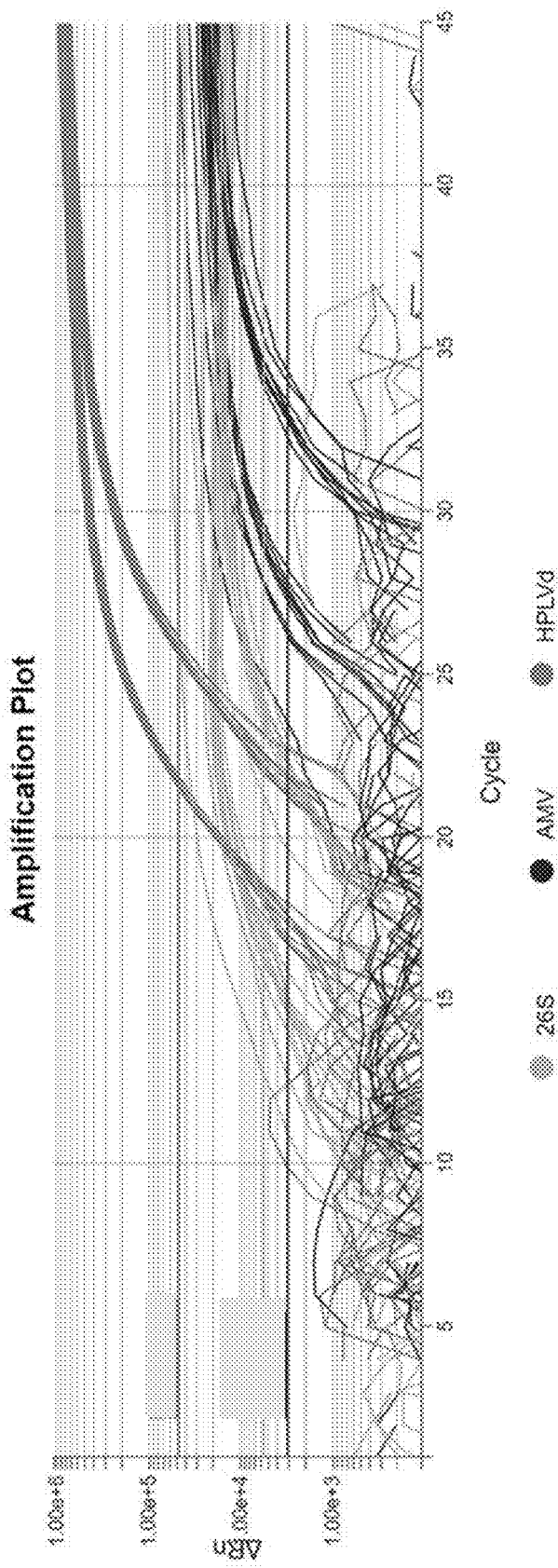
FIG 11B contd
B-D p5

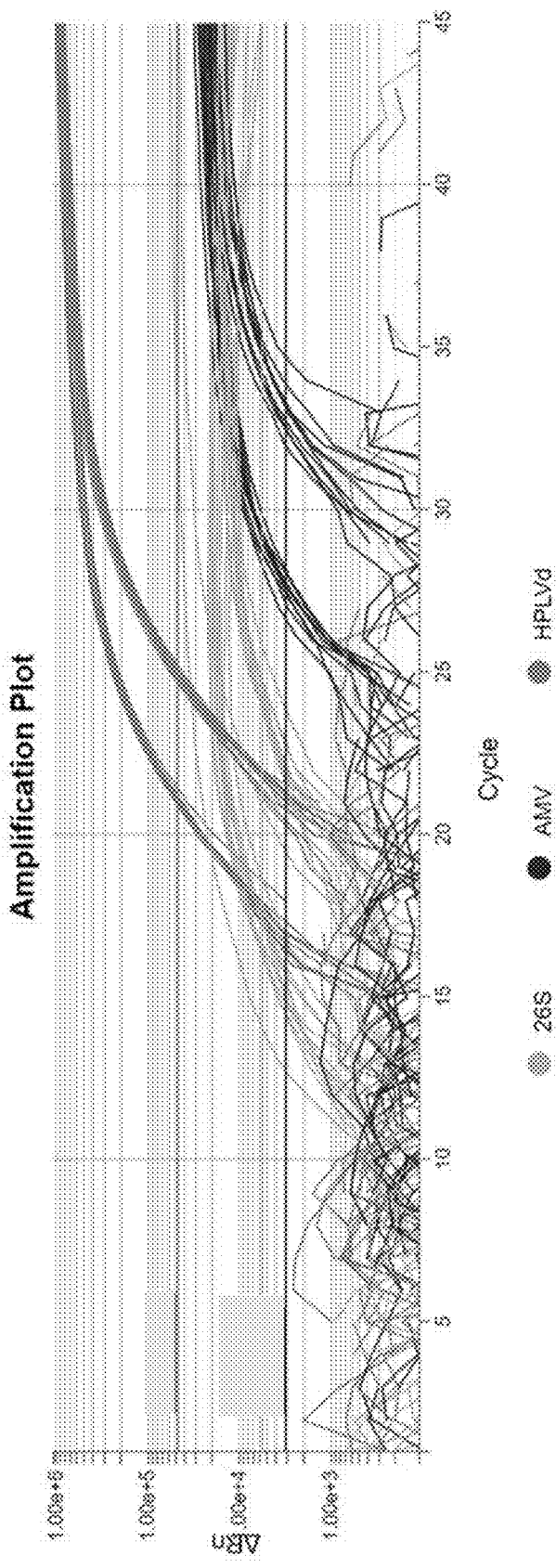
FIG 11B contd
B-E p5

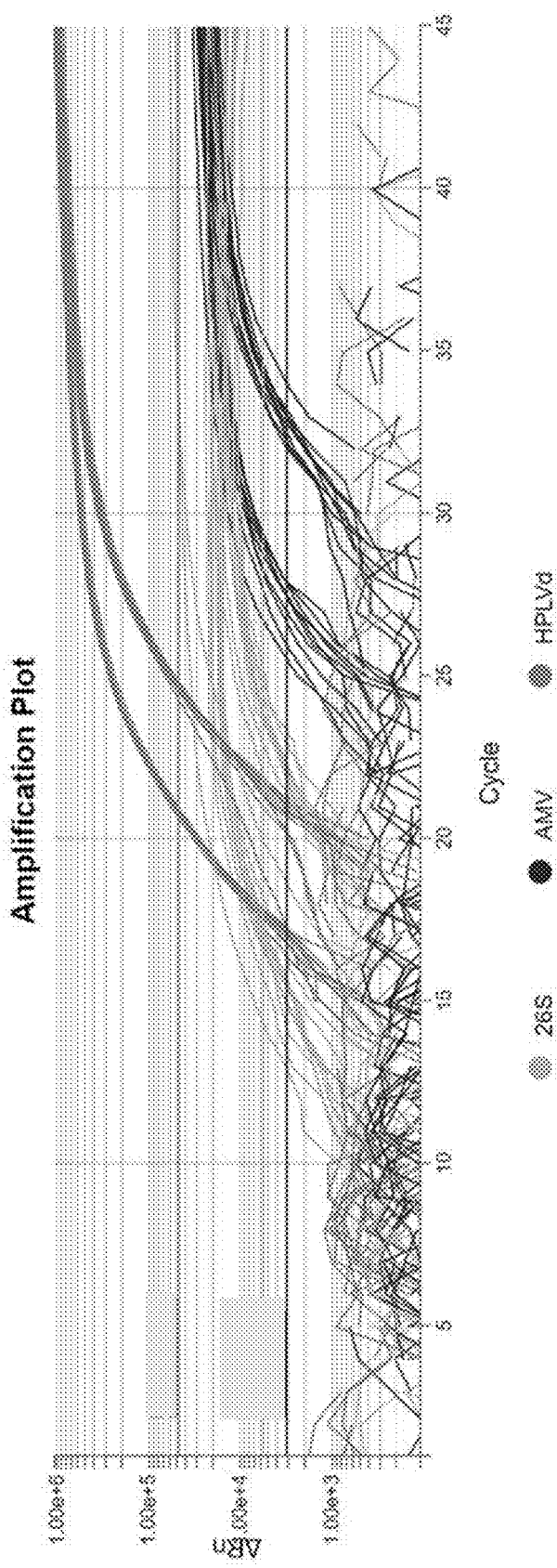
FIG 11B contd
B-F p5

FIG 12A

| Well Position | Sample | Target | Reporter | Amp Status | Cq | Primer/Probe | Result |
|---|---|---|---|---|---|---|---|
| B1 | CW14T520 M001 Rep 1 | 26S | VIC | Amp | 20.21909314 | 26S / p1 | Reaction Positive |
| B1 | CW14T520 M001 Rep 1 | AMV | CY5 | No Amp | Undetermined | AMV / p1 | AMV Negative |
| B1 | CW14T520 M001 Rep 1 | HPLVd | FAM | No Amp | Undetermined | HPLVd B-F / p4 | HPLVd Negative |
| B2 | CW14T520 M002 Rep 1 | 26S | VIC | Amp | 21.22218508 | 26S / p1 | Reaction Positive |
| B2 | CW14T520 M002 Rep 1 | AMV | CY5 | No Amp | Undetermined | AMV / p1 | AMV Negative |
| B2 | CW14T520 M002 Rep 1 | HPLVd | FAM | No Amp | Undetermined | HPLVd B-F / p4 | HPLVd Negative |
| B3 | Abagail Symptomatic Leaf Rep 1 | 26S | VIC | Amp | 21.43302092 | 26S / p1 | Reaction Positive |
| B3 | Abagail Symptomatic Leaf Rep 1 | AMV | CY5 | No Amp | Undetermined | AMV / p1 | AMV Negative |
| B3 | Abagail Symptomatic Leaf Rep 1 | HPLVd | FAM | Amp | 22.88486122 | HPLVd B-F / p4 | HPLVd Positive |
| B4 | CW14T520 M001 Rep 2 | 26S | VIC | Amp | 21.22532893 | 26S / p1 | Reaction Positive |
| B4 | CW14T520 M001 Rep 2 | AMV | CY5 | No Amp | Undetermined | AMV / p1 | AMV Negative |
| B4 | CW14T520 M001 Rep 2 | HPLVd | FAM | No Amp | Undetermined | HPLVd B-F / p4 | HPLVd Negative |
| B5 | CW14T520 M002 Rep 2 | 26S | VIC | Amp | 22.71611575 | 26S / p1 | Reaction Positive |
| B5 | CW14T520 M002 Rep 2 | AMV | CY5 | No Amp | Undetermined | AMV / p1 | AMV Negative |
| B5 | CW14T520 M002 Rep 2 | HPLVd | FAM | No Amp | Undetermined | HPLVd B-F / p4 | HPLVd Negative |
| B6 | Abagail Symptomatic Leaf Rep 2 | 26S | VIC | Amp | 21.70684867 | 26S / p1 | Reaction Positive |
| B6 | Abagail Symptomatic Leaf Rep 2 | AMV | CY5 | No Amp | Undetermined | AMV / p1 | AMV Negative |
| B6 | Abagail Symptomatic Leaf Rep 2 | HPLVd | FAM | Amp | 23.26663459 | HPLVd B-F / p4 | HPLVd Positive |
| D1 | Abagail Symptomatic Leaf Rep 1 | 26S | VIC | Amp | 23.35268689 | 26S / p1 | Reaction Positive |
| D1 | Abagail Symptomatic Leaf Rep 1 | BCTV | CY5 | Amp | 24.52087325 | BCTV / p1 | BCTV Positive |
| D1 | Abagail Symptomatic Leaf Rep 1 | HPLVd | FAM | Amp | 23.31174086 | HPLVd B-F / p4 | HPLVd Positive |
| D2 | Abagail Symptomatic Leaf Rep 2 | 26S | VIC | Amp | 22.49532071 | 26S / p1 | Reaction Positive |
| D2 | Abagail Symptomatic Leaf Rep 2 | BCTV | CY5 | Amp | 24.87691766 | BCTV / p1 | BCTV Positive |

FIG 12A contd

| Sample | Target | Dye | Amp | Ct | Assay | Result |
|---|---|---|---|---|---|---|
| D2 | Abagail Symptomatic Leaf Rep 2 | HPLVd | FAM | Amp | 23.5305483 | HPLVd B-F / p4 | HPLVd Positive |
| D3 | Abagail Symptomatic Leaf Rep 1 | 26S | VIC | Amp | 24.1966921 | 26S / p1 | Reaction Positive |
| D3 | Abagail Symptomatic Leaf Rep 1 | BCTV | CY5 | Amp | 25.4627802 | BCTV / p1 | BCTV Positive |
| D3 | Abagail Symptomatic Leaf Rep 1 | HPLVd | FAM | Amp | 24.09313776 | HPLVd B-F / p4 | HPLVd Positive |
| D4 | Abagail Symptomatic Leaf Rep 2 | 26S | VIC | Amp | 23.81804523 | 26S / p1 | Reaction Positive |
| D4 | Abagail Symptomatic Leaf Rep 2 | BCTV | CY5 | Amp | 25.47055053 | BCTV / p1 | BCTV Positive |
| D4 | Abagail Symptomatic Leaf Rep 2 | HPLVd | FAM | Amp | 24.26595102 | HPLVd B-F / p4 | HPLVd Positive |
| G1 | HPLVd Positive Control 5ng Input | 26S | VIC | Amp | 20.91903799 | 26S / p1 | Reaction Positive |
| G1 | HPLVd Positive Control 5ng Input | AMV | CY5 | No Amp | Undetermined | AMV / p1 | AMV Negative |
| G1 | HPLVd Positive Control 5ng Input | HPLVd | FAM | Amp | 17.66479686 | HPLVd B-F / p4 | HPLVd Positive |
| G2 | HPLVd Positive Control 1ng Input | 26S | VIC | Amp | 24.00834565 | 26S / p1 | Reaction Positive |
| G2 | HPLVd Positive Control 1ng Input | AMV | CY5 | No Amp | Undetermined | AMV / p1 | AMV Negative |
| G2 | HPLVd Positive Control 1ng Input | HPLVd | FAM | Amp | 20.07355726 | HPLVd B-F / p4 | HPLVd Positive |
| G4 | AMV Positive Control | 26S | VIC | Amp | 31.75318076 | 26S / p1 | Reaction Positive |
| G4 | AMV Positive Control | AMV | CY5 | Amp | 15.27723581 | AMV / p1 | AMV Positive |
| G4 | AMV Positive Control | HPLVd | FAM | No Amp | Undetermined | HPLVd B-F / p4 | HPLVd Negative |
| H10 | NTC | 26S | VIC | No Amp | Undetermined | 26S / p1 | Reaction Negative |
| H10 | NTC | AMV | CY5 | No Amp | Undetermined | AMV / p1 | AMV Negative |
| H10 | NTC | HPLVd | FAM | No Amp | Undetermined | HPLVd B-F / p4 | HPLVd Negative |
| H11 | NTC | 26S | VIC | No Amp | Undetermined | 26S / p1 | Reaction Negative |
| H11 | NTC | AMV | CY5 | No Amp | Undetermined | AMV / p1 | AMV Negative |
| H11 | NTC | HPLVd | FAM | No Amp | Undetermined | HPLVd B-F / p4 | HPLVd Negative |
| H12 | NTC | 26S | VIC | No Amp | Undetermined | 26S / p1 | Reaction Negative |
| H12 | NTC | BCTV | CY5 | No Amp | Undetermined | BCTV / p1 | BCTV Negative |
| H12 | NTC | HPLVd | FAM | No Amp | Undetermined | HPLVd B-F / p4 | HPLVd Negative |

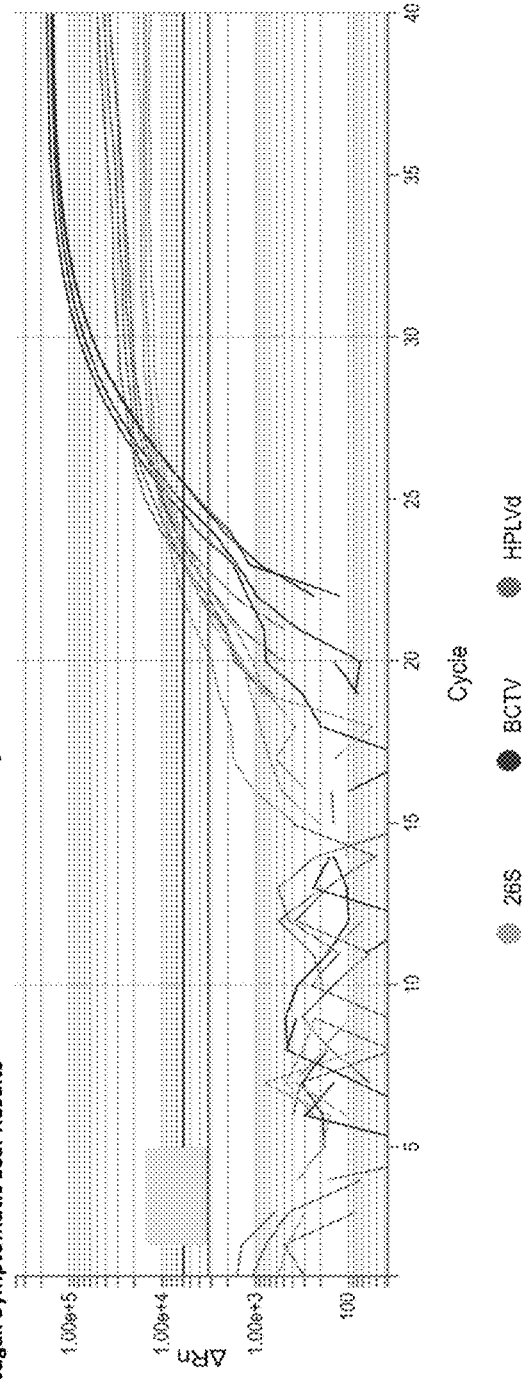
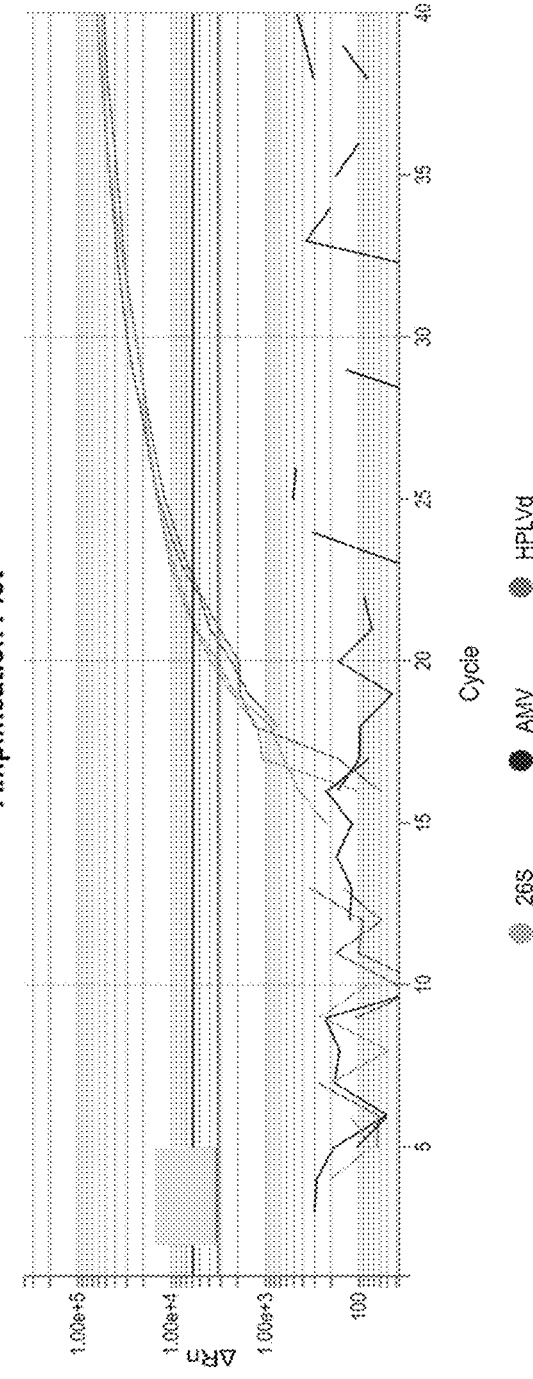
FIG 12B contd
Abagail Symptomatic Leaf Results

FIG 13A

| Well Position | Sample | Target | Reporter | Amp Status | Cq | Primer/Probe | Result |
|---|---|---|---|---|---|---|---|
| G7 | 0.01ng HPLVd Positive Control | BCTV | CY5 | Amp | 34.95988254 | BCTV / p1 | BCTV Positive |
| G7 | 0.01ng HPLVd Positive Control | HPLVd | FAM | Amp | 31.52873679 | HPLVd B-F / p3 | HPLVd Positive |
| G7 | 0.01ng HPLVd Positive Control | 26S | VIC | Amp | 26.8732961 | 26S / p1 | Reaction Positive |
| G4 | 0.1ng HPLVd Positive Control | BCTV | CY5 | Amp | 31.98348495 | BCTV / p1 | BCTV Positive |
| G4 | 0.1ng HPLVd Positive Control | HPLVd | FAM | Amp | 28.67429297 | HPLVd B-F / p3 | HPLVd Positive |
| G4 | 0.1ng HPLVd Positive Control | 26S | VIC | Amp | 22.50891776 | 26S / p1 | Reaction Positive |
| G2 | 1ng HPLVd Positive Control | BCTV | CY5 | Amp | 27.18605449 | BCTV / p1 | BCTV Positive |
| G2 | 1ng HPLVd Positive Control | HPLVd | FAM | Amp | 23.79594849 | HPLVd B-F / p3 | HPLVd Positive |
| G2 | 1ng HPLVd Positive Control | 26S | VIC | Amp | 17.08774983 | 26S / p1 | Reaction Positive |
| B7 | BSC A | BCTV | CY5 | No Amp | Undetermined | BCTV / p1 | BCTV Negative |
| B7 | BSC A | HPLVd | FAM | No Amp | Undetermined | HPLVd B-F / p3 | HPLVd Negative |
| B7 | BSC A | 26S | VIC | Amp | 15.8378681 | 26S / p1 | Reaction Positive |
| D7 | BSC A | BCTV | CY5 | No Amp | Undetermined | BCTV / p1 | BCTV Negative |
| D7 | BSC A | HPLVd | FAM | No Amp | Undetermined | HPLVd B-F / p3 | HPLVd Negative |
| D7 | BSC A | 26S | VIC | Amp | 15.63262925 | 26S / p1 | Reaction Positive |
| B8 | BSC B | BCTV | CY5 | No Amp | Undetermined | BCTV / p1 | BCTV Negative |
| B8 | BSC B | HPLVd | FAM | No Amp | Undetermined | HPLVd B-F / p3 | HPLVd Negative |
| B8 | BSC B | 26S | VIC | Amp | 16.2127111 | 26S / p1 | Reaction Positive |
| D8 | BSC B | BCTV | CY5 | No Amp | Undetermined | BCTV / p1 | BCTV Negative |
| D8 | BSC B | HPLVd | FAM | No Amp | Undetermined | HPLVd B-F / p3 | HPLVd Negative |
| D8 | BSC B | 26S | VIC | Amp | 16.1177588 | 26S / p1 | Reaction Positive |
| B9 | BSC C | BCTV | CY5 | No Amp | Undetermined | BCTV / p1 | BCTV Negative |

FIG 13A contd

| | | | | | | |
|---|---|---|---|---|---|---|
| B9 | BSC C | HPLVd | FAM | Amp | 30.26745374 | HPLVd B-F / p3 | HPLVd Positive |
| B9 | BSC C | 26S | VIC | Amp | 16.62771212 | 26S / p1 | Reaction Positive |
| D9 | BSC C | BCTV | CY5 | No Amp | Undetermined | BCTV / p1 | BCTV Negative |
| D9 | BSC C | HPLVd | FAM | Amp | 33.04037004 | HPLVd B-F / p3 | HPLVd Positive |
| D9 | BSC C | 26S | VIC | Amp | 16.61417996 | 26S / p1 | Reaction Positive |
| B10 | BSC D | BCTV | CY5 | No Amp | Undetermined | BCTV / p1 | BCTV Negative |
| B10 | BSC D | HPLVd | FAM | No Amp | Undetermined | HPLVd B-F / p3 | HPLVd Negative |
| B10 | BSC D | 26S | VIC | Amp | 15.90805126 | 26S / p1 | Reaction Positive |
| D10 | BSC D | BCTV | CY5 | No Amp | Undetermined | BCTV / p1 | BCTV Negative |
| D10 | BSC D | HPLVd | FAM | No Amp | Undetermined | HPLVd B-F / p3 | HPLVd Negative |
| D10 | BSC D | 26S | VIC | Amp | 15.80136651 | 26S / p1 | Reaction Positive |
| B11 | BSC E | BCTV | CY5 | No Amp | Undetermined | BCTV / p1 | BCTV Negative |
| B11 | BSC E | HPLVd | FAM | No Amp | Undetermined | HPLVd B-F / p3 | HPLVd Negative |
| B11 | BSC E | 26S | VIC | Amp | 16.02732707 | 26S / p1 | Reaction Positive |
| D11 | BSC E | BCTV | CY5 | No Amp | Undetermined | BCTV / p1 | BCTV Negative |
| D11 | BSC E | HPLVd | FAM | No Amp | Undetermined | HPLVd B-F / p3 | HPLVd Negative |
| D11 | BSC E | 26S | VIC | Amp | 16.07800342 | 26S / p1 | Reaction Positive |
| B2 | ICC A | BCTV | CY5 | No Amp | Undetermined | BCTV / p1 | BCTV Negative |
| B2 | ICC A | HPLVd | FAM | No Amp | Undetermined | HPLVd B-F / p3 | HPLVd Negative |
| B2 | ICC A | 26S | VIC | Amp | 16.00283586 | 26S / p1 | Reaction Positive |
| D2 | ICC A | BCTV | CY5 | No Amp | Undetermined | BCTV / p1 | BCTV Negative |
| D2 | ICC A | HPLVd | FAM | No Amp | Undetermined | HPLVd B-F / p3 | HPLVd Negative |
| D2 | ICC A | 26S | VIC | Amp | 15.45848398 | 26S / p1 | Reaction Positive |
| B3 | ICC B | BCTV | CY5 | No Amp | Undetermined | BCTV / p1 | BCTV Negative |
| B3 | ICC B | HPLVd | FAM | Amp | 23.84101772 | HPLVd B-F / p3 | HPLVd Positive |
| B3 | ICC B | 26S | VIC | Amp | 15.84683278 | 26S / p1 | Reaction Positive |
| D3 | ICC B | BCTV | CY5 | No Amp | Undetermined | BCTV / p1 | BCTV Negative |
| D3 | ICC B | HPLVd | FAM | Amp | 23.31661367 | HPLVd B-F / p3 | HPLVd Positive |
| D3 | ICC B | 26S | VIC | Amp | 16.34671814 | 26S / p1 | Reaction Positive |
| B4 | ICC C | BCTV | CY5 | No Amp | Undetermined | BCTV / p1 | BCTV Negative |

FIG 13A contd

| | | | | | | |
|---|---|---|---|---|---|---|
| B4 | ICC C | HPLVd | FAM | No Amp | Undetermined | HPLVd B-F / p3 | HPLVd Negative |
| B4 | ICC C | 26S | VIC | Amp | 16.32740673 | 26S / p1 | Reaction Positive |
| D4 | ICC C | BCTV | CY5 | No Amp | Undetermined | BCTV/ p1 | BCTV Negative |
| D4 | ICC C | HPLVd | FAM | No Amp | Undetermined | HPLVd B-F / p3 | HPLVd Negative |
| D4 | ICC C | 26S | VIC | Amp | 16.12302755 | 26S / p1 | Reaction Positive |
| B5 | ICC D | BCTV | CY5 | No Amp | Undetermined | BCTV/ p1 | BCTV Negative |
| B5 | ICC D | HPLVd | FAM | No Amp | Undetermined | HPLVd B-F / p3 | HPLVd Negative |
| B5 | ICC D | 26S | VIC | Amp | 15.56563925 | 26S / p1 | Reaction Positive |
| D5 | ICC D | BCTV | CY5 | No Amp | Undetermined | BCTV/ p1 | BCTV Negative |
| D5 | ICC D | HPLVd | FAM | No Amp | Undetermined | HPLVd B-F / p3 | HPLVd Negative |
| D5 | ICC D | 26S | VIC | Amp | 15.32354113 | 26S / p1 | Reaction Positive |
| B6 | ICC E | BCTV | CY5 | No Amp | Undetermined | BCTV/ p1 | BCTV Negative |
| B6 | ICC E | HPLVd | FAM | No Amp | Undetermined | HPLVd B-F / p3 | HPLVd Negative |
| B6 | ICC E | 26S | VIC | Amp | 15.83519117 | 26S / p1 | Reaction Positive |
| D6 | ICC E | BCTV | CY5 | No Amp | Undetermined | BCTV/ p1 | BCTV Negative |
| D6 | ICC E | HPLVd | FAM | No Amp | Undetermined | HPLVd B-F / p3 | HPLVd Negative |
| D6 | ICC E | 26S | VIC | Amp | 16.23136647 | 26S / p1 | Reaction Positive |
| H11 | NTC | BCTV | CY5 | No Amp | Undetermined | BCTV/ p1 | BCTV Negative |
| H11 | NTC | HPLVd | FAM | No Amp | Undetermined | HPLVd B-F / p3 | HPLVd Negative |
| H11 | NTC | 26S | VIC | No Amp | Undetermined | 26S / p1 | 26S Negative |
| H12 | NTC | BCTV | CY5 | No Amp | Undetermined | BCTV/ p1 | BCTV Negative |
| H12 | NTC | HPLVd | FAM | No Amp | Undetermined | HPLVd B-F / p3 | HPLVd Negative |
| H12 | NTC | 26S | VIC | No Amp | Undetermined | 26S / p1 | 26S Negative |

FIG 14A

| Well Position | Sample | Target | Reporter | Amp Status | Cq | Primer Conc | Mastermix |
|---|---|---|---|---|---|---|---|
| C1 | 1ng Symptomatic Abagail Leaf RNA | BCTV | CY5 | Amp | 24.33821677 | 450nM | iTaq |
| C1 | 1ng Symptomatic Abagail Leaf RNA | HPLVd | FAM | Amp | 21.15692609 | 900nM | iTaq |
| C1 | 1ng Symptomatic Abagail Leaf RNA | 26S | VIC | Amp | 10.70044446 | 23.4nM | iTaq |
| C2 | 0.1ng Symptomatic Abagail Leaf RNA | BCTV | CY5 | Amp | 27.7540445 | 450nM | iTaq |
| C2 | 0.1ng Symptomatic Abagail Leaf RNA | HPLVd | FAM | Amp | 24.87655219 | 900nM | iTaq |
| C2 | 0.1ng Symptomatic Abagail Leaf RNA | 26S | VIC | Amp | 14.77032052 | 23.4nM | iTaq |
| C3 | 0.01ng Symptomatic Abagail Leaf RNA | BCTV | CY5 | Amp | 31.87471584 | 450nM | iTaq |
| C3 | 0.01ng Symptomatic Abagail Leaf RNA | HPLVd | FAM | Amp | 28.54013831 | 900nM | iTaq |
| C3 | 0.01ng Symptomatic Abagail Leaf RNA | 26S | VIC | Amp | 17.88130927 | 23.4nM | iTaq |
| C4 | 0.001ng Symptomatic Abagail Leaf RNA | BCTV | CY5 | No Amp | Undetermined | 450nM | iTaq |
| C4 | 0.001ng Symptomatic Abagail Leaf RNA | HPLVd | FAM | Amp | 32.47128731 | 900nM | iTaq |
| C4 | 0.001ng Symptomatic Abagail Leaf RNA | 26S | VIC | Amp | 21.55862761 | 23.4nM | iTaq |
| C5 | 0.0001ng Symptomatic Abagail Leaf RNA | BCTV | CY5 | No Amp | Undetermined | 450nM | iTaq |
| C5 | 0.0001ng Symptomatic Abagail Leaf RNA | HPLVd | FAM | Inconclusive | 34.84194086 | 900nM | iTaq |
| C5 | 0.0001ng Symptomatic Abagail Leaf RNA | 26S | VIC | Amp | 25.43336318 | 23.4nM | iTaq |
| C6 | 0.00001ng Symptomatic Abagail Leaf RNA | BCTV | CY5 | No Amp | Undetermined | 450nM | iTaq |
| C6 | 0.00001ng Symptomatic Abagail Leaf RNA | HPLVd | FAM | No Amp | Undetermined | 900nM | iTaq |
| C6 | 0.00001ng Symptomatic Abagail Leaf RNA | 26S | VIC | No Amp | Undetermined | 23.4nM | iTaq |
| C7 | NTC | BCTV | CY5 | No Amp | Undetermined | 450nM | iTaq |
| C7 | NTC | HPLVd | FAM | No Amp | Undetermined | 900nM | iTaq |
| C7 | NTC | 26S | VIC | No Amp | Undetermined | 23.4nM | iTaq |
| C8 | 1ng Positive Control | BCTV | CY5 | Amp | 24.44812946 | 450nM | iTaq |
| C8 | 1ng Positive Control | HPLVd | FAM | Amp | 21.68318107 | 900nM | iTaq |
| C8 | 1ng Positive Control | 26S | VIC | Amp | 11.72413946 | 23.4nM | iTaq |
| G1 | 1ng AMV spike and TCD Pooled RNA | AMV | CY5 | Amp | 13.84828883 | 450nM | iTaq |
| G1 | 1ng AMV spike and TCD Pooled RNA | HPLVd | FAM | Amp | 18.36052828 | 900nM | iTaq |

FIG 14A contd

| | | | | | | |
|---|---|---|---|---|---|---|
| G1 | 1ng AMV spike and TCD Pooled RNA | 26S | VIC | Amp | 10.32564803 | 23.4nM | iTaq |
| G2 | 0.1ng AMV spike and TCD Pooled RNA | AMV | CY5 | Amp | 17.85641364 | 450nM | iTaq |
| G2 | 0.1ng AMV spike and TCD Pooled RNA | HPLVd | FAM | Amp | 22.4890639 | 900nM | iTaq |
| G2 | 0.1ng AMV spike and TCD Pooled RNA | 26S | VIC | Amp | 11.67075882 | 23.4nM | iTaq |
| G3 | 0.01ng AMV spike and TCD Pooled RNA | AMV | CY5 | Amp | 21.69561573 | 450nM | iTaq |
| G3 | 0.01ng AMV spike and TCD Pooled RNA | HPLVd | FAM | Amp | 25.74137437 | 900nM | iTaq |
| G3 | 0.01ng AMV spike and TCD Pooled RNA | 26S | VIC | Amp | 18.97335898 | 23.4nM | iTaq |
| G4 | 0.001ng AMV spike and TCD Pooled RNA | AMV | CY5 | Amp | 25.25304798 | 450nM | iTaq |
| G4 | 0.001ng AMV spike and TCD Pooled RNA | HPLVd | FAM | Amp | 29.8181847 | 900nM | iTaq |
| G4 | 0.001ng AMV spike and TCD Pooled RNA | 26S | VIC | Amp | 22.13525428 | 23.4nM | iTaq |
| G5 | 0.0001ng AMV spike and TCD Pooled RNA | AMV | CY5 | Amp | 28.44117448 | 450nM | iTaq |
| G5 | 0.0001ng AMV spike and TCD Pooled RNA | HPLVd | FAM | Amp | 31.9625561 | 900nM | iTaq |
| G5 | 0.0001ng AMV spike and TCD Pooled RNA | 26S | VIC | Amp | 25.26483098 | 23.4nM | iTaq |
| G6 | 0.00001ng AMV spike and TCD Pooled RNA | AMV | CY5 | Inconclusive | 31.93296591 | 450nM | iTaq |
| G6 | 0.00001ng AMV spike and TCD Pooled RNA | HPLVd | FAM | No Amp | Undetermined | 900nM | iTaq |
| G6 | 0.00001ng AMV spike and TCD Pooled RNA | 26S | VIC | No Amp | Undetermined | 23.4nM | iTaq |
| G7 | NTC | AMV | CY5 | No Amp | Undetermined | 450nM | iTaq |
| G7 | NTC | HPLVd | FAM | No Amp | Undetermined | 900nM | iTaq |
| G7 | NTC | 26S | VIC | No Amp | Undetermined | 23.4nM | iTaq |

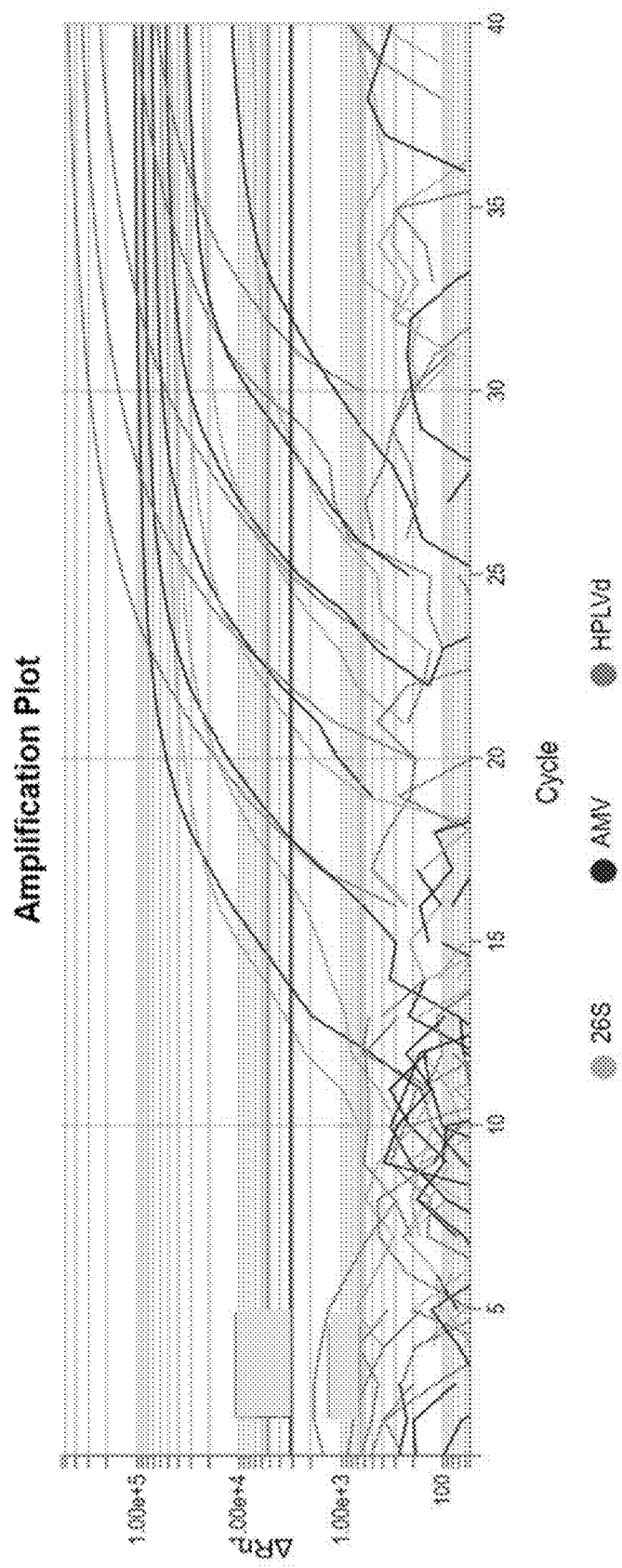
FIG 14B contd

Abagail Leaf Standard Curve

FIG 14C contd
AMV Spike and TCD Pooled RNA
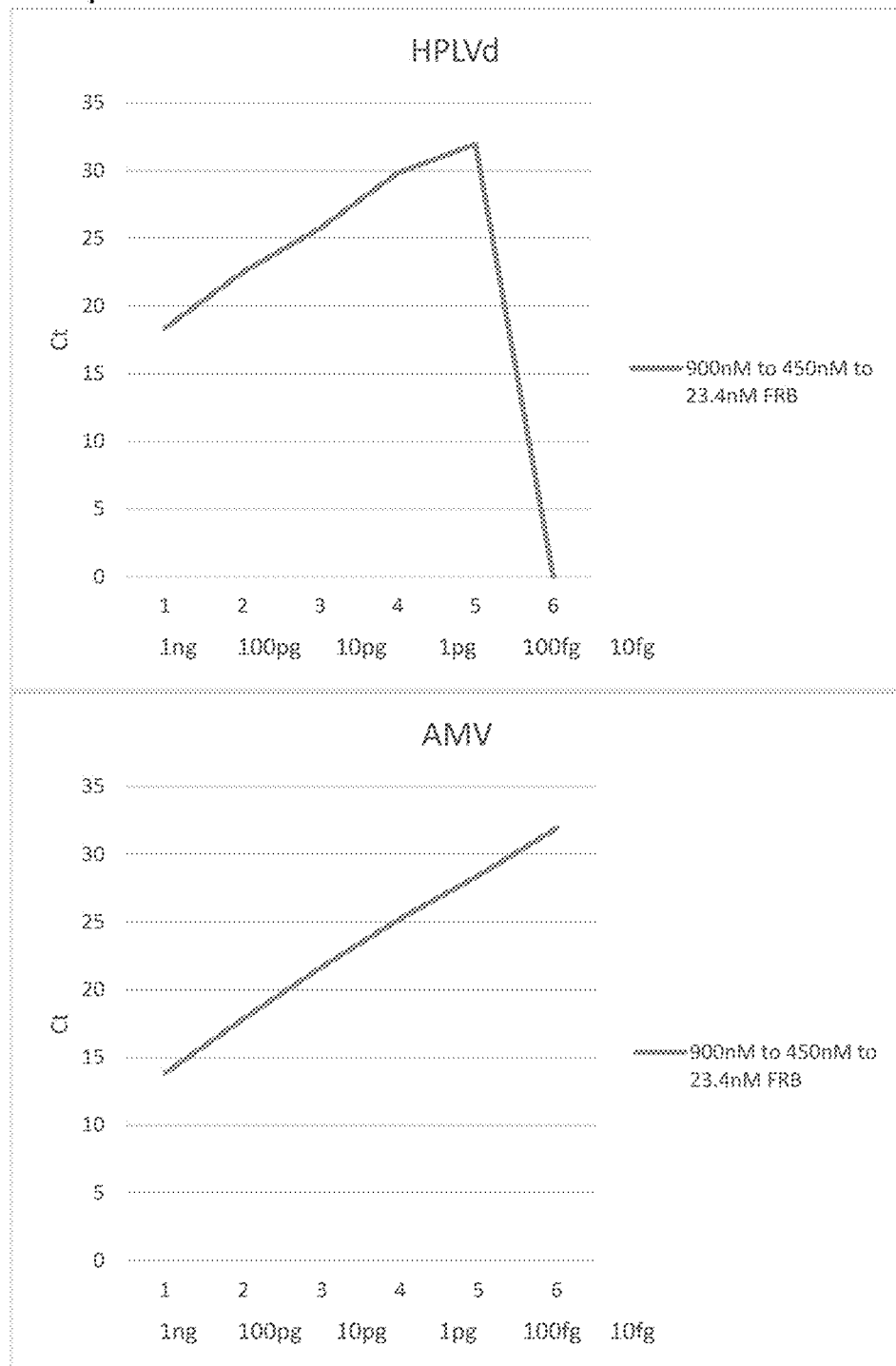

FIG 16

| Well | Sample | Target | Reporter | Amp Status | Cq | Result | Assay |
|---|---|---|---|---|---|---|---|
| B10 | DAY-A20 | HPLVd p2 | ROX | Amp | 26.31962 | HPLVd Positive | HPLVd B-F p2 |
| B10 | DAY-A20 | HPLVd p4 | FAM | Amp | 26.0218 | HPLVd Positive | HPLVd B-F p4 |
| B10 | DAY-A20 | 26S | VIC | Amp | 14.93542 | Reaction Positive | 26S P1 |
| B11 | DAY-A20 | HPLVd p2 | ROX | Amp | 28.33416 | HPLVd Positive | HPLVd B-F p2 |
| B11 | DAY-A20 | HPLVd p4 | FAM | Amp | 27.89989 | HPLVd Positive | HPLVd B-F p4 |
| B11 | DAY-A20 | 26S | VIC | Amp | 15.69233 | Reaction Positive | 26S P1 |
| B2 | FRB 011-8-8A | HPLVd p2 | ROX | No Amp | Undetermined | HPLVd Negative | HPLVd B-F p2 |
| B2 | FRB 011-8-8A | HPLVd p4 | FAM | No Amp | Undetermined | HPLVd Negative | HPLVd B-F p4 |
| B2 | FRB 011-8-8A | 26S | VIC | Amp | 17.73309 | Reaction Positive | 26S P1 |
| B3 | FRB 011-8-8A | HPLVd p2 | ROX | No Amp | Undetermined | HPLVd Negative | HPLVd B-F p2 |
| B3 | FRB 011-8-8A | HPLVd p4 | FAM | No Amp | Undetermined | HPLVd Negative | HPLVd B-F p4 |
| B3 | FRB 011-8-8A | 26S | VIC | Amp | 16.65805 | Reaction Positive | 26S P1 |
| B4 | FRB 011-8-8A-1 | HPLVd p2 | ROX | No Amp | Undetermined | HPLVd Negative | HPLVd B-F p2 |
| B4 | FRB 011-8-8A-1 | HPLVd p4 | FAM | No Amp | Undetermined | HPLVd Negative | HPLVd B-F p4 |
| B4 | FRB 011-8-8A-1 | 26S | VIC | Amp | 14.15981 | Reaction Positive | 26S P1 |
| B5 | FRB 011-8-8A-1 | HPLVd p2 | ROX | No Amp | Undetermined | HPLVd Negative | HPLVd B-F p2 |
| B5 | FRB 011-8-8A-1 | HPLVd p4 | FAM | No Amp | Undetermined | HPLVd Negative | HPLVd B-F p4 |
| B5 | FRB 011-8-8A-1 | 26S | VIC | Amp | 14.29878 | Reaction Positive | 26S P1 |
| B6 | FRB 011-8-20 A | HPLVd p2 | ROX | No Amp | Undetermined | HPLVd Negative | HPLVd B-F p2 |
| B6 | FRB 011-8-20 A | HPLVd p4 | FAM | No Amp | Undetermined | HPLVd Negative | HPLVd B-F p4 |
| B6 | FRB 011-8-20 A | 26S | VIC | Amp | 14.19101 | Reaction Positive | 26S P1 |

FIG 16 contd

| | FRB 011-8-20 A | HPLVd p2 | ROX | No Amp | Undetermined | HPLVd Negative | HPLVd B-F p2 |
|---|---|---|---|---|---|---|---|
| B7 | FRB 011-8-20 A | HPLVd p4 | FAM | No Amp | Undetermined | HPLVd Negative | HPLVd B-F p4 |
| B7 | FRB 011-8-20 A | 26S | VIC | Amp | 16.64927 | Reaction Positive | 26S P1 |
| B8 | FRB 011-8-1B M | HPLVd p2 | ROX | Amp | Undetermined | HPLVd Negative | HPLVd B-F p2 |
| B8 | FRB 011-8-1B M | HPLVd p4 | FAM | No Amp | Undetermined | HPLVd Negative | HPLVd B-F p4 |
| B8 | FRB 011-8-1B M | 26S | VIC | Amp | 14.22231 | Reaction Positive | 26S P1 |
| B9 | FRB 011-8-1B M | HPLVd p2 | ROX | No Amp | Undetermined | HPLVd Negative | HPLVd B-F p2 |
| B9 | FRB 011-8-1B M | HPLVd p4 | FAM | No Amp | Undetermined | HPLVd Negative | HPLVd B-F p4 |
| B9 | FRB 011-8-1B M | 26S | VIC | Amp | 15.12058 | Reaction Positive | 26S P1 |
| C10 | DAY-A27 | HPLVd p2 | ROX | Amp | 34.3125 | HPLVd Positive | HPLVd B-F p2 |
| C10 | DAY-A27 | HPLVd p4 | FAM | Amp | 35.11119 | HPLVd Positive | HPLVd B-F p4 |
| C10 | DAY-A27 | 26S | VIC | Amp | 18.02419 | Reaction Positive | 26S P1 |
| C11 | DAY-A27 | HPLVd p2 | ROX | Amp | 31.33813 | HPLVd Positive | HPLVd B-F p2 |
| C11 | DAY-A27 | HPLVd p4 | FAM | Amp | 31.89628 | HPLVd Positive | HPLVd B-F p4 |
| C11 | DAY-A27 | 26S | VIC | Amp | 17.17136 | Reaction Positive | 26S P1 |
| C2 | DAY-A3 | HPLVd p2 | ROX | Amp | 33.0226 | HPLVd Positive | HPLVd B-F p2 |
| C2 | DAY-A3 | HPLVd p4 | FAM | Amp | 32.56004 | HPLVd Positive | HPLVd B-F p4 |
| C2 | DAY-A3 | 26S | VIC | Amp | 16.98961 | Reaction Positive | 26S P1 |
| C3 | DAY-A3 | HPLVd p2 | ROX | Amp | 29.21596 | HPLVd Positive | HPLVd B-F p2 |
| C3 | DAY-A3 | HPLVd p4 | FAM | Amp | 29.39937 | HPLVd Positive | HPLVd B-F p4 |
| C3 | DAY-A3 | 26S | VIC | Amp | 15.82733 | Reaction Positive | 26S P1 |
| C4 | DAY-A19 | HPLVd p2 | ROX | Amp | 30.69804 | HPLVd Positive | HPLVd B-F p2 |
| C4 | DAY-A19 | HPLVd p4 | FAM | Amp | 30.72965 | HPLVd Positive | HPLVd B-F p4 |

FIG 16 contd

| | | | | | | | |
|---|---|---|---|---|---|---|---|
| C4 | DAY-A19 | 26S | VIC | Amp | 15.15794 | Reaction Positive | 26S P1 |
| C5 | DAY-A19 | HPLVd p2 | ROX | Amp | 30.50372 | HPLVd Positive | HPLVd B-F p2 |
| C5 | DAY-A19 | HPLVd p4 | FAM | Amp | 30.43022 | HPLVd Positive | HPLVd B-F p4 |
| C5 | DAY-A19 | 26S | VIC | Amp | 13.15757 | Reaction Positive | 26S P1 |
| C6 | DAY-A4 | HPLVd p2 | ROX | Amp | 31.40811 | HPLVd Positive | HPLVd B-F p2 |
| C6 | DAY-A4 | HPLVd p4 | FAM | Amp | 31.82313 | HPLVd Positive | HPLVd B-F p4 |
| C6 | DAY-A4 | 26S | VIC | Amp | 16.52849 | Reaction Positive | 26S P1 |
| C7 | DAY-A4 | HPLVd p2 | ROX | Amp | 32.00379 | HPLVd Positive | HPLVd B-F p2 |
| C7 | DAY-A4 | HPLVd p4 | FAM | Amp | 31.70292 | HPLVd Positive | HPLVd B-F p4 |
| C7 | DAY-A4 | 26S | VIC | Amp | 13.93661 | Reaction Positive | 26S P1 |
| C8 | DAY-A23 | HPLVd p2 | ROX | No Amp | Undetermined | HPLVd Negative | HPLVd B-F p2 |
| C8 | DAY-A23 | HPLVd p4 | FAM | No Amp | Undetermined | HPLVd Negative | HPLVd B-F p4 |
| C8 | DAY-A23 | 26S | VIC | Amp | 16.06745 | Reaction Positive | 26S P1 |
| C9 | DAY-A23 | HPLVd p2 | ROX | No Amp | Undetermined | HPLVd Negative | HPLVd B-F p2 |
| C9 | DAY-A23 | HPLVd p4 | FAM | No Amp | Undetermined | HPLVd Negative | HPLVd B-F p4 |
| C9 | DAY-A23 | 26S | VIC | Amp | 16.15033 | Reaction Positive | 26S P1 |
| D10 | DAY-A11 | HPLVd p2 | ROX | Amp | 31.47093 | HPLVd Positive | HPLVd B-F p2 |
| D10 | DAY-A11 | HPLVd p4 | FAM | Amp | 31.91306 | HPLVd Positive | HPLVd B-F p4 |
| D10 | DAY-A11 | 26S | VIC | Amp | 14.51171 | Reaction Positive | 26S P1 |
| D11 | DAY-A11 | HPLVd p2 | ROX | Amp | 27.55887 | HPLVd Positive | HPLVd B-F p2 |
| D11 | DAY-A11 | HPLVd p4 | FAM | Amp | 27.25021 | HPLVd Positive | HPLVd B-F p4 |
| D11 | DAY-A11 | 26S | VIC | Amp | 16.38894 | Reaction Positive | 26S P1 |
| D2 | DAY-108 | HPLVd p2 | ROX | Amp | 24.95187 | HPLVd Positive | HPLVd B-F p2 |

FIG 16 contd

| | | | | | | | |
|---|---|---|---|---|---|---|---|
| D2 | DAY-108 | HPLVd p4 | FAM | Amp | 24.77473 | HPLVd Positive | HPLVd B-F p4 |
| D2 | DAY-108 | 26S | VIC | Amp | 13.6634 | Reaction Positive | 26S P1 |
| D3 | DAY-108 | HPLVd p2 | ROX | Amp | 32.81162 | HPLVd Positive | HPLVd B-F p2 |
| D3 | DAY-108 | HPLVd p4 | FAM | Amp | 32.86027 | HPLVd Positive | HPLVd B-F p4 |
| D3 | DAY-108 | 26S | VIC | Amp | 14.827 | Reaction Positive | 26S P1 |
| D4 | DAY-A13 | HPLVd p2 | ROX | Amp | 30.91073 | HPLVd Positive | HPLVd B-F p2 |
| D4 | DAY-A13 | HPLVd p4 | FAM | Amp | 30.72905 | HPLVd Positive | HPLVd B-F p4 |
| D4 | DAY-A13 | 26S | VIC | Amp | 14.38861 | Reaction Positive | 26S P1 |
| D5 | DAY-A13 | HPLVd p2 | ROX | Amp | 29.8004 | HPLVd Positive | HPLVd B-F p2 |
| D5 | DAY-A13 | HPLVd p4 | FAM | Amp | 29.68322 | HPLVd Positive | HPLVd B-F p4 |
| D5 | DAY-A13 | 26S | VIC | Amp | 14.83726 | Reaction Positive | 26S P1 |
| D6 | DAY-A24 | HPLVd p2 | ROX | Amp | 29.69204 | HPLVd Positive | HPLVd B-F p2 |
| D6 | DAY-A24 | HPLVd p4 | FAM | Amp | 29.53751 | HPLVd Positive | HPLVd B-F p4 |
| D6 | DAY-A24 | 26S | VIC | Amp | 15.94621 | Reaction Positive | 26S P1 |
| D7 | DAY-A24 | HPLVd p2 | ROX | Amp | 31.89676 | HPLVd Positive | HPLVd B-F p2 |
| D7 | DAY-A24 | HPLVd p4 | FAM | Amp | 32.29111 | HPLVd Positive | HPLVd B-F p4 |
| D7 | DAY-A24 | 26S | VIC | Amp | 14.29752 | Reaction Positive | 26S P1 |
| D8 | DAY-A5 | HPLVd p2 | ROX | Amp | 30.83802 | HPLVd Positive | HPLVd B-F p2 |
| D8 | DAY-A5 | HPLVd p4 | FAM | Amp | 31.17707 | HPLVd Positive | HPLVd B-F p4 |
| D8 | DAY-A5 | 26S | VIC | Amp | 15.74671 | Reaction Positive | 26S P1 |
| D9 | DAY-A5 | HPLVd p2 | ROX | Amp | 34.8094 | HPLVd Positive | HPLVd B-F p2 |
| D9 | DAY-A5 | HPLVd p4 | FAM | Amp | 35.78432 | HPLVd Positive | HPLVd B-F p4 |
| D9 | DAY-A5 | 26S | VIC | Amp | 13.73412 | Reaction Positive | 26S P1 |

FIG 16 contd

| | | | | | | | |
|---|---|---|---|---|---|---|---|
| E10 | PBB 051 | HPLVd p2 | ROX | No Amp | Undetermined | HPLVd Negative | HPLVd B-F p2 |
| E10 | PBB 051 | HPLVd p4 | FAM | No Amp | Undetermined | HPLVd Negative | HPLVd B-F p4 |
| E10 | PBB 051 | 26S | VIC | Amp | 14.59361 | Reaction Positive | 26S P1 |
| E11 | PBB 051 | HPLVd p2 | ROX | No Amp | Undetermined | HPLVd Negative | HPLVd B-F p2 |
| E11 | PBB 051 | HPLVd p4 | FAM | No Amp | Undetermined | HPLVd Negative | HPLVd B-F p4 |
| E11 | PBB 051 | 26S | VIC | Amp | 14.49587 | Reaction Positive | 26S P1 |
| E2 | BSC1 | HPLVd p2 | ROX | No Amp | Undetermined | HPLVd Negative | HPLVd B-F p2 |
| E2 | BSC1 | HPLVd p4 | FAM | No Amp | Undetermined | HPLVd Negative | HPLVd B-F p4 |
| E2 | BSC1 | 26S | VIC | Amp | 14.95978 | Reaction Positive | 26S P1 |
| E3 | BSC1 | HPLVd p2 | ROX | No Amp | Undetermined | HPLVd Negative | HPLVd B-F p2 |
| E3 | BSC1 | HPLVd p4 | FAM | No Amp | Undetermined | HPLVd Negative | HPLVd B-F p4 |
| E3 | BSC1 | 26S | VIC | Amp | 14.07246 | Reaction Positive | 26S P1 |
| E4 | PBB 059 | HPLVd p2 | ROX | No Amp | Undetermined | HPLVd Negative | HPLVd B-F p2 |
| E4 | PBB 059 | HPLVd p4 | FAM | No Amp | Undetermined | HPLVd Negative | HPLVd B-F p4 |
| E4 | PBB 059 | 26S | VIC | Amp | 14.4904 | Reaction Positive | 26S P1 |
| E5 | PBB 059 | HPLVd p2 | ROX | No Amp | Undetermined | HPLVd Negative | HPLVd B-F p2 |
| E5 | PBB 059 | HPLVd p4 | FAM | No Amp | Undetermined | HPLVd Negative | HPLVd B-F p4 |
| E5 | PBB 059 | 26S | VIC | Amp | 16.82814 | Reaction Positive | 26S P1 |
| E6 | PBB 046 | HPLVd p2 | ROX | Amp | 29.29484 | HPLVd Positive | HPLVd B-F p2 |
| E6 | PBB 046 | HPLVd p4 | FAM | Amp | 29.60477 | HPLVd Positive | HPLVd B-F p4 |
| E6 | PBB 046 | 26S | VIC | Amp | 12.82739 | Reaction Positive | 26S P1 |
| E7 | PBB 046 | HPLVd p2 | ROX | Amp | 29.66409 | HPLVd Positive | HPLVd B-F p2 |
| E7 | PBB 046 | HPLVd p4 | FAM | Amp | 29.62681 | HPLVd Positive | HPLVd B-F p4 |

FIG 16 contd

| | | | | | | Reaction | |
|---|---|---|---|---|---|---|---|
| E7 | PBB 046 | 26S | VIC | Amp | 13.75348 | Positive | 26S P1 |
| E8 | PBB 052 | HPLVd p2 | ROX | No Amp | Undetermined | HPLVd Negative | HPLVd B-F p2 |
| E8 | PBB 052 | HPLVd p4 | FAM | No Amp | Undetermined | HPLVd Negative | HPLVd B-F p4 |
| E8 | PBB 052 | 26S | VIC | Amp | 11.29344 | Reaction Positive | 26S P1 |
| E9 | PBB 052 | HPLVd p2 | ROX | No Amp | Undetermined | HPLVd Negative | HPLVd B-F p2 |
| E9 | PBB 052 | HPLVd p4 | FAM | No Amp | Undetermined | HPLVd Negative | HPLVd B-F p4 |
| E9 | PBB 052 | 26S | VIC | Amp | 9.438463 | Reaction Positive | 26S P1 |
| F10 | PBB 021 | HPLVd p2 | ROX | No Amp | Undetermined | HPLVd Negative | HPLVd B-F p2 |
| F10 | PBB 021 | HPLVd p4 | FAM | No Amp | Undetermined | HPLVd Negative | HPLVd B-F p4 |
| F10 | PBB 021 | 26S | VIC | Amp | 16.52574 | Reaction Positive | 26S P1 |
| F11 | PBB 021 | HPLVd p2 | ROX | No Amp | Undetermined | HPLVd Negative | HPLVd B-F p2 |
| F11 | PBB 021 | HPLVd p4 | FAM | No Amp | Undetermined | HPLVd Negative | HPLVd B-F p4 |
| F11 | PBB 021 | 26S | VIC | Amp | 16.59513 | Reaction Positive | 26S P1 |
| F2 | PBB 053 | HPLVd p2 | ROX | No Amp | Undetermined | HPLVd Negative | HPLVd B-F p2 |
| F2 | PBB 053 | HPLVd p4 | FAM | No Amp | Undetermined | HPLVd Negative | HPLVd B-F p4 |
| F2 | PBB 053 | 26S | VIC | Amp | 16.67927 | Reaction Positive | 26S P1 |
| F3 | PBB 053 | HPLVd p2 | ROX | No Amp | Undetermined | HPLVd Negative | HPLVd B-F p2 |
| F3 | PBB 053 | HPLVd p4 | FAM | No Amp | Undetermined | HPLVd Negative | HPLVd B-F p4 |
| F3 | PBB 053 | 26S | VIC | Amp | 16.5699 | Reaction Positive | 26S P1 |
| F4 | PBB 054 | HPLVd p2 | ROX | No Amp | Undetermined | HPLVd Negative | HPLVd B-F p2 |
| F4 | PBB 054 | HPLVd p4 | FAM | No Amp | Undetermined | HPLVd Negative | HPLVd B-F p4 |
| F4 | PBB 054 | 26S | VIC | Amp | 15.8514 | Reaction Positive | 26S P1 |
| F5 | PBB 054 | HPLVd p2 | ROX | No Amp | Undetermined | HPLVd Negative | HPLVd B-F p2 |

FIG 16 contd

| | | | | | | HPLVd Negative | HPLVd B-F p4 |
|---|---|---|---|---|---|---|---|
| F5 | PBB 054 | HPLVd p4 | FAM | No Amp | Undetermined | | |
| F5 | PBB 054 | 26S | VIC | Amp | 15.35759 | Reaction Positive | 26S P1 |
| F6 | PBB 045 | HPLVd p2 | ROX | No Amp | Undetermined | HPLVd Negative | HPLVd B-F p2 |
| F6 | PBB 045 | HPLVd p4 | FAM | No Amp | Undetermined | HPLVd Negative | HPLVd B-F p4 |
| F6 | PBB 045 | 26S | VIC | Amp | 15.27669 | Reaction Positive | 26S P1 |
| F7 | PBB 045 | HPLVd p2 | ROX | No Amp | Undetermined | HPLVd Negative | HPLVd B-F p2 |
| F7 | PBB 045 | HPLVd p4 | FAM | No Amp | Undetermined | HPLVd Negative | HPLVd B-F p4 |
| F7 | PBB 045 | 26S | VIC | Amp | 15.08082 | Reaction Positive | 26S P1 |
| F8 | PBB 047 | HPLVd p2 | ROX | No Amp | Undetermined | HPLVd Negative | HPLVd B-F p2 |
| F8 | PBB 047 | HPLVd p4 | FAM | No Amp | Undetermined | HPLVd Negative | HPLVd B-F p4 |
| F8 | PBB 047 | 26S | VIC | Amp | 11.79076 | Reaction Positive | 26S P1 |
| F9 | PBB 047 | HPLVd p2 | ROX | No Amp | Undetermined | HPLVd Negative | HPLVd B-F p2 |
| F9 | PBB 047 | HPLVd p4 | FAM | No Amp | Undetermined | HPLVd Negative | HPLVd B-F p4 |
| F9 | PBB 047 | 26S | VIC | Amp | 15.5282 | Reaction Positive | 26S P1 |
| H9 | NTC | HPLVd p2 | ROX | No Amp | Undetermined | HPLVd Negative | HPLVd B-F p2 |
| H9 | NTC | HPLVd p4 | FAM | No Amp | Undetermined | HPLVd Negative | HPLVd B-F p4 |
| H9 | NTC | 26S | VIC | No Amp | Undetermined | Reaction Negative | 26S P1 |
| H10 | NTC | HPLVd p2 | ROX | No Amp | Undetermined | HPLVd Negative | HPLVd B-F p2 |
| H10 | NTC | HPLVd p4 | FAM | No Amp | Undetermined | HPLVd Negative | HPLVd B-F p4 |
| H10 | NTC | 26S | VIC | No Amp | Undetermined | Reaction Negative | 26S P1 |
| H11 | PTC | HPLVd p2 | ROX | Amp | 18.61372 | HPLVd Positive | HPLVd B-F p2 |
| H11 | PTC | HPLVd p4 | FAM | Amp | 18.05948 | HPLVd Positive | HPLVd B-F p4 |
| H11 | PTC | 26S | VIC | Amp | 8.049097 | Reaction Positive | 26S P1 |

FIG 16 contd
| H12 | PTC | HPLVd p2 | ROX | Amp | 18.86945 | HPLVd Positive | HPLVd B-F p2 |
| H12 | PTC | HPLVd p4 | FAM | Amp | 17.74228 | HPLVd Positive | HPLVd B-F p4 |
| H12 | PTC | 26S | VIC | Amp | 8.01413 | Reaction Positive | 26S P1 |
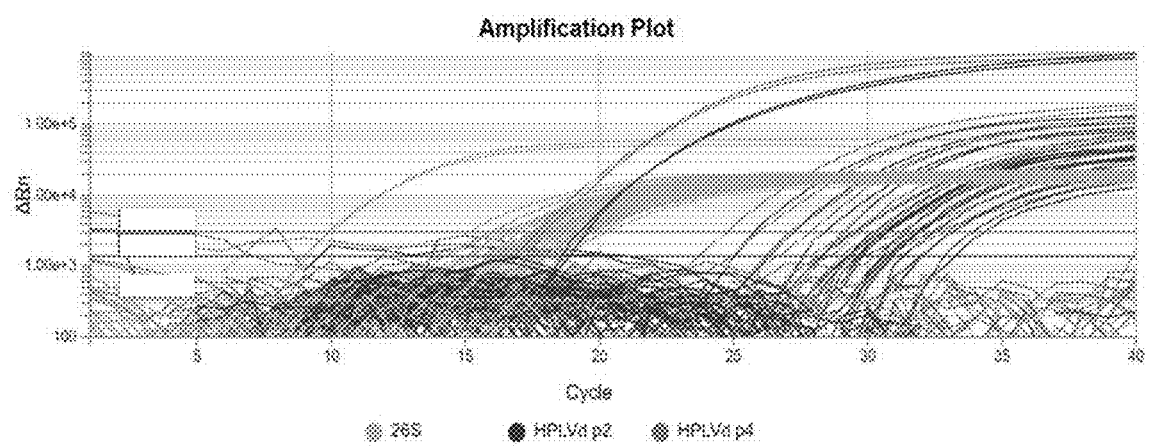

FIG. 17

LAMP HPLVd Method Validation

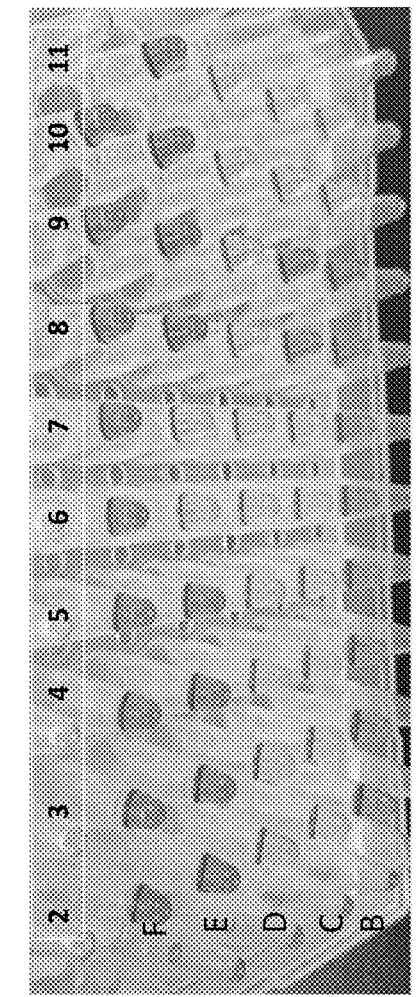

| Sample | Well Prep1 | Well Prep2 | Run Date | Location | qPCR & LAMP Result |
|---|---|---|---|---|---|
| FRB 011-8-8A | B2 | B3 | 20210217 | Salinas | HPLVd Negative |
| FRB 011-8-8A-1 | B4 | B5 | 20210217 | Salinas | HPLVd Negative |
| FRB 011-8-20 A | B6 | B7 | 20210217 | Salinas | HPLVd Negative |
| FRB 011-8-1B M | B8 | B9 | 20210217 | Salinas | HPLVd Negative |
| DAY-A20 | B10 | B11 | 20210217 | Salinas | HPLVd Positive |
| DAY-A3 | C2 | C3 | 20210217 | Salinas | HPLVd Positive |
| DAY-A19 | C4 | C5 | 20210217 | Salinas | HPLVd Positive |
| DAY-A4 | C6 | C7 | 20210217 | Salinas | HPLVd Positive |
| DAY-A23 | C8 | C9 | 20210217 | Salinas | HPLVd Negative |
| DAY-A27 | C10 | C11 | 20210217 | Salinas | HPLVd Positive |
| DAY-108 | D2 | D3 | 20210217 | Salinas | HPLVd Positive |
| DAY-A13 | D4 | D5 | 20210217 | Salinas | HPLVd Positive |
| DAY-A24 | D6 | D7 | 20210217 | Salinas | HPLVd Positive |
| DAY-A5 | D8 | D9 | 20210217 | Salinas | HPLVd Positive |
| DAY-A11 | D10 | D11 | 20210217 | Salinas | HPLVd Positive |
| BSC1 | E2 | E3 | 20210217 | Salinas | HPLVd Negative |
| PBB 059 | E4 | E5 | 20210217 | Salinas | HPLVd Negative |
| PBB 046 | E6 | E7 | 20210217 | Salinas | HPLVd Positive |
| PBB 052 | E8 | E9 | 20210217 | Salinas | HPLVd Negative |
| PBB 051 | E10 | E11 | 20210217 | Salinas | HPLVd Negative |
| PBB 053 | F2 | F3 | 20210217 | Salinas | HPLVd Negative |
| PBB 054 | F4 | F5 | 20210217 | Salinas | HPLVd Negative |
| PBB 045 | F6 | F7 | 20210217 | Salinas | HPLVd Negative |
| PBB 047 | F8 | F9 | 20210217 | Salinas | HPLVd Negative |

HPLVd LAMP Primer Mix 1
45 min

| Control | Well | Result |
|---|---|---|
| PTC | H12 | HPLVd Positive |
| NTC | F10 H11 | HPLVd Negative |

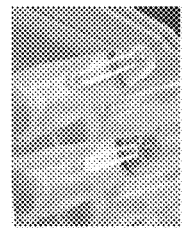

SEQUENCE LISTING

```
<160> NUMBER OF SEQ ID NOS: 123

<210> SEQ ID NO 1
<211> LENGTH: 256
<212> TYPE: DNA
<213> ORGANISM: Hop latent viroid

<400> SEQUENCE: 1
ctggggaata cactacgtga cttacctgta tggtggcaag ggctcgaaga gggatccccg      60
gggaaaccta ctcgagcgag gcggagatcg agcgccagtt cgtgcgcggc gacctgaagt     120
tgcttcggct tcttcttgtt cgcgtcctgc gtggaacggc tccttcttca caccagccgg     180
agttggaaac tacccggtgg atacaactct tgagcgccga gctttacctg cagaagttca     240
```
cataaaaagt gccccct                                                    256

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctacgtgact tacctgtatg gtggc                                            25

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcacgaact ggcgctcg                                                    18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggaaacct actcgagcg                                                   19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttcaggtcg ccgcgcacg                                                   19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggaaacctac tcgagcgagg cg                                               22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgaagaagg agccgttcca                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgggtagttt ccaactccg                                                19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgaggcggag atcgagcgc                                                19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgggtagtt tccaactccg                                               20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagatcgagc gccagttcg                                                19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accgggtagt tccaactcc g                                              21

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agatcgagcg ccagttcg                                                 18

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agagttgtat tcaccgggta gtttcc                                          26

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15 gcactttta tgtgaacttc tgc                                              23

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tcgtgcgcgg cgacct                                                     16

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cggagatcga gcgccagtt                                                  19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tgcgcggcga cctgaagt                                                   18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
aggcggagat cgagcgcca                                                  19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tcctgcgtgg aacggctcc                                                  19

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agggctcgaa gagggatc                                                   18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
taagctcggc gctcaaga                                                   18

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgaagcaact tcaggtcgcc gcccggggaa acctactcg                            39

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttctccttg ttcgcgtcct gcccgggtag tttccaactc c                         41

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccggggaaa cctactcg                                                   18

```
<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgaagcaact tcaggtcgcc g                                                 21

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccgggtagtt tccaactcc                                                    19

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cttctccttg ttcgcgtcct gc                                                22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggctccttct tcacaccagc c                                                 21

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agggctcgaa gagggatc                                                     18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
taagctcggc gctcaaga                                                     18

<210> SEQ ID NO 32
```

<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgaagcaact tcaggtcgcc gcccggggaa acctactcg                          39

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttctccttg ttcgcgtcct gcatccaccg ggtagtttcc aa                      42

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cccggggaaa cctactcg                                                 18

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgaagcaact tcaggtcgcc g                                             21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atccaccggg tagtttccaa                                               20

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cttctccttg ttcgcgtcct gc                                            22

<210> SEQ ID NO 38
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggctccttct tcacaccagc c                                           21

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agggctcgaa gagggatc                                               18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttaagctcgg cgctcaag                                               18

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgaagcaact tcaggtcgcc gcccggggaa acctactcg                        39

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttctccttg ttcgcgtcct gcagttgtat ccaccgggta gt                    42

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cccggggaaa cctactcg                                               18

<210> SEQ ID NO 44
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 44
cgaagcaact tcaggtcgcc g                                              21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agttgtatcc accgggtagt                                                20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cttctccttg ttcgcgtcct gc                                             22

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acaccagccg gagttgg                                                   17

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agggctcgaa gagggatc                                                  18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttaagctcgg cgctcaag                                                  18

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgaagcaact tcaggtcgcc gcccggggaa acctactcg                                  39

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cttctccttg ttcgcgtcct gcccgggtag tttccaactc c                               41

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cccggggaaa cctactcg                                                         18

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgaagcaact tcaggtcgcc g                                                     21

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccgggtagtt tccaactcc                                                        19

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cttctccttg ttcgcgtcct gc                                                    22

<210> SEQ ID NO 56
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 56
ggctccttct tcacaccagc c                                           21

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gccaccatac aggtaagtca cgtag                                       25

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgagcgccag ttcgtgcg                                               18

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgctcgagta ggtttcccc                                              19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cgtgcgcggc gacctgaag                                              19

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgcctcgctc gagtaggttt cc                                          22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic

```
    primer

<400> SEQUENCE: 62
tggaacggct ccttcttcac                                                   20

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cggagttgga aactacccg                                                    19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcgctcgatc tccgcctcg                                                    19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cggagttgga aactacccgg                                                   20

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cgaactggcg ctcgatctc                                                    19

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cggagttgga aactacccgg t                                                 21

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 68
cgaactggcg ctcgatct                                                    18

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggaaactacc cggtgaatac aactct                                           26

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gcagaagttc acataaaaag tgc                                              23

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
aggtcgccgc gcacga                                                      16

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
aactggcgct cgatctccg                                                   19

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
acttcaggtc gccgcgca                                                    18

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 74
tggcgctcga tctccgcct                                                19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
ggagccgttc cacgcagga                                                19

<210> SEQ ID NO 76
<211> LENGTH: 256
<212> TYPE: DNA
<213> ORGANISM: Hop latent viroid

<400> SEQUENCE: 76
aggggcactt tttatgtgaa cttctgcagg taaagctcgg cgctcaagag ttgtatccac   60
cgggtagttt ccaactccgg ctggtgtgaa gaaggagccg ttccacgcag gacgcgaaca   120
agaagaagcc gaagcaactt caggtcgccg cgcacgaact ggcgctcgat ctccgcctcg   180
ctcgagtagg ttttccccggg gatccctctt cgagcccttg ccaccataca ggtaagtcac   240
gtagtgtatt ccccag                                                   256

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtgacttacc tgtatggtgg caa                                           23

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ctcgctcgag taggtttccc c                                             21

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
gggctcgaag agggatcccc                                               20

<210> SEQ ID NO 80
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 80
ttggtcttca cagctcctac c                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
aagtccagac agagggctac g                                              21

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctcctaccca tgcgggaat                                                 19

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tctctcgacc caaacttcgt tg                                             22

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcgttgaatc ggtatgaggg a                                              21

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
taggacaagg ttgggtgtgg                                                20

<210> SEQ ID NO 86
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 86
gtctttgcct tcccggtaat ct                                              22

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
tgcgggaatg caaaaccaaa atttca                                          26

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
tgcgggaatg caaaaycaaa atttca                                          26

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
gaygcgcagc ctgagggatc                                                 20

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ggtcaaagaa tgatcccagt ccggt                                           25

<210> SEQ ID NO 91
<211> LENGTH: 2037
<212> TYPE: DNA
<213> ORGANISM: Alfalfa mosaic virus

<400> SEQUENCE: 91
gttttaaaac cattttcaaa atattccaat tcaactcaat taacgctttt acagtgtaat      60
tcgtactttt cgtaagtaag tttctgtaaa agcgtttctt gttttaatttt ggtctaacac    120 gtaattcgta ctcttcgtga gtaagttgtg ttagccatac ctatccttta aatttctgtc    180
aatttaaaaa gaaatcatt cccatttgcg taattcgtac tcttcgtgag taagttgtaa     240
atggagaata caaaaacaaa tgcctcgagt tctggaatgt cttcttcctc cagcttttca    300
gtgtcttatg ctgaggaaat gttactagct gatgaagttt caaaaattaa ctcaatgtcg    360

-continued

```
attctgggtc ctaatcagct aaagctctgc actcaattgg tgctgtctaa tggagcagcg    420
ccagtagttt taagccttgt gtcaaaggaa aagaaatcga ttttaaatcg tatgcttcct    480
aagattggac agaggatgta cgtccatcac tcggctattt acctccttta tatgccaaac    540
atactgaaaa gttcttcagg gagcatcacc ttgaaacttt ttaatgaagc tacaggagag    600
ttagtggatg ttgacaccga ccatgatgct acccaggcat gtatatttgc tggacgttac    660
ccccggagta ttctggcgaa agatgcagcg aaaggacacg acttgaaatt agtcgtccac    720
gctgttgctt cgaccaatgc gaactccgct gtcggtgttc tataccccat ttgggaagat    780
gagttgagca gaaagcagat cctcgaaagg ggtgccgatt tcctaaagtt tccaattgct    840
gagaccgagc cagtccgcga tctcttaaat gctgggaagt tgacggactt tgttcttgat    900
aggacaaggt tgggtgtggg gtcaaagaat gatcccagtc cggttctttt agaaccaaga    960
gctaagatta ccgggaaggc aaagacagtt tttattcccg aaggtcctag tgttcctaat   1020
accactataa atggtatggc accaacggtg cgtatagatg ccggttctcc aaagggtctt   1080
ggagttccga aagggtttac atatgaaagt tttattaaag atgaaatatt acccgatcat   1140
tgatcggtaa tgggccgttt ttatttttaa ttttctttca attacttcca tcatgagttc   1200
ttcacaaaag aaagctggtg ggaaagctgg taaacctact aaacgttctc agaactatgc   1260
tgccttacgc aaagctcaac tgccgaagcc tccggcgttg aaagtcccgg ttgtaaaacc   1320
gacgaatact atactgccac agacgggctg cgtgtggcaa agcctcggga cccctctgag   1380
tctgagctct tttaatgggc tcggcgtgag attcctctac agttttctga aggatttcgc   1440
gggacctcgg atcctcgaag aggatctgat ttacaggatg gtgttttcca taacaccgtc   1500
ctatgccggc accttttgtc tcactgatga cgtgacgact gaggatggta gggccgttgc   1560
gcatggtaat cccatgcaag aatttcctca tggcgcgttt cacgctaatg agaagttcgg   1620
gtttgagttg gtcttcacag ctcctaccca tgcgggaatg caaaaccaaa atttcaagca   1680
ttcctatgcc gtagccctct gtctggactt cgacgcgcag cctgagggat ctaaaaatcc   1740
ctcataccga ttcaacgaag tttgggtcga gagaaaggcg ttcccgcgag cagggcccct   1800
ccgcagtttg attactgtgg ggctgctcga cgaagctgac gatcttgatc gtcattgatg   1860
taccccatta atttgggatg ccaaagtcat ttgatgctga cctccactgg gtggattaag   1920
gtcaaggtat gaagtcctat tcgctcctga taggatcgac ttcatattgc ttatatatgt   1980
gctaacgcac atatataaat gctcatgcaa aactgcatga atgcccctaa gggatgc      2037
```

<210> SEQ ID NO 92
<211> LENGTH: 221
<212> TYPE: PRT
<213> ORGANISM: Alfalfa mosaic virus

<400> SEQUENCE: 92

```
Met Ser Ser Ser Gln Lys Lys Ala Gly Gly Lys Ala Gly Lys Pro Thr
1               5                   10                  15

Lys Arg Ser Gln Asn Tyr Ala Ala Leu Arg Lys Ala Gln Leu Pro Lys
            20                  25                  30

Pro Pro Ala Leu Lys Val Pro Val Val Lys Pro Thr Asn Thr Ile Leu
        35                  40                  45

Pro Gln Thr Gly Cys Val Trp Gln Ser Leu Gly Thr Pro Leu Ser Leu
    50                  55                  60

Ser Ser Phe Asn Gly Leu Gly Val Arg Phe Leu Tyr Ser Phe Leu Lys
65                  70                  75                  80
```

Asp Phe Ala Gly Pro Arg Ile Leu Glu Glu Asp Leu Ile Tyr Arg Met
                85                  90                  95

Val Phe Ser Ile Thr Pro Ser Tyr Ala Gly Thr Phe Cys Leu Thr Asp
            100                 105                 110

Asp Val Thr Thr Glu Asp Gly Arg Ala Val Ala His Gly Asn Pro Met
        115                 120                 125

Gln Glu Phe Pro His Gly Ala Phe His Ala Asn Glu Lys Phe Gly Phe
    130                 135                 140

Glu Leu Val Phe Thr Ala Pro Thr His Ala Gly Met Gln Asn Gln Asn
145                 150                 155                 160

Phe Lys His Ser Tyr Ala Val Ala Leu Cys Leu Asp Phe Asp Ala Gln
                165                 170                 175

Pro Glu Gly Ser Lys Asn Pro Ser Tyr Arg Phe Asn Glu Val Trp Val
            180                 185                 190

Glu Arg Lys Ala Phe Pro Arg Ala Gly Pro Leu Arg Ser Leu Ile Thr
        195                 200                 205

Val Gly Leu Leu Asp Glu Ala Asp Asp Leu Asp Arg His
    210                 215                 220

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gacctttcag agtggatcaa tttcc                                          25

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gaaagacctc gccttcttct agg                                            23

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ccagcctttc tagcagtrtc gacca                                          25

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcgaggacgc ttctgtatct t                                              21

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
aagcmcttar gtcctggact atac                                          24

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
gggcyggaga gtttaacgaa ggy                                           23

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gctgcatcat tagccgtctg                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ccttccaccs caacttccar                                               20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
accccagtcg acgtaatcac cgt                                           23

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
agcgatttgc ggaggttgt                                                19

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
aacaggcgac gaaatcaaca					20

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 104
agtggattcg gaactgatgt tgttgg					26

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
gmagaaagac ctcgccttct					20

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 106
ccatcaagag atagagsctc tgaccc					26

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
agaagggttc gagtgagagc					20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
gagggaaact tcggagggaa					20

<210> SEQ ID NO 109

```
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
atcgctgcgg gcctccacca                                                  20

<210> SEQ ID NO 110
<211> LENGTH: 381
<212> TYPE: DNA
<213> ORGANISM: Beet curly top virus

<400> SEQUENCE: 110
atgggacctt tcagagtgga tcaatttcca gacaattatc cagcctttct agcagtatcg      60
accagttgtt tcttaaggta caacaggtgg tgtatactag gtatccatca agagatagag     120
cctctgaccc tagaagaagg cgaggtcttt ctgcaattcc agaaggaagt caagaagcta     180
ctgaggtgta aggtcaactt tcataggaag tgttcgttgt atgaggaaat atacaagaaa     240
tacgtataca atgtcccaga aaagaaaggt gaatcctcaa agtgcgtggc cgaagaagag     300
gaggactact acgacttcga ggaaatacca atggaggaga cctgtgacaa aaacaggac      360 tccgaagtta aagatgtatg a                                               381

<210> SEQ ID NO 111
<211> LENGTH: 126
<212> TYPE: PRT
<213> ORGANISM: Beet curly top virus

<400> SEQUENCE: 111

Met Gly Pro Phe Arg Val Asp Gln Phe Pro Asp Asn Tyr Pro Ala Phe
1               5                   10                  15

Leu Ala Val Ser Thr Ser Cys Phe Leu Arg Tyr Asn Arg Trp Cys Ile
            20                  25                  30

Leu Gly Ile His Gln Glu Ile Glu Pro Leu Thr Leu Glu Glu Gly Glu
        35                  40                  45

Val Phe Leu Gln Phe Gln Lys Glu Val Lys Lys Leu Leu Arg Ser Lys
    50                  55                  60

Val Asn Phe His Arg Lys Cys Ser Leu Tyr Glu Glu Ile Tyr Lys Glu
65                  70                  75                  80

Tyr Val Tyr Asn Val Pro Glu Lys Lys Gly Glu Ser Ser Lys Cys Val
                85                  90                  95

Ala Glu Glu Glu Asp Tyr Tyr Asp Phe Glu Glu Ile Pro Met Glu
            100                 105                 110

Glu Ile Cys Asp Lys Lys Gln Asp Ser Glu Val Lys Asp Val
        115                 120                 125

<210> SEQ ID NO 112
<211> LENGTH: 267
<212> TYPE: DNA
<213> ORGANISM: Beet curly top virus

<400> SEQUENCE: 112
atgatggtct gtctaccaga ctggttattt ttgctatttta tcttcagtat tctactgcaa     60
tcaggtacca acttttatgg gacctttcag agtggatcaa tttccagaca attatccagc    120 cttttctagca gtatcgacca gttgtttctt aaggtacaac aggtggtgta tactaggtat   180
```

```
ccatcaagag atagagcctc tgaccctaga agaaggcgag gtctttctgc aattccagaa      240
ggaagtcaag aagctactga ggtgtaa                                          267

<210> SEQ ID NO 113
<211> LENGTH: 88
<212> TYPE: PRT
<213> ORGANISM: Beet curly top virus

<400> SEQUENCE: 113

Met Met Val Cys Leu Pro Asp Trp Leu Phe Leu Leu Phe Ile Phe Ser
1               5                   10                  15

Ile Leu Leu Gln Ser Gly Thr Asn Phe Tyr Gly Thr Phe Gln Ser Gly
            20                  25                  30

Ser Ile Ser Arg Gln Leu Ser Ser Leu Ser Ser Ser Ile Asp Gln Leu
        35                  40                  45

Phe Leu Lys Val Gln Gln Val Val Tyr Thr Arg Asn Pro Ser Arg Asp
    50                  55                  60

Arg Ala Ser Asp Pro Arg Arg Arg Gly Leu Ser Ala Ile Pro Glu
65                  70                  75                  80

Gly Ser Glu Glu Ala Thr Glu Val
                85

<210> SEQ ID NO 114
<211> LENGTH: 1077
<212> TYPE: DNA
<213> ORGANISM: Beet curly top virus

<400> SEQUENCE: 114 ttacaggga gattgaccttt gcgaggacgc ttctgtatct ttatcaaaga gagggccgga      60
gagtttaacg aaggttgaat tctgtatagt ccaggaccta aggcttcat tttctgattt      120 atctaggaag tcctggtaag agctgccttc gcctggattg cataatataa tactaggaat    180 accacccttta atgacacgtg gttttccata ctttaagttt gtctgccact ctctttgtgc   240
gcctatgagg tgtttccaat gcttcatctt taagtaagct gggtctacgt catcaatgac    300
gttatataaa acatcatcgt gatatgtttt taaactaaaa tctaaatggc cgatatata    360 attatgaggt cctaatgatc tagcccacat tgttttaccc gttctagaat caccctctat   420
gattatacta ttatatctaa aaggccgcgc agcggcatcc accccgaaat aagagtcggc   480
ccattcttga acaatttctg gaactcgagt gaaagaagat tgtgggaatg gaggttgata   540
aatatctggt ggaggaagaa aaatggcttc taaattaggt ttaaggttgt gatactgaaa   600
aataaatttt tctgggagtt tctcccttat tatttgcagt gcttcagctg cattacctgc    660
atttaatgct tctgctgctg catcattagc cgtctgctgg cctcctctag cagatcttcc   720
gtcgacttga aatgtacccc agtcgacgta atcaccgtcc ttctcgatgt attgtttaac   780
atcggatgca gattttgctc cctggaagtt ggggtggaag gtggagcttg aggaaggatg    840
ggtgatgtcg aagtgtctag ggtttctgaa ttgtgcttta cctttgaatt ggatgagggc    900
gtggagatgc agagacccat cctgatgttt ttcctgggat actctaataa ataatttatc   960
agatgggcaa ggaatatttt tcaatatttc cagagcatct tcttttataa ctgaacatcg  1020
tgggtatgtg agaaagatat ttttggcttt aatttgaaat gaaggtgatc gaggcat     1077

<210> SEQ ID NO 115
<211> LENGTH: 358
<212> TYPE: PRT
<213> ORGANISM: Beet curly top virus
```

<400> SEQUENCE: 115

```
Met Pro Arg Ser Pro Ser Phe Gln Ile Lys Ala Lys Asn Ile Phe Leu
1               5                   10                  15

Thr Tyr Pro Arg Cys Ser Ile Ile Lys Glu Asp Ala Leu Glu Ile Leu
            20                  25                  30

Lys Asn Ile Pro Cys Pro Ser Asp Lys Leu Phe Ile Arg Val Ser Gln
        35                  40                  45

Glu Lys His Gln Asp Gly Ser Leu His Leu His Ala Leu Ile Gln Phe
    50                  55                  60

Lys Gly Lys Ala Gln Phe Arg Asn Pro Arg His Phe Asp Ile Thr His
65                  70                  75                  80

Pro Ser Ser Ser Thr Phe His Pro Asn Phe Gln Gly Ala Lys Ser
                85                  90                  95

Ala Ser Asp Val Lys Gln Tyr Ile Glu Lys Asp Gly Asp Tyr Val Asp
            100                 105                 110

Trp Gly Thr Phe Gln Val Asp Gly Arg Ser Ala Arg Gly Gly Gln Gln
            115                 120                 125

Thr Ala Asn Asp Ala Ala Glu Ala Leu Asn Ala Gly Asn Ala Ala
    130                 135                 140

Glu Ala Leu Gln Ile Ile Arg Glu Lys Leu Pro Glu Lys Phe Ile Phe
145                 150                 155                 160

Gln Tyr His Asn Leu Lys Pro Asn Leu Glu Ala Ile Phe Leu Pro Pro
                165                 170                 175

Pro Asp Ile Tyr Gln Pro Pro Phe Pro Leu Ser Ser Phe Thr Arg Val
            180                 185                 190

Pro Glu Ile Val Gln Glu Trp Ala Asp Ser Tyr Phe Gly Leu Asp Pro
            195                 200                 205

Ala Ala Arg Pro Phe Arg Tyr Asn Ser Ile Ile Ile Glu Gly Asp Ser
    210                 215                 220

Arg Thr Gly Lys Thr Met Trp Ala Arg Cys Leu Gly Pro His Asn Tyr
225                 230                 235                 240

Ile Thr Gly His Leu Asp Phe Ser Leu Lys Thr Tyr Ser Asp Asn Val
                245                 250                 255

Leu Tyr Asn Val Ile Asp Asp Val Asp Pro Asn Tyr Leu Lys Met Lys
            260                 265                 270

His Trp Lys His Leu Ile Gly Ala Gln Arg Glu Trp Gln Thr Asn Leu
        275                 280                 285

Lys Tyr Gly Lys Pro Arg Val Ile Lys Gly Gly Ile Pro Ser Ile Ile
    290                 295                 300

Leu Cys Asn Pro Gly Glu Gly Ser Ser Tyr Gln Asp Phe Leu Asn Lys
305                 310                 315                 320

Ser Glu Asn Glu Ala Leu Arg Ser Trp Thr Leu Gln Asn Ser Val Phe
                325                 330                 335

Ala Lys Leu Thr Ser Pro Leu Phe Asp Asn Asn Gln Glu Ala Ser Ser
            340                 345                 350

Gln Asp Gln Ser Ser Leu
        355
```

<210> SEQ ID NO 116
<211> LENGTH: 444
<212> TYPE: DNA
<213> ORGANISM: Beet curly top virus

<400> SEQUENCE: 116

```
ttaattgaga ttgaagattg acgctccagt acccaatcca gttggttctt caaggctctc      60
aaaaaacggt ctccagtcaa tgtcctgtgt gatccagtta tcgtcaaatc gatccagcac     120
ttgtgtaggt tgagcgattt gcggaggttg tggttgaatc tcatctggac ttttagttga     180
tatatcgttc cgaatctctc gaaccatagt agtttgaagt agagtggatt cggaactgat     240
gttgttggtg ttgatttcgt cgcctgttcc agggtaatag gtagttccgt gcgaaaatcc     300
gtgatggcat tcatgatgaa ttgtgaagtg acacttacag gggagattga ccttgcgagg     360
acgcttctgt atctttatca aagagagggc cggagagttt aacgaaggtt gaattctgta     420
tagtccagga cctaagggct tcat                                            444

<210> SEQ ID NO 117
<211> LENGTH: 147
<212> TYPE: PRT
<213> ORGANISM: Beet curly top virus

<400> SEQUENCE: 117

Met Lys Pro Leu Gly Pro Gly His Tyr Lys Ile Gln Ser Ser Pro Asn
1               5                   10                  15

Ser Gln Val Leu Ser Leu Ile Thr Ile Lys Lys Arg Pro Arg Lys Ile
            20                  25                  30

Asn Leu Pro Cys Lys Cys His Phe Thr Ile His His Glu Cys His Gln
        35                  40                  45

Gly Phe Ser His Arg Gly Thr His Tyr Ser Ala Thr Ser Asp Glu Ile
    50                  55                  60

His Thr Arg Gly Leu Gly Thr Glu Ser Thr Val Pro Gln Thr Pro Gly
65                  70                  75                  80

Leu Leu Pro Tyr Arg Ala Ser Leu Ser Thr Glu Ser Pro Asp Lys Ile
                85                  90                  95

Gln Pro Gln Pro Pro Gln Ile Leu Glu Ser Ser Gln Val Leu Asp Arg
            100                 105                 110

Phe Asp Asp His Trp Ile Thr Gln Asp Ile Asp Trp Arg Pro Phe Phe
        115                 120                 125

Glu Ser Leu Glu Glu Pro Ser Arg Gln Gly Asn Gln Lys Thr Ile Phe
    130                 135                 140

Ser Leu Asn
145

<210> SEQ ID NO 118
<211> LENGTH: 267
<212> TYPE: DNA
<213> ORGANISM: Beet curly top virus

<400> SEQUENCE: 118
ttacacctca gtagcttctt gacttccttc tggaattgca gaaagacctc gccttcttct      60
agggtcagag gctctatctc ttgatggata cctagtatac accacctgtt gtaccttaag    120
aaacaactgg tcgatactgc tagaaaggct ggataattgt ctggaaattg atccactctg    180
aaaggtccca taaagttgg tacctgattg cagtagaata ctgaagataa atagcaaaaa     240
taaccagtct ggtagacaga ccatcat                                        267

<210> SEQ ID NO 119
<211> LENGTH: 85
<212> TYPE: PRT
<213> ORGANISM: Beet curly top virus
```

<400> SEQUENCE: 119

Met Gly Leu Cys Ile Ser Thr Pro Ser Asn Ser Lys Val Lys His
1               5                   10                  15

Asn Ser Glu Thr Leu Asp Thr Ser Thr Ser Leu Ile Leu Pro Gln Ala
            20                  25                  30

Pro Pro Ser Thr Pro Thr Ser Arg Glu Gln Asn Leu His Pro Met Leu
        35                  40                  45

Asn Asn Thr Ser Arg Arg Thr Val Ile Thr Ser Thr Gly Val His Phe
    50                  55                  60

Lys Ser Thr Glu Asp Leu Leu Glu Glu Ala Ser Arg Arg Leu Met Met
65                  70                  75                  80

Gln Gln Gln Lys His
            85

<210> SEQ ID NO 120
<211> LENGTH: 411
<212> TYPE: DNA
<213> ORGANISM: Beet curly top virus

<400> SEQUENCE: 120
ttaatacaat ttcattgcaa tactagtata ttgaattaca ctactgacga aattgaaacg     60
cttatacaat atataattga aaatacgaat aatttatta attgagattg aagattgacg    120
ctccagtacc caatccagtt ggttcttcaa ggctctcaaa aaacggtctc cagtcaatgt    180
cctgtgtgat ccagttatcg tcaaatcgat ccagcacttg tgtaggttga gcgatttgcg    240
gaggttgtgg ttgaatctca tctggacttt tagttgatat atcgttccga atctctcgaa    300
ccatagtagt ttgaagtaga gtggattcgg aactgatgtt gttggtgttg atttcgtcgc    360
ctgttccagg gtaataggta gttccgtgcg aaaatccgtg atggcattca t             411

<210> SEQ ID NO 121
<211> LENGTH: 136
<212> TYPE: PRT
<213> ORGANISM: Beet curly top virus

<400> SEQUENCE: 121

Met Asn Val Ile Arg Asp Phe Arg Thr Glu Glu Pro Ile Thr Leu Gln
1               5                   10                  15

Gln Ala Thr Lys Ser Ile Pro Val Asp Leu Val Pro Asn Pro Leu Tyr
            20                  25                  30

Leu Lys Leu Gln Asp Phe Phe Arg Thr Gly Pro Val Tyr Gln Leu Lys
        35                  40                  45

Val Gln Ile Arg Phe Asn His Asn Leu Arg Lys Tyr Leu Asn Leu His
    50                  55                  60

Lys Cys Trp Ile Asp Leu Thr Ile Thr Gly Ser His Arg Thr Leu Thr
65                  70                  75                  80

Gly Asp Arg Phe Leu Arg Val Leu Lys Asn Gln Val Asp Arg Glu Ile
                85                  90                  95

Lys Lys Arg Ser Ser Leu Ser Ile Asn Ile Val Thr Glu Ile Leu Asn
            100                 105                 110

His Val Leu Tyr Ser Thr Phe Asn Phe Val Asn Ser Val Ile Gln Tyr
        115                 120                 125

Thr Ser Ile Ala Met Lys Leu Tyr
    130                 135

<210> SEQ ID NO 122

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ctggggaata cactacgtga ct                                              22

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
aggggcactt tttatgtgaa ct                                              22
```

METHODS AND COMPOSITIONS FOR PATHOGEN DETECTION IN PLANTS

RELATED PATENT APPLICATIONS

This patent application is a continuation of U.S. patent application Ser. No. 17/334,400, filed May 28, 2021, naming Christopher Stephen PAULI et al. as inventors, entitled METHODS AND COMPOSITIONS FOR PATHOGEN DETECTION IN PLANTS, which claims priority to U.S. Provisional Patent Application No. 63/032,155 filed on May 29, 2020, entitled METHODS AND COMPOSITIONS FOR PATHOGEN DETECTION IN PLANTS, naming Christopher Stephen PAULI et al. as inventors. The entire content of the foregoing patent application is incorporated herein by reference for all purposes.

SEQUENCE LISTING

The instant application contains a Sequence Listing which has been submitted electronically in ASCII format and is hereby incorporated by reference in its entirety. Said ASCII copy, created on Jul. 19, 2021, is named FRB-1003-UTt_SL.txt and is 42,885 bytes in size.

FIELD

The technology relates in part to methods and compositions for detecting one or more pathogens in plants. In some aspects, the technology relates to methods and compositions for detecting hops latent viroid in plants. In some aspects, the technology relates to methods and compositions for detecting hops latent viroid in *cannabis* plants. In some aspects, the technology relates to methods and compositions for classifying a hops latent viroid genotype. In certain aspects, the technology relates to methods and compositions for determining the presence, absence and/or amount of one or more pathogens in plants, either independently or simultaneously. In aspects, the pathogen is a virus or viroid. In some aspects, the virus or viroid is selected from among one or more of Hops Latent Viroid (HpLVd), Beet Curly Top Virus (BCTV) and Alfalfa Mosaic Virus (AMV).

BACKGROUND

*Cannabis* is a genus of flowering plants that includes at least three species, *Cannabis sativa, Cannabis indica*, and *Cannabis ruderalis*, as determined by plant phenotypes and secondary metabolite profiles (chemotype). Both marijuana and hemp plants are in this genus and produce a unique family of terpeno-phenolic compounds called cannabinoids. The cannabinoids typically produced in greatest abundance are cannabidiol (CBD) and Δ9-tetrahydrocannabinol (THC). CBD and THC have been shown to have different physiological effects when ingested. *Cannabis* is used to produce hemp fiber and hemp oil, for medicinal purposes, and as a recreational drug. Hemp cultivars of *cannabis* are bred to produce minimal levels of THC, while marijuana cultivars are bred to produce higher levels of THC. CBD has been shown to have a number of medically useful effects such as anti-inflammatory, anti-convulsant, antioxidant, antiemetic, anxiolytic and antipsychotic effects, and THC is psychoactive. In general, the maximum THC content of hemp is 0.3% and any *cannabis* with a THC content of greater than 0.3% is considered to be marijuana.

*Cannabis* plants can be susceptible to infection by pathogens. Pathogens may include viruses, viroids, bacteria, fungi, nematodes, and/or any organisms that can cause disease in plants. Certain pathogens can reduce the quality and/or productivity of plants, and in certain instances, pathogens can cause plant death. Pathogens can be introduced and spread to host plants in a variety of ways. For example, bacterial and fungal spores can be transmitted by wind, rain, and/or soil. Certain pathogens can be spread through insects, transplants, infected seeds, irrigation water contaminated equipment, and humans.

One pathogen capable of infecting *Cannabis* plants is the hops latent viroid (HpLVd). Symptoms of a hops latent viroid infection may include reduction or lack of oil, small heads, misshapen leaves, leaves that are yellowish in color, brittle stems, an outwardly horizontal plant structure, and reduced flower mass and trichomes, although some plants infected with hops latent viroid or a hops latent viroid variant may be asymptomatic. Other pathogens with similar deleterious effects include viruses such as Beet Curly Top Virus (BCTV) and Alfalfa Mosaic Virus (AMV). Given the potentially detrimental effects of hops latent viroid infection and viruses such as BCTV and AMV in *Cannabis* plants, there is a need for accurate diagnostics of hops latent viroid and/or other pathogenic infection and for an assessment of the relationship between hops latent viroid or other pathogenic variants and presentation of symptoms.

SUMMARY

Provided herein are diagnostics for detecting presence, absence and/or amount of pathogens in plant cultivars. In certain aspects, provided are accurate diagnostics for HpLVd infection and for an assessment of the relationship between hops latent viroid variants and presentation of symptoms. Such diagnostics are useful given the potentially detrimental effects of hops latent viroid infection in plant cultivars (e.g., *Cannabis* plant cultivars).

Provided in certain aspects are diagnostics that specifically and reproducibly identify more than one pathogen in plant cultivars, independently or simultaneously, e.g., in multiplexed methods. Such diagnostics are useful given the plethora of pathogens that can infect plant cultivars (e.g., *Cannabis* plant cultivars), including other plant viruses such as AMV and BCTV.

Provided herein, in some aspects, are methods for analyzing nucleic acid from a plant sample, comprising contacting nucleic acid of a plant sample with one or more polynucleotide primer pairs under amplification conditions, thereby generating one or more amplification products; and analyzing the amplification products; where the majority or all of the one or more polynucleotide primer pairs hybridize to subsequences of SEQ ID NO:1 if present in the nucleic acid of the plant sample under the amplification conditions; the subsequences of SEQ ID NO:1 to which the majority or all of the polynucleotide primers hybridize under the amplification conditions contain no variant nucleotide position; and each subsequence of SEQ ID NO:1 between the subsequences to which the one or more primer pairs hybridize contain one or more variant nucleotide positions.

Also provided herein, in some aspects, are methods for generating nucleic acid amplification products from a plant sample, comprising contacting nucleic acid of a plant sample with one or more polynucleotide primer pairs under amplification conditions, thereby generating one or more amplification products, where the majority or all of the one or more polynucleotide primer pairs hybridize to subsequences of SEQ ID NO:1 if present in the nucleic acid of the plant sample under the amplification conditions; the subsequences of SEQ ID NO:1 to which the majority or all of the polynucleotide primers hybridize under the amplification conditions contain no variant nucleotide position; and each subsequence of SEQ ID NO:1 between the subsequences to which the one or more primer pairs hybridize contain one or more variant nucleotide positions.

Also provided herein, in some aspects, are methods for analyzing nucleic acid from a plant sample, comprising a) contacting nucleic acid of a plant sample with a first set of polynucleotide primers under amplification conditions, thereby generating a first set of amplification products, where i) the majority or all of the primers in the first set of polynucleotide primers hybridize to subsequences of SEQ ID NO:1 if present in the nucleic acid of the plant sample under the amplification conditions, ii) the subsequences of SEQ ID NO:1 to which the majority or all of the primers in the first set of polynucleotide primers hybridize under the amplification conditions contain no variant nucleotide position, and iii) each subsequence of SEQ ID NO:1 between the subsequences to which the primers in the first set of polynucleotide primers hybridize contain one or more variant nucleotide positions; b) contacting the nucleic acid of the plant sample with a second set of polynucleotide primers under the amplification conditions, thereby generating a second set of amplification products, where i) the majority or all of the primers in the second set of polynucleotide primers hybridize to subsequences of SEQ ID NO:1 if present in the nucleic acid of the plant sample under the amplification conditions, and ii) the subsequences of SEQ ID NO:1 to which the majority or all of the primers in the second set of polynucleotide primers hybridize under the amplification conditions contain one or more variant nucleotide positions; and c) analyzing the first and second sets of amplification products.

Also provided herein, in some aspects, are methods for generating nucleic acid amplification products from a plant sample, comprising a) contacting nucleic acid of a plant sample with a first set of polynucleotide primers under amplification conditions, thereby generating a first set of amplification products, where i) the majority or all of the primers in the first set of polynucleotide primers hybridize to subsequences of SEQ ID NO:1 if present in the nucleic acid of the plant sample under the amplification conditions, ii) the subsequences of SEQ ID NO:1 to which the majority or all of the primers in the first set of polynucleotide primers hybridize under the amplification conditions contain no variant nucleotide position, and iii) each subsequence of SEQ ID NO:1 between the subsequences to which the primers in the first set of polynucleotide primers hybridize contain one or more variant nucleotide positions; and b) contacting the nucleic acid of the plant sample with a second set of polynucleotide primers under the amplification conditions, thereby generating a second set of amplification products, where i) the majority or all of the primers in the second set of polynucleotide primers hybridize to subsequences of SEQ ID NO:1 if present in the nucleic acid of the plant sample under the amplification conditions, and ii) the subsequences of SEQ ID NO:1 to which the majority or all of the primers in the second set of polynucleotide primers hybridize under the amplification conditions contain one or more variant nucleotide positions.

Also provided herein, in some aspects, are methods for analyzing nucleic acid from a plant sample, comprising contacting nucleic acid of a plant sample with a plurality of polynucleotide primer pairs under amplification conditions, thereby preparing a mixture; and analyzing nucleic acid of the mixture; where the majority or all of the polynucleotide primer pairs hybridize to subsequences of SEQ ID NO:1 if present in the nucleic acid of the plant sample under the amplification conditions; the subsequences of SEQ ID NO:1 to which the majority or all of the polynucleotide primers hybridize under the amplification conditions contain no variant nucleotide position or one variant nucleotide position; and each subsequence of SEQ ID NO:1 between the subsequences to which the primer pairs hybridize contain two or more variant nucleotide positions.

Also provided herein, in some aspects, are methods for preparing a nucleic acid mixture comprising contacting nucleic acid of a plant sample with a plurality of polynucleotide primer pairs under amplification conditions, thereby preparing a mixture, where the majority or all of the polynucleotide primer pairs hybridize to subsequences of SEQ ID NO:1 if present in the nucleic acid of the plant sample under the amplification conditions; the subsequences of SEQ ID NO:1 to which the majority or all of the polynucleotide primers hybridize under the amplification conditions contain no variant nucleotide position or one variant nucleotide position; and each subsequence of SEQ ID NO:1 between the subsequences to which the primer pairs hybridize contain two or more variant nucleotide positions.

Also provided herein, in some aspects, are compositions comprising one or more polynucleotide primer pairs where each polynucleotide of the one or more primer pairs is identical, or substantially identical, to a subsequence of SEQ ID NO:1, or complement thereof; each subsequence of SEQ ID NO:1, or complement thereof, to which each polynucleotide is identical, or substantially identical, contains no variant nucleotide position; and each target sequence of SEQ ID NO:1 between the subsequences, or complements thereof, to which the polynucleotides of the one or more primer pairs are identical, or substantially identical, comprises one or more variant nucleotide positions.

Also provided herein, in some aspects, are compositions comprising a) a first set of polynucleotide primers where i) each polynucleotide of the a first set of polynucleotide primers is identical, or substantially identical, to a subsequence of SEQ ID NO:1, or complement thereof, ii) each subsequence of SEQ ID NO:1, or complement thereof, to which each polynucleotide is identical, or substantially identical, contains no variant nucleotide position, and iii) each target sequence of SEQ ID NO:1 between the subsequences, or complements thereof, to which the polynucleotides of the first set of polynucleotide primers are identical, or substantially identical, comprises one or more variant nucleotide positions; and b) a second set of polynucleotide primers where i) each polynucleotide of the second set of polynucleotide primers is identical, or substantially identical, to a subsequence of SEQ ID NO:1, or complement thereof, and ii) each subsequence of SEQ ID NO:1, or complement thereof, to which each polynucleotide is identical, or substantially identical, contains one or more variant nucleotide positions.

Also provided herein, in some aspects, is a method for determining the presence, absence and/or amount of a pathogen in a plant cultivar, comprising: (a) obtaining a nucleic acid sample from the plant cultivar; (b) contacting the nucleic acid sample with at least one polynucleotide primer pair under amplification conditions and amplifying the sample, thereby preparing an amplified nucleic acid mixture, wherein, if the pathogen is present, the polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical (i.e., not identical) to any subsequence of the nucleic acid of the plant genome, or to any complement thereof; and (c) determining the presence, absence and/or amount of at least one amplicon that is 300 base pairs or less and is an amplification product of the polynucleotide primer pair in the amplified nucleic acid mixture of (b), thereby determining the presence, absence and/or amount of a pathogen in the plant cultivar.

In certain aspects, provided herein is a method of preparing a nucleic acid mixture from a plant cultivar, comprising:
(a) obtaining a nucleic acid sample from the plant cultivar; and
(b) preparing an amplified nucleic acid mixture by contacting the nucleic acid sample with at least one polynucleotide primer pair under amplification conditions and amplifying the sample, wherein, if the pathogen is present, the polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical to any subsequence of the nucleic acid of the plant genome, or to any complement thereof. In aspects, the method further comprises, determining the presence, absence and/or amount of at least one amplicon that is 300 base pairs or less and is an amplification product of the polynucleotide primer pair in the amplified nucleic acid mixture of (b), thereby determining the presence, absence and/or amount of a pathogen in the plant cultivar.

In aspects, in any of the methods provided herein, the subsequence of the nucleic acid of the pathogen, or the complement thereof, is in a region of overlap between two genes in the genome of the pathogen. In certain aspects, the pathogen is a virus or viroid. In aspects, the virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

Also provided herein, in certain aspects, are multiplexed methods of determining the presence, absence and/or amount of one or more pathogens in one or more plant cultivars. In certain aspects, the multiplexed method comprises one or more of:
(1) determining the presence, absence and/or amount of more than one non-overlapping amplicon of a pathogen that may have infected a plant cultivar;
(2) determining the presence, absence and/or amount of more than one pathogen that may have infected a plant cultivar by determining the presence, absence and/or amount of one or more amplicons of each pathogen;
(3) determining the presence, absence and/or amount of one or more pathogens in a plurality of plant cultivars.

In aspects, the multiplexed methods provided herein are for determining the presence, absence and/or amount of one or more of the following pathogens in a plant cultivar: In aspects, the virus is selected from among one or more of Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV). In aspects, the virus is selected from among one or more of Hops Latent Viroid (HpLVd), Alfalfa Mosaic Virus (AMV), Beet Curly Top Virus (BCTV).

In any of the methods provided herein, in certain aspects, determining the presence, absence and/or amount of one or more amplicons of a plant pathogen is by quantitative PCR (qPCR), or quantitative RT-PCR (RT-qPCR). In aspects, the one or more amplicons are quantified using a polynucleotide probe sequence. In certain aspects, an amplicon of at least one pathogen is quantified with more than one polynucleotide probe sequence, wherein the polynucleotide probe sequences hybridize to non-overlapping regions of the subsequence of the pathogen that is amplified to generate the amplicon.

In aspects, if the presence, absence and/or amount of one pathogen in the plant cultivar is to be determined, more than one amplicon can be obtained by amplifying more than one subsequence of the nucleic acid of the pathogen, or complements thereof, using more than one polynucleotide primer pair, and determining the presence, absence and/or amount of the pathogen by determining the presence, absence and/or amount of at least two amplicons that are 300 base pairs or less and are amplification products of the more than one polynucleotide primer pair in the amplified nucleic acid mixture, thereby determining the presence, absence and/or amount of a pathogen in the plant cultivar. In certain aspects, if the presence, absence and/or amount of a plurality of pathogens in the plant cultivar is to be determined, more than one amplicon can be obtained by amplifying more than one subsequence of the nucleic acid of more than one of the plurality of pathogens, or complements thereof, using more than one polynucleotide primer pair for each of the more than one pathogens, and determining the presence, absence and/or amount of the more than one pathogens by determining the presence, absence and/or amount of at least two amplicons for each pathogen that are 300 base pairs or less and are amplification products of the more than one polynucleotide primer pair in each of the more than one pathogens of the amplified nucleic acid mixture of, thereby determining the presence, absence and/or amount of the more than one pathogens in the plant cultivar.

In aspects, determining the presence, absence and/or amount of amplicons obtained by a polynucleotide primer pair specifically hybridizing to and amplifying one or more subsequences of one or more plant pathogens is by RT-qPCR or qPCR, and the one or more amplicons, if present, are quantified using polynucleotide probes. A Cq value can be determined for each polynucleotide probe, whereby, if the Cq value is above a threshold value, the presence and/or amount of an amplicon is determined, thereby determining the presence and/or amount of a pathogen in a plant cultivar and if the Cq value is below a threshold value, the absence of an amplicon is determined, thereby determining the absence of a pathogen in a plant cultivar. In certain aspects, more than one non-overlapping probe is used to quantify an amplicon obtained by a polynucleotide primer pair specifically hybridizing to and amplifying a subsequence of a plant pathogen and, if the Cq value obtained with a first polynucleotide probe sequence is significantly different than the Cq value obtained with any of the other non-overlapping polynucleotide probe sequences, a variant in the genotype of the pathogen is identified and, if the Cq value obtained with a first polynucleotide probe sequence is similar to the Cq values obtained with any of the other non-overlapping polynucleotide probe sequences, the genotype of the pathogen is identified as not comprising a variant genotype of the pathogen. In aspects, the presence or absence of a variant in the genotype of the pathogen is correlated to the infectivity of the pathogen. In aspects, more than one non-overlapping subsequence of a pathogen is amplified to obtain and quantify more than one amplicon and, based on the relative Cq values for each amplicon, the presence or absence of a variant in the genotype of the pathogen is identified. In aspects, the presence or absence of a variant in the genotype of the pathogen is correlated to the infectivity of the pathogen. In some aspects, the presence or absence of a variant in the genotype of the pathogen is correlated to resistance or susceptibility of the plant to infection by the pathogen comprising the genotype or a variant thereof. As used herein, Cq, Cp and Ct values are measures of the same cycle threshold value using different software, e.g., Thermofisher Scientific, Waltham, Mass. (Cq), Roche Diagostics, Indianapolis, Ind. (Cp) and Bio-Rad Diagnostics, Hercules, Calif. (Ct).

In aspects of the methods provided herein, a positive control amplicon is generated using a polynucleotide primer pair that is capable of specifically hybridizing to and amplifying a subsequence of the nucleic acid of the plant genome, or to a complement thereof, wherein the subsequence of the nucleic acid of the plant genome, or the complement thereof, is non-identical to any subsequence of the nucleic acid of the pathogen, or to any complement thereof; and determining the presence, absence and/or amount of at least one amplicon that is an amplification product of the polynucleotide primer pair that is capable of specifically hybridizing to and amplifying a subsequence of the nucleic acid of the plant genome, thereby determining whether the amplification conditions are effective for generating amplicons. In aspects, the subsequence of the nucleic acid of the plant genome comprises all or part of a gene selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin.

In any of the methods provided herein, in aspects, the subsequence of the nucleic acid of the pathogen, or the complement thereof, comprises all or a portion of at least one gene that is conserved among species of that pathogen. In aspects, the at least one gene that is conserved among species of the pathogen is selected from among RNA-3 coat protein, SS-ds-DNA Regulator protein, Movement Protein, Pathogenesis Enhancer Protein, Rolling Circle Replication Protein, Cell Cycle Regulator Protein and Replication Enhancer Protein.

In aspects, the pathogen is Alfalfa Mosaic Virus (AMV). In certain aspects, the subsequence of the nucleic acid of the pathogen to which the polynucleotide primer pair is capable of hybridizing comprises SEQ ID NO:91, or a portion of SEQ ID NO:91, or a complement of SEQ ID NO:91, or a portion of the complement of SEQ ID NO:91.

In certain aspects, the pathogen is HpLVd. In aspects, the subsequence of the nucleic acid of the pathogen to which the polynucleotide primer pair is capable of hybridizing comprises SEQ ID NO:1, or a portion of SEQ ID NO:1, or a complement of SEQ ID NO:1, or a portion of the complement of SEQ ID NO:1.

In certain aspects, the pathogen is BCTV. In aspects, the subsequence of the nucleic acid of the pathogen to which the polynucleotide primer pair is capable of hybridizing is selected from among SEQ ID NOS:110, 112, 114, 116, 118 or 120, or a portion of SEQ ID NOS:110, 112, 114, 116, 118 or 120, or a complement of SEQ ID NOS:110, 112, 114, 116, 118 or 120, or a portion of the complement of SEQ ID NOS:110, 112, 114, 116, 118 or 120, or to regions of overlap that spans any two of SEQ ID NOS:110, 112, 114, 116, 118 or 120 in the genome of the pathogen.

In aspects of the methods provided herein, the presence, absence and/or amount of more than one pathogen selected from among Hops Latent Viroid (HpLVd), Alfalfa Mosaic Virus (AMV) and Beet Curly Top Virus (BCTV) is determined simultaneously. In certain aspects, the plant cultivar is a *Cannabis* cultivar. In aspects, the method is a multiplexed method in which the presence, absence and/or amount of one or more pathogens is determined in a plurality of plant cultivars. In aspects, one, a portion, or all of the plant cultivars of the plurality is/are *Cannabis* cultivars.

Any of the methods provided herein can, in certain aspects, be performed on a solid support. In aspects, the solid support comprises a bead, column, capillary, disk, filter, dipstick, membrane, wafer, comb, pin or a chip.

Also provided herein, in aspects, is a method of preparing a polynucleotide primer pair for specifically hybridizing to and amplifying nucleic acid of a plant pathogen, comprising:
  (a) Identifying a polynucleotide primer pair that is capable of specifically hybridizing to and amplifying a polynucleotide comprising a subsequence of the nucleic acid of a plant pathogen, or a complement thereof, wherein the plant is capable of being infected by the pathogen and the subsequence of the nucleic acid of the pathogen, or the complement thereof, is non-identical to any subsequence of the nucleic acid of the plant genome, or to any complement thereof;
  (b) identifying whether the subsequence of the nucleic acid of the pathogen is conserved among species of the pathogen; and
  (c) if the subsequence of the nucleic acid of the pathogen is conserved among species of the pathogen, preparing the polynucleotide primer pair.

Also provided, in certain aspects, are compositions comprising one or more polynucleotide primer pairs prepared by the methods provided herein. Also provided herein, in certain aspects, are compositions comprising one or more polynucleotide primer pairs used in the methods provided herein for specifically hybridizing to and amplifying nucleic acid of a plant pathogen and, optionally, one or more polynucleotide probes provided herein for quantifying one or more amplicons generated using the one or more polynucleotide primer pairs. In aspects, provided herein are kits comprising one or more of the compositions provided herein, and instructions for use.

Also provided herein, in aspects, are solid supports, comprising:
  single-stranded nucleic acid from a plant cultivar; and
  one or more polynucleotide primer pairs used in the methods provided herein or one or more polynucleotide primer pairs prepared by the methods provided herein for specifically hybridizing to and amplifying nucleic acid of a plant pathogen. In aspects, the solid support comprises a bead, column, capillary, disk, filter, dipstick, membrane, wafer, comb, pin or a chip.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIGS. 11A-11B depict a validation analysis of multiplexed determination of the presence, absence and/or amount of pathogen in HpLVd-positive Cannabis cultivar samples spiked with AMV. FIG. 11A is a Table listing the Cq values for the reaction conditions tested, and FIG. 11B shows the amplification plots for various primer and probe sets as indicated on the top left of each plot.

FIGS. 12A-12B depict multiplexed RT-qPCR for determining the presence, absence and/or amount of HpLVd, AMV and BCTV in Cannabis cultivars. FIG. 12A is a Table listing the Cq values for the reaction conditions tested, and FIG. 12B shows the amplification plots for samples and targets as indicated.

FIGS. 13A-13B depict the reproducibility of multiplexed RT-qPCR for determining the presence, absence and/or amount of HpLVd and BCTV in RNA from pooled leaf samples of Cannabis cultivars. FIG. 13A is a Table listing the Cq values for the reaction conditions tested, and FIG. 13B shows the amplification plots for samples and targets as indicated.

FIGS. 14A-14C depict the sensitivity of multiplexed RT-qPCR as measured by a standard curve. FIG. 14A is a Table listing the Cq values for the reaction conditions tested, and FIG. 14B shows the amplification plots for samples and targets as indicated. FIG. 14C depicts standard curves for the detection of HpLVd, AMV and BCTV.

FIG. 16 depicts validation of a High throughput RT-qPCR Method for detection of pathogens in a plant.

FIG. 17 depicts a High throughput LAMP Method for detection of pathogens in a plant.

DETAILED DESCRIPTION

Figure 1:
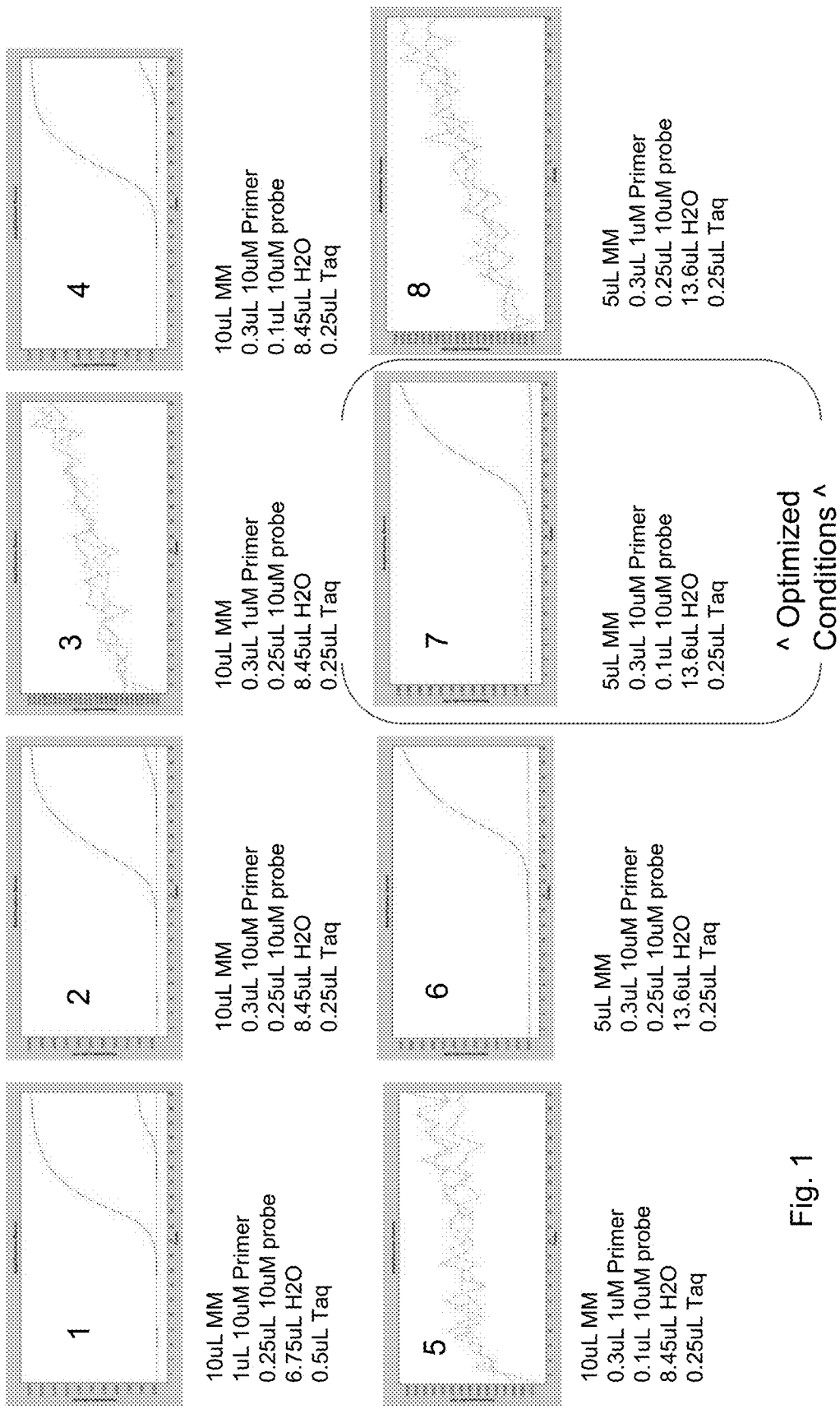
FIG. 1 shows results of an optimization of general assay components for a hops latent viroid RT-qPCR method for primer pair A-G (A-fwd, ϵ-rev) and probe p1. MM, master mix.

Provided herein are methods and compositions for determining the presence, absence and/or amount of a pathogen in a plant cultivar, which include: (a) obtaining a nucleic acid sample from the plant cultivar; (b) contacting the nucleic acid sample with at least one polynucleotide primer pair under amplification conditions and amplifying the sample, thereby preparing an amplified nucleic acid mixture, wherein, if the pathogen is present, the polynucleotide primer pair is capable of specifically hybridizing to and amplifying a subsequence of the nucleic acid of the pathogen, or to a complement thereof, wherein the subsequence of the nucleic acid of the pathogen, or the complement thereof, is not identical (i.e., non-identical) to any subsequence of the nucleic acid of the plant genome, or to any complement thereof; and (c) determining the presence, absence and/or amount of at least one amplicon that is 300 base pairs or less and is an amplification product of the polynucleotide primer pair in the amplified nucleic acid mixture of (b), thereby determining the presence, absence and/or amount of a pathogen in the plant cultivar.

In certain embodiments, the plant is a member of the Rosidae subclass. In embodiments, the plant is a Cannabis plant. Any type of Cannabis plant can be analyzed according to the methods provided herein including, but not limited to, Type 1 (THC-dominant), Type 2 (Mixed ratio—CBD&THC), Type 3 (CBD-dominant), Type 4 (CBG-dominant) and Type 5 (Varin-dominant).

The methods and compositions provided herein can, in certain embodiments, be used in a multiplexed format to analyze one or more of: (1) more than one pathogen in a single plant cultivar; (2) more than one subsequence of a single pathogen; (3) a single subsequence of a pathogen quantified using more than one polynucleotide probe for quantification of the amplicon obtained by a polynucleotide primer pair that is capable of specifically hybridizing to and amplifying a subsequence of the nucleic acid of the pathogen; and/or (4) one or more pathogens in a plurality of plant cultivars.

The polynucleotide primer pair for specifically hybridizing to and amplifying a subsequence of the nucleic acid of the pathogen, or to a complement thereof, binds to a subsequence of the nucleic acid of the pathogen, or the complement thereof, that is non-identical to any subsequence of the nucleic acid of the plant genome, or to any complement thereof.

In the methods and compositions provided herein, in embodiments, the polynucleotide primer pairs for specifically hybridizing to and amplifying a subsequence of the nucleic acid of the pathogen are designed to amplify a subsequence that is non-identical to any subsequence of the nucleic acid of the plant genome, thereby permitting specific detection of the plant pathogen and avoiding non-specific detection of sequences of the plant nucleic acid. In certain embodiments, the subsequence of the nucleic acid of the pathogen is in a coding region, thereby permitting the detection of pathogens that are actively expressing proteins and/or are replicating in the plant (e.g., detecting RNA or cDNA of a plant virus, rather than latent virus). In embodiments, the subsequence of the nucleic acid of the pathogen is in a region of overlap between the coding sequences of more than one protein expressed by the pathogen, thereby permitting better confirmation of the identity of the pathogen. In certain embodiments, the identity and/or genotypic variation in a pathogen can be determined by amplifying more than one non-overlapping subsequence of the nucleic acid pathogen, using more than one polypeptide primer pair.

In embodiments, the amplicons generated by specific hybridization and amplification of such subsequences of the nucleic acid of the pathogen can be quantified, e.g., by qPCR or RT-qPCR, e.g., using polynucleotide probes. In such quantification methods, the presence, absence and/or amount of an amplicon is determined by the threshold value of a signal or a parameter, such as a Cq (used interchangeably with Ct) value. In general, a value above (or that crosses) a threshold value indicates that an amplicon (and, therefore, the corresponding pathogen) is present, and a value at or below the threshold value indicates that the amplicon (and, therefore, the corresponding pathogen) is absent. Threshold values can be determined by methods known to those of skill in the art, including, e.g., by obtaining a standard curve (see, e.g., Example 6). The term "Cq" value (or "Ct" value), as used herein, refers to the number of cycles required for a signal, such as a fluorescent signal obtained by labelling the primers and/or templates for amplification, to exceed the background signal (e.g., fluorescence).

In certain embodiments, an amplicon generated by amplifying a subsequence of the nucleic acid of a pathogen can be quantified using more than one non-overlapping polynucleotide probe, and differences between the Cq values of the non-overlapping polynucleotide probes can provide information regarding the presence or absence of genotypic variation in the pathogen.

The pathogens can include viruses, viroids, bacteria, fungi, nematodes, and/or any organisms that can cause disease in plants. In certain embodiments, the pathogen is a virus. The virus can be a DNA virus or an RNA virus. In embodiments, the virus is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV). In certain embodiments, the presence, absence and/or amount of more than one pathogen is determined simultaneously in one or more plant cultivars. In embodiments, the virus is selected from among Hops Latent Viroid (HpLVd), Alfalfa Mosaic Virus (AMV) and Beet Curly Top Virus (BCTV).

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art and may be found, for example, in Current Protocols in Molecular Biology, John Wiley & Sons, N.Y., 6.3.1-6.3.6 (1989); either aqueous or non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e., lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile. As used herein: stringency of hybridization in determining percentage mismatch are those conditions understood by those of skill in the art and typically are substantially equivalent to the following: 1) high stringency: 0.1×SSPE, 0.1% SDS, 65° C.; 2) medium stringency: 0.2×SSPE, 0.1% SDS, 50° C.; 3) low stringency: 1.0×SSPE, 0.1% SDS, 50° C. It is understood that equivalent stringencies may be achieved using alternative buffers, salts and temperatures.

The terms "specifically hybridizes," "specific hybridization" and the like, as used herein, refers to conditions under which a polynucleotide primer pair preferentially hybridizes to a particular subsequence, e.g., of the nucleic acid of a pathogen, and hybridizes to a substantially lesser degree, e.g., 5% or less, such as 5%, 4%, 3%, 2%, 1% or 0%, or between 0% to 1%, 2%, 3%, 4% or 5% or less, to any other subsequence of the nucleic acid of the pathogen, or to subsequences of the nucleic acid of any other pathogens, or to subsequences of the nucleic acid of a plant cultivar. In embodiments, the specific hybridization is under conditions of high stringency, or under conditions of medium stringency.

In embodiments of the methods and compositions provided herein, the polynucleotide primer pairs specifically hybridize to and amplify a subsequence of a nucleic acid of a pathogen that is non-identical to one or more of: (1) any of the other subsequences of the nucleic acid of the pathogen, or complements thereof; (2) subsequences of the nucleic acid of any other pathogens, or complements thereof; and (3) subsequences of the nucleic acid of the genome of the plant cultivar. A sequence that is non-identical to another subsequence, or complement thereof, such as being non-identical to another subsequence of the plant genome, such as a *Cannabis* genome, generally refers to a sequence containing one or more mismatched nucleotides when compared to another subsequence of equivalent length (e.g., identical length, a length that is about 95%, about 96%, about 97%, about 98%, about 99%, about 100%, about 101%, about 102%, about 103%, about 104% or about 105% of the length of the subsequence to which it is compared, or a length that is longer or shorter by one nucleotide, two nucleotides, or three nucleotides than the subsequence to which it is compared) in the plant genome (e.g., *Cannabis* genome, such as the CS10 *Cannabis* genome). In certain embodiments, the length of the sequence to which the subsequence of equivalent length is compared is about 15 nucleotides to about 30 nucleotides, or a length that is about 95%, about 96%, about 97%, about 98%, about 99%, about 100%, about 101%, about 102%, about 103%, about 104% or about 105% of a sequence of length between about 15 nucleotides to about 30 nucleotides.

The polynucleotide primer pairs of the methods and compositions provided herein generally are between about 15 nucleotides to about 30 nucleotides in length, generally about 16, 17, 18, 19, 20, 21, 22, 23, 24, 25, 26, 27, 28, 29 or 30 nucleotides in length, or about 18, 19, 20, 21, 22, 23, 24, 25, 26 or 27 nucleotides in length. In some embodiments, the nucleic acid subsequence of the pathogen, to which a polynucleotide primer pair specifically hybridizes and amplifies, comprises a non-identical sequence comprising at least one, two, three, four, five, six, seven, eight, nine or ten or more mismatches when compared to any other subsequence of equivalent length (e.g., any subsequence of equivalent length within the nucleic acid of the pathogen, or subsequences of the nucleic acid of other pathogens, or subsequences of the nucleic acid of the plant genome). In embodiments, the nucleic acid subsequence of the pathogen, to which a polynucleotide primer pair specifically hybridizes and amplifies, is unique and comprises at least one mismatch when compared to one or more of the following subsequences: (i) any other subsequence of equivalent length in the same pathogen, or (ii) any other subsequence of equivalent length in another pathogen (e.g., one or more other pathogens), or (iii) to any other subsequence of equivalent length in the nucleic acid of the plant genome, or (iv) a combination of (i) and (ii), or (ii) and (iii), or (i) and (iii), or (i), (ii) and (iii). In certain embodiments, the nucleic acid subsequence of the pathogen, to which a polynucleotide primer pair specifically hybridizes and amplifies, is unique and includes at least one mismatch when compared to any other subsequence of equivalent length in the nucleic acid of the plant genome.

The subsequence of the nucleic acid of the pathogen that is amplified using the methods and compositions provided herein generally is about 300 base pairs or less, generally of a size that permits specific detection of the pathogen while substantially avoiding non-specific amplification of sequences of the plant genome and providing better consistency and reproducibility in melting characteristics of the amplicons. In embodiments, the size of the product that is amplified by the prepared polynucleotide primer pair is between about 50 base pairs to about 300 base pairs, or about 300, 290, 280, 275, 270, 265, 260, 255, 250, 245, 240, 235, 230, 225, 220, 215, 210, 205 or 200 base pairs or less. In embodiments, the size of the product that is amplified by the polynucleotide primer pair is between about 40 base pairs to about 200 base pairs, or between about 50 base pairs to about 150 base pairs. In some embodiments, the nucleic acid sequence of the amplicon is non-identical to and comprises a sequence comprising at least one, two, three, four, five, six, seven, eight, nine or ten or more mismatches when compared to any subsequence of equivalent length (e.g., any subsequence of equivalent length within the nucleic acid of the pathogen, or subsequences of the nucleic acid of other pathogens, or subsequences of the nucleic acid of the plant genome). In embodiments, the nucleic acid sequence of the amplicon is unique and comprises at least one mismatch when compared to one or more of any other subsequences of the pathogen, or to any other subsequences of any other pathogens, or to any subsequence of the nucleic acid of the plant genome. In certain embodiments, the nucleic acid sequence of the amplicon is unique and comprises at least one mismatch when compared to any subsequence of the nucleic acid of the plant genome.

The primers of the polynucleotide primer pairs of the methods and compositions provided herein generally share a high degree of sequence identity to the subsequence, or complement thereof, to which they specifically hybridize and amplify. In some embodiments, each polynucleotide in each primer pair comprises a sequence that is at least about 90%, 91%, 92%, 93%, 94%, 95%, 96%, 97%, 98%, 99% or 100% identical to a subsequence, or complement thereof, to which it specifically hybridizes and amplifies. For example, a polynucleotide primer pair that specifically hybridizes to a particular subsequence, e.g., of the nucleic acid of a pathogen, would hybridize to a substantially lesser degree, e.g., 5% or less, such as 5%, 4%, 3%, 2%, 1% or 0%, or between 0% to 1%, 2%, 3%, 4% or 5% or less, to any other non-identical subsequence of the nucleic acid of the pathogen, or to non-identical subsequences of the nucleic acid of any other pathogens, or to non-identical subsequences of the nucleic acid of a plant cultivar.

Provided herein are methods and compositions for detecting the presence, absence and/or amount of pathogens, such as viruses, in a plant. In embodiments, the pathogen is a virus or viroid selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV). The term "virus," as used herein, refers to an infective organism comprising nucleic acid and protein, wherein the organism multiplies by infecting a host organism, such as a plant or animal, that is different than the virus. A "viroid," as used herein, refers to an infective organism comprising nucleic acid, generally without protein, and smaller than a virus. Viroids, like viruses, can multiply by infecting a host organism that is different than the viroid. Both "virus" and "viroid," as used herein, are terms of art known to and understood by those of skill in the art.

In certain embodiments, provided herein are methods for detecting the presence, absence and/or amount of pathogens such as hops latent viroid (HpLvd), AMV and BCTV in a plant sample (e.g., a *Cannabis* plant sample). Also provided herein are methods and compositions for identifying an HpLVd, AMV or BCTV genotype in a plant sample. Also provided herein are methods and compositions for classifying an HpLVd, AMV or BCTV genotype (e.g., associating one or more disease phenotypes in a plant (e.g., a *Cannabis* plant) with a particular HpLVd genotype). Also provided herein are methods and compositions for identifying an HpLVd, AMV or BCTV genetic variation signature in a plant sample. Also provided herein are methods and compositions for classifying an HpLVd, AMV or BCTV genetic variation signature (e.g., associating one or more disease phenotypes in a plant sample (e.g., a *Cannabis* plant) with a particular HpLVd, AMV or BCTV genetic variation signature). As used herein, "a plant sample" refers to applying a method and/or composition described herein to one plant sample in an assay, multiple plant samples each in a separate assay for each sample, multiple plant samples in a single assay, and any combination of the foregoing.

In aspects of the methods and compositions provided herein, the genome of the pathogen can be amplified and sequenced to identify a wild-type or genotypic variant of the pathogen. In certain aspects, amplification of the genome from a known pathogen-positive sample can serve as a positive control when performing the methods provided herein. In aspects, the method is qPCR and in certain aspects, the method is RT-qPCR.

In embodiments, the methods provided herein are performed on cellulose paper that includes chemicals that lyse the plant cells and denature the proteins while retaining the DNA for amplification and/or detection. In embodiments, the cellulose paper is a FTA® card (Whatman).

Hops Latent Viroid (HpLVd), Alfalfa Mosaic Virus (AMV) and Beet Curly Top Virus (BCTV)

Hops Latent Viroid (HpLVd)

Provided herein are methods for analyzing nucleic acid from a plant sample. In some embodiments, the analysis comprises detecting the presence, absence or amount of a hops latent viroid (HpLVd) in the plant sample (e.g., a *Cannabis* plant sample). In some embodiments, the analysis comprises determining one or more genotypes of a hops latent viroid (HpLVd). In some embodiments, the analysis comprises determining a genetic variation signature of a hops latent viroid (HpLVd). The hops latent viroid (HpLVd), which also may be referred to as hop latent viroid, HLV, HLVd, or Putative *Cannabis* Infectious Agent (PCIA), was first characterized as a pathogen in *Humulus lupulus* (hop) plants that can impact yield and secondary metabolite production. Such yield and metabolite impacts generally are more pronounced in *cannabis* plants. HpLVd infections in *cannabis* may result in symptoms, or disease phenotypes, such as loss of vigor, stunting, reduction in yield, reduction in potency, and/or changes in morphology (sometimes collectively referred to as "dudding"). Methods for treating plants infected with one or more pathogens (e.g., HpLVd) include thermotherapy (i.e., heat treatment), cold treatment, light treatment, plant growth regulator treatment (e.g., hormone treatment), and combinations thereof. One method for treating plants infected with HpLVd, or suspected of being infected with HpLVd, is thermotherapy (i.e., heat treatment). Such heat treatment typically reduces HpLVd levels, but may also lead to the accumulation of sequence variability in the HpLVd genome. Sequence variations induced by heat treatment may be referred to as thermomutants.

The complete sequence of the HpLVd genome (provided as GENBANK accession no. NC_003611.1) is:

```
                                          (SEQ ID NO: 1)
CTGGGGAATACACTACGTGACTTACCTGTATGGTG

GCAAGGGCTCGAAGAGGGATCCCCGGGGAAACCTA

CTCGAGCGAGGCGGAGATCGAGCGCCAGTTCGTGC

GCGGCGACCTGAAGTTGCTTCGGCTTCTTCTTGTT

CGCGTCCTGCGTGGAACGGCTCCTTCTTCACACCA

GCCGGAGTTGGAAACTACCCGGTGGATACAACTCT

TGAGCGCCGAGCTTTACCTGCAGAAGTTCACATAA

AAAGTGCCCCT.
```

The reverse complement of the HpLVd genome also is contemplated herein:

```
                                         (SEQ ID NO: 76)
AGGGGCACTTTTTATGTGAACTTCTGCAGGTAAAG

CTCGGCGCTCAAGAGTTGTATCCACCGGGTAGTTT

CCAACTCCGGCTGGTGTGAAGAAGGAGCCGTTCCA

CGCAGGACGCGAACAAGAAGAAGCCGAAGCAACTT

CAGGTCGCCGCGCACGAACTGGCGCTCGATCTCCG

CCTCGCTCGAGTAGGTTTCCCCGGGGATCCCTCTT

CGAGCCCTTGCCACCATACAGGTAAGTCACGTAGT

GTATTCCCCAG.
```

Also provided herein are methods for detecting the presence or absence of HpLVd variants and/or mutants (e.g., thermomutants). HpLVd variants and/or mutants (e.g., thermomutants) may include any HpLVd having one or more nucleotide substitutions, deletions, and/or insertions (e.g., relative to SEQ ID NO:1). Non-limiting examples of HpLVd variants and/or mutants include Hop latent viroid isolate H2 (GENBANK accession no. EF613183.1), Hop latent viroid 'thermomutant' T75 (GENBANK accession no. AJ290409.1), Hop latent viroid isolate CV1 (GENBANK accession no. MK791751.1), Hop latent viroid isolate Y7 (GENBANK accession no. EF613192.1), Hop latent viroid isolate S5 (GENBANK accession no. EF613188.1), Hop latent viroid isolate K7 (GENBANK accession no. EF613185.1), Hop latent viroid 'thermomutant' T92 (GEN BANK accession no. AJ290410.1), Hop latent viroid 'thermomutant' T59 (GEN BANK accession no. AJ290407.1), Hop latent viroid 'thermomutant' T61 (GEN BANK accession no. AJ290408.1), Hop latent viroid isolate A2 (GENBANK accession no. EF613181.1), Hop latent viroid 'thermomutant' T50 (GENBANK accession no. AJ290406.1), Hop latent viroid 'thermomutant' T40 (GENBANK accession no. AJ290405.1), Hop latent viroid 'thermomutant' T229 (GENBANK accession no. AJ290412.1), Hop latent viroid 'thermomutant' T218 (GENBANK accession no. AJ290411.1), Hop latent viroid 'thermomutant' T15 (GENBANK accession no. AJ290404.1), Hop latent viroid isolate GVdC_HLVd01 (GENBANK accession no. KT600318.1), Hop latent viroid isolate GVdC_HLVd02 (GENBANK accession no. KT600317.1), and Hop latent viroid sequence (GENBANK accession no. X07397.1). HpLVd variants and/or mutants (e.g., thermomutants) may include substitutions at one or more of the following nucleotide positions (numbering relative to SEQ ID NO:1): 7, 10, 12, 26, 27, 28, 29, 30, 33, 35, 43, 59, 121, 128, 134, 150, 157, 162, 168, 169, 177, 200, 225, 229, 247, 248, and 253. Examples of thermomutant substitutions include A to G at position 7 of SEQ ID NO:1, A to G at position 12 of SEQ ID NO:1, C to A at position 26 of SEQ ID NO:1, U to A at position 27 of SEQ ID NO:1, G to A at position 28 of SEQ ID NO:1, A to G at position 30 of SEQ ID NO:1, G to A at position 33 of SEQ ID NO:1, G to A at position 35 of SEQ ID NO:1, C to U at position 43 of SEQ ID NO:1, G to A at position 128 of SEQ ID NO:1, C to U at position 150 of SEQ ID NO:1, C to U at position 157 of SEQ ID NO:1, C to A at position 162 of SEQ ID NO:1, U to C at position 168 of SEQ ID NO:1, C to U at position 169 of SEQ ID NO:1, C to U at position 177 of SEQ ID NO:1, U to C at position 229 of SEQ ID NO:1, A to G at position 247 of SEQ ID NO:1, A to C at position 248 of SEQ ID NO:1, C to U at position 253 of SEQ ID NO:1, and C to A at position 255 of SEQ ID NO:1. HpLVd variants and/or mutants (e.g., thermomutants) may include one or more nucleotide insertions or deletions (e.g., deletion of U at position 225 of SEQ ID NO:1).

In aspects of any of the methods provided herein, the entire 256 base pair genome of the HpLVd viroid can be amplified and sequenced to identify a wild-type pathogen or genotypic variant thereof. In certain aspects, amplification of the HpLVd genome from a known positive sample can be used as a positive control in the methods provided herein. In certain aspects, the method is qPCR. In aspects, the method is RT-qPCR. An example of a primer set for amplifying the HpLVd genome is provided in the Table below:

| | Sequence (5'->3') | Template strand | Length | Start | Stop | Tm | GC% | Self complementarity | Self 3' complementarity |
|---|---|---|---|---|---|---|---|---|---|
| Forward primer | CTGGGGAATACACTACGTGACT (SEQ ID NO: 122) | Plus | 22 | 1 | 22 | 59.24 | 50 | 4 | 2 |
| Reverse primer | AGGGGCACTTTTTATGTGAACT (SEQ ID NO: 123) | Minus | 22 | 256 | 235 | 58.16 | 40.91 | 3 | 1 |
| Product length | 256 | | | | | | | | |

Alfalfa Mosaic Virus (AMV)

In some embodiments, the analysis comprises detecting the presence, absence and/or amount of an Alfalfa Mosaic Virus (AMV) in the plant sample (e.g., a *Cannabis* plant sample). In some embodiments, the analysis comprises determining one or more genotypes of an AMV. In some embodiments, the analysis comprises determining a genetic variation signature of an AMV. Alfalfa mosaic virus (AMV), also known as Lucerne Mosaic Virus or Potato Calico Virus, is a phytopathogen that is found worldwide and can damage a large variety of over 600 plant species, including commercially important crops such as *Cannabis*. The genetic material of AMV consists of 3 linear single strands RNAs (RNA 1, RNA 2 and RNA 3) and a subgenomic RNA (RNA 4) which is obtained by transcription of the negative-sense strand of RNA 3. Symptoms caused by AMV infection vary from wilting, white flecks, malformation like dwarfing, ringspots, mottles, mosaics and necrosis depending on the virus strain, host variety, stage of growth at infection and environmental conditions. The virus can be detected in each part of the host plant, while the virions are mainly found in the cytoplasm of the infected plant, as inclusion bodies.

Provided herein are methods and compositions for determining the presence, absence and/or amount of AMV in a plant cultivar. In the methods and compositions provided herein, polynucleotide primer pairs are used to specifically hybridize to and amplify a subsequence of the nucleic acid of AMV, or a complement thereof, where the primer pairs and/or the subsequence are non-identical to any subsequence, or complement thereof, of equivalent length in the nucleic acid of the plant genome. In embodiments, the subsequence of the nucleic acid of AMV that is amplified is a conserved sequence. In certain embodiments, the subsequence of the nucleic acid of AMV, or a portion thereof, is in a coding region, or in a region of overlap between more than one gene of the nucleic acid of the AMV, or in a region of overlap between more than one coding region of the nucleic acid of the AMV.

In certain embodiments, the subsequence of the nucleic acid of the AMV that is amplified is a subsequence of RNA 3, having the sequence set forth below as SEQ ID NO:91 (GenBank Accession No: NC_002025.1):

```
                                            (SEQ ID NO: 91)
  1 GTTTTAAAAC CATTTTCAAA ATATTCCAAT

TCAACTCAAT TAACGCTTTT ACAGTGTAAT

61 TCGTACTTTT CGTAAGTAAG TTTCTGTAAA

AGCGTTTCTT GTTTTAATTT GGTCTAACAC

121 GTAATTCGTA CTCTTCGTGA GTAAGTTGTG

TTAGCCATAC CTATCCTTTA AATTTCTGTC

181 AATTTAAAAA GAAATCATT CCCATTTGCG

TAATTCGTAC TCTTCGTGAG TAAGTTGTAA

241 ATGGAGAATA CAAAAACAAA TGCCTCGAGT

TCTGGAATGT CTTCTTCCTC CAGCTTTTCA

301 GTGTCTTATG CTGAGGAAAT GTTACTAGCT

GATGAAGTTT CAAAAATTAA CTCAATGTCG

361 ATTCTGGGTC CTAATCAGCT AAAGCTCTGC

ACTCAATTGG TGCTGTCTAA TGGAGCAGCG

421 CCAGTAGTTT TAAGCCTTGT GTCAAAGGAA

AAGAAATCGA TTTTAAATCG TATGCTTCCT

481 AAGATTGGAC AGAGGATGTA CGTCCATCAC

TCGGCTATTT ACCTCCTTTA TATGCCAAAC
```

-continued

```
 541 ATACTGAAAA GTTCTTCAGG GAGCATCACC
     TTGAAACTTT TTAATGAAGC TACAGGAGAG
 601 TTAGTGGATG TTGACACCGA CCATGATGCT
     ACCCAGGCAT GTATATTTGC TGGACGTTAC
 661 CCCCGGAGTA TTCTGGCGAA AGATGCAGCG
     AAAGGACACG ACTTGAAATT AGTCGTCCAC
 721 GCTGTTGCTT CGACCAATGC GAACTCCGCT
     GTCGGTGTTC TATACCCCAT TTGGGAAGAT
 781 GAGTTGAGCA GAAAGCAGAT CCTCGAAAGG
     GGTGCCGATT TCCTAAAGTT TCCAATTGCT
 841 GAGACCGAGC CAGTCCGCGA TCTCTTAAAT
     GCTGGGAAGT TGACGGACTT TGTTCTTGAT
 901 AGGACAAGGT TGGGTGTGGG GTCAAAGAAT
     GATCCCAGTC CGGTTCTTTT AGAACCAAGA
 961 GCTAAGATTA CCGGGAAGGC AAAGACAGTT
     TTTATTCCCG AAGGTCCTAG TGTTCCTAAT
1021 ACCACTATAA ATGGTATGGC ACCAACGGTG
     CGTATAGATG CCGGTTCTCC AAAGGGTCTT
1081 GGAGTTCCGA AAGGGTTTAC ATATGAAAGT
     TTTATTAAAG ATGAAATATT ACCCGATCAT
1141 TGATCGGTAA TGGGCCGTTT TTATTTTTAA
     TTTTCTTTCA ATTACTTCCA TCATGAGTTC
1201 TTCACAAAAG AAAGCTGGTG GGAAAGCTGG
     TAAACCTACT AAACGTTCTC AGAACTATGC
1261 TGCCTTACGC AAAGCTCAAC TGCCGAAGCC
     TCCGGCGTTG AAAGTCCCGG TTGTAAAACC
1321 GACGAATACT ATACTGCCAC AGACGGGCTG
     CGTGTGGCAA AGCCTCGGGA CCCCTCTGAG
1381 TCTGAGCTCT TTTAATGGGC TCGGCGTGAG
     ATTCCTCTAC AGTTTTCTGA AGGATTTCGC
1441 GGGACCTCGG ATCCTCGAAG AGGATCTGAT
     TTACAGGATG GTGTTTTCCA TAACACCGTC
1501 CTATGCCGGC ACCTTTTGTC TCACTGATGA
     CGTGACGACT GAGGATGGTA GGGCCGTTGC
1561 GCATGGTAAT CCCATGCAAG AATTTCCTCA
     TGGCGCGTTT CACGCTAATG AGAAGTTCGG
1621 GTTTGAGTTG GTCTTCACAG CTCCTACCCA
     TGCGGGAATG CAAAACCAAA ATTTCAAGCA
1681 TTCCTATGCC GTAGCCCTCT GTCTGGACTT
     CGACGCGCAG CCTGAGGGAT CTAAAAATCC
1741 CTCATACCGA TTCAACGAAG TTTGGGTCGA
     GAGAAAGGCG TTCCCGCGAG CAGGGCCCCT
1801 CCGCAGTTTG ATTACTGTGG GGCTGCTCGA
     CGAAGCTGAC GATCTTGATC GTCATTGATG
1861 TACCCCATTA ATTTGGGATG CCAAAGTCAT
     TTGATGCTGA CCTCCACTGG GTGGATTAAG
1921 GTCAAGGTAT GAAGTCCTAT TCGCTCCTGA
     TAGGATCGAC TTCATATTGC TTATATATGT
1981 GCTAACGCAC ATATATAAAT GCTCATGCAA
     AACTGCATGA ATGCCCCTAA GGGATGC.
```

In embodiments, the subsequence is selected from the region of the RNA 3 that encodes the coat protein, whose amino acid sequence is set forth below as SEQ ID NO:92 (GenBank Accession No: NP_041195.1):

```
(SEQ ID NO: 92)
MSSSQKKAGGKAGKPTKRSQNYAALRKAQLPKPPA

LKVPVVKPTNTILPQTGCVWQSLGTPLSLSSFNGL

GVRFLYSFLKDFAGPRILEEDLIYRMVFSITPSYA
GTFCLTDDVTTEDGRAVAHGNPMQEFPHGAFHANE
KFGFELVFTAPTHAGMQNQNFKHSYAVALCLDFDA
QPEGSKNPSYRFNEVVVVERKAFPRAGPLRSLITV
GLLDEADDLDRH
```

Beet Curly Top Virus (BCTV)

In some embodiments, the analysis comprises detecting the presence, absence and/or amount of a Beet Curly Top Virus (BCTV) in the plant sample (e.g., a *Cannabis* plant sample). In some embodiments, the analysis comprises determining one or more genotypes of a BCTV. In some embodiments, the analysis comprises determining a genetic variation signature of a BCTV.

BCTV was first discovered in 1888 in the Western parts of the United States. The virus was not fully recognized until 1907, when people started to realize a loss in crop yield that was attributable to the virus. In addition to the Unites States, BCTV has been known to affect other parts of the world including Mexico, South America, the Mediterranean basin, and the Middle East.

BCTV has been known to affect more than 300 plant species from 44 different families. It is a DNA virus containing a single-stranded circular DNA that is encapsulated in a twinned icosahedral capsid. The virus DNA contains a monopartite genome that is made up of three viral sense and four complementary open reading frames (ORFS C1-C4). The ORF Complementary 1 (C1) contains the code for the replication initiator protein (Rep) which is responsible for initiating replication in a host plant cell. C3 also plays an important role in the replication process. C2 is involved in causing the disease (pathogenicity), while C4 plays an important role in developing the major symptoms that comes with the virus, such as hyperplasia, curling of the leaves, and deformation. Symptom of infection include: vein swelling (the earliest and most common symptom), leaf curling, yellowing of leaves with purple veins, necrosis and hyperplasia of the phloem, fruit deformation, premature fruit ripening, reduced fruit quality and yield, stunting and the death of young seedlings.

Provided herein are methods and compositions for determining the presence, absence and/or amount of BCTV in a plant cultivar. In the methods and compositions provided herein, polynucleotide primer pairs are used to specifically hybridize to and amplify a subsequence of the nucleic acid of BCTV, or a complement thereof, where the primer pairs and/or the subsequence are non-identical to any subsequence, or complement thereof, of equivalent length in the nucleic acid of the plant genome. In embodiments, the subsequence of the nucleic acid of BCTV that is amplified is a conserved sequence. In certain embodiments, the subsequence of the nucleic acid of BCTV, or a portion thereof, is in a coding region. In embodiments, the subsequence of the nucleic acid of BCTV, or a portion thereof, is in a coding region, or in a region of overlap between more than one gene of the nucleic acid of the BCTV, or in a region of overlap between more than one coding region of the nucleic acid of the BCTV. For sequences of the BCTV genome and proteins encoded therein, see, for example, GenBank Accession No: KX867057

In certain embodiments, the subsequence of the nucleic acid of the BCTV that is amplified is a subsequence of:

```
(a) SEQ ID NO: 110
(Nucleic acid encoding the
SS-ds-DNA-Regulator Protein):
ATGGGACCTTTCAGAGTGGATCAATTTCCAGACAA

TTATCCAGCCTTTCTAGCAGTATCGACCAGTTGTT

TCTTAAGGTACAACAGGTGGTGTATACTAGGTATC

CATCAAGAGATAGAGCCTCTGACCCTAGAAGAAGG

CGAGGTCTTTCTGCAATTCCAGAAGGAAGTCAAGA

AGCTACTGAGGTGTAAGGTCAACTTTCATAGGAAG

TGTTCGTTGTATGAGGAAATATACAAGAAATACGT

ATACAATGTCCCAGAAAAGAAAGGTGAATCCTCAA

AGTGCGTGGCCGAAGAAGAGGAGGACTACTACGAC

TTCGAGGAAATACCAATGGAGGAGACCTGTGACAA

AAAACAGGACTCCGAAGTTAAAGATGTATGA,
where the SS-ds- DNA-Regulator Protein
has the sequence set forth in
SEQ ID NO: 111:

MGPFRVDQFPDNYPAFLAVSTSCFLRYNRWCILGI

HQEIEPLTLEEGEVFLQFQKEVKKLLRSKVNFHRK

CSLYEEIYKEYVYNVPEKKGESSKCVAEEEEDYYD

FEEIPMEEICDKKQDSEVKDV
(SEQ ID NO: 111);

(b) SEQ ID NO: 112
(Nucleic acid encoding
the Movement Protein):
ATGATGGTCTGTCTACCAGACTGGTTATTTTTGCT

ATTTATCTTCAGTATTCTACTGCAATCAGGTACCA

ACTTTTATGGGACCTTTCAGAGTGGATCAATTTCC

AGACAATTATCCAGCCTTTCTAGCAGTATCGACCA
```

```
-continued
GTTGTTTCTTAAGGTACAACAGGTGGTGTATACTA

GGTATCCATCAAGAGATAGAGCCTCTGACCCTAGA

AGAAGGCGAGGTCTTTCTGCAATTCCAGAAGGAAG

TCAAGAAGCTACTGAGGTGTAA,
where the Movement Protein has the
sequence set forth in SEQ ID NO: 113:

MMVCLPDWLFLLFIFSILLQSGTNFYGTFQSGSIS

RQLSSLSSSIDQLFLKVQQVVYTRNPSRDRASDPR

RRRGLSAIPEGSEEATEV
(SEQ ID NO: 113);

(c) SEQ ID NO: 114 (Nucleic acid
encoding the Rolling Circle
Replication Protein (RCR)):
TTACAGGGGAGATTGACCTTGCGAGGACGCTTCTG

TATCTTTATCAAAGAGAGGGCCGGAGAGTTTAACG

AAGGTTGAATTCTGTATAGTCCAGGACCTAAGGGC

TTCATTTTCTGATTTATCTAGGAAGTCCTGGTAAG

AGCTGCCTTCGCCTGGATTGCATAATATAATACTA

GGAATACCACCTTTAATGACACGTGGTTTTCCATA

CTTTAAGTTTGTCTGCCACTCTCTTTGTGCGCCTA

TGAGGTGTTTCCAATGCTTCATCTTTAAGTAAGCT

GGGTCTACGTCATCAATGACGTTATATAAAACATC

ATCGTGATATGTTTTTAAACTAAAATCTAAATGGC

CCGATATATAATTATGAGGTCCTAATGATCTAGCC

CACATTGTTTTACCCGTTCTAGAATCACCCTCTAT

GATTATACTATTATATCTAAAAGGCCGCGCAGCGG

CATCCACCCCGAAATAAGAGTCGGCCCATTCTTGA

ACAATTTCTGGAACTCGAGTGAAAGAAGATTGTGG

GAATGGAGGTTGATAAATATCTGGTGGAGGAAGAA

AAATGGCTTCTAAATTAGGTTTAAGGTTGTGATAC

TGAAAAATAAATTTTTCTGGGAGTTTCTCCCTTAT

TATTTGCAGTGCTTCAGCTGCATTACCTGCATTTA

ATGCTTCTGCTGCTGCATCATTAGCCGTCTGCTGG

CCTCCTCTAGCAGATCTTCCGTCGACTTGAAATGT

ACCCCAGTCGACGTAATCACCGTCCTTCTCGATGT

ATTGTTTAACATCGGATGCAGATTTTGCTCCCTGG

AAGTTGGGGTGGAAGGTGGAGCTTGAGGAAGGATG

GGTGATGTCGAAGTGTCTAGGGTTTCTGAATTGTG

CTTTACCTTTGAATTGGATGAGGGCGTGGAGATGC

AGAGACCCATCCTGATGTTTTCCTGGGATACTCT

AATAAATAATTTATCAGATGGGCAAGGAATATTTT

TCAATATTTCCAGAGCATCTTCTTTTATAACTGAA

CATCGTGGGTATGTGAGAAAGATATTTTTGGCTTT

AATTTGAAATGAAGGTGATCGAGGCAT,
``` where the RCR protein has the
sequence set forth in SEQ ID NO: 115:

MPRSPSFQIKAKNIFLTYPRCSIIKEDALEILKNI

PCPSDKLFIRVSQEKHQDGSLHLHALIQFKGKAQF

RNPRHFDITHPSSSSTFHPNFQGAKSASDVKQYIE

KDGDYVDWGTFQVDGRSARGGQQTANDAAAEALNA

GNAAEALQIIREKLPEKFIFQYHNLKPNLEA!FLP

PPDIYQPPFPLSSFTRVPE1VQEWADSYFGLDPAA

RPFRYNSIIIEGDSRTGKTMWARCLGPHNYITGHL

DFSLKTYSDNVLYNVIDDVDPNYLKMKHWKHLIGA

QREWQTNLKYGKPRVIKGGIPSIILCNPGEGSSYQ

DFLNKSENEALRSVVTLQNSVFAKLTSPLFDNNQE

ASSQDQSSL (SEQ ID NO: 115);

(d) SEQ ID NO: 116 (Nucleic acid
encoding the Pathogenesis
Enhancement Protein):
TTAATTGAGATTGAAGATTGACGCTCCAGTACCCA

ATCCAGTTGGTTCTTCAAGGCTCTCAAAAAACGGT

CTCCAGTCAATGTCCTGTGTGATCCAGTTATCGTC

AAATCGATCCAGCACTTGTGTAGGTTGAGCGATTT

GCGGAGGTTGTGGTTGAATCTCATCTGGACTTTTA

GTTGATATATCGTTCCGAATCTCTCGAACCATAGT

AGTTTGAAGTAGAGTGGATTCGGAACTGATGTTGT

TGGTGTTGATTTCGTCGCCTGTTCCAGGGTAATAG

GTAGTTCCGTGCGAAAATCCGTGATGGCATTCATG

ATGAATTGTGAAGTGACACTTACAGGGGAGATTGA

CCTTGCGAGGACGCTTCTGTATCTTTATCAAAGAG

AGGGCCGGAGAGTTTAACGAAGGTTGAATTCTGTA

TAGTCCAGGACCTAAGGGCTTCAT,
where the Pathogenesis Enhancement
Protein has the sequence set forth
in SEQ ID NO: 117:

MKPLGPGHYKIQSSPNSQVLSLITIKKRPRKINLP

CKCHFTIHHECHQGFSHRGTHYSATSDEIHTRGLG

TESTVPQTPGLLPYRASLSTESPDKIQPQPPQILE

SSQVLDRFDDHWITQDIDWRPFFESLEEPSRQGNQ

KTIFSLN (SEQ ID NO: 117);

(e) SEQ ID NO: 118 (Nucleic acid
encoding the Cell Cycle Regulator
Protein):
TTACACCTCAGTAGCTTCTTGACTTCCTTCTGGAA

TTGCAGAAAGACCTCGCCTTCTTCTAGGGTCAGAG

GCTCTATCTCTTGATGGATACCTAGTATACACCAC

CTGTTGTACCTTAAGAAACAACTGGTCGATACTGC

TAGAAAGGCTGGATAATTGTCTGGAAATTGATCCA

CTCTGAAAGGTCCCATAAAAGTTGGTACCTGATTG

CAGTAGAATACTGAAGATAAATAGCAAAAATAACC

AGTCTGGTAGACAGACCATCAT,
where the Cell Cycle Regulator Protein
has the sequence set forth in
SEQ ID NO: 119:

MGLCISTPSSNSKVKHNSETLDTSTSLILPQAPPS

TPTSREQNLHPMLNNTSRRTVITSTGVHFKSTEDL

LEEASRRLMMQQQKH (SEQ ID NO: 119);

(f) SEQ ID NO: 120 (Nucleic acid
encoding the Replication Enhancer
Protein):
TTAATACAATTTCATTGCAATACTAGTATATTGAA

TTACACTACTGACGAAATTGAAACGCTTATACAAT

ATATAATTGAAAATACGAATAATTTTATTAATTGA

GATTGAAGATTGACGCTCCAGTACCCAATCCAGTT

GGTTCTTCAAGGCTCTCAAAAAACGGTCTCCAGTC

AATGTCCTGTGTGATCCAGTTATCGTCAAATCGAT

CCAGCACTTGTGTAGGTTGAGCGATTTGCGGAGGT

TGTGGTTGAATCTCATCTGGACTTTTAGTTGATAT

ATCGTTCCGAATCTCTCGAACCATAGTAGTTTGAA

GTAGAGTGGATTCGGAACTGATGTTGTTGGTGTTG

ATTTCGTCGCCTGTTCCAGGGTAATAGGTAGTTCC

GTGCGAAAATCCGTGATGGCATTCAT,
where the Replication Enhancer Protein
has the sequence set forth in
SEQ ID NO: 121:

MNVIRDFRTEEPITLQQATKSIPVDLVPNPLYLKL

QDFFRTGPVYQLKVQIRFNHNLRKYLNLHKCWIDL

TITGSHRTLTGDRFLRVLKNQVDREIKKRSSLSIN

IVTEILNHVLYSTFNFVNSVIQYTSIAMKLY
(SEQ ID NO: 121);

or
regions of overlap that span any two of SEQ ID NOS:110, 112, 114, 116, 118 or 120 in the genome of BCTV. In embodiments, the subsequence of the nucleic acid of the pathogen to which the polynucleotide primer pair is capable of hybridizing is in a region of overlap that spans:
(i) the gene encoding the SS-ds-DNA Regulator Protein (SEQ ID NO:110) and the gene encoding Movement Protein (SEQ ID NO:112);
(ii) the gene encoding the Pathogenesis Enhancement Protein (SEQ ID NO:116) and the gene encoding the Rolling Circle Replication Protein (SEQ ID NO:114);
(iii) the gene encoding the Rolling Circle Replication Protein (SEQ ID NO:114) and the gene encoding the Cell Cycle Regulator Protein (SEQ ID NO:118); or
(iv) the gene encoding the Pathogenesis Enhancement Protein (SEQ ID NO:116) and the gene encoding the Replication Enhancer Protein (SEQ ID NO:120).

Pathogen Detection

Provided herein are methods for analyzing nucleic acid from a plant sample. Also provided herein are methods for generating nucleic acid amplification products from a plant sample. Also provided herein are methods for preparing a nucleic acid mixture. In certain embodiments, the methods provided herein determine the presence, absence and/or amount of a pathogen in the plant sample. A method herein may comprise contacting nucleic acid of a plant sample with a polynucleotide primer pair under amplification conditions. In some embodiments, a method herein comprises contacting nucleic acid of a plant sample with one or more polynucleotide primer pairs under amplification conditions. In some embodiments, a method herein comprises contacting nucleic acid of a plant sample with a plurality of polynucleotide primer pairs under amplification conditions. A plurality of primer pairs may comprise two or more polynucleotide primer pairs, three or more polynucleotide primer pairs, four or more polynucleotide primer pairs, five or more polynucleotide primer pairs, six or more polynucleotide primer pairs, seven or more polynucleotide primer pairs, eight or more polynucleotide primer pairs, nine or more polynucleotide primer pairs, or ten or more polynucleotide primer pairs. The primers described in this section may, in certain embodiments, be referred to as primary primers, a first set of primers, and/or thermomutant-resistant primers. For HpLVd, examples of primary primers, a first set of primers, and/or thermomutant-resistant primers are provided in Table 1 (primers labeled tm-resistant). The reverse complement for each primer also is contemplated herein.

In some embodiments, a method comprises generating one or more amplification products. Amplification products may be generated by any suitable amplification method described herein or known in the art (e.g., polymerase chain reaction (PCR)). Suitable amplification conditions include any conditions that can generate an amplification product, when a target nucleic acid is contacted with primers that are capable of hybridizing to the target nucleic acid. In some embodiments, a method comprises generating a mixture (e.g., a mixture of two or more amplification product species). A mixture of two or more amplification product species may be generated when two or more primer pairs hybridize to different regions of a target nucleic acid. Such amplification product species may have different lengths and/or different nucleotide sequences, which may include overlapping and/or non-overlapping sequences.

Generally, a primer pair comprises a forward primer and a reverse primer. Two primer pairs may comprise two different forward primer species (e.g., A-fwd and B-fwd) and two different reverse primer species (e.g., A-rev, B-rev); may comprise one forward primer species (e.g., A-fwd) and two different reverse primer species (e.g., A-rev, B-rev); or may comprise two different forward primer species (e.g., A-fwd and B-fwd) and one reverse primer species (e.g., A-rev), provided the combination of forward and reverse primer species is capable of generating two amplification product species. Further forward and reverse primer combinations are contemplated for additional primer pairs. For HpLVd, an example of forward and reverse primer pairing combinations, with the corresponding amplification product species, is provided in Table 2 herein.

Examples of Certain HpLVd Primer Pairs

In some embodiments, polynucleotide primer pairs hybridize to subsequences of SEQ ID NO:1 (i.e., subsequences of the HpLVd genome). Generally, polynucleotide primer pairs hybridize to subsequences of SEQ ID NO:1 if the subsequences are present in the nucleic acid of a plant sample (e.g., when the plant has been infected with HpLVd). Furthermore, polynucleotide primer pairs do not hybridize to subsequences of SEQ ID NO:1 if the subsequences are not present in the nucleic acid of a plant sample (e.g., when the plant has not been infected with HpLVd). In some embodiments, when a plurality of primer pairs is used, a majority of the polynucleotide primer pairs hybridize to subsequences of SEQ ID NO:1. A majority of the polynucleotide primer pairs may refer to greater than 50% of the primer pairs. For example, a majority of the polynucleotide primer pairs may refer to greater than 60% of the primer pairs, greater than 70% of the primer pairs, greater than 80% of the primer pairs, or greater than 90% of the primer pairs. In some embodiments, all (e.g., 100%) of the polynucleotide primer pairs hybridize to subsequences of SEQ ID NO:1.

In some embodiments, the subsequences of SEQ ID NO:1 to which the polynucleotide primers hybridize (also referred to as primer hybridization sites) contain no variant nucleotide position. A variant nucleotide position refers to a nucleotide (or base) at a given position in SEQ ID NO:1 that may be mutated (e.g., during thermotherapy) and/or differs among various HpLVd strains (e.g., may contain a reference allele or an alternate allele). A subsequence containing no variant position refers to a subsequence where each base is not subject to mutation (e.g., during thermotherapy) and has no known alternative variants (i.e., no known nucleotide substitutions, insertions, or deletions at each position).

In some embodiments, the subsequences of SEQ ID NO:1 to which the polynucleotide primers hybridize contain one variant nucleotide position. A subsequence containing one variant position refers to a subsequence where one base is subject to mutation (e.g., during thermotherapy) and/or is a known alternative variant (i.e., a known nucleotide substitution, insertion, or deletion at the variant position).

In some embodiments, each subsequence of SEQ ID NO:1 between the subsequences to which the primer pairs hybridize contain one or more variant nucleotide positions. As noted above, a variant nucleotide position refers to a nucleotide at a given position in SEQ ID NO:1 that may be mutated (e.g., during thermotherapy) and/or differs among various HpLVd strains. A subsequence of SEQ ID NO:1 between the subsequences to which the primer pairs hybridize may be referred to as a target sequence. A target sequence generally refers to a subsequence of SEQ ID NO:1 between two primer hybridization sites, and generally does not include the primer hybridization sites themselves. Thus, the variant positions described for a target sequence do not include positions in the primer hybridization sites. In some embodiments, a target sequence comprises one variant nucleotide position. In some embodiments, a target sequence comprises two or more variant nucleotide positions. In some embodiments, a target sequence comprises three or more variant nucleotide positions. In some embodiments, a target sequence comprises four or more variant nucleotide positions. In some embodiments, a target sequence comprises five or more variant nucleotide positions. In some embodiments, a target sequence comprises six or more variant nucleotide positions. In some embodiments, a target sequence comprises seven or more variant nucleotide positions. In some embodiments, a target sequence comprises eight or more variant nucleotide positions. In some embodiments, a target sequence comprises nine or more variant nucleotide positions. In some embodiments, a target sequence comprises ten or more variant nucleotide positions.

In some embodiments, each polynucleotide in each primer pair comprises a sequence that is non-identical to any subsequence, or complement thereof, in a *cannabis* genome. In some embodiments, each polynucleotide in each primer pair comprises a sequence that is non-identical to any subsequence, or complement thereof, in a *Cannabis sativa* genome, *Cannabis indica* genome, or *Cannabis ruderalis* genome. Examples of *cannabis* genomes include CS10, Arcata Trainwreck, Grape Stomper, Citrix, Black 84, Headcheese, Red Eye OG, Tahoe OG, Master Kush, Chem 91, Domnesia, Sour Tsunami, Sour Tsunami_x_CK, Tibor_1_2016, 80 E-1, 80 E-2, 80 E-3, Harlox, Saint Jack, Herijuana, Mothers Milk_5, Black Beauty, Sour Diesel, JL_1, JL_2, JL_3, JL_4, JL_5, JL_6, JL_father, BBCC_x_JL_father, JL_mother, JL_mother_p, IdaliaFT_1, Fedora17_6_1, Carmal_1_2016, CS_1_2016, ElCam_1_2016, C3/USO-1, Carmagnola_3, and Merino_S_1. In some embodiments, each polynucleotide in each primer pair comprises a sequence that is non-identical to any subsequence, or complement thereof, in a CS10 *Cannabis* genome (GENBANK assembly accession: GCA_900626175.1; REFSEQ assembly accession: GCF_900626175.1).

A sequence that is non-identical to any subsequence, or complement thereof, in a *Cannabis* genome generally refers to a sequence comprising one or more mismatched nucleotides when compared to any subsequence, or complement thereof, in a *Cannabis* genome (e.g., CS10 *Cannabis* genome). In some embodiments, each polynucleotide in each primer pair comprises a sequence comprising at least two mismatches when compared to any subsequence, or complement thereof, in a *cannabis* genome (e.g., CS10 *Cannabis* genome). In some embodiments, each polynucleotide in each primer pair comprises a sequence comprising at least three mismatches when compared to any subsequence, or complement thereof, in a *cannabis* genome (e.g., CS10 *Cannabis* genome). In some embodiments, each polynucleotide in each primer pair comprises a sequence comprising at least four mismatches when compared to any subsequence, or complement thereof, in a *cannabis* genome (e.g., CS10 *Cannabis* genome). In some embodiments, each polynucleotide in each primer pair comprises a sequence comprising at least five mismatches when compared to any subsequence, or complement thereof, in a *cannabis* genome (e.g., CS10 *Cannabis* genome). In some embodiments, each polynucleotide in each primer pair comprises a sequence comprising at least six mismatches when compared to any subsequence, or complement thereof, in a *Cannabis* genome (e.g., CS10 *Cannabis* genome). In some embodiments, each polynucleotide in each primer pair comprises a sequence comprising at least seven mismatches when compared to any subsequence, or complement thereof, in a *cannabis* genome (e.g., CS10 *Cannabis* genome). In some embodiments, each polynucleotide in each primer pair comprises a sequence comprising at least eight mismatches when compared to any subsequence, or complement thereof, in a *cannabis* genome (e.g., CS10 *Cannabis* genome). In some embodiments, each polynucleotide in each primer pair comprises a sequence comprising at least nine mismatches when compared to any subsequence, or complement thereof, in a *Cannabis* genome (e.g., CS10 *Cannabis* genome). In some embodiments, each polynucleotide in each primer pair comprises a sequence comprising at least ten mismatches when compared to any subsequence, or complement thereof, in a *Cannabis* genome (e.g., CS10 *Cannabis* genome).

The primers provided herein generally share a high degree of sequence identity to a subsequence, or complement thereof, of SEQ ID NO:1. In some embodiments, each polynucleotide in each primer pair comprises a sequence that is at least about 90% identical to a subsequence, or complement thereof, of SEQ ID NO:1. In some embodiments, each polynucleotide in each primer pair comprises a sequence that is at least about 95% identical to a subsequence, or complement thereof, of SEQ ID NO:1. In some embodiments, each polynucleotide in each primer pair comprises a sequence that is 100% identical to a subsequence, or complement thereof, of SEQ ID NO:1.

The primers provided herein generally hybridize to regions of the HpLVd genome that are free of thermomutant sites (i.e., nucleotide positions susceptible to mutation under heat treatment conditions). Such primers may be referred to as thermomutant-resistant primers. Example regions of the HpLVd genome that are free of thermomutant sites include the subsequence between nucleotide position 60 and nucleotide position 102 of SEQ ID NO:1, the subsequence between nucleotide position 89 and nucleotide position 119 of SEQ ID NO:1, and subsequence between nucleotide position 178 and nucleotide position 198 of SEQ ID NO:1. In some embodiments, each forward primer hybridizes to a subsequence between nucleotide position 60 and nucleotide position 102 of SEQ ID NO:1. In some embodiments, each reverse primer hybridizes to a subsequence between nucleotide position 89 and nucleotide position 119 of SEQ ID NO:1, or hybridizes to a subsequence between nucleotide position 178 and nucleotide position 198 of SEQ ID NO:1.

In some embodiments, the subsequences of SEQ ID NO:1 to which the polynucleotide primers hybridize (i.e., primer hybridization sites) contain no thermomutant positions (thermomutant sites). Thermomutant positions may be chosen from one or more of nucleotide position 7 of SEQ ID NO:1, nucleotide position 10 of SEQ ID NO:1, nucleotide position 12 of SEQ ID NO:1, nucleotide position 26 of SEQ ID NO:1, nucleotide position 27 of SEQ ID NO:1, nucleotide position 28 of SEQ ID NO:1, nucleotide position 29 of SEQ ID NO:1, nucleotide position 30 of SEQ ID NO:1, nucleotide position 33 of SEQ ID NO:1, nucleotide position 35 of SEQ ID NO:1, nucleotide position 43 of SEQ ID NO:1, nucleotide position 59 of SEQ ID NO:1, nucleotide position 121 of SEQ ID NO:1, nucleotide position 128 of SEQ ID NO:1, nucleotide position 134 of SEQ ID NO:1, nucleotide position 150 of SEQ ID NO:1, nucleotide position 157 of SEQ ID NO:1, nucleotide position 162 of SEQ ID NO:1, nucleotide position 168 of SEQ ID NO:1, nucleotide position 169 of SEQ ID NO:1, nucleotide position 177 of SEQ ID NO:1, nucleotide position 200 of SEQ ID NO:1, nucleotide position 225 of SEQ ID NO:1, nucleotide position 229 of SEQ ID NO:1, nucleotide position 247 of SEQ ID NO:1, nucleotide position 248 of SEQ ID NO:1, and nucleotide position 253 of SEQ ID NO:1.

Forward primers provided herein (i.e., thermomutant-resistant forward primers) generally share a high degree of sequence identity to a subsequence, or complement thereof, of SEQ ID NO:1. In some embodiments, one or more forward primers (i.e., one or more thermomutant-resistant forward primers) independently are chosen from a polynucleotide comprising a sequence that is at least about 90% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13). In some embodiments, one or more forward primers (i.e., one or more thermomutant-resistant forward primers) independently are chosen from a polynucleotide comprising a sequence that is at least about 95% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13). In some embodiments, one or more forward primers (i.e., one or more thermomutant-resistant forward primers) independently are chosen from a polynucleotide comprising a sequence that is 100% identical to GGGGAAACC-TACTCGAGCG (SEQ ID NO:4), GGAAACC-TACTCGAGCGAGGCG (SEQ ID NO:6), CGAGGCG-GAGATCGAGCGC (SEQ ID NO:9), GAGATCGAGCGCCAGTTCG (SEQ ID NO:11), and AGATCGAGCGCCAGTTCG (SEQ ID NO:13).

Reverse primers provided herein (i.e., thermomutant-resistant reverse primers) generally share a high degree of sequence identity to a subsequence, or complement thereof, of SEQ ID NO:1. In some embodiments, one or more reverse primers (i.e., one or more thermomutant-resistant reverse primers) independently are chosen from a polynucleotide comprising a sequence that is at least about 90% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12). In some embodiments, one or more reverse primers (i.e., one or more thermomutant-resistant reverse primers) independently are chosen from a polynucleotide comprising a sequence that is at least about 95% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12). In some embodiments, one or more reverse primers (i.e., one or more thermomutant-resistant reverse primers) independently are chosen from a polynucleotide comprising a sequence that is 100% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

A plurality of polynucleotide primer pairs generally comprises a plurality of forward primers and a plurality of reverse primers. In some embodiments, a plurality of forward primers comprises GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13); and a plurality of reverse primers comprises CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), ACCGGGTAGTTTCCAACTCCG (SEQ ID NO:12), and AGAGTTGTATTCACCGGGTAGTTTCC (SEQ ID NO:14). In some embodiments, a plurality of forward primers consists of GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13); and a plurality of reverse primers consists of CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

In certain embodiments, an additional example of a thermomutant-specific polynucleotide primer pair is as follows:

(Forward Primer) HpLVd_1-Fwd:
(SEQ ID NO: 77)
GTGACTTACCTGTATGGTGGCAA (Reverse Primer) HpLVd_1-Rev:
(SEQ ID NO: 78)
CTCGCTCGAGTAGGTTTCCCC In embodiments, the amplicon generated by amplifying a subsequence of the HpLVd genome is quantitated using the polynucleotide probe having the following sequence:

HpLVd_Probe:
(SEQ ID NO: 79)
GGGCTCGAAGAGGGATCCCC

The specifications for the above polynucleotide primer pair (SEQ ID NOS:77 and 78) and the above polynucleotide probe (SEQ ID NO:79) are set forth in Table 16 below:

TABLE 16

| | Sequence (5'->3') | Template strand | Length | Start | Stop | Tm | GC % | Self complementarity | Self 3' complementarity |
|---|---|---|---|---|---|---|---|---|---|
| HpLVd_1-Fwd | GTGACTTACCTGTATGGTGGCAA (SEQ ID NO: 77) | Plus | 23 | 17 | 39 | 60.56 | 47.83 | 4.00 | 2.00 |
| HpLVd_1-Rev | CTCGCTCGAGTAGGTTTCCCC (SEQ ID NO: 78) | Minus | 21 | 80 | 60 | 62.22 | 61.90 | 6.00 | 0.00 |
| HpLVd_1-probe | GGGCTCGAAGAGGGATCCCC (SEQ ID NO: 79) | Plus | 20 | 40 | 59 | 57.98 | 70.00 | | |
| Product length | 64 | | | | | | | | |

Examples of Certain AMV Primer Pairs

In some embodiments, polynucleotide primer pairs hybridize to subsequences of the AMV genome. In embodiments, polynucleotide primer pairs hybridize to subsequences of SEQ ID NO:91. Generally, polynucleotide primer pairs hybridize to subsequences of SEQ ID NO:91 if the subsequences are present in the nucleic acid of a plant sample (e.g., when the plant has been infected with AMV). Furthermore, generally, polynucleotide primer pairs substantially do not hybridize to subsequences of SEQ ID NO:91 if the subsequences are not present in the nucleic acid of a plant sample (e.g., when the plant has not been infected with AMV). In some embodiments, when a plurality of primer pairs is used, a majority of the polynucleotide primer pairs hybridize to subsequences of SEQ ID NO:91. A majority of the polynucleotide primer pairs may refer to greater than 50% of the primer pairs. For example, a majority of the polynucleotide primer pairs may refer to greater than 60% of the primer pairs, greater than 70% of the primer pairs, greater than 80% of the primer pairs, or greater than 90% of the primer pairs. In some embodiments, all (e.g., 100%) of the polynucleotide primer pairs hybridize to subsequences of SEQ ID NO:91.

In some embodiments, each polynucleotide in each primer pair comprises a sequence that is non-identical to any subsequence, or complement thereof, in a *cannabis* genome. In some embodiments, each polynucleotide in each primer pair comprises a sequence that is non-identical to any subsequence, or complement thereof, in a *Cannabis sativa* genome, *Cannabis indica* genome, or *Cannabis ruderalis* genome. Examples of *cannabis* genomes include CS10, Arcata Trainwreck, Grape Stomper, Citrix, Black 84, Headcheese, Red Eye OG, Tahoe OG, Master Kush, Chem 91, Domnesia, Sour Tsunami, Sour Tsunami_x_CK, Tibor_1_2016, 80 E-1, 80 E-2, 80 E-3, Harlox, Saint Jack, Herijuana, Mothers Milk_5, Black Beauty, Sour Diesel, JL_1, JL_2, JL_3, JL_4, JL_5, JL_6, JL_father, BBCC_x_JL_father, JL_mother, JL_mother_p, IdaliaFT_1, Fedora17_6_1, Carmal_1_2016, CS_1_2016, ElCam_1_2016, C3/USO-1, Carmagnola_3, and Merino_S_1. In some embodiments, each polynucleotide in each primer pair comprises a sequence that is non-identical to any subsequence, or complement thereof, in a CS10 *Cannabis* genome (GENBANK assembly accession: GCA_900626175.1; REFSEQ assembly accession: GCF_900626175.1).

The primers provided herein generally share a high degree of sequence identity to a subsequence, or complement thereof, of SEQ ID NO:91. In some embodiments, each polynucleotide in each primer pair comprises a sequence that is at least about 90% identical, or between about 90% to about 100% identical, to a subsequence, or complement thereof, of SEQ ID NO:91. In some embodiments, each polynucleotide in each primer pair comprises a sequence that is at least about 95%, 96%, 97%, 98% or 99% identical to a subsequence, or complement thereof, of SEQ ID NO:91. In some embodiments, each polynucleotide in each primer pair comprises a sequence that is 100% identical to a subsequence, or complement thereof, of SEQ ID NO:91.

In certain embodiments, the primer pairs that hybridize to subsequences of SEQ ID NO:91 are shown in Table 12 below:

TABLE 12

| | Sequence (5'->3') | Length | Start | Stop |
|---|---|---|---|---|
| A-fwd | TTGGTCTTCACAGCTCCTACC (SEQ ID NO: 80) | 21 | 1628 | 1648 |
| A-rev | AAGTCCAGACAGAGGGCTACG (SEQ ID NO: 81) | 21 | 1710 | 1690 |
| B-fwd | CTCCTACCCATGCGGGAAT (SEQ ID NO: 82) | 22 | 1641 | 1659 |
| B-rev | TCTCTCGACCCAAACTTCGTTG (SEQ ID NO: 83) | 19 | 1774 | 1753 |

TABLE 12-continued

| | Sequence (5'->3') | Length | Start | Stop |
|---|---|---|---|---|
| C-rev | TCGTTGAATCGGTATGAGGGA (SEQ ID NO: 84) | 20 | 1758 | 1738 |
| D-fwd | TAGGACAAGGTTGGGTGTGG (SEQ ID NO: 85) | 20 | 900 | 919 |
| D-rev | GTCTTTGCCTTCCCGGTAATCT (SEQ ID NO: 86) | 22 | 986 | 965 |

Examples of lengths of amplicons that can be generated using combinations of forward and reverse primers from among those set forth in Table 12 above are shown in Table 13, below:

TABLE 13

| | Arev | Brev | Crev |
|---|---|---|---|
| Afwd | 82 | 146 | 130 |
| Bfwd | 69 | 133 | 117 |

In certain embodiments, the amplicons that are generated are quantified. In embodiments, the amplicons are quantified by RT-qPCR or by qPCR. In embodiments, the polynucleotide probes for quantifying the amplicons generated by hybridizing polynucleotide primer pairs to subsequences of SEQ ID NO:91 are as shown below in Table 14:

TABLE 14

| | Sequence (SEQ ID NO) | Start | Stop |
|---|---|---|---|
| Probe A | TGCGGGAATGCAAAACCAAAATTTCA (87) | 1651 | 1676 |
| Probe A-degen | TGCGGGAATGCAAAAYCAAAATTTCA (88) | 1651 | 1676 |
| Probe B | GAYGCGCAGCCTGAGGGATC (89) | 1712 | 1731 |
| Probe D | GGTCAAAGAATGATCCCAGTCCGGT (90) | 920 | 944 |

Examples of Certain BCTV Primer Pairs

In some embodiments, polynucleotide primer pairs hybridize to subsequences of the BCTV genome. In embodiments, polynucleotide primer pairs hybridize to subsequences of SEQ ID NOS:110, 112, 114, 116, 118 or 120, or a portion of SEQ ID NOS:110, 112, 114, 116, 118 or 120, or a complement of SEQ ID NOS:110, 112, 114, 116, 118 or 120, or a portion of the complement of SEQ ID NOS:110, 112, 114, 116, 118 or 120, or to regions of overlap that span more than one of SEQ ID NOS:110, 112, 114, 116, 118 or 120 in the genome of the pathogen. Generally, polynucleotide primer pairs hybridize to any of the subsequences of the BCTV genome if the subsequences are present in the nucleic acid of a plant sample (e.g., when the plant has been infected with BCTV). Furthermore, generally, polynucleotide primer pairs substantially do not hybridize to subsequences of the BCTV genome if the subsequences are not present in the nucleic acid of a plant sample (e.g., when the plant has not been infected with BCTV). In some embodiments, when a plurality of primer pairs is used, a majority of the polynucleotide primer pairs hybridize to subsequences of the BCTV genome. A majority of the polynucleotide primer pairs may refer to greater than 50% of the primer pairs. For example, a majority of the polynucleotide primer pairs may refer to greater than 60% of the primer pairs, greater than 70% of the primer pairs, greater than 80% of the primer pairs, or greater than 90% of the primer pairs. In some embodiments, all (e.g., 100%) of the polynucleotide primer pairs hybridize to subsequences of SEQ ID NO:91.

In some embodiments, each polynucleotide in each primer pair comprises a sequence that is non-identical to any subsequence, or complement thereof, in a *Cannabis* genome. In some embodiments, each polynucleotide in each primer pair comprises a sequence that is non-identical to any subsequence, or complement thereof, in a *Cannabis sativa* genome, *Cannabis* indica genome, or *Cannabis ruderalis* genome. Examples of *cannabis* genomes include CS10, Arcata Trainwreck, Grape Stomper, Citrix, Black 84, Headcheese, Red Eye OG, Tahoe OG, Master Kush, Chem 91, Domnesia, Sour Tsunami, Sour Tsunami_x_CK, Tibor_1_2016, 80 E-1, 80 E-2, 80 E-3, Harlox, Saint Jack, Herijuana, Mothers Milk_5, Black Beauty, Sour Diesel, JL_1, JL_2, JL_3, JL_4, JL_5, JL_6, JL_father, BBCC_x_JL_father, JL_mother, JL_mother_p, IdaliaFT_1, Fedora17_6_1, Carmal_1_2016, CS_1_2016, ElCam_1_2016, C3/USO-1, Carmagnola_3, and Merino_S_1. In some embodiments, each polynucleotide in each primer pair comprises a sequence that is non-identical to any subsequence, or complement thereof, in a CS10 *Cannabis* genome (GENBANK assembly accession: GCA_900626175.1; REFSEQ assembly accession: GCF_900626175.1).

The primers provided herein generally share a high degree of sequence identity to a subsequence, or complement thereof, of SEQ ID NO:110, 112, 114, 116, 118 or 120, or a portion of SEQ ID NO:110, 112, 114, 116, 118 or 120, or a complement of SEQ ID NO:110, 112, 114, 116, 118 or 120, or a portion of the complement of SEQ ID NOS:110, 112, 114, 116, 118 or 120, or to regions of overlap that span more than one of SEQ ID NOS:110, 112, 114, 116, 118 or 120 in the genome of the BCTV pathogen. In some embodiments, each polynucleotide in each primer pair comprises a sequence that is at least about 90% identical, or between about 90% to about 100% identical, to a subsequence, or complement thereof, of SEQ ID NO:110, 112, 114, 116, 118 or 120, or a portion of SEQ ID NO:110, 112, 114, 116, 118 or 120, or a complement of SEQ ID NO:110, 112, 114, 116, 118 or 120, or a portion of the complement of SEQ ID NOS:110, 112, 114, 116, 118 or 120, or to regions of overlap that span more than one of SEQ ID NOS:110, 112, 114, 116, 118 or 120 in the genome of the BCTV pathogen. In some embodiments, each polynucleotide in each primer pair comprises a sequence that is at least about 95%, 96%, 97%, 98% or 99% identical to a subsequence, or complement thereof, of of SEQ ID NO:110, 112, 114, 116, 118 or 120, or a portion of SEQ ID NO:110, 112, 114, 116, 118 or 120, or a complement of SEQ ID NO:110, 112, 114, 116, 118 or 120, or a portion of the complement of SEQ ID NOS:110, 112, 114, 116, 118 or 120, or to regions of overlap that span more than one of SEQ ID NOS:110, 112, 114, 116, 118 or 120 in the genome of the BCTV pathogen. In some embodiments, each polynucleotide in each primer pair comprises a sequence that is 100% identical to a subsequence, or complement thereof, of of SEQ ID NO:110, 112, 114, 116, 118 or 120, or a portion of SEQ ID NO:110, 112, 114, 116, 118 or 120, or a complement of SEQ ID NO:110, 112, 114, 116, 118 or 120, or a portion of the complement of SEQ ID NOS:110, 112, 114, 116, 118 or 120, or to regions of overlap that span more than one of SEQ ID NOS:110, 112, 114, 116, 118 or 120 in the genome of the BCTV pathogen.

In embodiments, the subsequence of the nucleic acid of BCTV to which the polynucleotide primer pair hybridizes is in a region of overlap that spans:
(i) the gene encoding the SS-ds-DNA Regulator Protein (SEQ ID NO:110) and the gene encoding Movement Protein (SEQ ID NO:112);
(ii) the gene encoding the Pathogenesis Enhancement Protein (SEQ ID NO:116) and the gene encoding the Rolling Circle Replication Protein (SEQ ID NO:114);
(iii) the gene encoding the Rolling Circle Replication Protein (SEQ ID NO:114) and the gene encoding the Cell Cycle Regulator Protein (SEQ ID NO:118); or
(iv) the gene encoding the Pathogenesis Enhancement Protein (SEQ ID NO:116) and the gene encoding the Replication Enhancer Protein (SEQ ID NO:120).

In certain embodiments, the polynucleotide primer pairs, and the polynucleotide probe sequences for quantitating the resulting amplicons, are shown in Table 15 below:

TABLE 15

| | Sequence (5'->3') (SEQ ID NO) | Length | Start | Stop |
|---|---|---|---|---|
| Fwd_DRP_MP | GACCTTTCAGAGTGGATCAATTTCC (93) | 25 | 334 | 358 |
| Rev_DRP_MP | GAAAGACCTCGCCTTCTTCTAGG (94) | 23 | 480 | 458 |
| Rev-2_DRP_MP_Degen | GMAGAAAGACCTCGCCTTCT (105) | | | |
| Probe_DRP_MP | CCAGCCTTTCTAGCAGTRTCGACCA (95) | 25 | 369 | 393 |
| Probe-2_DRP_MP_Degen | CCATCAAGAGATAGAGCTCTGACCC (106) | | | |
| Fwd_PE_RCRI | GCGAGGACGCTTCTGTATCTT (96) | 21 | 1781 | 1801 |
| Degen_Rev_PE_RCRI | AAGCMCTTARGTCCTGGACTATAC (97) | 24 | 1867 | 1844 |
| Degen_Probe_PE_RCRI | GGGCYGGAGAGTTTAACGAAGGY (98) | 23 | 1813 | 1835 |
| Fwd_RCRI_CCR | GCTGCATCATTAGCCGTCTG (99) | 20 | 2437 | 2456 |
| Degen_Rev_RCRI_CCR | CCTTCCACCSCAACTTCCAR (100) | 20 | 2581 | 2562 |
| Probe_RCRI_CCR | ACCCCAGTCGACGTAATCACCGT (101) | 23 | 2496 | 2518 |

TABLE 15-continued

| | Sequence (5'->3') (SEQ ID NO) | Length | Start | Stop |
|---|---|---|---|---|
| Fwd_PE_RE | AGCGATTTGCGGAGGTTGT (102) | 19 | 1559 | 1577 |
| Rev_PE_RE | AACAGGCGACGAAATCAACA (103) | 20 | 1694 | 1675 |
| Probe_PE_RE | AGTGGATTCGGAACTGATGTTGTTGG (104) | 26 | 1649 | 1674 |

DNA Regulator Protein (SEQ ID NO: 110) and the gene encoding Movement Protein (SEQ ID NO: 112).
PE_RCRI primers and probe: targeting region of overlap between gene encoding the Pathogenesis Enhancement Protein (SEQ ID NO: 116) and the gene encoding the Rolling Circle Replication Protein (SEQ ID NO: 114).
RCRI_CCR primers and probe: targeting region of overlap between gene encoding the Rolling Circle Replication Protein (SEQ ID NO: 114) and the gene encoding the Cell Cycle Regulator Protein (SEQ ID NO: 118).
PE_RE primers and probe: targeting region of overlap between gene encoding the Pathogenesis Enhancement Protein (SEQ ID NO: 116) and the gene encoding the Replication Enhancer Protein (SEQ ID NO: 120).
**DRP_MP primers and probe: targeting region of overlap between gene encoding the SS-ds- Certain Primers that Hybridize to Subsequences of the Plant Genome In embodiments of the methods provided herein, a positive control amplicon is generated using a polynucleotide primer pair that is capable of specifically hybridizing to and amplifying a subsequence of the nucleic acid of the plant genome, or to a complement thereof, wherein the subsequence of the nucleic acid of the plant genome, or the complement thereof, is non-identical to any subsequence of the nucleic acid of the pathogen, or to any complement thereof; and determining the presence, absence and/or amount of at least one amplicon that is an amplification product of the polynucleotide primer pair that is capable of specifically hybridizing to and amplifying a subsequence of the nucleic acid of the plant genome, thereby determining whether the amplification conditions are effective for generating amplicons. In embodiments, the subsequence of the nucleic acid of the plant genome comprises all or part of a gene selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin. In embodiments, the plant genome is a *Cannabis* genome.

In embodiments, the polynucleotide primer pair hybridizes to a subsequence of 26S rRNA. An example of a polynucleotide primer pair that hybridizes to a subsequence of 26S rRNA is the following:

```
Forward Primer
26_S_Fwd:
                                        (SEQ ID NO: 107)
AGAAGGGTTCGAGTGAGAGC Reverse Primer
26_S_Rev:
                                        (SEQ ID NO: 108)
GAGGGAAACTTCGGAGGGAA
```

In certain embodiments, the amplicon generated by hybridizing to and amplifying a subsequence of 26S rRNA are quantified using a polynucleotide probe (e.g., by RT-qPCR or qPCR). An example of a 26S rRNA polynucleotide probe sequence is as follows:

```
26S probe:
                                        (SEQ ID NO: 109)
ATCGCTGCGGGCCTCCACCA.
```

Methods for Analyzing Nucleic Acids

Provided herein are methods for analyzing nucleic acids. In embodiments, the methods are for analyzing nucleic acids to determine the presence, absence and/or amount of a plant pathogen in a plant. The nucleic acids can be analyzed using a variety of methods that include, but are not limited to, RT-qPCR, qPCR, RT-PCR, and PCR ran on cDNA. The genotype of the plant pathogen can be determined using, e.g., amplified nucleic acids (low level or high level amplification) and/or high resolution melting analysis (HRM). A high-resolution melting (HRM) endpoint assay using the polynucleotide primer pairs that specifically hybridize to and amplify a subsequence of the nucleic acid from a pathogen, as provided herein, can permit genetic classification of the variant of the pathogen (e.g., HpLVd, AMV, BCTV or any combination thereof) that infects a plant cultivar. These primers can be used as molecular markers to identify, e.g., symptomatic vs asymptomatic pathogenic variants, as well as identify, e.g., pathogenic variants that spread more easily or pathogenic variants to which the plants have acquired resistance. The methods provided herein can be used analyze a single plant pathogen using a single polynucleotide primer pair and a single polynucleotide probe, or can be performed as a multiplexed method for analyzing one or more of: (a) a single polynucleotide primer pair and more than one polynucleotide probe sequence for analyzing a pathogen; differences in the Cq values that might be obtained using the different probes can provide information regarding possible mutations (genotypic variants) in the pathogen; (b) more than one polynucleotide primer pair to analyze more than one non-overlapping subsequence (including, in embodiments, a polynucleotide probe sequence for each non-overlapping subsquence) of a pathogen; differences in the Cq values that might be obtained for the polynucleotide probes can provide information regarding possible mutations (genotypic variants) in the pathogen; (c) more than one polynucleotide primer pair to simultaneously analyze more than one pathogen that may have infected the plant, e.g., one or more of among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

In embodiments, the presence or absence of a wild-type or genotypic variant pathogen in a plant, as identified by the methods provided herein, can be correlated to susceptibility of the plant to infection by the wild-type pathogen and/or genotypic variants thereof, e.g., whether the plant is infected and symptomatic, infected but asymptomatic, or altogether resistant to infection. In aspects, if the plant is identified as resistant to infection or by the pathogen and/or a genotypic variant thereof, or asymptomatic, the plant is identified as desirable for breeding, or as desirable for cultivating as a crop. In aspects, the methods provided herein can be used as a way to produce, such as by self-breeding, inbreeding, and outcrossing, offspring that are resistant to infection by a pathogen or an identified genetic variant thereof. For example, when two plants that have latent infections of HpLVd (infected but asymptomatic) are bred, about 8% of the progeny are resistant to HpLVd infection. Selective breeding and selection by identifying pathogen-resistant or asymptomatic plants according to the methods provided herein can, in aspects, be used to "clean" a field containing infected plants by gradually replacing such plants with resistant or asymptomatic progeny plants. In aspects, the plant is of the Rosidae family. In certain aspects, the plant is a *Cannabis* plant.

In some embodiments, methods herein comprise analyzing nucleic acid from a plant sample. In some embodiments, methods herein comprise analyzing nucleic acid from a *Cannabis* plant sample. In some embodiments, methods herein comprise analyzing nucleic acid from a pathogen. In some embodiments, methods herein comprise analyzing nucleic acid from a pathogen that has infected a plant. In some embodiments, methods herein comprise analyzing nucleic acid from a pathogen that is a virus selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV). In some embodiments, methods herein comprise analyzing nucleic acid from a Hops Latent Viroid that has infected a *Cannabis* plant. In some embodiments, methods herein comprise analyzing nucleic acid from one or more viruses selected from among a Hops Latent Viroid (HpLVd), Alfalfa Mosaic Virus (AMV) and Beet Curly Top Virus (BCTV) that has infected a plant. In embodiments, the plant is a *Cannabis* plant.

In some embodiments, the plant (e.g., a *Cannabis* plant) has been subjected to thermotherapy (has been heat treated). In embodiments, the pathogen is hops latent viroid (HpLVd). In some embodiments, the plant (e.g., a *Cannabis* plant) has not been subjected to thermotherapy (has not been heat treated). Thermotherapy (or heat treatment) generally refers to a process of maintaining living plants in a chamber or room where light and temperature can be manipulated throughout a 24 hour time period, typically providing long days of light and temperatures near 100° F. for at least 16 hours and typically a lower temperature (such as 25° C. to 40° C.) during the dark period. Often the conditions are adjusted as appropriate to maintain the genetics of the plant being treated with the goal of causing virus escape when explants are removed from the plants after the heating period.

In some embodiments, analyzing comprises detecting the presence or absence and/or amount of one or more pathogens in a plant. A plant may be a *Cannabis* plant. A pathogen may be a Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV), or any combination thereof.

HpLVd

A plant may be a *Cannabis* plant. A pathogen may be a Hops Latent Viroid (HpLVd). Accordingly, in some embodiments, analyzing comprises detecting the presence or absence of a hops latent viroid (HpLVd) in a *Cannabis* plant. Presence of a hops latent viroid (HpLVd) in a *Cannabis* plant may be determined according to amplification products generated using one or more primer pairs that specifically amplify subsequences of a hops latent viroid (HpLVd) (e.g., the primer pairs provided herein). In some embodiments, the presence of a hops latent viroid (HpLVd) in a *cannabis* plant may be determined according to one or more amplification products generated using one or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to two or more amplification products generated using two or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to three or more amplification products generated using three or more primer pairs that specifically amplify subsequences of a hops latent viroid (HpLVd) (e.g., primer pairs provided herein). In some embodiments, the presence of a hops latent viroid (HpLVd) in a *cannabis* plant may be determined according to four or more amplification products generated using four or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to five or more amplification products generated using five or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to six or more amplification products generated using six or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to seven or more amplification products generated using seven or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to eight or more amplification products generated using eight or more primer pairs that specifically amplify subsequences of a hops latent viroid (HpLVd) (e.g., primer pairs provided herein). In some embodiments, the presence of a hops latent viroid (HpLVd) in a *cannabis* plant may be determined according to nine or more amplification products generated using nine or more primer pairs that specifically amplify subsequences of a hops latent viroid (HpLVd) (e.g., primer pairs provided herein). In some embodiments, the presence of a hops latent viroid (HpLVd) in a *Cannabis* plant may be determined according to ten or more amplification products generated using ten or more primer pairs that specifically amplify subsequences of a hops latent viroid (HpLVd) (e.g., primer pairs provided herein).

In some embodiments, analyzing comprises detecting one or more genotypes in a hops latent viroid. A genotype generally refers to a part of the genetic information of an organism or pathogen (e.g., virus or viroid), which may determine one or more of its characteristics or traits (phenotypes). A genotype of a virus or viroid may refer to a particular mutation or a combination of mutations, a genetic variation or a combination or genetic variations, and/or an allele or a combination of alleles. A genotype may specify whether an organism or viroid has a reference allele or an alternate allele at a particular locus. In some embodiments, analyzing comprises detecting a genetic variation in a hops latent viroid genome. A genotype for a hops latent viroid may specify a reference allele for a particular locus in the hops latent viroid genome. A reference allele may refer to a nucleotide present at a particular position as provided in SEQ ID NO:1. A genotype for a hops latent viroid may specify an alternate allele for a particular locus in the hops latent viroid genome. An alternate allele may refer to a variant nucleotide present at a particular position in SEQ ID NO:1 (i.e., a nucleotide that is different from the nucleotide at that position in SEQ ID NO:1).

Any suitable method for genotype assessment may be used for detecting a genetic variation in a hops latent viroid genome, such as, for example, nucleic acid sequencing (examples of which are described herein) and/or a high resolution melting (HRM) assay described herein. Generally, a sequencing process and/or an HRM assay are performed in conjunction with a nucleic acid amplification method described herein (e.g., using the amplification primers provided herein). In some embodiments, one or more genetic variations may be determined according to the presence and/or absence of amplification products generated using certain amplification primers provided herein. Such primers are distinct from the primers described above (i.e., primary primers, first set of primers, thermomutant-resistant primers) and may be referred to as further primers, secondary primers, a second set of primers, thermomutant-specific, and/or thermomutant-sensitive primers. For example, certain amplification primers provided herein hybridize to subsequences of the hops latent viroid genome that contain variant positions (e.g., thermomutant-specific primers). The presence of a variant nucleotide in the hops latent viroid genome can result in the failure of a thermomutant-specific primer to hybridize to its corresponding HpLVd subsequence carrying the variant nucleotide. Such hybridization failure results in an absence of certain amplification product or products, and the absence of a certain amplification product or products can be indicative of the presence of at least one genetic variation in the HpLVd subsequence. Examples of further primers, secondary primers, a second set of primers, thermomutant-specific, and/or thermomutant-sensitive primers are provided in Table 1 (primers labeled tm-specific). The reverse complement for each primer also is contemplated herein.

In some embodiments, detecting one or more genetic variations in the hops latent viroid comprises contacting the nucleic acid of the plant sample with one or more further polynucleotide primers (e.g., primers distinct from the first set of primers described above). The nucleic acid of the plant sample may be contacted with the further polynucleotide primer(s) under amplification conditions. The amplification conditions may be the same amplification conditions as described above for the first set of primers, or may be a different amplification conditions. The amplification reaction may be the same amplification reaction as described above for the first set of primers, or may be a different amplification reaction. In some embodiments, one amplification reaction is performed using a combination of primers from the first set and primers from the second set. In some embodiments, certain forward primers from the first set pair with certain reverse primers from the second set, and vice versa (see, e.g., Table 1 and Table 2).

In some embodiments, the further polynucleotide primers hybridize to subsequences of SEQ ID NO:1 (i.e., subsequences of the HpLVd genome that have not been mutated (e.g., subsequences containing no thermomutations)). Generally, the further polynucleotide primers hybridize to subsequences of SEQ ID NO:1 if the subsequences are present in the nucleic acid of a plant sample (e.g., when the plant has been infected with HpLVd, and where the variant positions in the subsequences contain no mutations). Furthermore, the further polynucleotide primers do not hybridize to subsequences of SEQ ID NO:1 if the subsequences are not present in the nucleic acid of a plant sample (e.g., when the plant has not been infected with HpLVd, or when an HpLVd subsequence contains a mutation). In some embodiments, when a plurality of further polynucleotide primers is used, a majority of the polynucleotide further polynucleotide primers hybridize to subsequences of SEQ ID NO:1. A majority of the further polynucleotide primers may refer to greater than 50% of the further primers. For example, a majority of the further polynucleotide primers may refer to greater than 60% of the further primers, greater than 70% of the further primers, greater than 80% of the further primers, or greater than 90% of the further primers. In some embodiments, all (e.g., 100%) of the further polynucleotide primers hybridize to subsequences of SEQ ID NO:1 (i.e., subsequences of the HpLVd genome that have not been mutated (e.g., subsequences containing no thermomutations)).

In some embodiments, the subsequences of SEQ ID NO:1 to which the further polynucleotide primers hybridize (also referred to as further primer hybridization sites) contain one or more variant nucleotide positions. As noted above, a variant nucleotide position refers to a nucleotide (or base) at a given position in SEQ ID NO:1 that may be mutated (e.g., during thermotherapy) and/or differs among various HpLVd strains (e.g., may contain a reference allele or an alternate allele). A subsequence containing one or more variant positions refers to a subsequence where at least one base is subject to mutation (e.g., during thermotherapy) and/or has at least one known alternative variant (i.e., a known nucleotide substitution, insertion, or deletion at the variant position).

In some embodiments, each further polynucleotide primer comprises a sequence that is non-identical to any subsequence, or complement thereof, in a *cannabis* genome (e.g., a CS10 *Cannabis* genome, and/or any *cannabis* genome described herein). As noted above, a sequence that is non-identical to any subsequence, or complement thereof, in a *cannabis* genome generally refers to a sequence comprising one or more mismatched nucleotides when compared to any subsequence, or complement thereof, in a *cannabis* genome (e.g., CS10 *Cannabis* genome). In some embodiments, each further polynucleotide primer comprises a sequence comprising at least two, three, four, five, six, seven, eight, nine, or ten mismatches when compared to any subsequence, or complement thereof, in a *cannabis* genome (e.g., CS10 *Cannabis* genome). In some embodiments, each further polynucleotide primer comprises a sequence comprising at least six mismatches when compared to any subsequence, or complement thereof, in a *cannabis* genome (e.g., CS10 *Cannabis* genome).

The further primers provided herein (i.e., thermomutant-specific primers) generally share a high degree of sequence identity to a subsequence, or complement thereof, of SEQ ID NO:1. In some embodiments, each further primer comprises a sequence that is at least about 90% identical to a subsequence, or complement thereof, of SEQ ID NO:1. In some embodiments, each further primer comprises a sequence that is at least about 95% identical to a subsequence, or complement thereof, of SEQ ID NO:1. In some embodiments, each further primer comprises a sequence that is 100% identical to a subsequence, or complement thereof, of SEQ ID NO:1.

In some embodiments, one or more further polynucleotide primers (i.e., one or more thermomutant-specific primers) independently are chosen from a polynucleotide comprising a sequence that is at least about 90% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15). In some embodiments, one or more further polynucleotide primers (i.e., one or more thermomutant-specific primers) independently are chosen from a polynucleotide comprising a sequence that is at least about 95% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15). In some embodiments, one or more further polynucleotide primers (i.e., one or more thermomutant-specific primers) independently are chosen from a polynucleotide comprising a sequence that is 100% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15). In some embodiments, one or more further polynucleotide primers (i.e., one or more thermomutant-specific primers) comprise CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15). In some embodiments, one or more further polynucleotide primers (i.e., one or more thermomutant-specific primers) consist of CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

In some embodiments, a primer provided herein (e.g., a further primer herein) comprises a polynucleotide where one or more nucleotide positions contain a nonstandard nucleotide and/or a degenerate nucleotide. A nonstandard nucleotide may be, for example, a non-natural base, a modified base, or a universal base. A universal base is a base capable of indiscriminately base pairing with each of the four standard nucleotide bases: A, C, G and T. Universal bases that may be incorporated into a primer herein include, but are not limited to, inosine, deoxyinosine, 2'-deoxyinosine (dI, dInosine), nitroindole, 5-nitroindole, and 3-nitropyrrole (e.g., 5' nitroindole, deoxyinosine, deoxynebularine). A degenerate nucleotide typically refers to a mixture of nucleotides at a given position and may be represented by a letter other than A, T, G or C. For example, a degenerate nucleotide may be represented by R (A or G), Y (C or T), S (G or C), W (A or T), K (G or T), M (A or C), B (C or G or T), D (A or G or T), H (A or C or T), V (A or C or G), or N (any base), for example. Such symbols for degenerate nucleotides are part of the International Union of Pure and Applied Chemistry (IUPAC) standard nomenclature for nucleotide base sequence names and represent degenerate or nonstandard nucleotides that can bind multiple nucleotides. For example, an "M" in a primer or probe would include a mixture of A and C at that position, and thus could bind to either T or G in a complementary DNA strand. An "N" in a primer or probe would include a mixture of A, T, G and C at that position, and thus could bind to any nucleotide at that position in the complementary DNA strand.

In some embodiments, analyzing comprises detecting one or more genetic variations in a hops latent viroid genome. In some embodiments, analyzing comprises detecting two or more genetic variations in a hops latent viroid genome. In some embodiments, analyzing comprises detecting three or more genetic variations in a hops latent viroid genome. In some embodiments, analyzing comprises detecting four or more genetic variations in a hops latent viroid genome. In some embodiments, analyzing comprises detecting five or more genetic variations in a hops latent viroid genome. In some embodiments, analyzing comprises detecting six or more genetic variations in a hops latent viroid genome. In some embodiments, analyzing comprises detecting seven or more genetic variations in a hops latent viroid genome. In some embodiments, analyzing comprises detecting eight or more genetic variations in a hops latent viroid genome. In some embodiments, analyzing comprises detecting nine or more genetic variations in a hops latent viroid genome. In some embodiments, analyzing comprises detecting ten or more genetic variations in a hops latent viroid genome.

A genetic variation may refer to a nucleotide insertion, a nucleotide deletion, or a nucleotide substitution. An example of a nucleotide deletion in the hops latent viroid (HpLVd) genome is a deletion of the nucleotide at position 225 of SEQ ID NO:1. A nucleotide substitution may be referred to as a single nucleotide variation, single nucleotide mutation, or single nucleotide polymorphism (SNP). A single nucleotide variation generally refers to a variant nucleotide at a particular position in the HpLVd genome (SEQ ID NO:1). A variant nucleotide (also referred to as a variant allele) generally refers to a nucleotide other than the nucleotide present at that position in SEQ ID NO:1. For example, position 1 of SEQ ID NO:1 is a C nucleotide, and a variant nucleotide at that position would be any nucleotide other than a C nucleotide (e.g., A, T, or G nucleotide). Examples of single nucleotide variations in the hops latent viroid (HpLVd) genome include a variant nucleotide at position 7 of SEQ ID NO:1, a variant nucleotide at position 10 of SEQ ID NO:1, a variant nucleotide at position 12 of SEQ ID NO:1, a variant nucleotide at position 26 of SEQ ID NO:1, a variant nucleotide at position 27 of SEQ ID NO:1, a variant nucleotide at position 28 of SEQ ID NO:1, a variant nucleotide at position 29 of SEQ ID NO:1, a variant nucleotide at position 30 of SEQ ID NO:1, a variant nucleotide at position 33 of SEQ ID NO:1, a variant nucleotide at position 35 of SEQ ID NO:1, a variant nucleotide at position 43 of SEQ ID NO:1, a variant nucleotide at position 59 of SEQ ID NO:1, a variant nucleotide at position 121 of SEQ ID NO:1, a variant nucleotide at position 128 of SEQ ID NO:1, a variant nucleotide at position 134 of SEQ ID NO:1, a variant nucleotide at position 150 of SEQ ID NO:1, a variant nucleotide at position 157 of SEQ ID NO:1, a variant nucleotide at position 162 of SEQ ID NO:1, a variant nucleotide at position 168 of SEQ ID NO:1, a variant nucleotide at position 169 of SEQ ID NO:1, a variant nucleotide at position 177 of SEQ ID NO:1, a variant nucleotide at position 200 of SEQ ID NO:1, a variant nucleotide at position 225 of SEQ ID NO:1, a variant nucleotide at position 229 of SEQ ID NO:1, a variant nucleotide at position 247 of SEQ ID NO:1, a variant nucleotide at position 248 of SEQ ID NO:1, and a variant nucleotide at position 253 of SEQ ID NO:1.

In some embodiments, a method for analyzing nucleic acid from a plant sample, comprises a) contacting nucleic acid of a plant sample with a first set of polynucleotide primers under amplification conditions, thereby generating a first set of amplification products, where i) the majority or all of the primers in the first set of polynucleotide primers hybridize to subsequences of SEQ ID NO:1 if present in the nucleic acid of the plant sample under the amplification conditions, ii) the subsequences of SEQ ID NO:1 to which the majority or all of the primers in the first set of polynucleotide primers hybridize under the amplification conditions contain no variant nucleotide position, and iii) each subsequence of SEQ ID NO:1 between the subsequences to which the primers in the first set of polynucleotide primers hybridize contain one or more variant nucleotide positions; b) contacting the nucleic acid of the plant sample with a second set of polynucleotide primers under the amplification conditions, thereby generating a second set of amplification products, where i) the majority or all of the primers in the second set of polynucleotide primers hybridize to subsequences of SEQ ID NO:1 if present in the nucleic acid of the plant sample under the amplification conditions, and ii) the subsequences of SEQ ID NO:1 to which the majority or all of the primers in the second set of polynucleotide primers hybridize under the amplification conditions contain one or more variant nucleotide positions; and c) analyzing the first and second sets of amplification products.

In some embodiments, analyzing comprises detecting a genetic variation signature (e.g., a genetic variation signature for a hops latent viroid genome). Generally, a genetic variation signature comprises genotypes determined at a plurality of variant nucleotide positions. A particular genetic variation signature may comprise reference allele genotypes, alternate (i.e., variant) allele genotypes, or a combination of reference allele genotypes and alternate (i.e., variant) allele genotypes. Thus, a genetic variation signature may comprise a combination of variant and non-variant identities for a plurality of nucleotide positions in a hops latent viroid genome. A genetic variation signature in certain contexts may be referred to as a serotype, a serovar, a barcode, or a haplotype.

In some embodiments, a genetic variation signature comprises genotypes determined at two or more variant nucleotide positions in a hops latent viroid genome. In some embodiments, a genetic variation signature comprises genotypes determined at three or more variant nucleotide positions in a hops latent viroid genome. In some embodiments, a genetic variation signature comprises genotypes determined at four or more variant nucleotide positions in a hops latent viroid genome. In some embodiments, a genetic variation signature comprises genotypes determined at five or more variant nucleotide positions in a hops latent viroid genome. In some embodiments, a genetic variation signature comprises genotypes determined at six or more variant nucleotide positions in a hops latent viroid genome. In some embodiments, a genetic variation signature comprises genotypes determined at seven or more variant nucleotide positions in a hops latent viroid genome. In some embodiments, a genetic variation signature comprises genotypes determined at eight or more variant nucleotide positions in a hops latent viroid genome. In some embodiments, a genetic variation signature comprises genotypes determined at nine or more variant nucleotide positions in a hops latent viroid genome. In some embodiments, a genetic variation signature comprises genotypes determined at ten or more variant nucleotide positions in a hops latent viroid genome.

In some embodiments, analyzing comprises identifying a hops latent viroid trait according to one or more genetic variations in a hops latent viroid genome. In some embodiments, analyzing comprises identifying a hops latent viroid trait according to a genetic variation signature determined for a hops latent viroid genome. Identifying a hops latent viroid trait according to one or more genetic variations and/or a genetic variation signature may be referred to as classifying a genotype; associating one or more phenotypes of an infected plant (e.g., an infected *cannabis* plant) with one or more genotypes and/or genetic variations for a pathogen (e.g., HpLVd); and/or associating one or more disease phenotypes in a plant (e.g., a *Cannabis* plant) with a particular HpLVd genotype. A hops latent viroid trait (or phenotypic trait) may refer to any distinguishing quality or characteristic of the viroid itself and/or phenotype expressed by a plant infected by the viroid. In some embodiments, a method comprises identifying an HpLVd trait or segment of the HpLVd genome that is an indicator of whether a particular HpLVd variant in a particular cultivar is more or less virulent/symptomatic. Without being limited by theory, HpLVd RNA may be complementary to certain genes, or fragments thereof, in the plant, which, when hybridized, may prevent the plant gene expression by acting as a silencing/interfering RNA type molecule. In some embodiments, a method herein comprises matching genotypes of HpLVd with *cannabis* phenotypes and/or *cannabis* genotypes that either confer resistance to infection or susceptibility to infection, such that *cannabis* genotypes susceptible to certain HpLVd genotypes may be identified and/or *cannabis* plants resistant to HpLVd may be bred.

A hops latent viroid trait may include, for example, infectiousness and or contagiousness of the viroid; presence or absence of symptoms in an infected plant; type, pervasiveness, and/or severity of symptoms in an infected plant; degree of recovery of an infected plant; and/or responsiveness to treatment. Symptoms of an infected plant may include, for example, loss of vigor, stunting, abnormal stretching, reduction in yield, reduction in potency, changes in morphology, reduction or lack of oil, small trichome heads, malformed trichomes, misshapen leaves, leaves that are yellowish in color, brittle stems, an outwardly horizontal plant structure, and reduced flower mass and trichomes.

AMV, BCTV

A plant may be a *Cannabis* plant and a pathogen may be an Alfalfa Mosaic Virus (AMV) or a Beet Curly Top Virus (BCTV). Accordingly, in some embodiments, analyzing comprises detecting the presence, absence and/or amount of AMV or BCTV in a *Cannabis* plant. In some embodiments, analyzing comprises detecting the presence, absence and/or amount of HpLVd, AMV or BCTV or any combination thereof (e.g., HpLVd and AMV; or AMV and BCTV; or HpLVd and BCTV; or HpLVd and AMV and BCTV) in a *Cannabis* plant. Presence of AMV or BCTV in a *Cannabis* plant may be determined according to amplification products generated using one or more polynucleotide primer pairs that specifically amplify subsequences of an AMV or a BCTV (e.g., the polynucleotide primer pairs provided herein). In some embodiments, the presence of AMV or BCTV in a *Cannabis* plant may be determined according to one or more amplification products generated using one or more primer pairs that specifically amplify subsequences of AMV or BCTV, respectively (e.g., the polynucleotide primer pairs provided herein). In some embodiments, the presence of AMV or BCTV in a *Cannabis* plant may be determined according to two or more amplification products generated using two or more primer pairs that specifically amplify subsequences of AMV or BCTV, respectively (e.g., the polynucleotide primer pairs provided herein). In some embodiments, the presence of AMV or BCTV in a *Cannabis* plant may be determined according to three or more amplification products generated using three or more primer pairs that specifically amplify subsequences of AMV or BCTV, respectively (e.g., the polynucleotide primer pairs provided herein). In some embodiments, the presence of AMV or BCTV in a *Cannabis* plant may be determined according to four or more amplification products generated using four or more primer pairs that specifically amplify subsequences of AMV or BCTV, respectively (e.g., the polynucleotide primer pairs provided herein). In some embodiments, the presence of AMV or BCTV in a *Cannabis* plant may be determined according to five or more amplification products generated using five or more primer pairs that specifically amplify subsequences of AMV or BCTV, respectively (e.g., the polynucleotide primer pairs provided herein). In some embodiments, the presence of AMV or BCTV in a *Cannabis* plant may be determined according to six or more amplification products generated using six or more primer pairs that specifically amplify subsequences of AMV or BCTV, respectively (e.g., the polynucleotide primer pairs provided herein). In some embodiments, the presence of AMV or BCTV in a *Cannabis* plant may be determined according to seven or more amplification products generated using seven or more primer pairs that specifically amplify subsequences of AMV or BCTV, respectively (e.g., the polynucleotide primer pairs provided herein). In some embodiments, the presence of AMV or BCTV in a *Cannabis* plant may be determined according to eight or more amplification products generated using eight or more primer pairs that specifically amplify subsequences of AMV or BCTV, respectively (e.g., the polynucleotide primer pairs provided herein). In some embodiments, the presence of AMV or BCTV in a *Cannabis* plant may be determined according to nine or more amplification products generated using nine or more primer pairs that specifically amplify subsequences of AMV or BCTV, respectively (e.g., the polynucleotide primer pairs provided herein). In some embodiments, the presence of AMV or BCTV in a *Cannabis* plant may be determined according to ten or more amplification products generated using ten or more primer pairs that specifically amplify subsequences of AMV or BCTV, respectively (e.g., the polynucleotide primer pairs provided herein).

In embodiments, analyzing comprises detecting one or more variants. A variant generally refers to a change in the sequence of the nucleic acid and/or proteins encoded by the nucleic acid, such as an insertion, deletion, or substitution (mutation). In some embodiments, analyzing comprises detecting one or more genotypes in AMV or BCTV. A genotype generally refers to a part of the genetic information of an organism or pathogen (e.g., viroid), which may determine one or more of its characteristics or traits (phenotypes). A genotype of a virus may refer to a particular mutation or a combination of mutations, a genetic variation or a combination or genetic variations, and/or an allele or a combination of alleles. A genotype may specify whether an organism or pathogen has a reference allele or an alternate allele at a particular locus. In some embodiments, analyzing comprises detecting a genetic variation in one or more of HpLVd, AMV and BCTV. A genotype for HpLVd may specify a reference allele for a particular locus in the HpLVd genome. A reference allele may refer to a nucleotide present at a particular position as provided in SEQ ID NO:1. A genotype for a HpLVd may specify an alternate allele for a particular locus in the HpLVd genome. An alternate allele may refer to a variant nucleotide present at a particular position in SEQ ID NO:1 (i.e., a nucleotide that is different from the nucleotide at that position in SEQ ID NO:1).

A genotype for AMV may specify a reference allele for a particular locus in the AMV genome. A reference allele may refer to a nucleotide present at a particular position as provided in SEQ ID NO:91. A genotype for a AMV may specify an alternate allele for a particular locus in the AMV genome. An alternate allele may refer to a variant nucleotide present at a particular position in SEQ ID NO:91 (i.e., a nucleotide that is different from the nucleotide at that position in SEQ ID NO:91). A genotype for BCTV may specify a reference allele for a particular locus in the BCTV genome. A reference allele may refer to a nucleotide present at a particular position as provided in one or more of SEQ ID NOS:110, 112, 114, 116, 118 and 120. A genotype for a BCTV may specify an alternate allele for a particular locus in the BCTV genome. An alternate allele may refer to a variant nucleotide present at a particular position in one or more of SEQ ID NOS:110, 112, 114, 116, 118 and 120 (i.e., a nucleotide that is different from the nucleotide at the corresponding position in SEQ ID NOS:110, 112, 114, 116, 118 and 120, respectively).

Any suitable method for genotype assessment may be used for detecting a genetic variation in a genome of a pathogen, such as, for example, nucleic acid sequencing (examples of which are described herein) and/or a high resolution melting (HRM) assay described herein. Generally, a sequencing process and/or an HRM assay are performed in conjunction with a nucleic acid amplification method described herein (e.g., using the amplification primers provided herein). In some embodiments, one or more genetic variations may be determined according to the presence and/or absence of amplification products generated using certain amplification primers provided herein.

Also provided herein, in certain aspects, are multiplexed methods of determining the presence, absence and/or amount of one or more pathogens in one or more plant cultivars. In certain aspects, the multiplexed method comprises one or more of:

(1) determining the presence, absence and/or amount of more than one non-overlapping amplicon of a pathogen that may have infected a plant cultivar;
(2) determining the presence, absence and/or amount of more than one pathogen that may have infected a plant cultivar by determining the presence, absence and/or amount of one or more amplicons of each pathogen;
(3) determining the presence, absence and/or amount of one or more pathogens in a plurality of plant cultivars;
(4) quantifying an amplicon of a pathogen using more than one non-overlapping polynucleotide probe.

Any of the plant pathogens described herein and known to those of skill in the art can be analyzed in the multiplexed methods provided herein. In embodiments, the multiplexed methods provided herein can be used to analyze more than one pathogen, where the one or more, two or more or three or more pathogens analyzed are selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV). In certain embodiments, the multiplexed methods provided herein can be used to analyze more than one pathogen, where one or more, two or more or three or more pathogens analyzed are selected from among Hops Latent Viroid (HpLVd), Alfalfa Mosaic Virus (AMV) and Beet Curly Top Virus (BCTV). In any of the multiplexed methods provided herein, a positive control amplicon can be generated using a polynucleotide primer pair that is capable of specifically hybridizing to and amplifying a subsequence of the nucleic acid of the plant genome, or to a complement thereof, wherein the subsequence of the nucleic acid of the plant genome, or the complement thereof, is non-identical to any subsequence of the nucleic acid of the pathogen, or to any complement thereof; and determining the presence, absence and/or amount of at least one amplicon that is an amplification product of the polynucleotide primer pair that is capable of specifically hybridizing to and amplifying a subsequence of the nucleic acid of the plant genome, thereby determining whether the amplification conditions are effective for generating amplicons. In embodiments, the subsequence of the nucleic acid of the plant genome comprises all or part of a gene selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin. In certain embodiments, the subsequence of the nucleic acid of the plant genome comprises all or part of the 26SrRNA gene.

Examples of configurations of a multiplexed method are provided below. These examples depict various combinations for determining the presence, absence and/or amount of one or more pathogens selected from among HpLVd, AMV and BCTV, with or without and an internal (plant genome specific) positive control (IPC), with each amplicon and/or polynucleotide probe uniquely labeled, such as with a unique fluorescent label.

Multiplex 1:
HpLVd: B-fwd (SEQ ID NO:4) with F-rev (SEQ ID NO:12) using Probe 1, 2, 3, 4, or 5 (SEQ ID NOS:16-20)
AMV: A-fwd (SEQ ID NO:80) with A-rev (SEQ ID NO:81) with Probe A (SEQ ID NO:87)
BCTV: PE_RE_fwd (SEQ ID NO:102) with PE_RE_Rev (SEQ ID NO:103) and PE_RE_Probe (SEQ ID NO:104)
IPC: 26S rRNA-fwd (SEQ ID NO:107) with 26S rRNA-rev (SEQ ID NO:108) and 26S rRNA Probe (SEQ ID NO:109)

Multiplex 2:
HpLVd: C-fwd (SEQ ID NO:6) with E-Rev (SEQ ID NO:10) using Probe 1, 3, or 5 (SEQ ID NOS: 16, 18 and 20, respectively)
AMV: B-fwd (SEQ ID NO:82) with B-rev (SEQ ID NO:83) with Probe B (SEQ ID NO:89)
BCTV: RCRI_CCR_Fwd (SEQ ID NO:99) with Degen_RCRI_CCR_Rev (SEQ ID NO:100) with RCRI_C-CR_Probe (SEQ ID NO:101)
IPC: 26S rRNA-fwd (SEQ ID NO:107) with 26S rRNA-rev (SEQ ID NO:108) and 26S rRNA Probe (SEQ ID NO:109)

Multiplex 3:
HpLVd: D-fwd (SEQ ID NO:9) with D-rev (SEQ ID NO:8) using Probe 1, 3, or 5 (SEQ ID NOS: 16, 18 and 20, respectively)
AMV: A-fwd (SEQ ID NO:80) with C-rev (SEQ ID NO:84) with Probe A (SEQ ID NO:87) or B (SEQ ID NO:89)
BCTV: DRP_MP_Fwd (SEQ ID NO:93) with DRP_MP_Rev (SEQ ID NO:94) using DRP_MP_Probe (SEQ ID NO:95)
IPC: 26S rRNA-fwd (SEQ ID NO:107) with 26S rRNA-rev (SEQ ID NO:108) and 26S rRNA Probe (SEQ ID NO:109)

In embodiments, a single pathogen can be analyzed in a multiplexed format using more than one set of polynucleotide primer pairs. Examples of this configuration are depicted below:

Multiplex 4 (Pathogen—HpLVd):
B-fwd (SEQ ID NO:4) with F-rev (SEQ ID NO:12) using Probe 1, 2, 3, 4, or 5 (SEQ ID NOS:16-20)
E-fwd (SEQ ID NO:11) with E-Rev (SEQ ID NO:10) using Probe 3 or 5 (SEQ ID NO:18 or 20, respectively)
D-fwd (SEQ ID NO:9) with D-rev (SEQ ID NO:8) using Probe 1, 3, or 5 (SEQ ID NOS: 16, 18 and 20, respectively)
IPC: 26S rRNA-fwd (SEQ ID NO:107) with 26S rRNA-rev (SEQ ID NO:108) and 26S rRNA Probe (SEQ ID NO:109)

Multiplex 5 (Pathogen—HpLVd):
F-fwd (SEQ ID NO:13) with F-rev (SEQ ID NO:12) using Probe 3 or 5 (SEQ ID NO:18 or 20, respectively)
D-fwd (SEQ ID NO:9) with D-rev (SEQ ID NO:8) using Probe 1, 3, or 5 (SEQ ID NOS: 16, 18 and 20, respectively)
B-fwd (SEQ ID NO:4) with B-rev (SEQ ID NO:5) using Probe 2 or 4 (SEQ ID NO:17 or 19, respectively)

Multiplex 6 (Pathogen—AMV):
A-fwd (SEQ ID NO:80) with A-rev (SEQ ID NO:81) with Probe A (SEQ ID NO:87)
B-fwd (SEQ ID NO:82) with B-rev (SEQ ID NO:83) with Probe B (SEQ ID NO:89)
IPC: 26S rRNA-fwd (SEQ ID NO:107) with 26S rRNA-rev (SEQ ID NO:108) and 26S rRNA Probe (SEQ ID NO:109)

Multiplex 7 (Pathogen—BCTV): (DNA virus, therefore, could be run on cDNA as RT-qPCR multiplex or on gDNA (genomic DNA) as qPCR multiplex)

PE_RE_fwd (SEQ ID NO:102) with PE_RE_Rev (SEQ ID NO:103) and PE_RE_Probe (SEQ ID NO:104)

RCRI_CCR_Fwd (SEQ ID NO:99) with Degen_R-CRI_CCR_Rev (SEQ ID NO:100) with RCRI_CCR_Probe (SEQ ID NO:101)

DRP_MP_Fwd (SEQ ID NO:93) with DRP_MP_Rev (SEQ ID NO:94) using DRP_MP_Probe (SEQ ID NO:95)

IPC: 26S rRNA-fwd (SEQ ID NO:107) with 26S rRNA-rev (SEQ ID NO:108) and 26S rRNA Probe (SEQ ID NO:109)

In certain embodiments, more than one pathogen can be analyzed in a multiplexed format using more than one set of polynucleotide primer pairs targeting unique regions with uniquely labeled probes as depicted below. In embodiments, an IPC may not be analyzed in the multiplex.

Multiplex 8 (Pathogens—BCTV and HpLVd):
BCTV-1: PE_RE_fwd (SEQ ID NO:102) with PE_RE_Rev (SEQ ID NO:103) and PE_RE_Probe (SEQ ID NO:104)
BCTV-2: RCRI_CCR_Fwd (SEQ ID NO:99) with Degen_RCRI_CCR_Rev (SEQ ID NO:100) with RCRI_CR_Probe (SEQ ID NO:101)
HpLVd-1: B-fwd (SEQ ID NO:4) with F-rev (SEQ ID NO:12) using Probe 1, 2, 3, 4, or 5 (SEQ ID NOS:16-20)
HpLVd-2: D-fwd (SEQ ID NO:9) with D-rev (SEQ ID NO:8) using Probe 1, 3, or 5 (SEQ ID NOS: 16, 18 and 20, respectively)

Multiplex 9 (Pathogens—BCTV and AMV):
BCTV-1: PE_RE_fwd (SEQ ID NO:102) with PE_RE_Rev (SEQ ID NO:103) and PE_RE_Probe (SEQ ID NO:104)
BCTV-2: RCRI_CCR_Fwd (SEQ ID NO:99) with Degen_RCRI_CCR_Rev (SEQ ID NO:100) with RCRI_CR_Probe (SEQ ID NO:101)
AMV-1: A-fwd (SEQ ID NO:80) with A-rev (SEQ ID NO:81) with Probe A (SEQ ID NO:87)
AMV-2: B-fwd (SEQ ID NO:82) with B-rev (SEQ ID NO:83) with Probe B (SEQ ID NO:89)

Multiplex 10 (Pathogens—HpLVd and AMV):
HpLVd-1: B-fwd (SEQ ID NO:4) with F-rev (SEQ ID NO:12) using Probe 1, 2, 3, 4, or 5 (SEQ ID NOS:16-20)
HpLVd-2: D-fwd (SEQ ID NO:9) with D-rev (SEQ ID NO:8) using Probe 1, 3, or 5 (SEQ ID NOS: 16, 18 and 20, respectively)
AMV-1: A-fwd (SEQ ID NO:80) with A-rev (SEQ ID NO:81) with Probe A (SEQ ID NO:87)
AMV-2: B-fwd (SEQ ID NO:82) with B-rev (SEQ ID NO:83) with Probe B (SEQ ID NO:89)

In certain embodiments, the multiplexed methods provided herein include amplifying more than one non-overlapping subsequences of the genome of a pathogen, thereby generating more than one amplicon and providing additional verification regarding the presence, absence and/or amount of the pathogen. Differences in Cq values for each of the amplicons may provide information regarding the presence of a variant of the pathogen and/or the presence of a change in genotype when compared to the nucleic acid and/or genotype of the wild-type pathogen. Examples of such "multi-amplicon" multiplex reactions are depicted below:

Multiplex 11 (Pathogen—AMV):
AMV-A-Fwd (SEQ ID NO:80) with AMV-C-Rev (SEQ ID NO:84) using Probe A-degen (SEQ ID NO:88)
AMV-D-Fwd (SEQ ID NO:85) with AMV-D-Rev (SEQ ID NO:86) using Probe D (SEQ ID NO:90)

OR

AMV-A-Fwd (SEQ ID NO:80) with AMV-B-Rev (SEQ ID NO:83) using Probe B (SEQ ID NO:89)
AMV-D-Fwd (SEQ ID NO:85) with AMV-D-Rev (SEQ ID NO:86) using Probe D (SEQ ID NO:90)

Multiplex 12 (Pathogen—BCTV):
Fwd_PE_RCRI (SEQ ID NO:96) with Degen_Rev_PE_RCRI (SEQ ID NO:97) using Degen_Probe_PE_RCRI (SEQ ID NO:98)
Fwd_RCRI_CCR (SEQ ID NO:99) with Degen_Rev_RCRI_CCR (SEQ ID NO:100) using Probe_RCRI_CCR (SEQ ID NO:101)

In certain embodiments, the multiplexed methods provided herein include using more than one non-overlapping polynucleotide probe to quantitate a single amplicon of a plant pathogen. In embodiments, the relative Cq values for each polynucleotide probe can indicate whether or not genomic variations (insertions, deletions, mutations) are present within the amplicon. Examples of such multiplex reactions are depicted below:

Multiplex 13 (Pathogen—BCTV):
Fwd_DRP_MP (SEQ ID NO:93) with Rev-2_DRP_MP_Degen (SEQ ID NO:105) using Probe-2_DRP_MP_Degen (SEQ ID NO:106)
DRP_MP_Fwd (SEQ ID NO:93) with DRP_MP_Rev (SEQ ID NO:94) using DRP_MP_Probe (SEQ ID NO:95)

Multiplex 14 (Pathogen—AMV):
AMV-A-Fwd (SEQ ID NO:80) with AMV-C-Rev (SEQ ID NO:84) using Probe A-degen (SEQ ID NO:88) & Probe B (SEQ ID NO:89)

OR

AMV-A-Fwd (SEQ ID NO:80) with AMV-B-Rev (SEQ ID NO:83) using Probe A-degen (SEQ ID NO:88) & Probe B (SEQ ID NO:89)

In certain embodiments, when the pathogen is HpLVd, the multiplexed methods provided herein can determine the extent of mutation in the genome of the viroid (e.g., due to heating) by comparing Cq values of a polynucleotide probe used to quantify an amplicon obtained using a thermomutant specific pair of polynucleotide primers and a polynucleotide probe used to quantify an amplicon obtained using a thermomutant resistant pair of polynucleotide primers. Examples of such multiplexing reactions are depicted below:

Multiplex 15 (Pathogen—HpLVd):
HpLVd_1-Fwd (SEQ ID NO:77) with HpLVd_1-rev (SEQ ID NO:78) using HpLVd_1 Probe (SEQ ID NO:79) (Thermomutant-Specific)
F-Fwd (SEQ ID NO:13) with F-Rev (SEQ ID NO:12) using Probes 3 and/or 5 (SEQ ID NOS:18 and/or 20, respectively) (Thermomutant-Resistant)

OR

HpLVd_1-Fwd (SEQ ID NO:77) with HpLVd_1-rev (SEQ ID NO:78) using HpLVd_1 Probe (SEQ ID NO:79) (Thermomutant-Specific)
E-Fwd (SEQ ID NO:11) with E-Rev (SEQ ID NO:10) using Probes 3 and/or 5 (SEQ ID NOS:18 and/or 20, respectively) (Thermomutant-Resistant)

Multiplex 16 (Pathogen—HpLVd):
E-Fwd (SEQ ID NO:11) with E-Rev (SEQ ID NO:10) using Probes 3 and 5 (SEQ ID NOS:18 and 20, respectively) (Thermomutant-Resistant)

OR

F-Fwd (SEQ ID NO:13) with F-Rev (SEQ ID NO:12) using Probes 3 and 5 (SEQ ID NOS:18 and 20, respectively)

(Thermomutant-Resistant)

OR (for Triplicate Verification)

B-Fwd (SEQ ID NO:4) with F-rev (SEQ ID NO:12) using Probe combinations (2, 3, & 5 (SEQ ID NOS:17, 18 and 20, respectively) OR 1, 4, & 5 (SEQ ID NOS:16, 19 and 20, respectively)).

Samples

Provided herein are methods and compositions for processing, preparing, and/or analyzing nucleic acid. Nucleic acid or a nucleic acid mixture utilized in methods and compositions described herein may be isolated from a sample (e.g., a test sample) obtained from a plant. A plant can be any plant capable of being infected by a hops latent viroid (HpLVd) (e.g., *Humulus lupulus* (hop) plant, *Cannabis* plant). A plant can be any plant capable of being infected by a plant pathogen. A plant can be any plant capable of being infected by one or more pathogen (plant virus) selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

The term *Cannabis* generally refers to a genus of flowering plants in the family Cannabaceae, which contains at least 3 species: *Cannabis sativa, Cannabis indica,* and *Cannabis ruderalis*. A plant may be a plant infected with HpLVd or other plant pathogen, a plant suspected of being infected with HpLVd or other plant pathogen, a plant treated for an HpLVd or other pathogenic infection (e.g., heat treated), a plant recovering from an HpLVd or other pathogenic infection, a plant with a history of HpLVd infections, a plant obtaining an HpLVd or other pathogenic screen, a plant sharing a cultivation space with another plant infected with HpLVd or other plant pathogen, a plant grown in a cultivation space with a history of HpLVd or other pathogenic infections, a plant derived from a plant infected with HpLVd (e.g., derived from a cutting of a plant infected with HpLVd) or other plant pathogens, a plant subjected to a cleaning process, and/or a cutting or explant thereof. The term cleaning generally refers to a process of removing one or more contaminants from a plant. If the contaminant is a pathogen (e.g., HpLVd, AMV, BCTV), example methods include one or more of thermotherapy of meristems, chemotherapy, meristem-tip culture, and use of chemicals in a media.

In some embodiments, a plant may be a cutting or explant of a whole plant. The term cutting generally refers to a section of a plant that is the starting material for vegetative propagation (i.e., asexual plant reproduction). The term explant, with reference to plant tissue culture, generally refers to living plant tissue that is removed from the natural site of growth and placed in sterile medium for culture. This can be of any tissue type such as leaves, roots, stems, or any portion taken from a plant and used to initiate tissue culture.

A nucleic acid sample may be isolated or obtained from any type of suitable biological (i.e., plant) specimen or sample (e.g., a test sample). A nucleic acid sample may be isolated or obtained from a single plant cell, a plurality of plant cells (e.g., cultured plant cells), plant cell culture media, conditioned plant cell culture media, or plant tissue (e.g., leaves, roots, stems).

A sample may be heterogeneous. For example, a sample may include more than one cell type and/or one or more nucleic acid species. In some instances, a sample may include host plant nucleic acid and pathogen nucleic acid. In some instances, a sample may include nucleic acid from a *Cannabis* genome and nucleic acid from the genome of a plant pathogen, such as an HpLVd, AMV or BCTV genome. In some instances, a sample may include a minority nucleic acid species and a majority nucleic acid species. In some instances, a sample may include plant cells and/or nucleic acid from a single plant or may include plant cells and/or nucleic acid from multiple plants.

Nucleic Acid

Provided herein are methods and compositions for processing, preparing, and/or analyzing nucleic acid. The terms nucleic acid(s), nucleic acid molecule(s), nucleic acid fragment(s), target nucleic acid(s), nucleic acid template(s), template nucleic acid(s), nucleic acid target(s), target nucleic acid(s), polynucleotide(s), polynucleotide fragment(s), target polynucleotide(s), polynucleotide target(s), and the like may be used interchangeably throughout the disclosure. The terms refer to nucleic acids of any composition from, such as DNA (e.g., complementary DNA (cDNA; synthesized from any RNA or DNA of interest), genomic DNA (gDNA), genomic DNA fragments, mitochondrial DNA (mtDNA), recombinant DNA (e.g., plasmid DNA), and the like), RNA (e.g., message RNA (mRNA), short inhibitory RNA (siRNA), ribosomal RNA (rRNA), transfer RNA (tRNA), microRNA, transacting small interfering RNA (ta-siRNA), natural small interfering RNA (nat-siRNA), small nucleolar RNA (snoRNA), small nuclear RNA (snRNA), long non-coding RNA (lncRNA), non-coding RNA (ncRNA), transfer-messenger RNA (tmRNA), precursor messenger RNA (pre-mRNA), small Cajal body-specific RNA (scaRNA), piwi-interacting RNA (piRNA), endoribonuclease-prepared siRNA (esiRNA), small temporal RNA (stRNA), signal recognition RNA, telomere RNA, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plant, a viroid, a plasmid, autonomously replicating sequence (ARS), mitochondria, centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid may be used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense," "plus" strand or "minus" strand, "forward" reading frame or "reverse" reading frame) and double-stranded polynucleotides. The term "gene" refers to a section of DNA involved in producing a polypeptide chain; and generally includes regions preceding and following the coding region (leader and trailer) involved in the transcription/translation of the gene product and the regulation of the transcription/translation, as well as intervening sequences (introns) between individual coding regions (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

Target nucleic acids may be any nucleic acids of interest. Nucleic acids may be polymers of any length composed of deoxyribonucleotides (i.e., DNA bases), ribonucleotides (i.e., RNA bases), or combinations thereof, e.g., 10 bases or longer, 20 bases or longer, 50 bases or longer, 100 bases or longer, 200 bases or longer, 300 bases or longer, 400 bases or longer, 500 bases or longer, 1000 bases or longer, 2000 bases or longer, 3000 bases or longer, 4000 bases or longer, 5000 bases or longer. In certain aspects, nucleic acids are polymers composed of deoxyribonucleotides (i.e., DNA bases), ribonucleotides (i.e., RNA bases), or combinations thereof, e.g., 10 bases or less, 20 bases or less, 50 bases or less, 100 bases or less, 200 bases or less, 300 bases or less, 400 bases or less, 500 bases or less, 1000 bases or less, 2000 bases or less, 3000 bases or less, 4000 bases or less, or 5000 bases or less.

Nucleic acid may be single or double stranded. Single stranded DNA (ssDNA), for example, can be generated by denaturing double stranded DNA by heating or by treatment with alkali, for example. Accordingly, in some embodiments, ssDNA is derived from double-stranded DNA (dsDNA).

Nucleic acid (e.g., nucleic acid targets, polynucleotides, primers, polynucleotide primers, polynucleotide primer pairs, sequences, and subsequences) may be described herein as being complementary to another nucleic acid, hybridizing to another nucleic acid, and/or being capable of hybridizing to another nucleic acid. The terms "complementary" or "complementarity" or "hybridization" generally refer to a nucleotide sequence that base-pairs by non-covalent bonds to a region of a nucleic acid (e.g., a primer that hybridizes to a subsequence of HpLVd or other plant pathogen, a primer that is complementary to a subsequence of HpLVd or other plant pathogen). In the canonical Watson-Crick base pairing, adenine (A) forms a base pair with thymine (T), and guanine (G) pairs with cytosine (C) in DNA. In RNA, thymine (T) is replaced by uracil (U). Thus, A is complementary to T and G is complementary to C. In RNA, A is complementary to U and vice versa. In a DNA-RNA duplex, A (in a DNA strand) is complementary to U (in an RNA strand). Typically, "complementary" or "complementarity" or "hybridize" or "capable of hybridizing" refers to a nucleotide sequence that is at least partially complementary. These terms may also encompass duplexes that are fully complementary such that every nucleotide in one strand is complementary or hybridizes to every nucleotide in the other strand in corresponding positions.

In certain instances, a nucleotide sequence may be partially complementary to a target, in which not all nucleotides are complementary to every nucleotide in the target nucleic acid in all the corresponding positions. For example, a primer may be perfectly (i.e., 100%) complementary to an HpLVd or other plant pathogen subsequence, or a primer may share some degree of complementarity to an HpLVd or other plant pathogen subsequence which is less than perfect (e.g., 70%, 75%, 85%, 90%, 95%, 99%). In some embodiments, a primer (e.g., a thermomutant-resistant primer) is 100% complementary to an HpLVd subsequence. In some embodiments, a plurality of primers (e.g., a plurality of thermomutant-resistant primers) are 100% complementary to HpLVd subsequences.

The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions× 100). When a position in one sequence is occupied by the same nucleotide as the corresponding position in the other sequence, then the molecules are identical at that position.

In some embodiments, nucleic acids in a mixture of nucleic acids are analyzed. A mixture of nucleic acids can comprise two or more nucleic acid species having the same or different nucleotide sequences, different lengths, different origins (e.g., genomic origins, cell or tissue origins, host vs. pathogen, sample origins, subject origins, and the like), different amplification products (e.g., amplification products generated from different sets of primer pairs), or combinations thereof. In some embodiments, a mixture of nucleic acids comprises a plurality amplification product species generated from different sets of primer pairs (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more amplification product species). In some embodiments, a mixture of nucleic acids comprises single-stranded nucleic acid and double-stranded nucleic acid. In some embodiment, a mixture of nucleic acids comprises DNA and RNA. In some embodiment, a mixture of nucleic acids comprises ribosomal RNA (rRNA) and messenger RNA (mRNA). Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be derived from one or more plant sources by methods known in the art. Any suitable method can be used for isolating, extracting and/or purifying DNA from a plant sample, non-limiting examples of which include methods of DNA preparation (e.g., described by Sambrook and Russell, Molecular Cloning: A Laboratory Manual 3d ed., 2001), various commercially available reagents or kits, such as DNeasy®, RNeasy®, QIAprep®, QIAquick®, and QIAamp®, nucleic acid isolation/purification kits by Qiagen, Inc. (Germantown, Md.); DNAzol®, ChargeSwitch®, Purelink®, GeneCatcher® nucleic acid isolation/purification kits by Life Technologies, Inc. (Carlsbad, Calif.); NucleoMag®, NucleoSpin®, and Nucleo-Bond® nucleic acid isolation/purification kits by Clontech Laboratories, Inc. (Mountain View, Calif.), DNA/RNA extraction kits from Zymo Research (e.g., ZYMOBIOMICS DNA Mini Kit, ZYMOBIOMICS DNA/RNA Miniprep Kit, ZYMOCLEAN gel DNA recovery); the like or combinations thereof.

Nucleic acid may be provided for conducting methods described herein with or without processing of the sample(s) containing the nucleic acid. In some embodiments, nucleic acid is provided for conducting methods described herein after processing of the sample(s) containing the nucleic acid. For example, a nucleic acid can be extracted, isolated, purified, partially purified and/or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a test subject (e.g., a plant). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. In certain examples, pathogen nucleic acid can be purified from a mixture comprising pathogen and host nucleic acid. In certain examples, HpLVd or other plant pathogen genomic DNA can be purified from a mixture comprising HpLVd or other plant pathogen genomic DNA and *Cannabis* genomic DNA. In some embodiments, nucleic acid is provided for conducting methods described herein without prior processing of the sample(s) containing the nucleic acid. For example, nucleic acid may be analyzed directly from a sample without prior extraction, purification, partial purification, and/or amplification.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. In some embodiments, a plant is exposed to thermotherapy (heat treatment) prior to providing nucleic acid for a method described herein. Nucleic acid may be provided in any suitable form useful for conducting an analysis (e.g., genotype analysis, sequence analysis).

Primers

Primers useful for detection, amplification, quantification, sequencing and/or analysis of nucleic acid are provided. The term "primer" as used herein refers to a nucleic acid that includes a nucleotide sequence capable of hybridizing or annealing to a target nucleic acid, at or near (e.g., adjacent to) a specific region of interest. Primers can allow for specific determination of a target nucleic acid nucleotide sequence or detection of the target nucleic acid (e.g., presence or absence of a sequence), or feature thereof, for example. A primer typically is a synthetic sequence. The term "specific" or "specificity," as used herein, refers to the binding or hybridization of one molecule to another molecule, such as a primer for a target polynucleotide. That is, "specific" or "specificity" refers to the recognition, contact, and formation of a stable complex between two molecules, as compared to substantially less recognition, contact, or complex formation of either of those two molecules with other molecules. As used herein, the terms "anneal" and "hybridize" refer to the formation of a stable complex between two molecules. The terms "primer," "polynucleotide," "oligo," or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 15, 16, 17, 18, 19, 20, 21, 22, 23, 24, 25, 26, 27, 28, 29 or 30 nucleotides in length, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of primers can be effected by native acrylamide gel electrophoresis or by anion-exchange high-performance liquid chromatography (HPLC), for example, as described in Pearson and Regnier, *J. Chrom.*, 255:137-149, 1983.

In some embodiments, a primer provided herein (e.g., a further primer herein) comprises a polynucleotide where one or more nucleotide positions contain a nonstandard nucleotide and/or a degenerate nucleotide. A nonstandard nucleotide may be, for example, a non-natural base, a modified base, or a universal base. A universal base is a base capable of indiscriminately base pairing with each of the four standard nucleotide bases: A, C, G and T. Universal bases that may be incorporated into a primer herein include, but are not limited to, inosine, deoxyinosine, 2'-deoxyinosine (dI, dInosine), nitroindole, 5-nitroindole, and 3-nitropyrrole (e.g., 5' nitroindole, deoxyinosine, deoxynebularine). A degenerate nucleotide typically refers to a mixture of nucleotides at a given position and may be represented by a letter other than A, T, G or C. For example, a degenerate nucleotide may be represented by R (A or G), Y (C or T), S (G or C), W (A or T), K (G or T), M (A or C), B (C or G or T), D (A or G or T), H (A or C or T), V (A or C or G), or N (any base), for example. Such symbols for degenerate nucleotides are part of the International Union of Pure and Applied Chemistry (IUPAC) standard nomenclature for nucleotide base sequence names and represent degenerate or nonstandard nucleotides that can bind multiple nucleotides. For example, an "M" in a primer or probe would include a mixture of A and C at that position, and thus could bind to either T or G in a complementary DNA strand. An "N" in a primer or probe would include a mixture of A, T, G and C at that position, and thus could bind to any nucleotide at that position in the complementary DNA strand.

All or a portion of a primer sequence may be complementary or substantially complementary to a target nucleic acid. As referred to herein, "substantially complementary" with respect to sequences refers to nucleotide sequences that will hybridize with each other. The stringency of the hybridization conditions can be altered to tolerate varying amounts of sequence mismatch. Included are target and primer sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more up to 100% complementary to each other.

Primers that are substantially complimentary to a target nucleic acid sequence are also substantially identical to the complement of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more up to 100% identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/ sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5 M sodium phosphate, 7% SDS at 65° C., followed by one or more washes at 0.2×SSC, 1% SDS at 65° C. Stringent hybridization temperatures can also be altered (i.e., lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile. Features of primers described herein may also apply to probes, such as, for example, the qPCR probes provided herein. The reverse complement of each primer and probe described herein also is contemplated herein.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a modification such as one or more nonstandard nucleotides, non-natural nucleotides, universal bases, degenerate nucleotides, inosines, abasic sites, locked nucleic acids, minor groove binders, duplex stabilizers (e.g., acridine, spermidine), Tm modifiers or any modifier that changes the binding properties of the primers or probes. A primer, in certain embodiments, may contain a detectable molecule or entity (e.g., a fluorophore, radioisotope, colorimetric agent, particle, enzyme, and the like).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are: optical properties, electrical properties, magnetic properties, chemical properties and time or speed through an opening of known size.

Amplification

Nucleic acids may be amplified under amplification conditions. The term "amplify," "amplification," "amplification reaction," "amplifying," "amplified," or "amplification conditions" as used herein refers to subjecting a target nucleic acid (e.g., HpLVd, AMV, BCTV genomic DNA) in a sample to a process that linearly or exponentially generates amplicon nucleic acids having the same or substantially the same nucleotide sequence as the target nucleic acid (e.g., HpLVd, AMV, BCTV genomic DNA), or part (i.e., subsequence) thereof. In certain embodiments, the term "amplified" or "amplification" or "amplification conditions" refers to a method that comprises a polymerase chain reaction (PCR). Nucleic acid may be amplified using a suitable amplification process. Nucleic acid amplification typically involves enzymatic synthesis of nucleic acid amplicons (copies), which contain a sequence complementary to a nucleotide sequence being amplified.

In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, for example, and also may reduce amplification biases due to nucleotide sequence or species abundance of the target. In some embodiments, a one-time primer extension may be used may be performed as a prelude to linear or exponential amplification.

Any suitable amplification technique can be utilized. Amplification of methods include, but are not limited to, polymerase chain reaction (PCR); ligation amplification (or ligase chain reaction (LCR)); amplification methods based on the use of Q-beta replicase or template-dependent polymerase (e.g., U.S. Patent Publication Number US20050287592); helicase-dependent isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA), and transcription-associated amplification (TAA). Non-limiting examples of PCR amplification methods include standard PCR, AFLP-PCR, allele-specific PCR, Alu-PCR, asymmetric PCR, colony PCR, hot start PCR, inverse PCR (IPCR), in situ PCR (ISH), intersequence-specific PCR (ISSR-PCR), long PCR, multiplex PCR, nested PCR, quantitative PCR (qPCR), reverse transcriptase PCR (RT-PCR), reverse transcriptase quantitative PCR (RT-qPCR), TAQMAN qPCR, real time PCR, single cell PCR, solid phase PCR, combinations thereof, and the like. Reagents and hardware for conducting PCR are commercially available.

A generalized description of an amplification process is as follows. Primers and target nucleic acid are contacted, and complementary sequences hybridize to one another, for example. Primers can hybridize to a target nucleic acid, at or near (e.g., adjacent to, abutting, and the like) a sequence of interest. A reaction mixture, containing components necessary for enzymatic functionality, is added to the primer-target nucleic acid hybrid, and amplification can occur under suitable conditions. Components of an amplification reaction may include, but are not limited to, e.g., primers (e.g., individual primers, primer pairs, a plurality of primer pairs, and the like) a polynucleotide template (e.g., target nucleic acid), polymerase, nucleotides, dNTPs and the like. In some embodiments, non-naturally occurring nucleotides or nucleotide analogs, such as analogs containing a detectable label (e.g., fluorescent or colorimetric label), may be used for example. Any suitable polymerase may be selected which may include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermo-stable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for transcription mediated amplification (TMA) reactions, for example.

PCR conditions can be dependent upon primer sequences, target abundance, and the desired amount of amplification, and therefore, any suitable PCR protocol may be selected. PCR is typically carried out as an automated process with a thermostable enzyme. In this process, the temperature of the reaction mixture is cycled through a denaturing step, a primer-annealing step, and an extension reaction step automatically. Some PCR protocols also include an activation step and a final extension step. Machines specifically adapted for this purpose are commercially available. A non-limiting example of a PCR protocol that may be suitable for embodiments described herein is as follows: treating the sample at 95° C. for 2 minutes; repeating 40 cycles of 95° C. for 15 seconds and 60° C. for 30 seconds. Additional examples of suitable PCR protocols are provided in Examples 1 and 2. A completed PCR reaction can optionally be kept at 4° C. until further action is desired. Multiple cycles frequently are performed using a commercially available thermal cycler. Suitable isothermal amplification processes also may be applied, in certain embodiments.

In some embodiments, an amplification product may include naturally occurring nucleotides, non-naturally occurring nucleotides, nucleotide analogs and the like and combinations of the foregoing. An amplification product often has a nucleotide sequence that is identical to or substantially identical to a sample nucleic acid nucleotide sequence or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

In some embodiments where a target nucleic acid is RNA, prior to the amplification step, a DNA copy (cDNA) of the RNA transcript of interest may be synthesized. A cDNA can be synthesized by reverse transcription, which can be carried out as a separate step, or in a homogeneous reverse transcription-polymerase chain reaction (RT-PCR), a modification of the polymerase chain reaction for amplifying RNA.

Amplification also can be accomplished using digital PCR, in certain embodiments. Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation).

Amplification reactions may be performed as individual amplification reactions, where one primer pair is used for each reaction and the presence or absence of one amplification product is detected. In some embodiments, multiple individual amplification reactions may be performed (i.e., carried out in separate containers) using a different set of primers for each reaction, and the presence or absence of an amplification product is detected for each individual reaction. In some embodiments, amplification reactions are performed as multiplex amplification reactions (i.e., a plurality of amplification reactions performed in a single container), where a plurality of primer pairs is used for the multiplex reaction, and the presence or absence of more than one amplification product is detected. Both individual amplification reactions and multiplex amplification reactions are contemplated for the primers provided herein.

In some embodiments, when the plant pathogen is HpLVd, a method herein comprises generating nucleic acid amplification products from a plant sample. Such method may comprise a) contacting nucleic acid of a plant sample with a first set of polynucleotide primers under amplification conditions, thereby generating a first set of amplification products, where i) the majority or all of the primers in the first set of polynucleotide primers hybridize to subsequences of SEQ ID NO:1 if present in the nucleic acid of the plant sample under the amplification conditions, ii) the subsequences of SEQ ID NO:1 to which the majority or all of the primers in the first set of polynucleotide primers hybridize under the amplification conditions contain no variant nucleotide position, and iii) each subsequence of SEQ ID NO:1 between the subsequences to which the primers in the first set of polynucleotide primers hybridize contain one or more variant nucleotide positions; and b) contacting the nucleic acid of the plant sample with a second set of polynucleotide primers under the amplification conditions, thereby generating a second set of amplification products, where i) the majority or all of the primers in the second set of polynucleotide primers hybridize to subsequences of SEQ ID NO:1 if present in the nucleic acid of the plant sample under the amplification conditions, and ii) the subsequences of SEQ ID NO:1 to which the majority or all of the primers in the second set of polynucleotide primers hybridize under the amplification conditions contain one or more variant nucleotide positions. In some embodiments, a method herein comprises analyzing the first and second sets of amplification products.

Quantitative PCR

In some embodiments, an amplification method comprises a quantifiable amplification method. For example, levels of HpLVd, AMV, BCTV or other plant pathogen may be measured using a quantitative PCR (qPCR) approach (e.g., on cDNA generated from RNA from a plant sample), or a reverse transcriptase quantitative PCR (RT-qPCR) approach (e.g., on RNA from a plant sample). Quantitative PCR (qPCR), which also may be referred to a real-time PCR, monitors the amplification of a targeted nucleic acid molecule during a PCR reaction (i.e., in real time). This method may be used quantitatively (quantitative real-time PCR) and semi-quantitatively (i.e., above/below a certain amount of nucleic acid molecules; semi-quantitative real-time PCR).

Methods for qPCR include use of non-specific fluorescent dyes that intercalate with double-stranded DNA, and sequence-specific DNA probes labelled with a fluorescent reporter, which generally allows detection after hybridization of the probe with its complementary sequence. Quantitative PCR methods typically are performed in a thermal cycler with the capacity to illuminate each sample with a beam of light of at least one specified wavelength and detect the fluorescence emitted by an excited fluorophore.

For non-specific detection, a DNA-binding dye binds to all double-stranded (ds) DNA during PCR. An increase in DNA product during PCR therefore leads to an increase in fluorescence intensity measured at each cycle. For qPCR using dsDNA dyes, the reaction typically is prepared like a basic PCR reaction, with the addition of fluorescent dsDNA dye. Then the reaction is run in a real-time PCR instrument, and after each cycle, the intensity of fluorescence is measured with a detector (the dye only fluoresces when bound to the dsDNA (i.e., the PCR product)). In certain applications, multiple target sequences may be monitored in a tube by using different types of dyes.

For specific detection, fluorescent reporter probes detect only the DNA containing the sequence complementary to the probe. Accordingly, use of the reporter probe increases specificity, and enables performing the technique even in the presence of other dsDNA. Using different types of labels, fluorescent probes may be used in multiplex assays for monitoring several target sequences in the same tube. This method typically uses a DNA-based probe with a fluorescent reporter at one end and a quencher of fluorescence at the opposite end of the probe. The close proximity of the reporter to the quencher prevents detection of its fluorescence. During PCR, the probe is broken down by the 5' to 3' exonuclease activity of the polymerase, which breaks the reporter-quencher proximity and thus allows unquenched emission of fluorescence, which can be detected after excitation with a laser. An increase in the product targeted by the reporter probe at each PCR cycle therefore causes a proportional increase in fluorescence due to the breakdown of the probe and release of the reporter.

In some embodiments, a method herein comprises contacting nucleic acid of a plant sample with one or more primer pairs and one or more quantitative PCR probes. Polynucleotide primers and polynucleotide probes can be designed and or used as provided herein, e.g., to determine the presence, absence and/or amount of a pathogen in a plant.

For example, when the pathogen is HpLVd, certain primers provided herein (e.g., primers provided in Table 1) may be used in combination with certain qPCR probes (e.g., probes provided in Table 5). Examples of specific combinations of primers and probes that can identify HpLVd in a plant sample are provided in Table 4. These combinations may be used on a cDNA template or an RNA template that is extracted from the plant. In some embodiments, one or more quantitative PCR probes are chosen from one or more of TCGTGCGCGGCGACCT (SEQ ID NO:16), CGGAGATCGAGCGCCAGTT (SEQ ID NO:17), TGCGCGGCGACCTGAAGT (SEQ ID NO:18), AGGCG- GAGATCGAGCGCCA (SEQ ID NO:19), and TCCTGCGTGGAACGGCTCC (SEQ ID NO:20). The reverse complement of each of the probes also is contemplated herein.

In some embodiments, a quantitative PCR probe (e.g., a probe set forth as SEQ ID NO:16, SEQ ID NO:17, SEQ ID NO:18, SEQ ID NO:19, and/or SEQ ID NO:20) comprises a polynucleotide where one or more nucleotide positions contain a nonstandard nucleotide and/or a degenerate nucleotide. Nonstandard nucleotides and degenerate nucleotide are described above. In some embodiments, a quantitative PCR probe (e.g., a probe set forth as SEQ ID NO:16, SEQ ID NO:17, SEQ ID NO:18, SEQ ID NO:19, and/or SEQ ID NO:20) comprises a polynucleotide where two or more nucleotide positions contain a nonstandard nucleotide and/or a degenerate nucleotide. In some embodiments, a quantitative PCR probe (e.g., a probe set forth as SEQ ID NO:16, SEQ ID NO:17, SEQ ID NO:18, SEQ ID NO:19, and/or SEQ ID NO:20) comprises a polynucleotide where three or more nucleotide positions contain a nonstandard nucleotide and/or a degenerate nucleotide. In some embodiments, a quantitative PCR probe (e.g., a probe set forth as SEQ ID NO:16, SEQ ID NO:17, SEQ ID NO:18, SEQ ID NO:19, and/or SEQ ID NO:20) comprises a polynucleotide where four or more nucleotide positions contain a nonstandard nucleotide and/or a degenerate nucleotide. In some embodiments, a quantitative PCR probe (e.g., a probe set forth as SEQ ID NO:16, SEQ ID NO:17, SEQ ID NO:18, SEQ ID NO:19, and/or SEQ ID NO:20) comprises a polynucleotide where five or more nucleotide positions contain a nonstandard nucleotide and/or a degenerate nucleotide.

Loop Mediated Isothermal Amplification (LAMP)

In some embodiments, an amplification method comprises loop mediated isothermal amplification (LAMP). Loop-mediated isothermal amplification (LAMP) is a single-tube technique useful for nucleic acid amplification. Reverse transcription loop-mediated isothermal amplification (RT-LAMP) combines LAMP with a reverse transcription step for the detection of RNA. LAMP is typically performed under isothermal conditions. In contrast to a polymerase chain reaction (PCR) technology, which is typically performed using a series of alternating temperature cycles, isothermal amplification is performed at a constant temperature, and does not require a thermal cycler.

In LAMP, a target sequence is amplified at a constant temperature (e.g., between about 60° C. to about 65° C.) using a plurality of primer pairs (e.g., two primer pairs, three primer pairs) and a polymerase (e.g., a polymerase with high strand displacement activity). In certain applications, four different primers may be used to amplify six distinct regions on a target sequence, for example, which may increase specificity. An additional pair of loop primers can further accelerate the reaction.

The amplification product can be detected via photometry (i.e., measuring the turbidity caused by magnesium pyrophosphate precipitate in solution as a byproduct of amplification). This generally allows for visualization by the naked eye or by photometric detection approaches (e.g., for small volumes). In certain applications, the reaction can be followed in real-time either by measuring turbidity or by fluorescence using intercalating dyes (e.g., SYTO 9, SYBR green). Certain dyes may be used to create a visible color change that can be seen with the naked eye without the need for specialized equipment. Dye molecules intercalate or directly label the DNA, and in turn can be correlated with the number of copies initially present. Accordingly, certain variations of LAMP may be quantitative. Detection of LAMP amplification products also may be achieved using manganese loaded calcein, which starts fluorescing upon complexation of manganese by pyrophosphate during in vitro DNA synthesis. Another method for visual detection of LAMP amplification products by the naked eye is based on the ability of the products to hybridize with complementary gold-bound single-stranded DNA, which prevents a red to purple-blue color change that would otherwise occur during salt-induced aggregation of the gold particles.

A number of LAMP visualization technologies are known to those of skill in the art (see, e.g., Fischbach et al., *Biotechniques,* 58(4):189-194 (2015), the contents of which are incorporated in their entirety by reference herein). Examples of such visualization reagents, summarized in the Table below from Fischbach et al., include magnesium pyrophosphate, hydroxynaphthol blue (HNB), calcein, SYBR Green I, EvaGreen and the nucleic acid-specific dye, berberine, which emits a fluorescent signal under UV light after a positive LAMP reaction.

| | Turbidity | Hydroxy-naphthol blue | Calcein | SYBR Green I | EvaGreen | Berberine |
|---|---|---|---|---|---|---|
| Substance | Mg-pyro-phosphate (Mg-PPi) | Hydroxy-naphthol blue (HNB) | Calcein AM + MnCl$_2$ | SYBR Green I | EvaGreen | Berberine-SO4 |
| Origin | Amplification product | Synthetic | Synthetic | Synthetic | Synthetic | Natural |
| Toxicity | None | May cause eye irritation | May be harmful to skin and eyes | Mutation enhancer | Possible carcinogen | May be toxic in high concentrations |
| Detection Mechanism | Insoluble complex; precipitation | Decrease of free Mg$^{2+}$ | Decrease of free Mn$^{2+}$ | dsDNA intercalation | dsDNA intercalation | Small groove intercalation |
| Readout | Turbidity Absorbance: 400 nm | Absorption Absorbance: 650 nm | Fluorescence Excitation: 495 nm Emission: 515 nm | Fluorescence Excitation: 494 nm Emission: 521 nm | Fluorescence Excitation: 500 nm Emission: 530 nm | Fluorescence Excitation: 450 nm Emission: 530 nm |
| Effect on amplification | None | None | Manganesse may inhibit reaction | Not inhibiting when used O 5-1× | Not inhibiting when used O 5.1× | Not inhibiting (≤180 µM) |
| One-pot real-time assay | + + | − | + + + | + + + + | + + + + | + + + + |
| Equipment for real-time detection | Turbidometer | − | Fluorometer with FAM filter | Fluorometer with FAM filter | Fluorometer with FAM filter | Fluorometer with FAM filter |

|  | Turbidity | Hydroxy-naphthol blue | Calcein | SYBR Green I | EvaGreen | Berberine |
|---|---|---|---|---|---|---|
| One-pot end point assay | + + + | + + + + | + + + + | − | − | + + + (UV light with low background signal) |
| Equipment for end point detection | None (cordless centrifuge) | None | UV lamp (optional) | Not applicable | Not applicable | UV lamp |
| Evaluation of results | + Turbid − Clear | + Sky blue − Violet | + Green − Orange | + Fluorescence signal − No signal | + Fluorescence signal − No signal | + Fluorescence signal − signal |
| Percentage of overall costs * | 0 | <0.1 | <0.1 | 26.01 | 1.18 | 0.82 |
| Relative sensitivity * * | + + + | + + + | + + + | + + + | + + + | + + + |
| Field applicability * * * | + + + | + + + + | + + + + | + + | + + | + + + + |

Summary of features relevant for in-the-field loop-mediated isothermal amplification (LAMP) assays tested for detection of potato spindle tuber viroid (PSTVd).
Number of "+" describes the applicability/relevance of the feature.
* Overall costs represent the basic chemicals of common suppliers for one LAMP reaction, depending on reaction volume.
* * In our assays. Analytical sensitivity may depend on LAMP setup and has to be optimized separately.
* * * Depending on visualization.

In some embodiments, a method herein comprises contacting nucleic acid of a plant sample with a set of loop mediated isothermal amplification (LAMP) primers. For example, when the pathogen is HpLVd, a method herein may comprise contacting nucleic acid of a plant sample with a set of loop mediated isothermal amplification (LAMP) primers chosen from the primer sets provided in Tables 6-9 herein. In some embodiments, a LAMP primer set comprises the polynucleotides of SEQ ID NO:21 to SEQ ID NO:29. In some embodiments, a LAMP primer set comprises the polynucleotides of SEQ ID NO:30 to SEQ ID NO:38. In some embodiments, a LAMP primer set comprises the polynucleotides of a primer set comprising the polynucleotides of SEQ ID NO:39 to SEQ ID NO:47. In some embodiments, a LAMP primer set comprises the polynucleotides of SEQ ID NO:48 to SEQ ID NO:56.

Detection of Amplification Products

Amplification products generated by a method herein may be detected by a suitable detection process. Non-limiting examples of methods of detection include electrophoresis, nucleic acid sequencing, mass spectrometry, mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), Molecular Inversion Probe (MIP) technology from Affymetrix, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, coded microspheres, template-directed incorporation (TDI), fluorescence polarization, colorimetric oligonucleotide ligation assay (OLA), sequence-coded OLA, microarray ligation, ligase chain reaction, padlock probes, invader assay, hybridization using at least one probe, hybridization using at least one fluorescently labeled probe, cloning and sequencing, the use of hybridization probes and quantitative real time polymerase chain reaction (QRT-PCR), digital PCR, nanopore sequencing, chips, MYBAIT (Arbor Biosciences), SNPCHIP, various microarray platforms, and combinations thereof.

In some embodiments, amplification products are detected using electrophoresis. Any suitable electrophoresis method, whereby amplified nucleic acids are separated by size, may be used in conjunction with the methods provided herein, which include, but are not limited to, standard electrophoretic techniques and specialized electrophoretic techniques, such as, for example capillary electrophoresis (e.g., Capillary Zone Electrophoresis (CZE), also known as free-solution CE (FSCE), Capillary Isoelectric Focusing (CIEF), Isotachophoresis (ITP), Electrokinetic Chromatography (EKC), Micellar Electrokinetic Capillary Chromatography (MECC OR MEKC), Micro Emulsion Electrokinetic Chromatography (MEEKC), Non-Aqueous Capillary Electrophoresis (NACE), and Capillary Electrochromatography (CEC)). A non-limiting standard electrophoresis example is presented as follows. After running an amplified nucleic acid sample in an agarose or polyacrylamide gel, the gel may be labeled (e.g., stained) with ethidium bromide (see, Sambrook and Russell, Molecular Cloning: A Laboratory Manual 3d ed., 2001). The presence of a band of the same size as the standard control is an indication of the presence of a target nucleic acid sequence, the amount of which may then be compared to the control based on the intensity of the band, thus detecting and quantifying the target sequence of interest. In some embodiments, where a plurality of primer pairs is used in an amplification reaction, multiple amplification products of varying size may be detected using electrophoresis.

High Resolution Melting (HRM)

In some embodiments, nucleic acid is analyzed using a high resolution melting (HRM) endpoint assay. In some embodiments, an analysis comprises performing a high resolution melting (HRM) endpoint assay on amplification products (e.g., amplification products generated using primers provided herein). In some embodiments, an analysis comprises performing a high resolution melting (HRM)

endpoint assay on nucleic acid in a mixture (e.g., a mixture of amplification products generated using a plurality of primer pairs).

High resolution melt or high resolution melting (HRM) analysis is a technique useful for the detection of mutations, polymorphisms, and epigenetic differences in double-stranded DNA. Typically, amplification (e.g., a polymerase chain reaction (PCR)) is performed prior to HRM analysis to amplify a DNA region in which a mutation of interest is located. The HRM process involves a precise warming of the amplification product from around 50° C. up to around 95° C. At some point during this process, the melting temperature of the amplicon is reached and the two strands of DNA separate (i.e., melt apart).

The separation of strands may be monitored in real-time (e.g., using a fluorescent dye). Dyes that may be used for HRM include intercalating dyes, which specifically bind to double-stranded DNA and emit fluorescence when bound to DNA. At the start of an HRM analysis there is a high level of fluorescence in the sample because of the billions of copies of the amplicon. However, as the sample is heated up and the two strands of the DNA melt apart, presence of double stranded DNA decreases, and thus the fluorescence is reduced. In certain configurations, an HRM machine has a camera that monitors this process by measuring the fluorescence. The machine can plot the data (e.g., as a graph sometimes referred to as a melt curve), showing the level of fluorescence vs. temperature.

The melting temperature of an amplification product at which the two DNA strands come apart is a predictable parameter, and typically is dependent on the DNA sequence of the amplicon. When comparing two samples from two different plants infected with HpLVd or other plant pathogen, for example, amplification products from both samples should have the same shaped melt curve. However, if one plant is infected with an HpLVd or other pathogen carrying a mutation in the amplified region, this will alter the temperature at which the DNA strands melt apart. Accordingly, the two melt curves will be different. The difference may be subtle, but because HRM machines typically are capable of monitoring the HRM process in high resolution, it is generally possible to accurately document these changes and therefore identify if a mutation is present or not.

In some embodiments, an analysis comprises detecting one or more genetic variations (e.g., single nucleotide substitutions) in a hops latent viroid or other pathogen according to results obtained from a high resolution melting (HRM) endpoint assay. In some embodiments, an analysis comprises detecting two or more genetic variations (e.g., single nucleotide substitutions) in a hops latent viroid or other pathogen according to results obtained from a high resolution melting (HRM) endpoint assay. In some embodiments, an analysis comprises detecting three or more genetic variations (e.g., single nucleotide substitutions) in a hops latent viroid or other pathogen according to results obtained from a high resolution melting (HRM) endpoint assay. In some embodiments, an analysis comprises detecting four or more genetic variations (e.g., single nucleotide substitutions) in a hops latent viroid or other pathogen according to results obtained from a high resolution melting (HRM) endpoint assay. In some embodiments, an analysis comprises detecting five or more genetic variations (e.g., single nucleotide substitutions) in a hops latent viroid or other pathogen according to results obtained from a high resolution melting (HRM) endpoint assay. In some embodiments, an analysis comprises detecting six or more genetic variations (e.g., single nucleotide substitutions) in a hops latent viroid or other pathogen according to results obtained from a high resolution melting (HRM) endpoint assay. In some embodiments, an analysis comprises detecting seven or more genetic variations (e.g., single nucleotide substitutions) in a hops latent viroid or other pathogen according to results obtained from a high resolution melting (HRM) endpoint assay. In some embodiments, an analysis comprises detecting eight or more genetic variations (e.g., single nucleotide substitutions) in a hops latent viroid or other pathogen according to results obtained from a high resolution melting (HRM) endpoint assay. In some embodiments, an analysis comprises detecting nine or more genetic variations (e.g., single nucleotide substitutions) in a hops latent viroid or other pathogen according to results obtained from a high resolution melting (HRM) endpoint assay. In some embodiments, an analysis comprises detecting ten or more genetic variations (e.g., single nucleotide substitutions) in a hops latent viroid or other pathogen according to results obtained from a high resolution melting (HRM) endpoint assay.

Nucleic Acid Sequencing

In some embodiments, nucleic acid is sequenced. In some embodiments, amplified subsequences of HpLVd, AMV, BCTV or other plant pathogens ("amplification products") are sequenced by a sequencing process. In some embodiments, the sequencing process generates sequence reads (or sequencing reads). In some embodiments, a method herein comprises determining the sequence of an HpLVd, AMV, BCTV or other plant pathogen subsequence based on the sequence reads. In some embodiments, a method herein comprises determining the sequence of an HpLVd, AMV, BCTV or other plant pathogen genome based on the sequence reads. In some embodiments, a method herein comprises determining one or more HpLVd, AMV, BCTV or other genotypes based on the sequence reads.

Nucleic acid may be sequenced using any suitable sequencing platform, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first-generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments, MPS sequencing methods utilize a targeted approach, where specific chromosomes, genes or regions of interest are sequenced. For example, a targeted approach may include targeting specific regions of an HpLVd, AMV, BCTV or other plant pathogen genome for sequencing. In certain embodiments, a non-targeted approach is used where most or all nucleic acids in a sample are sequenced, amplified and/or captured randomly.

Non-limiting examples of sequencing platforms include a sequencing platform provided by Illumina® (e.g., HiSeq™

HiSeq™ 2000, MiSeq™ Genome Analyzer™, and Genome Analyzer™ II sequencing systems); Oxford Nanopore™ Technologies (e.g., MinION sequencing system), Ion Torrent™ (e.g., Ion PGM™ and/or Ion Proton™ sequencing systems); Pacific Biosciences (e.g., PACBIO RS II sequencing system); Life Technologies™ (e.g., SOLiD sequencing system); Roche (e.g., 454 GS FLX+ and/or GS Junior sequencing systems); Helicos True Single Molecule Sequencing; Ion semiconductor-based sequencing (e.g., as developed by Life Technologies), WildFire, 5500, 5500xl W and/or 5500xl W Genetic Analyzer based technologies (e.g., as developed and sold by Life Technologies, U.S. Patent Application Publication No. 2013/0012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing; or any other suitable sequencing platform. Other sequencing methods that may be used to conduct methods herein include digital PCR, sequencing by hybridization, nanopore sequencing, chromosome-specific sequencing (e.g., using DANSR (digital analysis of selected regions) technology), MYBAIT (Arbor Biosciences), SNPCHIP, and microarray platforms.

In some embodiments, the sequencing process is a highly multiplexed sequencing process. In certain instances, a full or substantially full sequence is obtained and sometimes a partial sequence is obtained. Nucleic acid sequencing generally produces a collection of sequence reads. As used herein, "reads" (e.g., "a read," "a sequence read") are short sequences of nucleotides produced by any sequencing process described herein or known in the art. Reads can be generated from one end of nucleic acid fragments (single-end reads), and sometimes are generated from both ends of nucleic acid fragments (e.g., paired-end reads, double-end reads). In some embodiments, a sequencing process generates short sequencing reads or "short reads." In some embodiments, the nominal, average, mean or absolute length of short reads sometimes is about 10 continuous nucleotides to about 250 or more contiguous nucleotides. In some embodiments, the nominal, average, mean or absolute length of short reads sometimes is about 50 continuous nucleotides to about 150 or more contiguous nucleotides.

The length of a sequence read is often associated with the particular sequencing technology utilized. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more. In some embodiments, sequence reads are of a mean, median, average or absolute length of about 100 bp to about 200 bp.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid.

In certain embodiments, "obtaining" nucleic acid sequence reads of a sample from a plant and/or "obtaining" nucleic acid sequence reads from one or more amplification products can involve directly sequencing nucleic acid to obtain the sequence information. In some embodiments, "obtaining" can involve receiving sequence information obtained directly from a nucleic acid by another.

In some embodiments, some or all nucleic acids in a sample are enriched and/or amplified (e.g., non-specifically, or specifically using amplification primers described herein) prior to or during sequencing. In certain embodiments, specific nucleic acid species or subsets in a sample are enriched and/or amplified prior to or during sequencing. In some embodiments, nucleic acid from a pathogen may be enriched and/or amplified prior to or during sequencing, while nucleic acid from a host plant is not enriched and/or amplified prior to or during sequencing. For example, nucleic acid from the HpLVd, AMV, BCTV or other plant pathogen genome may be enriched and/or amplified prior to or during sequencing, while nucleic acid from the *cannabis* genome is not enriched and/or amplified prior to or during sequencing. In some embodiments, nucleic acids in a sample are not enriched and/or amplified prior to or during sequencing.

In some embodiments, one nucleic acid sample from one plant is sequenced. In certain embodiments, nucleic acids from each of two or more samples are sequenced, where samples are from one plant or from different plants. In certain embodiments, nucleic acid samples from two or more biological samples are pooled, where each biological sample is from one plant or two or more plants, and the pool is sequenced. In the latter embodiments, a nucleic acid sample from each biological sample often is identified by one or more unique identifiers.

A sequencing method may utilize identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments, the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8-lane flow cell. Similarly, multiplexing using 48 identifiers, for example, allows simultaneous analysis of 384 samples (e.g., equal to the number of wells in a 384 well microwell plate) in an 8-lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments, a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. For example, primers specific for the HpLVd, AMV, BCTV or other plant pathogen genome may be used for a targeted enrichment, amplification and/or sequencing approach. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase-based extension) using sequence-specific primers and/or primer sets (e.g., primers provided herein). Sequence specific anchors often can be used as sequence-specific primers.

In some embodiments, nucleic acid is sequenced and the sequencing product (e.g., a collection of sequence reads) is processed prior to, or in conjunction with, an analysis of the sequenced nucleic acid. For example, sequence reads may be processed according to one or more of the following: aligning, mapping, filtering, counting, normalizing, weighting, generating a profile, and the like, and combinations thereof. Certain processing steps may be performed in any order and certain processing steps may be repeated.

Classifications and Uses Thereof

Methods described herein can provide an outcome indicative of one or more characteristics of a sample or pathogen described above. In some embodiments, methods described herein can provide an outcome indicative of one or more characteristics of a plant. In some embodiments, methods described herein can provide an outcome indicative of one or more characteristics of a *cannabis* plant. In some embodiments, methods described herein can provide an outcome indicative of one or more characteristics of a pathogen. In some embodiments, methods described herein can provide an outcome indicative of one or more characteristics of an HpLVd variant, an AMV variant, a BCTV variant, or other plant pathogen variant. Methods described herein sometimes provide an outcome indicative of a phenotype and/or presence or absence of a pathogen for a test sample (e.g., providing an outcome determinative of the presence or absence of a pathogen and/or phenotype, and/or an amount of a pathogen). For example, methods described herein sometimes provide an outcome indicative of a phenotype (e.g., a phenotype expressed by the plant and associated with an HpLVd, AMV, BCTV or other plant pathogen infection) and/or presence or absence of an HpLVd, AMV, BCTV or other plant pathogen infection for a plant sample (e.g., providing an outcome determinative of the presence or absence of an HpLVd, AMV, BCTV or other plant pathogen infection and/or phenotype associated with an HpLVd, AMV, BCTV or other plant pathogen infection). An outcome often is part of a classification process, and a classification (e.g., classification of one or more characteristics of a sample; classification of one or more characteristics of a pathogen (e.g., HpLVd, AMV, BCTV or other plant pathogen); classification of one or more phenotypes associated with a pathogen (e.g., HpLVd, AMV, BCTV or other plant pathogen); classification of one or more phenotypes associated with a particular variant of a pathogen (e.g., an HpLVd, AMV, BCTV or other plant pathogen variant); presence or absence of a genotype, phenotype, genetic variation, and/or infection (e.g., an HpLVd, AMV, BCTV or other plant pathogen infection) for a test sample (e.g., a *Cannabis* plant sample); presence or absence of a genotype, phenotype, genetic variation, and/or genetic variation signature for a pathogen (e.g., HpLVd, AMV, BCTV or other plant pathogen)) sometimes is based on and/or includes an outcome. An outcome and/or classification sometimes is based on and/or includes a result of data processing for a test sample that facilitates determining one or more characteristics of a sample (e.g., a *Cannabis* plant sample) or pathogen (e.g., HpLVd, AMV, BCTV or other plant pathogen) and/or presence or absence of a genotype, phenotype, genetic variation, genetic alteration, genetic variation signature, and/or infection in a classification process (e.g., a statistic value). An outcome and/or classification sometimes includes or is based on a score determinative of, or a call of, one or more characteristics of a sample (e.g., a *Cannabis* plant sample) or pathogen (e.g., HpLVd, AMV, BCTV or other plant pathogen) and/or presence or absence of a genotype, phenotype, genetic variation, genetic alteration, genetic variation signature, and/or infection (e.g., an HpLVd, AMV, BCTV or other plant pathogen infection). In certain embodiments, an outcome and/or classification includes a conclusion that predicts and/or determines one or more characteristics of a sample (e.g., a *Cannabis* plant sample) or pathogen (e.g., HpLVd, AMV, BCTV or other plant pathogen) and/or presence or absence of a genotype, phenotype, genetic variation, genetic alteration, genetic variation signature, and/or infection (e.g., an HpLVd, AMV, BCTV or other plant pathogen infection) in a classification process.

Any suitable expression of an outcome and/or classification can be provided. An outcome and/or classification sometimes is based on and/or includes one or more numerical values generated using a processing method described herein in the context of one or more considerations of probability. Non-limiting examples of values that can be utilized include a sensitivity, specificity, standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, ploidy value, fitted minority species fraction, area ratio, median level, the like or combination thereof. In some embodiments, an outcome and/or classification comprises a read density, a read density profile and/or a plot (e.g., a profile plot). In certain embodiments, multiple values are analyzed together, sometimes in a profile for such values (e.g., z-score profile, p-value profile, chi value profile, phi value profile, result of a t-test, value profile, the like, or combination thereof). A consideration of probability can facilitate determining one or more characteristics of a sample or pathogen; whether a plant is at risk of having, or has, a genotype, phenotype, genetic variation and/or infection; whether a pathogen has a genotype, genetic variation, or genetic variation signature; and/or whether a plant has a phenotype associated with a particular pathogen variant or strain, and an outcome and/or classification determinative of the foregoing sometimes includes such a consideration. In some embodiments, a consideration of probability can facilitate determining one or more characteristics of a *Cannabis* plant sample or an HpLVd, AMV, BCTV or other plant pathogen variant or strain; whether a *cannabis* plant is at risk of having, or has, a genotype, phenotype, genetic variation and/or HpLVd, AMV, BCTV or other plant pathogen infection; whether an HpLVd, AMV, BCTV or other plant pathogen variant or strain has a genotype, genetic variation, or genetic variation signature; and/or whether a *cannabis* plant has a phenotype associated with a particular HpLVd, AMV, BCTV or other plant pathogen variant or strain, and an outcome and/or classification determinative of the foregoing sometimes includes such a consideration.

In certain embodiments, an outcome and/or classification is based on and/or includes a conclusion that predicts and/or determines a risk or probability of the presence or absence of a genotype, phenotype, genetic variation and/or infection for a test sample (e.g., a test sample from a *cannabis* plant). In certain embodiments, an outcome and/or classification is based on and/or includes a conclusion that predicts and/or determines a risk or probability of the presence or absence of a genotype, genetic variation, and/or genetic variation signature a pathogen (e.g., HpLVd, AMV, BCTV or other plant pathogen). A conclusion sometimes is based on a value determined from a data analysis method described herein (e.g., a statistics value indicative of probability, certainty and/or uncertainty (e.g., standard deviation, median absolute deviation (MAD), measure of certainty, measure of confidence, measure of certainty or confidence that a value obtained for a test sample or pathogen is inside or outside a particular range of values, measure of uncertainty, measure of uncertainty that a value obtained for a test sample or pathogen is inside or outside a particular range of values, coefficient of variation (CV), confidence level, confidence interval (e.g., about 95% confidence interval), standard score (e.g., z-score), chi value, phi value, result of a t-test, p-value, sensitivity, specificity, the like or combination thereof). An outcome and/or classification sometimes is expressed in a laboratory test report for particular test sample (e.g., a *cannabis* plant sample) as a probability (e.g., odds ratio, p-value), likelihood, or risk factor, associated with the presence or absence of a genotype, phenotype, genetic variation and/or infection. An outcome and/or classification sometimes is expressed in a laboratory test report for particular pathogen (e.g., HpLVd, AMV, BCTV or other plant pathogen) as a probability (e.g., odds ratio, p-value), likelihood, or risk factor, associated with the presence or absence of a genotype, genetic variation, and/or genetic variation signature. An outcome and/or classification for a test sample (e.g., a *Cannabis* plant sample) sometimes is provided as "positive" or "negative" with respect a particular genotype, phenotype, genetic variation and/or infection. For example, an outcome and/or classification sometimes is designated as "positive" in a laboratory test report for a particular test sample (e.g., a *Cannabis* plant sample) where presence of a genotype, phenotype, genetic variation and/or infection is determined, and sometimes an outcome and/or classification is designated as "negative" in a laboratory test report for a particular test sample (e.g., a *Cannabis* plant sample) where absence of a genotype, phenotype, genetic variation and/or infection is determined. An outcome and/or classification for a pathogen (e.g., HpLVd, AMV, BCTV or other plant pathogen) sometimes is provided as "positive" or "negative" with respect a particular genotype, genetic variation, and/or genetic variation signature. For example, an outcome and/or classification sometimes is designated as "positive" in a laboratory test report for a particular pathogen (e.g., HpLVd, AMV, BCTV or other plant pathogen) where presence of a genotype, genetic variation, and/or genetic variation signature is determined, and sometimes an outcome and/or classification is designated as "negative" in a laboratory test report for a particular pathogen (e.g., HpLVd, AMV, BCTV or other plant pathogen) where absence of a genotype, genetic variation, and/or genetic variation signature is determined. An outcome and/or classification sometimes is determined and sometimes includes an assumption used in data processing.

There typically are four types of classifications generated in a classification process: true positive, false positive, true negative and false negative. The term "true positive" as used herein refers to presence of a genotype, phenotype, genetic variation, or infection correctly determined for a test sample. The term "false positive" as used herein refers to presence of a genotype, phenotype, genetic variation, or infection incorrectly determined for a test sample. The term "true negative" as used herein refers to absence of a genotype, phenotype, genetic variation, or infection correctly determined for a test sample. The term "false negative" as used herein refers to absence of a genotype, phenotype, genetic variation, or infection incorrectly determined for a test sample. Two measures of performance for a classification process can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, a laboratory test report generated for a classification process includes a measure of test performance (e.g., sensitivity and/or specificity) and/or a measure of confidence (e.g., a confidence level, confidence interval). A measure of test performance and/or confidence sometimes is obtained from a clinical validation study performed prior to performing a laboratory test for a test sample. In certain embodiments, one or more of sensitivity, specificity and/or confidence are expressed as a percentage. In some embodiments, a percentage expressed independently for each of sensitivity, specificity or confidence level, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A confidence interval expressed for a particular confidence level (e.g., a confidence level of about 90% to about 99.9% (e.g., about 95%)) can be expressed as a range of values, and sometimes is expressed as a range or sensitivities and/or specificities for a particular confidence level. Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome and/or classification is not due to chance) in certain embodiments is expressed as a standard score (e.g., z-score), a p-value, or result of a t-test. In some embodiments, a measured variance, confidence level, confidence interval, sensitivity, specificity and the like (e.g., referred to collectively as confidence parameters) for an outcome and/or classification can be generated using one or more data processing manipulations described herein.

In certain embodiments, an outcome and/or classification is provided using a suitable visual medium (e.g., a peripheral or component of a machine, e.g., a printer or display). A classification and/or outcome may be provided in the form of a report. A report typically comprises a display of an outcome and/or classification (e.g., a value, one or more characteristics of a sample or pathogen, an assessment or probability of presence or absence of a genotype, phenotype, genetic variation and/or infection; and/or an assessment or probability of a genotype, genetic variation, and/or genetic variation signature for a pathogen), sometimes includes an associated confidence parameter, and sometimes includes a measure of performance for a test used to generate the outcome and/or classification. A report sometimes includes a recommendation for a follow-up test (e.g., a test that confirms the outcome or classification).

A report can be displayed in a suitable format that facilitates determination of presence or absence of a genotype, phenotype, genetic variation, genetic variation signature, and/or infection. Non-limiting examples of formats suitable for use for generating a report include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, or combination of the foregoing.

A report may be generated by a computer and/or by human data entry, and can be transmitted and communicated using a suitable electronic medium (e.g., via the internet, via computer, via facsimile, from one network location to another location at the same or different physical sites), or by another method of sending or receiving data (e.g., mail service, courier service and the like). Non-limiting examples of communication media for transmitting a report include auditory file, computer readable file (e.g., pdf file), paper file, laboratory file, or any other medium described in the previous paragraph. A laboratory file may be in tangible form or electronic form (e.g., computer readable form), in certain embodiments. After a report is generated and transmitted, a report can be received by obtaining, via a suitable communication medium, a written and/or graphical representation comprising an outcome and/or classification, which upon review allows a qualified individual to make a determination as to one or more characteristics of a sample or pathogen; presence or absence of a genotype, phenotype, genetic variation and/or infection for a test sample (e.g., a *Cannabis* plant sample); and/or genotype, genetic variation, and/or genetic variation signature for a pathogen (e.g., HpLVd, AMV, BCTV or other plant pathogen).

An outcome and/or classification may be provided by and obtained from a laboratory (e.g., obtained from a laboratory file). A laboratory file can be generated by a laboratory that carries out one or more tests for determining one or more characteristics of a sample or pathogen; presence or absence of a genotype, phenotype, genetic variation and/or infection for a test sample (e.g., a *cannabis* plant sample); and/or genotype, genetic variation, and/or genetic variation signature for a pathogen (e.g., HpLVd, AMV, BCTV or other plant pathogen). Laboratory personnel (e.g., a laboratory manager) can analyze information associated with test samples (e.g., test profiles, reference profiles, test values, reference values, level of deviation) underlying an outcome and/or classification. For calls pertaining to presence or absence of a genotype, phenotype, genetic variation and/or infection that are close or questionable, laboratory personnel can re-run the same procedure using the same (e.g., aliquot of the same sample) or different test sample from a plant. A laboratory may be in the same location or different location (e.g., in another country) as personnel assessing the presence or absence of a genotype, phenotype, genetic variation and/or infection from the laboratory file. For example, a laboratory file can be generated in one location and transmitted to another location in which the information for a test sample therein is assessed by a qualified individual, and optionally, transmitted to the facility and/or grower from which the test sample was obtained. A laboratory sometimes generates and/or transmits a laboratory report containing a classification of presence or absence of a genotype, phenotype, a genetic variation, and/or an infection for a test sample (e.g., a *Cannabis* plant sample); and/or a genotype, genetic variation, and/or genetic variation signature for a pathogen (e.g., HpLVd, AMV, BCTV or other plant pathogen).

An outcome and/or classification sometimes is a component of a diagnosis for a plant, and sometimes an outcome and/or classification is utilized and/or assessed as part of providing a diagnosis for a test sample. For example, a qualified individual may analyze an outcome and/or classification and provide a diagnosis based on, or based in part on, the outcome and/or classification. In some embodiments, determination, detection or diagnosis of an infection, disease, and/or abnormality comprises use of an outcome and/or classification determinative of presence or absence of a genotype, phenotype, genetic variation and/or infection for a test sample (e.g., a *Cannabis* plant sample); and/or a genotype, genetic variation, and/or genetic variation signature for a pathogen (e.g., HpLVd, AMV, BCTV or other plant pathogen). Thus, provided herein are methods for diagnosing presence or absence of a genotype, phenotype, a genetic variation and/or an infection for a test sample (e.g., a *Cannabis* plant sample) according to an outcome or classification generated by methods described herein, and optionally according to generating and transmitting a laboratory report that includes a classification for presence or absence of the genotype, phenotype, a genetic variation and/or an infection for the test sample (e.g., a *Cannabis* plant sample). Also provided herein are methods for diagnosing presence or absence of a genotype, phenotype, a genetic variation and/or an infection for a test sample (e.g., a *Cannabis* plant sample) according to an outcome or classification generated by methods described herein for a genotype, genetic variation, and/or genetic variation signature for a pathogen (e.g., HpLVd, AMV, BCTV or other plant pathogen), and optionally according to generating and transmitting a laboratory report that includes a classification for presence or absence of the genotype, phenotype, a genetic variation and/or an infection for the test sample (e.g., a *cannabis* plant sample), and/or a classification of a genotype, genetic variation, and/or genetic variation signature for a pathogen (e.g., HpLVd, AMV, BCTV or other plant pathogen).

Machines, Software and Interfaces

Methods described herein (e.g., processing amplification results, processing high resolution melting (HRM) assay results, processing sequence read data, determining one or more characteristics of a sample or a pathogen based on sequence read data, associating one or more phenotypes of an infected plant (e.g., an infected *cannabis* plant) with one or more genotypes, genetic variations, and/or genetic variation signatures for a pathogen (e.g., HpLVd, AMV, BCTV or other plant pathogen), and/or providing an outcome) may be computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein.

Also provided are computer program products. A computer program product often includes a computer usable medium that includes a computer readable program code embodied therein, the computer readable program code adapted for being executed to implement a method, or part of a method, described herein. Computer usable media and readable program code are not transmission media (i.e., transmission signals per se). Computer readable program code often is adapted for being executed by a processor, computer, system, apparatus, or machine.

In some embodiments, methods described herein (e.g., processing amplification results, processing high resolution melting (HRM) assay results, processing sequence read data, determining one or more characteristics of a sample or a pathogen based on sequence read data, associating one or more phenotypes of an infected plant (e.g., an infected *Cannabis* plant) with one or more genotypes, genetic variations, and/or genetic variation signatures for a pathogen (e.g., HpLVd, AMV, BCTV or other plant pathogen), and/or providing an outcome) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Machines, software and interfaces may be used to conduct methods described herein. Using machines, software and interfaces, a user may enter, request, query or determine options for using particular information, programs or processes (e.g., processing amplification results, processing high resolution melting (HRM) assay results, processing sequence read data, determining one or more characteristics of a sample or a pathogen based on sequence read data, associating one or more phenotypes of an infected plant (e.g., an infected *cannabis* plant) with one or more genotypes, genetic variations, and/or genetic variation signatures for a pathogen (e.g., HpLVd, AMV, BCTV or other plant pathogen), and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for sequence read processing; send processed sequence read data to a computer system for further processing and/or yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine an outcome from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein. A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g., frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to a machine, peripheral, component or another module. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data and may include a module that specifically processes the data (e.g., a processing module that processes received data). The terms "obtaining" and "receiving" input information refers to receiving data by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads, genotypes, phenotypes, genetic variations, and/or genetic variation signatures. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining one or more characteristics of a sample.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Compositions

Provided in certain embodiments are compositions. Compositions useful for carrying out any of the methods described herein are provided. For example, compositions comprising any of the primers, primer pairs, primer sets, probes, and/or reverse complements thereof described herein are provided.

In some embodiments, a composition comprises one or more polynucleotide primer pairs (e.g., one or more polynucleotide primer pairs described herein). In some embodiments, each polynucleotide of the one or more primer pairs is identical, or substantially identical, to a subsequence of SEQ ID NO:1, or complement thereof. In some embodiments, each subsequence of SEQ ID NO:1, or complement thereof, to which each polynucleotide is identical, or substantially identical, contains no variant nucleotide position. In some embodiments, each target sequence of SEQ ID NO:1 between the subsequences, or complements thereof, to which the polynucleotides of the one or more primer pairs are identical, or substantially identical, (i.e., the subsequence between the primer hybridization sites) comprises one or more variant nucleotide positions.

In some embodiments, a composition comprises one or more further polynucleotide primers. In some embodiments, each polynucleotide of the one or more further polynucleotide primers is identical, or substantially identical, to a subsequence of SEQ ID NO:1, or complement thereof. In some embodiments, each subsequence of SEQ ID NO:1, or complement thereof, to which each polynucleotide is identical, or substantially identical, contains one or more variant nucleotide positions.

In some embodiments, a composition comprises a) a first set of polynucleotide primers where i) each polynucleotide of the a first set of polynucleotide primers is identical, or substantially identical, to a subsequence of SEQ ID NO:1, or complement thereof, ii) each subsequence of SEQ ID NO:1, or complement thereof, to which each polynucleotide is identical, or substantially identical, contains no variant nucleotide position, and iii) each target sequence of SEQ ID NO:1 between the subsequences, or complements thereof, to which the polynucleotides of the first set of polynucleotide primers are identical, or substantially identical, comprises one or more variant nucleotide positions; and b) a second set of polynucleotide primers where i) each polynucleotide of the second set of polynucleotide primers is identical, or substantially identical, to a subsequence of SEQ ID NO:1, or complement thereof, and ii) each subsequence of SEQ ID NO:1, or complement thereof, to which each polynucleotide is identical, or substantially identical, contains one or more variant nucleotide positions.

In some embodiments, a composition comprises at least one polynucleotide primer pair that is capable of specifically hybridizing to and amplifying a subsequence of the nucleic acid of Alfalfa Mosaic Virus (AMV). In certain embodiments, the subsequence of the nucleic acid of the Alfalfa Mosaic Virus (AMV) to which the polynucleotide primer pair is capable of hybridizing comprises SEQ ID NO:91, or a portion of SEQ ID NO:91, or a complement of SEQ ID NO:91, or a portion of the complement of SEQ ID NO:91. In embodiments, the at least one polynucleotide primer pair is selected from among: one primer selected from among those having the sequences set forth in SEQ ID NOS: 80, 82 and 85, or from among sequences that share 90%, 91%, 92%, 93%, 94%, 95%, 96%, 97%, 98%, 99% or more identity with the sequences set forth in SEQ ID NOS: 80, 82 and 85; and one primer selected from among those having the sequences set forth in SEQ ID NOS: 81, 83, 84 and 86; or from among sequences that share 90%, 91%, 92%, 93%, 94%, 95%, 96%, 97%, 98%, 99% or more identity with the sequences set forth in SEQ ID NOS: 81, 83, 84 and 86.

In some embodiments, a composition comprises at least one polynucleotide primer pair that is capable of specifically hybridizing to and amplifying a subsequence of the nucleic acid of Beet Curly Top Virus (BCTV). In certain embodiments, the subsequence of the nucleic acid of the pathogen to which the at least one polynucleotide primer pair is capable of hybridizing is selected from among SEQ ID NOS:110, 112, 114, 116, 118 or 120, or a portion of SEQ ID NOS:110, 112, 114, 116, 118 or 120, or a complement of SEQ ID NOS:110, 112, 114, 116, 118 or 120, or a portion of the complement of SEQ ID NOS:110, 112, 114, 116, 118 or 120, or to regions of overlap that span any two of SEQ ID NOS:110, 112, 114, 116, 118 or 120 in the genome of the pathogen. I embodiments, the subsequence of the nucleic acid of the pathogen to which the at least one polynucleotide primer pair is capable of hybridizing is in a region of overlap that spans:

(i) the gene encoding the SS-ds-DNA Regulator Protein (SEQ ID NO:110) and the gene encoding Movement Protein (SEQ ID NO:112);
(ii) the gene encoding the Pathogenesis Enhancement Protein (SEQ ID NO:116) and the gene encoding the Rolling Circle Replication Protein (SEQ ID NO:114);
(iii) the gene encoding the Rolling Circle Replication Protein (SEQ ID NO:114) and the gene encoding the Cell Cycle Regulator Protein (SEQ ID NO:118); or
(iv) the gene encoding the Pathogenesis Enhancement Protein (SEQ ID NO:116) and the gene encoding the Replication Enhancer Protein (SEQ ID NO:120). In certain embodiments, the polynucleotide primer pairs comprise:

for (i), the primer pair having the sequences set forth in SEQ ID NOS: 93 and 94 or sequences that share 90%, 91%, 92%, 93%, 94%, 95%, 96%, 97%, 98%, 99% or more identity with the sequences set forth in SEQ ID NOS: 93 and 94, or the primer pair having the sequences set forth in SEQ ID NOS: 93 and 105, or sequences that share 90%, 91%, 92%, 93%, 94%, 95%, 96%, 97%, 98%, 99% or more identity with the sequences set forth in SEQ ID NOS: 93 and 105;

for (ii), the primers having the sequences set forth in SEQ ID NOS: 96 and 97, or sequences that share 90%, 91%, 92%, 93%, 94%, 95%, 96%, 97%, 98%, 99% or more identity with the sequences set forth in SEQ ID NOS: 96 and 97;

for (iii), the primers having the sequences set forth in SEQ ID NOS: 99 and 100, or sequences that share 90%, 91%, 92%, 93%, 94%, 95%, 96%, 97%, 98%, 99% or more identity with the sequences set forth in SEQ ID NOS: 99 and 100; and for (iv), the primers having the sequences set forth in SEQ ID NOS: 102 and 103, or sequences that share 90%, 91%, 92%, 93%, 94%, 95%, 96%, 97%, 98%, 99% or more identity with the sequences set forth in SEQ ID NOS: 102 and 103.

Any of the compositions provided herein can further include one or more polynucleotide probes as provided herein, for quantifying amplicons generated by the polynucleotide primer pairs of the compositions provided herein.

Kits

Provided in certain embodiments are kits. The kits may include any components and compositions described herein (e.g., primers, primer pairs, primer sets (e.g., one or more LAMP primer sets), probes, and/or reverse complements thereof) useful for performing any of the methods described herein, in any suitable combination. Kits may further include any reagents, buffers, or other components useful for carrying out any of the methods described herein. For example, a kit may include one or more primer pairs described herein and one or more components for amplifying nucleic acid.

Kits may include components for amplifying nucleic acid. Kits for amplifying nucleic acid may be configured such that a user provides a DNA template (e.g., a cDNA template) or an RNA template. A kit for amplifying nucleic acid from an RNA template may further include reagents for reverse transcription (i.e., for generating cDNA).

Components of a kit may be present in separate containers, or multiple components may be present in a single container. In some embodiments, primers are provided such that each container contains a single primer pair (e.g., for individual amplification reactions). In some embodiments, primers are provided such that one container contains a plurality of primer pairs (e.g., for multiplex amplification reactions). Suitable containers include a single tube (e.g., vial), one or more wells of a plate (e.g., a 96-well plate, a 384-well plate, and the like), and the like.

Kits may also comprise instructions for performing one or more methods described herein and/or a description of one or more components described herein. For example, a kit may include instructions for using the amplification primers and/or probes described herein, to amplify nucleic acid (e.g., to amplify subsequences of an HpLVd, AMV, BCTV or other plant pathogen genome). In certain configurations, a kit may include instructions or a guide for interpreting the results of an amplification reaction. Instructions and/or descriptions may be in printed form and may be included in a kit insert. In some embodiments, instructions and/or descriptions are provided as an electronic storage data file present on a suitable computer readable storage medium, e.g., portable flash drive, DVD, CD-ROM, diskette, and the like. A kit also may include a written description of an internet location that provides such instructions or descriptions.

Solid Supports

Provided herein are solid supports that include nucleic acid from a plant sample and any of the polynucleotide primers provided herein. The nucleic acid and/or primers can directly be attached to the solid support, such as by covalent linkage, or can otherwise be associated with the solid support. For example, the primers can include, in addition to a sequence complementary to a unique subsequence of nucleic acid of the genome of a plant cultivar of interest, a sequence that is complementary to a nucleic acid sequence that is directly attached to the solid support. The solid supports that include the primers provided herein can be contacted with nucleic acid from a sample obtained from a plant cultivar, under conditions that facilitate hybridization of a primer to a corresponding subsequence of the genome of a plant pathogen that may have infected a plant cultivar of interest. The resulting hybrids can directly be analyzed, such as by a signal or a label, for the presence or absence of hybridized product containing one or more primers specifically bound to a unique subsequence of a pathogen in the nucleic acid of a plant sample. Alternately, the resulting hybrids can be subjected to polymerase-based amplification reaction conditions using, e.g., one or more labeled nucleotides that can be incorporated into an amplicon thereby identifying, based on the presence or absence of a label in the amplicon, whether or not a plant pathogen is plant cultivar of interest.

The term "solid support" or "solid phase" as used herein refers to a wide variety of materials including solids, semi-solids, gels, films, membranes, meshes, felts, composites, particles, and the like typically used to sequester molecules, and more specifically refers to an insoluble material with which nucleic acid can be associated. A solid support for use with processes described herein sometimes is selected in part according to size: solid supports having a size smaller than the size a microreactor sometimes are selected. Examples of solid supports for use with processes described herein include, without limitation, beads (e.g., microbeads, nanobeads), particles (e.g., microparticles, nanoparticles) and chips.

The terms "beads" and "particles" as used herein refer to solid supports suitable for associating with biomolecules, and more specifically nucleic acids. Beads may have a regular (e.g., spheroid, ovoid) or irregular shape (e.g., rough, jagged), and sometimes are non-spherical (e.g., angular, multi-sided). Particles or beads having a nominal, average or mean diameter less than the nominal, average, mean or minimum diameter of a microreactor can be utilized. Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 micrometers; about 1, 5, 10, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 80, 85, 90, 95, 100, 200, 300, 400, 500 micrometers.

A bead or particle can be made of virtually any insoluble or solid material. For example, the bead or particle can comprise or consist essentially of silica gel, glass (e.g., controlled-pore glass (CPG)), nylon, Sephadex®, Sepharose®, cellulose, a metal surface (e.g., steel, gold, silver, aluminum, silicon and copper), a magnetic material, a plastic material (e.g., polyethylene, polypropylene, polyamide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads®. Beads may also be made as solid particles or particles that contain internal voids.

The solid supports can be provided in a collection of solid supports. A solid support collection can include two or more different solid support species. The term "solid support species" as used herein refers to a solid support in association with one particular primer or primer pair provided herein, or a combination of different primers or primer pairs. In certain embodiments, a solid support includes about 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 650 or 700 or more primers that specifically bind to unique subsequences of one or more TPS genes or paralogs thereof in one or more plant cultivars of interest. The solid supports (e.g., beads) in the collection of solid supports can be homogeneous (e.g., all are Wang resin beads) or heterogeneous (e.g., some are Wang resin beads, and some are magnetic beads).

The primers generally are single-stranded and are of any type suitable for hybridizing sample nucleic acid (e.g., DNA, RNA, analogs thereof (e.g., peptide nucleic acid (PNA)), chimeras thereof (e.g., a single strand comprises RNA bases and DNA bases) and the like). The primers or nucleic acid from the plant cultivar sample can be associated with the solid support in any manner suitable for hybridization of the primers to nucleic acid from the plant cultivar. The primers or nucleic acid from the plant cultivar sample can be in association with a solid support by a covalent linkage or a non-covalent interaction. Non-limiting examples of non-covalent interactions include hydrophobic interactions (e.g., C18 coated solid support and tritylated nucleic acid), polar interactions (e.g., "wetting" association between nucleic acid/polyethylene glycol), pair interactions including without limitation, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA) and the like.

The primers provided herein also can be associated with a solid support by different methodology, which include, without limitation (i) sequentially synthesizing nucleic acid directly on a solid support, and (ii) synthesizing nucleic acid, providing the nucleic acid in solution phase and linking the nucleic acid to a solid support. The primers can be linked covalently at various sites in the nucleic acid to the solid support, such as (i) at a 1', 2', 3', 4' or 5' position of a sugar moiety or (ii) a pyrimidine or purine base moiety, of a terminal or non-terminal nucleotide of the nucleic acid, for example. The 5' terminal nucleotide of the primer can be linked to the solid support, in certain embodiments.

Methods for sequentially synthesizing nucleic acid directly on a solid support are known. For example, the 3' end of nucleic acid can be linked to the solid support (e.g., phosphoramidite method described in Caruthers, Science 230: 281-286 (1985)) or the 5' end of the nucleic acid can be linked to the solid support (e.g., Claeboe et al, *Nucleic Acids Res.* 31(19): 5685-5691 (2003)).

Methods for linking solution phase nucleic acid to a solid support also are known (e.g., U.S. Pat. No. 6,133,436, naming Koster et al. and entitled "Beads bound to a solid support and to nucleic acids" and WO 91/08307, naming Van Ness and entitled "Enhanced capture of target nucleic acid by the use of oligonucleotides covalently attached to polymers"). Examples include, without limitation, thioether linkages (e.g., thiolated nucleic acid); disulfide linkages (e.g., thiol beads, thiolated nucleic acid); amide linkages (e.g., Wang resin, amino-linked nucleic acid); acid labile linkages (e.g., glass beads, tritylated nucleic acid) and the like. Nucleic acid can be linked to a solid support without a linker or with a linker (e.g., S. S. Wong, "Chemistry of Protein Conjugation and Cross-Linking," CRC Press (1991), and G. T. Hermanson, "Bioconjugate Techniques," Academic Press (1995). A homo or hetero-biofunctional linker reagent, can be selected, and examples of linkers include without limitation N-succinimidyl(4-iodoacetyl) aminobenzoate (SIAB), dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-maleimidomethyl)cyclohexane-1-carboxylate (SMCC), 6-hydrazinonicotimide (HYNIC), 3-amino-(2-nitrophenyl)propionic acid and the like.

Nucleic acid can be synthesized using standard methods and equipment, such as the ABI®3900 High Throughput DNA Synthesizer and EXPEDITE®8909 Nucleic Acid Synthesizer, both of which are available from Applied Biosystems (Foster City, Calif.). Analogs and derivatives are described in U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; WO 00/56746; WO 01/14398, and related publications. Methods for synthesizing nucleic acids containing such analogs or derivatives are disclosed, for example, in the patent publications cited above and in U.S. Pat. Nos. 5,614,622; 5,739,314; 5,955,599; 5,962,674; 6,117,992; in WO 00/75372 and in related publications. In certain embodiments, analog nucleic acids include inosines, abasic sites, locked nucleic acids, minor groove binders, duplex stabilizers (e.g., acridine, spermidine) and/or other melting temperature modifiers (e.g., target nucleic acid, solid phase nucleic acid, and/or primer nucleic acid may comprise an analog).

The density of solid phase-bound primer molecules per solid support unit (e.g., one bead or one sample location of a chip) can be selected. A maximum density can be selected that allows for hybridization of sample nucleic acid from the plant cultivar to solid phase-bound primers. In certain embodiments, solid phase-bound primer density per solid support unit (e.g., nucleic acid molecules per bead) is about 5 nucleic acids to about 10,000 nucleic acids per solid support. The density of the solid phase-bound primer per unit solid support in some embodiments can be about 5, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 nucleic acids per solid support. In certain embodiments the density of the solid phase-bound primer per unit solid support is about 1 to 1 (e.g., one molecule of solid phase nucleic acid to one bead).

In certain embodiments, the solid supports can include any number of primer species useful for carrying out the analysis methods provided herein. Solid supports having primers attached or otherwise associated thereto can be provided in any convenient form for contacting a sample nucleic acid from a plant cultivar, such as solid or liquid form, for example. In certain embodiments, a solid support can be provided in a liquid form optionally containing one or more other components, which include without limitation one or more buffers or salts. Solid supports of a collection can be provided in one container or can be distributed across multiple containers.

Solid supports can be provided in an array in certain embodiments, or instructions can be provided to arrange solid supports in an array on a substrate. The term "array" as used herein can refer to an arrangement of sample locations (for nucleic acid samples from plant cultivars) on a single two-dimensional solid support, or an arrangement of solid supports across a two-dimensional surface. An array can be of any convenient general shape (e.g., circular, oval, square, rectangular). An array can be referred to as an "X by Y array" for square or rectangular arrays, where the array includes X number of sample locations or solid supports in one dimension and Y number of sample locations or solid supports in a perpendicular dimension. An array can be symmetrical (e.g., a 16 by 16 array) or non-symmetrical (e.g., an 8 by 16 array). An array may include any convenient number of sample locations or solid supports in any suitable arrangement. For example, X or Y independently can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 in some embodiments.

An array can contain one solid support species or multiple solid support species from a collection. The array can be arranged on any substrate suitable for sequence analysis or manufacture processes described herein. Examples of substrates include without limitation flat substrates, filter substrates, wafer substrates, etched substrates, substrates having multiple wells or pits (e.g., microliter (about 1 microliter, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900 and up to about 999 microliter volume), nanoliter (1 nanoliter, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900 and up to about 999 nanoliter volume), picoliter (1 picoliter, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900 and up to about 999 picoliter volume) wells or pits; wells having filter bottoms), substrates having one or more channels, substrates having one or more electrodes, chips and the like, and combinations thereof. Wells or pits of multiple well and pit substrates can contain one or more solid support units (e.g., each unit being a single bead or particle). Substrates can include a suitable material for conducting sequence analysis or nucleic acid manufacture processes described herein, including without limitation, fiber (e.g., fiber filters), glass (e.g., glass surfaces, fiber optic surfaces), metal (e.g., steel, gold, silver, aluminum, silicon and copper; metal coating), plastic (e.g., polyethylene, polypropylene, polyamide, polyvinylidenedifluoride), silicon and the like. In certain embodiments, the array can be a microarray or a nanoarray. A "nanoarray," often is an array in which solid support units are separated by about 0.1 nanometers to about 10 micrometers, for example from about 1 nanometer to about 1 micrometer (e.g. about 0.1 nanometers, 0.5, 1, 2, 3, 4, 5, 10, 20, 30, 40, 50, 60, 70, 80, 90, 100, 200, 300, 400, 500, 600, 700, 800, 900 nanometers, 1 micrometer, 2, 3, 4, 5, 6, 7, 8, 9, and up to about 10 micrometers). A "microarray" is an array in which solid support units are separated by more than 1 micrometer. The density of solid support units on arrays often is at least 100/cm$^2$, and can be 100/cm$^2$ to about 10,000/cm$^2$, 100/cm$^2$ to about 1,000/cm$^2$ or about 150, 200, 300, 400, 500, 600, 700, 800, 900, 1000, 2000, 3000, 4000, 5000, 6000, 7000, 8000, 9000 or 10000 solid support units/cm$^2$.

Applications/Uses

The methods provided herein can additionally provide an outcome indicative of one or more characteristics of a plant cultivar that may be infected by a pathogen, including, but not limited to:

In an in-grow application setting, in a molecular lab application setting, or as part of a kit of pathogen identification markers.

Identifying more or less active variants of the pathogen genome (e.g., HpLVd, AMV, BCTV or other pathogens or combinations thereof, e.g., in multiplexed settings) for transgenic experiments including CRISPR-cas9, Cre-Lox, and other genetic modification applications to inhibit, silence, or interfere with a more active variant or a less active variant.

Used in a cDNA microassay screening tool to identify presence and/or amount of pathogen RNA present in a given *Cannabis* cultivar.

Relating the amount of pathogen in a cell to the presentation or absence of symptoms in infected plants.

Relating the genotype of pathogen in a cell to the presentation or absence of symptoms in infected plants.

Relating a given pathogen (e.g., HpLVd, AMV, BCTV) genotype in the panel to determining the performance, yield, and growth characteristics of a given *Cannabis* cultivar.

Use of the markers (primers and/or the resulting amplicons) to verify if clean stock treatments have removed or mutated the pathogen genome from a given plant.

Identifying the mutant pathogen genome (e.g., HpLVd, AMV, BCTV) to identify detrimental SNPs within the pathogen genome that inhibit the viroid from affecting the host plants phenotype.

Use of the markers (primers and/or the resulting amplicons) to identify plant genotypes that are resistant to certain variants of the pathogen genome.

EXAMPLES

The examples set forth below illustrate certain embodiments and do not limit the technology.

Example 1: Examples of Protocols for: (1) Determining the Presence, Absence and/or Amount of a Pathogen in a Plant Cultivar; (2) Determining the Genotype of the Pathogen RNA Isolation Total RNA was isolated from fresh *Cannabis* leaf tissue samples using the Direct-zol RNA isolation kit and Zymo Research (Irvine, Calif.) Quick-RNA Plant Miniprep Kit with DNAase Digestion using manufacturer instructions. Purified RNA was prepared for quantification using the QuantiFluor HS-ssRNA System (Promega, Madison, Wis.) and quantified using a Quantus Fluorometer (Promega, Madison, Wis.), as per manufacturer's instructions. Quantified RNA was diluted to 5 ng/uL final working concentration and used as normalized input into either a first strand cDNA synthesis reaction or one-step reverse transcriptase real-time qPCR reactions.

cDNA Synthesis

Quantified RNA was used as input for cDNA synthesis using the SuperScript™ IV First-Strand Synthesis System (Thermo Fisher Scientific, Waltham, Mass.). cDNA synthesis reactions were prepared as follows: (1 μL 50 μM Oligo d(T)20 primer, 1 μL of 10 mM dNTP mix (10 mM each), 8 μL Template RNA (10 pg-5 pg total RNA or 10 pg-500 ng mRNA) up to 3 μL DEPC-treated water for 13 μL final volume). After mixing and briefly centrifuging, the RNA-primer mix reactions were heated at 65° C. for 5 minutes, and then incubated at 0° C. for 2 minutes on a veriti thermocycler.

Following annealing, the plate was pierced using a plate piercer and 7 uL Reverse transcriptase (RT) reaction mix was added to each reaction for a 20 uL final volume for cDNA synthesis. The RT reaction mix was prepared as follows: 4 μL of 5×SSIV Buffer, 1 μL of 100 mM DTT, 1 μL of Ribonuclease Inhibitor, 1 μL of SuperScript™ IV Reverse Transcriptase (200 U/μL)). The plate was sealed and briefly centrifuged and loaded on a veriti thermocycler for cDNA synthesis using the following protocol: incubate the combined reaction mixture at 50-55° C. for 10 minutes, inactivate the reaction by incubating it at 80° C. for 10 minutes, and hold at 4° C. The products of cDNA synthesis were prepared for quantification using the QuantiFluor HS-dsDNA System (Promega, Madison, Wis.) and quantified using a Quantus Fluorometer (Promega, Madison, Wis.), as per manufacturer's instructions. Quantitated cDNA was diluted to 2 ng/uL final working concentration and used as normalized input into either an end point PCR reaction or a Taqman real-time qPCR reaction.

Endpoint PCR with Gel Analysis 2.5 uL of normalized cDNA was used as input into 22.5 uL of PCR master mix prepared per reaction as follows: 12.5 uL 2× Promega Colorless GoTaq (Promega, Madison, Wis.), 0.1 uL of 100 uM Primer Mixes, and 9.5 uL Nuclease free Water (Ambion, Austin, Tex.). The reactions were subjected to the following thermocycler protocol: 1 cycle at 95° C. for 10 mins; 35 cycles at 95° C. for 40 sec, 60° C. for 2 mins, 72° C. for 2 mins; 1 cycle at 72° C. for 5 mins; 4° C. hold. End-point PCR reactions were analyzed by diluting 1:2 in nuclease-free water and 20 ul was loaded into each well of E-Gel™ EX Agarose Gels, 2%, 20 gels and ran for 10 minutes on 1-2% gel settings for the E-gel system.

Reverse Transcriptase Quantitative Polymerase Chain Reaction (RT-qPCR)

RT-qPCR analysis was performed in 10 μL reactions on a LIGHTCYCLER 480 qPCR (Roche Applied Systems, Germany) using the following protocol: 50° C. for 15 minutes hold, 95° C. for 2 minutes hold, followed by 40 cycles of: 95° C. for 15 seconds, 60° C. for 30 seconds. Each reaction contained: 2.5 μL of 5 ng/μL of the normalized RNA template used as input, 7.5 μL of SUPERSCRIPT III PLATINUM One-step RT-qPCR Master Mix (prepared per reaction as follows: 5 μL One step RT-qPCR Master Mix (Thermo Fisher Scientific, Waltham, Mass.), 0.3 μL 10 μM primer, 0.25 μL 10 μM probe, 13.6 μL H$_2$O, 0.25 μL TAQ). qPCR data was analyzed using the LIGHTCYCLER 480 software AbsQuant/2nd Derivative Max algorithm for calculating Cp values.

Quantitative Real-Time PCR TAQMAN Analysis qPCR analysis was performed in 10 μL reactions on a LIGHTCYCLER 480 qPCR (Roche Applied Systems, Germany) using the following protocol: 1 pre-incubation cycle (95° C. for 20 secs), 45 amplification cycles (95° C. for 1 second, 60° C. for 20 seconds, 72° C. for 20 seconds) with a single acquisition mode setting for each cycle at 60° C. annealing, followed by a final cooling cycle (40° C. for 30 seconds). Each reaction contained: 2.5 μL of 2 ng/μL of the normalized cDNA template used as input, 7.5 μL of TAQMAN Master Mix (prepared per reaction as follows: 5 uL of FASTTQ Advanced Reaction Mix (Applied Biosciences, Beverly Hills, Calif.), 0.3 μL 10 μM primer, 0.25 μL 10 μM probe, 13.6 μL H$_2$O, 0.25 μL TAQ). qPCR data was analyzed using the LIGHTCYCLER 480 software AbsQuant/2nd Derivative Max algorithm for calculating Cp values.

High Resolution Melt (HRM) Analysis

HRM analysis was performed in 10 μL reactions on a LIGHTCYCLER 480 qPCR (Roche Applied Systems, Germany) using the following protocol: 1 pre-incubation cycle (95° C. for 10 minutes), 45 amplification cycles (95° C. for 10 seconds, 60° C. for 15 seconds, 72° C. for 10 seconds), 1 cycle of HRM (95° C. for 1 minute, 40° C. for 1 minute, 65° C. for 1 second) and heat to 95° C. with 25 continuous acquisitions per degree (C.) followed by a final cooling cycle (40° C. for 10 seconds). Each reaction contained: 2.5 μL of 2 ng/μL of the diluted pre-amplified template, 7.5 μL of HRM Master Mix (prepared per reaction as follows: 5 μL 2× High Resolution Melting Master Mix containing HRM dye (Roche Applied Systems, Germany), 0.6 μL of 4 μM Primer Mix, 0.8 μL of 25 mM MgCl$_2$, 1.125 μL of nuclease-free water). High Resolution Melting data was analyzed using the LIGHTCYCLER 480 Melt Genotyping software. Fluorescence intensity as a function of temperature for each sample also was analyzed using R software custom scripts to determine statistical variation of melt curves.

Example 2: Methodologies to Identify Plants Affected by the Hops Latent Viroid (HpLVd) and Classify the Genotype of the Viroid This Example describes technology useful for identifying plants (e.g., *Cannabis* plants) infected with HpLVd and, in certain instances, classifying the genotype of the viroid. A variety of molecular technologies may be used depending on the application desired.

Applications include, for example, lab-based molecular diagnostics and in-field/cultivation facility diagnostics that can target of variety of genotypically different HpLVd genomes. Furthermore, this technology may be useful within the process of clean-stock micropropagation and tissue culture, where heat treatment is a common method to remove the viroid. Heat treatment can mutate the HpLVd genome in certain regions, which can render the viroid undetectable using existing primer designs. The primers provided in the Example overcome this by targeting conserved regions within thermomutants of HpLVd.

Components of the technology described in this Example include polymerase chain reaction (PCR) primers, loop mediated isothermal amplification (LAMP) primers, RT-PCR primers, probes, and reverse complements thereof. Primers and probes generally are about 15-30 nucleotide-long sequences that are complementary to various loci of the HpLVd genome with purposely mismatched bases to loci in the *Cannabis* genome CS10 *Cannabis* genome; GENBANK assembly accession: GCA_900626175.1; REFSEQ assembly accession: GCF_900626175.1) to prevent false positive results. Primer sequences provided in Table 1 below allow for the identification of plants that contain the HpLVd RNA, and, in certain instances, classification of the genotype of the viroid through various molecular technologies.

Amplification Primers and Amplification Products

One application of the amplification primers provided herein is a gel-electrophoresis endpoint assay. Any combination of forward and reverse primers shown in Table 1 may be used in conjunction with an RNA library or a cDNA library, and a corresponding size band (shown in Table 2) in a gel from a combination of primers may be observed. In addition to using the primers as described below, the primers also can be used on whole exome libraries, HpLVd specific libraries, and total RNA targeted cDNA libraries, as well as gene-specific cDNA synthesis as the first step after RNA extraction to create only HpLVd cDNA without any host plant cDNA being produced. All primer sets disclosed herein may be used within a gene-specific cDNA synthesis protocol to amplify a region of the HpLVd genome that could be identified through a gel size identification endpoint assay, or a high resolution melting (HRM) genotype endpoint assay, but only certain primers will work for gene-specific cDNA synthesis for a quantitative polymerase chain reaction (qPCR) endpoint. The amplicon lengths of each gene-specific cDNA target for each primer combination are shown in Table 2.

TABLE 1

Amplification primers

| Primer (type) | Sequence (5' to 3') | SEQ ID NO | Length | Start | Stop |
|---|---|---|---|---|---|
| A-fwd (tm-specific) | CTACGTGACTTACCTGTATGGTGGC | 2 | 25 | 13 | 37 |
| A-rev (tm-resistant) | CGCACGAACTGGCGCTCG | 3 | 18 | 106 | 89 |
| B-fwd (tm-resistant) | GGGGAAACCTACTCGAGCG | 4 | 19 | 60 | 78 |
| B-rev (tm-resistant) | CTTCAGGTCGCCGCGCACG | 5 | 19 | 119 | 101 |
| C-fwd (tm-resistant) | GGAAACCTACTCGAGCGAGGCG | 6 | 22 | 62 | 83 |
| C-rev (tm-specific) | GTGAAGAAGGAGCCGTTCCA | 7 | 20 | 171 | 152 |
| D-rev (tm-resistant) | CGGGTAGTTTCCAACTCCG | 8 | 19 | 196 | 178 |
| D-fwd (tm-resistant) | CGAGGCGGAGATCGAGCGC | 9 | 19 | 77 | 95 |
| E-rev (tm-resistant) | CCGGGTAGTTTCCAACTCCG | 10 | 20 | 197 | 178 |
| E-fwd (tm-resistant) | GAGATCGAGCGCCAGTTCG | 11 | 19 | 84 | 102 |
| F-rev (tm-resistant) | ACCGGGTAGTTTCCAACTCCG | 12 | 21 | 198 | 178 |
| F-fwd (tm-resistant) | AGATCGAGCGCCAGTTCG | 13 | 18 | 85 | 102 |
| G-rev (tm-specific) | AGAGTTGTATTCACCGGGTAGTTTCC | 14 | 26 | 210 | 185 |
| H-rev (tm-specific) | GCACTTTTTATGTGAACTTCTGC | 15 | 23 | 252 | 230 |

Several regions of the HpLVd genome were targeted for primer binding regions with the intent that certain regions of the genome would be more indicative of symptomatic plants than others. Certain mRNA transcripts from *cannabis* and hops can be complimentary to the HpLVd genome, and the primers were designed, in part, to genotype different regions of the HpLVd genome and find regions that can be complementary to *cannabis* transcripts and may cause a phenotypic change in the plant as a result of the infection.

Certain primers were designed to primarily target sites that are resistant to thermomutation, and may be referred to as thermomutant-resistant (tm-resistant) primers. Other primers (e.g., complementary to sequences towards the 3' and 5' ends of the HpLVd genome, where thermomutants are possible) were designed as variant-specific primers, and may be referred to as thermomutant-specific (tm-specific) primers. Using both types of primers, most of the HpLVd genome may be genotyped to identify SNPs in the genome that can cause symptoms in given cultivars.

Primers that bind to a site of variation (e.g., A-fwd, C-rev, G-rev, and H-rev) are considered thermomutant-specific primers, and are specific to a certain variant of HpLVd. Such primer targeting allows for amplification only virulent/symptomatic versions of the viroid, while avoiding non-symptomatic variants that were mutated during heat-shock treatment and may no longer affect the phenotype. Including thermo-mutant specific primers in the assays described herein allows for selection of more or less virulent/infectious/symptom-causing variants by targeting regions of thermomutation. In this Example, A-fwd hybridizes to a region containing potential thermomutant SNPs at nucleotide positions 26-30, 33, and 35 of SEQ ID NO:1. C-rev hybridizes to a region containing potential thermomutant SNPs at positions 157, 162, 168, and 169 of SEQ ID NO:1. G-rev hybridizes to a region containing potential thermomutant SNP at position 210 of SEQ ID NO:1. H-rev hybridizes to a region containing potential thermomutant SNPs at positions 247 and 248 of SEQ ID NO:1.

In certain instances, thermomutant-specific primers may be indicative of the presence or absence of HpLVd (e.g., in non-heat treated plants), and in certain instances, thermomutant-specific primers fail to detect the presence of HpLVd (e.g., in heat-treated plants containing one or more thermomutations in the primer binding region). In certain instances, thermomutant-specific primers are useful for genotyping the entire genome of HpLVd, and performing a secondary test if positive to determine if the plant has the specific variants being targeted using those primers (e.g., variants present in the amplicons). In one modified application, primers with the longest amplicons (e.g., A-fwd, G-rev, H-rev) may be used by allowing for non-specific binding by modifying the PCR protocol to have a greater annealing temperature (+5 degrees C. from protocol) which would allow these primers to overcome the few mismatches that may be present in a thermomutant. Additionally, certain known mutant sites could be targeted using modified versions of thermomutant-specific primers (e.g., modified versions of the thermomutant-specific primers listed in Table 1) by replacing one or more nucleotides at the mismatched sites with one or more nonstandard or degenerate nucleotides to allow for a wider range of amplification of the HpLVd genome variants. For example, one or more nonstandard or degenerate nucleotides may be incorporated in A-fwd that replace one or more nucleotides that correspond to nucleotide positions 26-30, 33, and/or 35 of SEQ ID NO:1. One or more nonstandard or degenerate nucleotides may be incorporated in C-rev that replace one or more nucleotides that correspond to nucleotide positions 157, 162, 168, and/or 169 of SEQ ID NO:1. A nonstandard or degenerate nucleotide may be incorporated in G-rev that replace the nucleotide that corresponds to nucleotide position 210 of SEQ ID NO:1. One or more nonstandard or degenerate nucleotides may be incorporated in H-rev that replace one or more nucleotides that correspond to nucleotide positions 247 and/or 248 of SEQ ID NO:1.

Primers that are designed to avoid binding to sites of variation (e.g., A-rev, B-fwd, B-rev, D-rev, D-fwd, E-rev, E-fwd, F-rev, and F-fwd) are considered thermomutant-resistant primers. Amplification products from such primers can be indicative of HpLVd infection, regardless of whether or not the plant was mutated under heat treatments. Such primers were designed to include thermomutant positions within the amplicon and not within the primed regions.

In certain applications, plants may be genotyped for variants present within an amplicon by amplification using thermomutant-resistant primers followed by a high resolution melt (HRM) assay or nucleotide sequencing. Additionally, plants may be genotyped for variants present within a primer binding site by amplification using thermomutant-specific primers, which provide a presence/absence answer to whether or not that variant is present.

Using multiple primers targeting multiple regions of the HpLVd genome in the methods described herein provides a robust verification that the viroid is present or absent, minimizing false-positive and false-negative rates. Additionally, the use of multiple primers targeting multiple regions allows for an identification of genotypes that correspond to symptomatic plants.

TABLE 2

Amplification products (bp)

|  | Arev | Brev | Crev | Drev | Erev | Frev | Grev | Hrev |
|---|---|---|---|---|---|---|---|---|
| Afwd | 93 | 106 | 158 | 183 | 184 | 185 | 197 | 239 |
| Bfwd | 46 | 59 | 111 | 136 | 137 | 138 | 150 | 192 |
| Cfwd | 44 | 57 | 109 | 134 | 135 | 136 | 148 | 190 |
| Dfwd | 29 | 42 | 94 | 119 | 120 | 121 | 133 | 175 |
| Efwd | 22 | 35 | 87 | 112 | 113 | 114 | 126 | 168 |
| Ffwd | 21 | 34 | 86 | 111 | 112 | 113 | 125 | 167 |

Specificity of HpLVd in the Order Rosidae

To determine the specificity of our primers, homology comparisons were performed between the HpLVd genome and other plants in the order Rosidae. Using Blastn, a word size of 7nt was searched for homology between the 256 bp of HpLVd with both the whole genome shotgun contigs of 625 databases of species and 369 databases of the transcriptome shotgun assembly databases included in the order Rosidae. The analysis showed that the HpLVd genome is not present within the genome or transcriptome of any other species of the order Rosidae, suggesting that the primers are specific to the HpLVd genome and will not amplify any off-target species of plant. Furthermore, in order to confirm these results, the primer combination (B-fwd with F-rev) was checked using NCBI's primer designer software that uses Primer3, to ensure both genomic and transcriptomic specificity in the order Rosidae, which was observed within a single-target amplification of only the HpLVd genome with no off-target RNA or DNA amplifications. Thus, the primers provided herein were confirmed as specific to HpLVd and will not amplify any species of the order Rosidae.

High Resolution Melt (HRM) Assay

Another method of using primers provided herein is a high resolution melt (HRM) endpoint assay. This type of assay allows the user to genetically classify a variant of the HpLVd (e.g., a variant that is affecting a given cultivar). The primers provided herein were designed so that the number of different primer combinations maximizes the likelihood of capturing nucleic acid differences. Such primer combinations may be useful for detecting (1) symptomatic vs asymptomatic HpLVd variants, (2) triggers that induce a switch from asymptomatic to symptomatic life cycle, (3) HpLVd variants that spread more easily, and (4) HpLVd variants that plants have gained resistance against. Primer set combinations shown with an asterisk (*) in Table 3 can be used within an HRM endpoint assay, on a cDNA or an RNA template under manufacturer's instructions (with the exception of certain thermocycler programs described herein).

TABLE 3

|  | Arev | Brev | Crev | Drev | Erev | Frev | Grev | Hrev |
|---|---|---|---|---|---|---|---|---|
| Afwd | * | * | * | * | * | * | * | * |
| Bfwd |  |  | * | * | * | * | * | * |
| Cfwd |  |  | * | * | * | * | * | * |
| Dfwd |  |  | * | * | * | * | * | * |
| Efwd |  |  | * | * | * | * | * | * |
| Ffwd |  |  | * | * | * | * | * | * |

High Resolution Melt (HRM) Analysis

HRM analysis was performed in 10 μL reactions on a LIGHTCYCLER 480 qPCR (Roche Applied Systems) using the following protocol: 1 pre-incubation cycle (95° C. for 10 minutes), 45 amplification cycles (95° C. for 10 seconds, 60° C. for 15 seconds, 72° C. for 10 seconds), 1 cycle of HRM (95° C. for 1 minute, 40° C. for 1 minute, 65° C. for 1 second) and heat to 95° C. with 25 continuous acquisitions per degree (C.) followed by a final cooling cycle (40° C. for 10 seconds). Each reaction contained: 2.5 μL of 2 ng/μL of the diluted pre-amplified template, 7.5 μL of HRM Master Mix (prepared per reaction as follows: 5 μL 2× High Resolution Melting Master Mix containing HRM dye (Roche Applied Systems), 0.6 μL of 4 μM Primer Mix, 0.8 μL of 25 mM $MgCl_2$, 1.125 μL of nuclease free water). High Resolution Melting data was analyzed using the LIGHTCYCLER 480 Melt Genotyping software. Fluorescence intensity as a function of temperature for each sample also was analyzed using R software custom scripts to determine statistical variation of melt curves.

Figure 8:
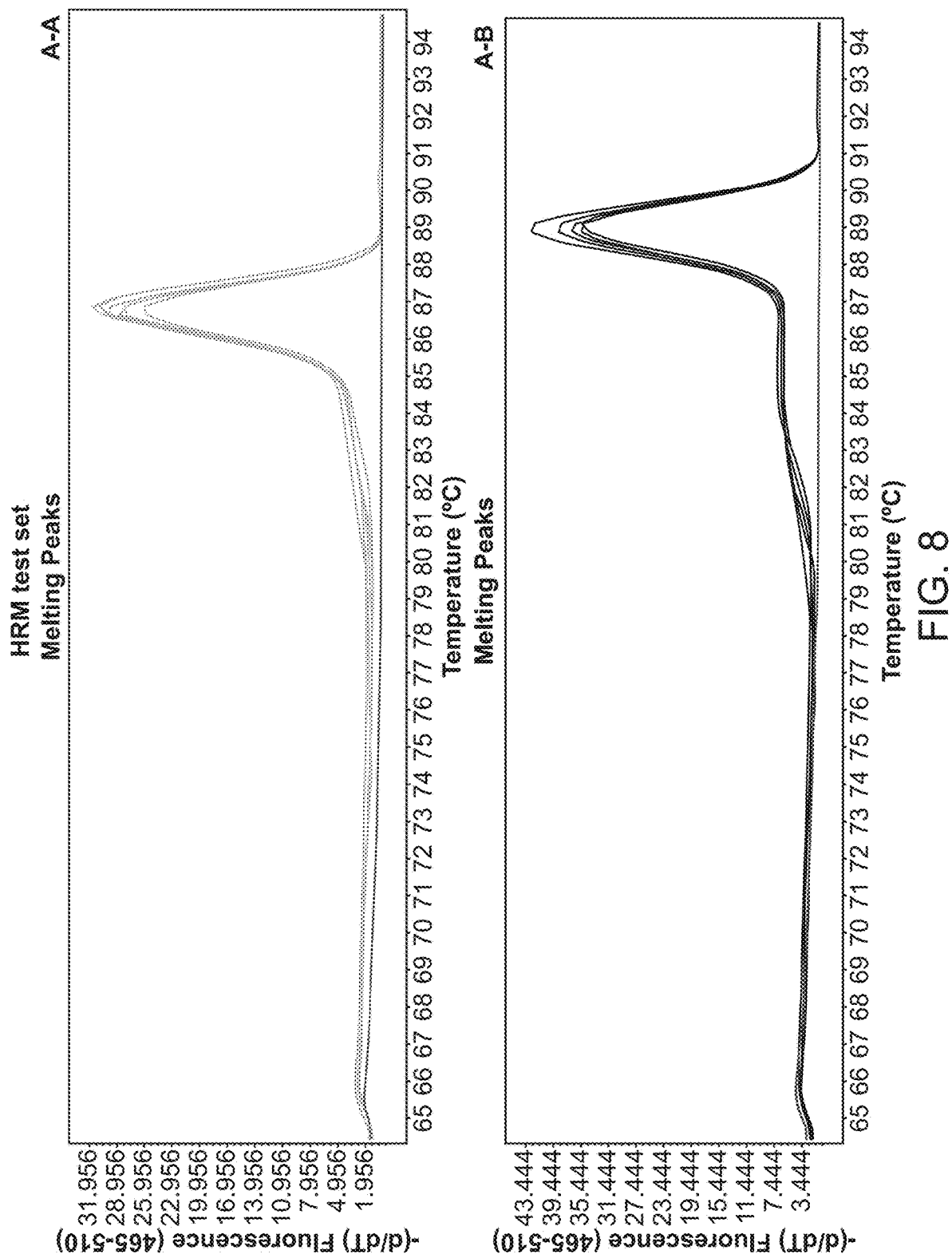
FIG. 8 shows results of melt curve genotyping analysis performed using primer pairs A-A (A-fwd, A-rev), A-B (A-fwd, B-rev), and A-C (A-fwd, C-rev).
Figure 8:
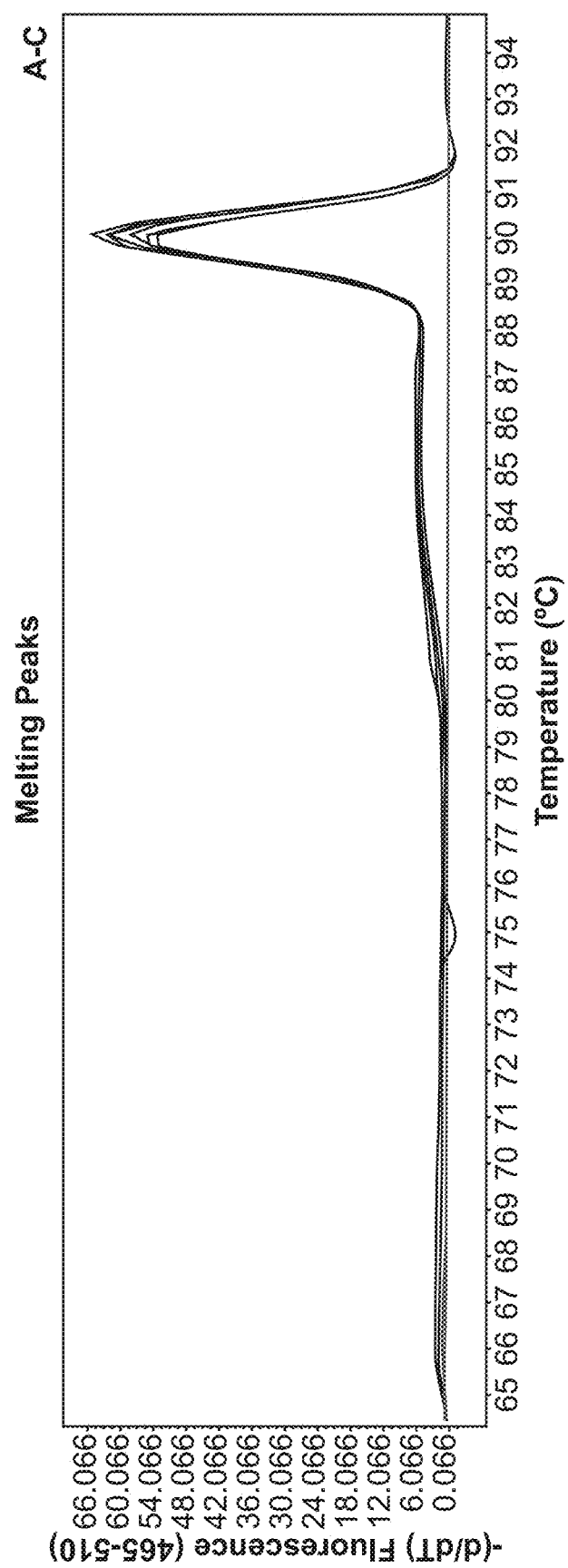

A melt curve genotyping analysis was performed with the following primer pairs: A-A, A-B, and A-C, and the results are shown in FIG. 8. For this assay, each condition was carried out in a duplex reaction on the Roche LIGHTCYCLER 480 real time instrument. Gel CZ1 was used as a positive control and no template was used as a negative control. The following known positive samples: BS2.1, Gel CZ4, and Gel CZ3 were analyzed for varying melting profiles of A-A, A-B, and A-C amplicons using the Roche LIGHTCYCLER 480 melt curve genotyping analysis algorithm. No differences in melt curve profiles were observed for the test samples and each test sample showed similar fluorescence values and melt curve temperature, indicating all the test samples had the same genotype. No amplification or fluorescence was observed in the no template control.

Quantitative Polymerase Chain Reaction (qPCR)

Another intended use of the primers provided herein is use in combination with the qPCR probes designated in Table 5. The combinations of primers and probes that identify the viroid are shown in Table 4. These combinations can be used on a cDNA template or an RNA template that is extracted from the cultivar for testing.

TABLE 4

|  | Arev | Brev | Crev | Drev | Erev | Frev | Grev | Hrev |
|---|---|---|---|---|---|---|---|---|
| Afwd |  | probe 2 | probe 1 | probe 1 | probe 1 | probe 1 | probe 1 | probe 1 |
|  |  | probe 4 | probe 2 | probe 2 | probe 2 | probe 2 | probe 2 | probe 2 |
|  |  |  | probe 3 | probe 3 | probe 3 | probe 3 | probe 3 | probe 3 |
|  |  |  | probe 4 | probe 4 | probe 4 | probe 4 | probe 4 | probe 4 |
|  |  |  |  | probe 5 | probe 5 | probe 5 | probe 5 | probe 5 |
| Bfwd |  | probe 2 | probe 1 | probe 1 | probe 1 | probe 1 | probe 1 | probe 1 |
|  |  | probe 4 | probe 2 | probe 2 | probe 2 | probe 2 | probe 2 | probe 2 |
|  |  |  | probe 3 | probe 3 | probe 3 | probe 3 | probe 3 | probe 3 |
|  |  |  | probe 4 | probe 4 | probe 4 | probe 4 | probe 4 | probe 4 |
|  |  |  |  | probe 5 | probe 5 | probe 5 | probe 5 | probe 5 |
| Cfwd |  |  | probe 1 | probe 1 | probe 1 | probe 1 | probe 1 | probe 1 |
|  |  |  | probe 3 | probe 3 | probe 3 | probe 3 | probe 3 | probe 3 |
|  |  |  |  | probe 5 | probe 5 | probe 5 | probe 5 | probe 5 |
| Dfwd |  |  | probe 1 | probe 1 | probe 1 | probe 1 | probe 1 | probe 1 |
|  |  |  | probe 3 | probe 3 | probe 3 | probe 3 | probe 3 | probe 3 |
|  |  |  |  | probe 5 | probe 5 | probe 5 | probe 5 | probe 5 |
| Efwd |  |  | probe 3 | probe 3 | probe 3 | probe 3 | probe 3 | probe 3 |
|  |  |  |  | probe 5 | probe 5 | probe 5 | probe 5 | probe 5 |
| Ffwd |  |  | probe 3 | probe 3 | probe 3 | probe 3 | probe 3 | probe 3 |
|  |  |  |  | probe 5 | probe 5 | probe 5 | probe 5 | probe 5 |

TABLE 5

| Probe | Sequence | SEQ ID NO | Start | Stop |
|---|---|---|---|---|
| Probe 1 | TCGTGCGCGGCGACCT | 16 | 100 | 115 |
| Probe 2 | CGGAGATCGAGCGCCAGTT | 17 | 81 | 100 |
| Probe 3 | TGCGCGGCGACCTGAAGT | 18 | 103 | 120 |
| Probe 4 | AGGCGGAGATCGAGCGCCA | 19 | 79 | 97 |
| Probe 5 | TCCTGCGTGGAACGGCTCC | 20 | 143 | 163 |

Example qPCR protocols performed with the primers and probes provided herein are described below.

Reverse Transcriptase Quantitative Polymerase Chain Reaction (RT-qPCR)

RT-qPCR analysis was performed in 10 μL reactions on a LIGHTCYCLER 480 qPCR (Roche Applied Systems) using the following protocol: 50° C. for 15 minutes hold, 95° C. for 2 minutes hold, followed by 40 cycles of: 95° C. for 15 seconds, 60° C. for 30 seconds). Each reaction contained: 2.5 μL of 5 ng/μL of the normalized RNA template used as input, 7.5 μL of SUPERSCRIPT III PLATINUM One-step RT-qPCR Master Mix (prepared per reaction as follows: 5 μL One step RT-qPCR Master Mix (ThermoFisher), 0.3 μL 10 μM primer, 0.10 μL-0.25 μL 10 μM probe, 13.6 μL $H_2O$, 0.25 μL TAQ). qPCR data was analyzed using the LIGHTCYCLER 480 software AbsQuant/2nd Derivative Max algorithm for calculating Cp values.

An optimization of general assay components for a hops latent viroid RT-qPCR method was performed, and the results are shown in FIG. 1. Eight conditions of varying RT-qPCR master mix compositions with different concentrations of primers, probe, water, and Taq for the primer pair A-G and probe p1 were tested. Each reaction tube contained the volumes described in FIG. 1 for each reagent component comprising a total volume of 19 μL. Three samples were tested in this experiment, 1) a known positive-GelCZ1, 2) a known negative-GG #4 5.1, and 3) no template (water). To each reaction, 1 μL of 5 ng/μL RNA or Water was used as template input for a final reaction volume of 20 μL. For this assay, each condition was carried out in a single reaction on the Roche LIGHTCYCLER 480 real time instrument. Conditions labeled in FIG. 1 as 1, 2, 4, 6, and 7 yielded detectable signals of fluorescence crossing a threshold value while conditions labeled in FIG. 1 as 3, 5, and 8 yielded no detectable signal as is called by the Roche LIGHTCYCLER analysis software 2nd derivative max analysis algorithm. Condition 7 was selected to perform subsequent downstream testing as it preserved master mix stock as well as had little to no background/late cycle amplification as was observed in the known negative sample for conditions 1, 2, and 4.

Figure 2:
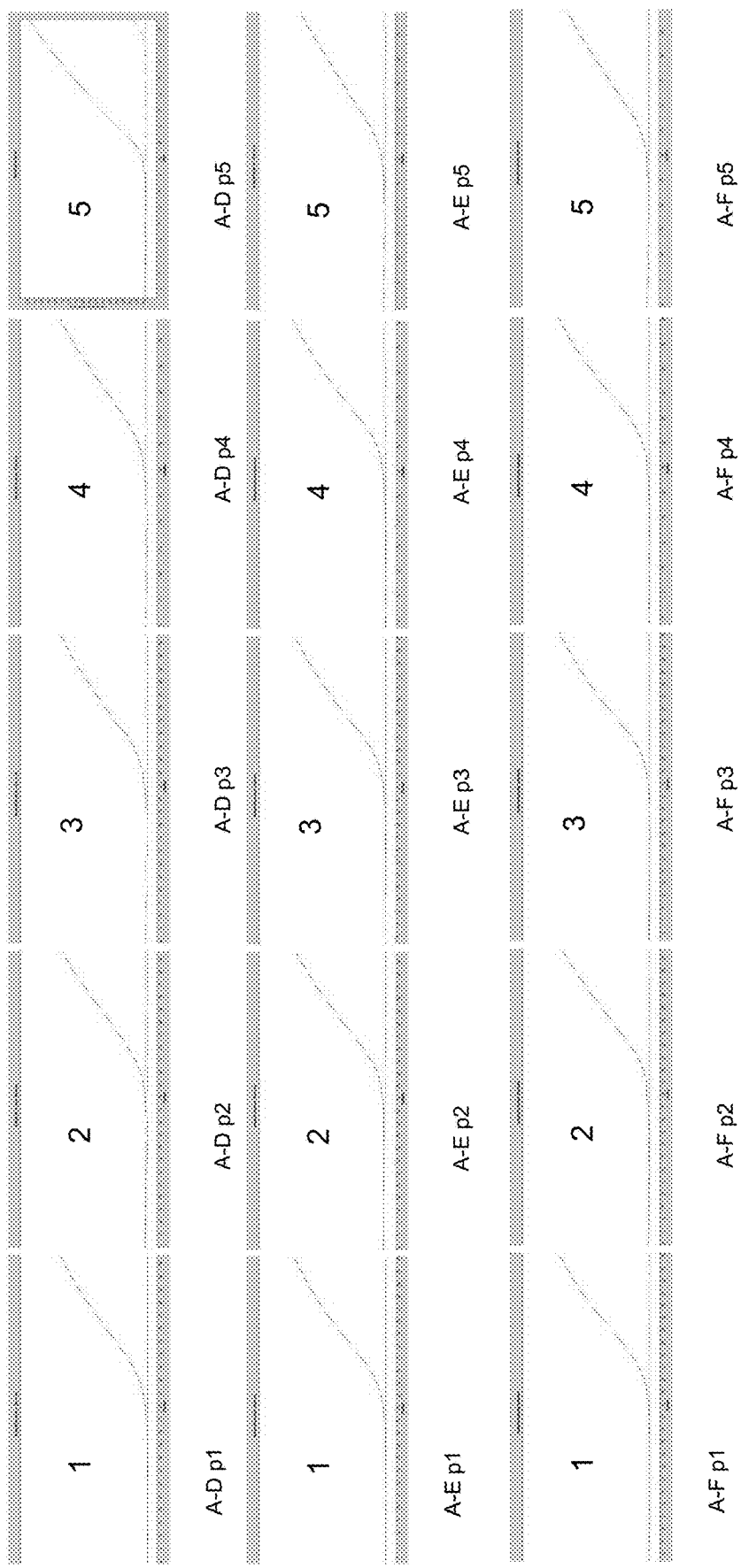
FIG. 2 shows results of an RT-qPCR analysis of primer/probe combinations for primer pairs A-D (A-fwd, D-rev), A-E (A-fwd, E-rev), and A-F (A-fwd, F-rev) and probes p1-p5 under optimized reaction condition 7.
Figure 3:
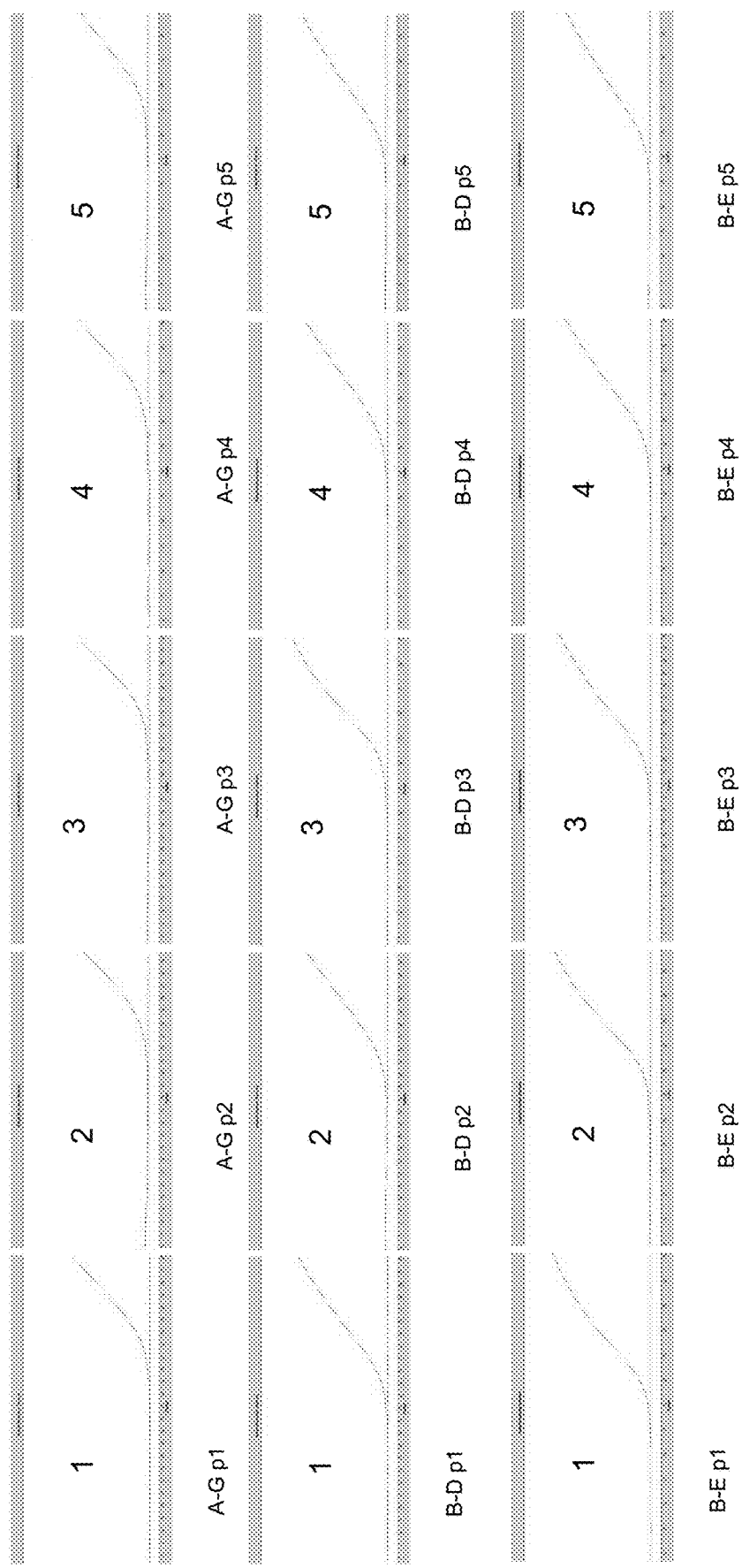
FIG. 3 shows results of an RT-qPCR analysis of primer/probe combinations for primer pairs A-G (A-fwd, G-rev), B-D (B-fwd, D-rev), and B-E (B-fwd, E-rev) and probes p1-p5 under optimized reaction condition 7.
Figure 4:
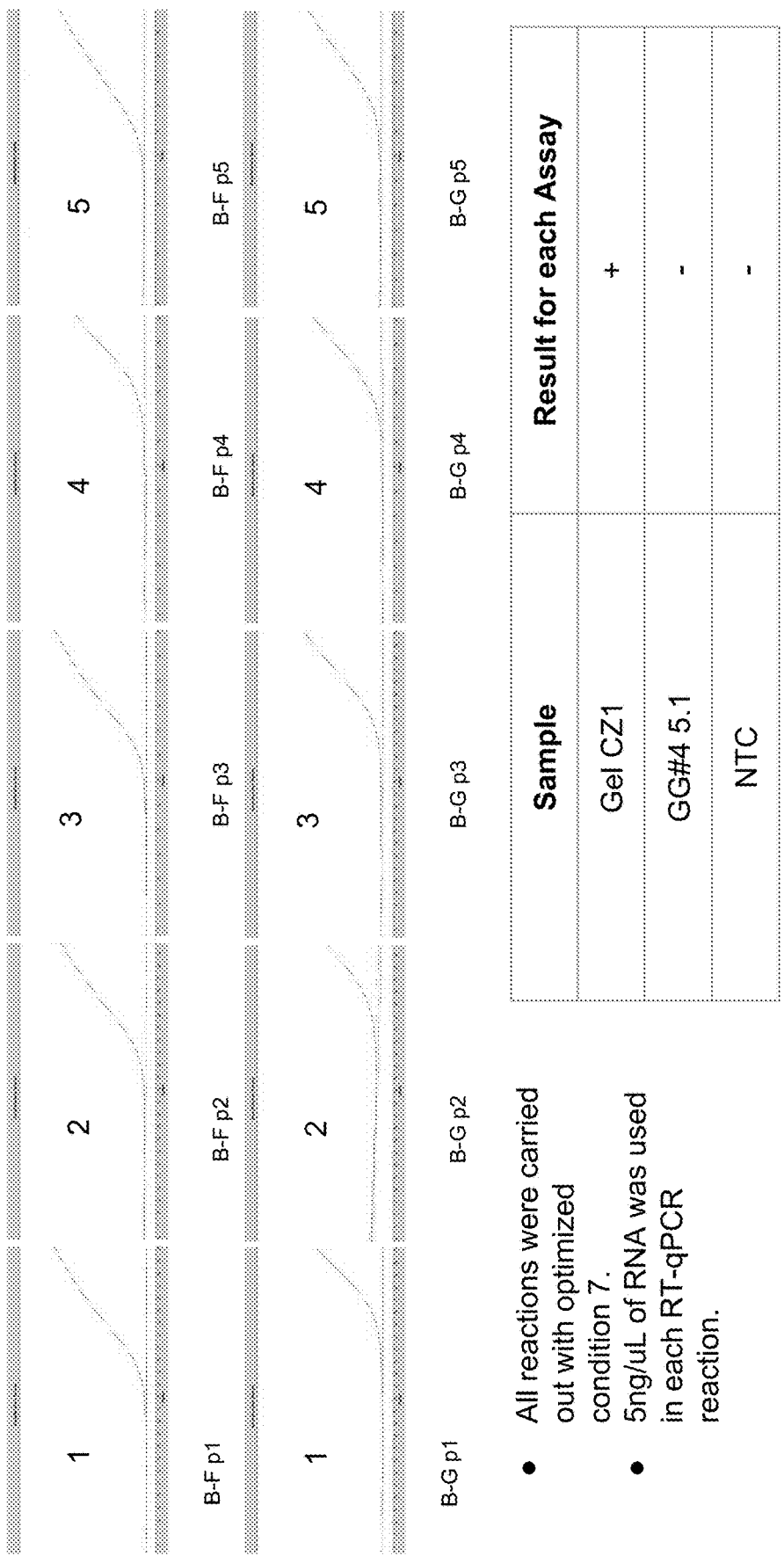
FIG. 4 shows results of an RT-qPCR analysis of primer/probe combinations for primer pairs B-F (B-fwd, F-rev) and B-G (B-fwd, G-rev) and probes p1-p5 under optimized reaction condition 7.

Further analysis of primer/probe combinations was performed for primer pairs A-D (FIG. 2), A-E (FIG. 2), A-F (FIG. 2), A-G (FIG. 3) B-D (FIG. 3), B-E (FIG. 3), B-F (FIG. 4), B-G (FIG. 4) each tested with probes p1-p5 with optimized reaction condition 7 (shown in FIG. 1). For this preliminary assay, each condition was carried out in a single reaction on the Roche LIGHTCYCLER 480 real time instrument. A reaction mix was prepared for each test sample with each reaction containing RT-qPCR components from condition 7 of: 5 µL Master mix, 0.3 µL 10 µM primer pair, 0.1 µL 10 µM probe, 13.6 µL nuclease free water, and 0.25 µL polymerase enzyme for 19 µL total reaction mix. Three samples were tested in this experiment, 1) a known positive-Gel CZ1, 2) a known negative-GG #4 5.1, and 3) no template (water). To each reaction, 1 µL of 5 ng/µL RNA or water was used as template input for a final reaction volume of 20 µL. In each assay, a positive fluorescent signal was detected and called by the Roche LIGHTCYCLER analysis software 2nd derivative max analysis algorithm for the Gel CZ1 positive sample and no signal was observed in the GG #4 5.1 negative sample or no template control.

Figure 5:
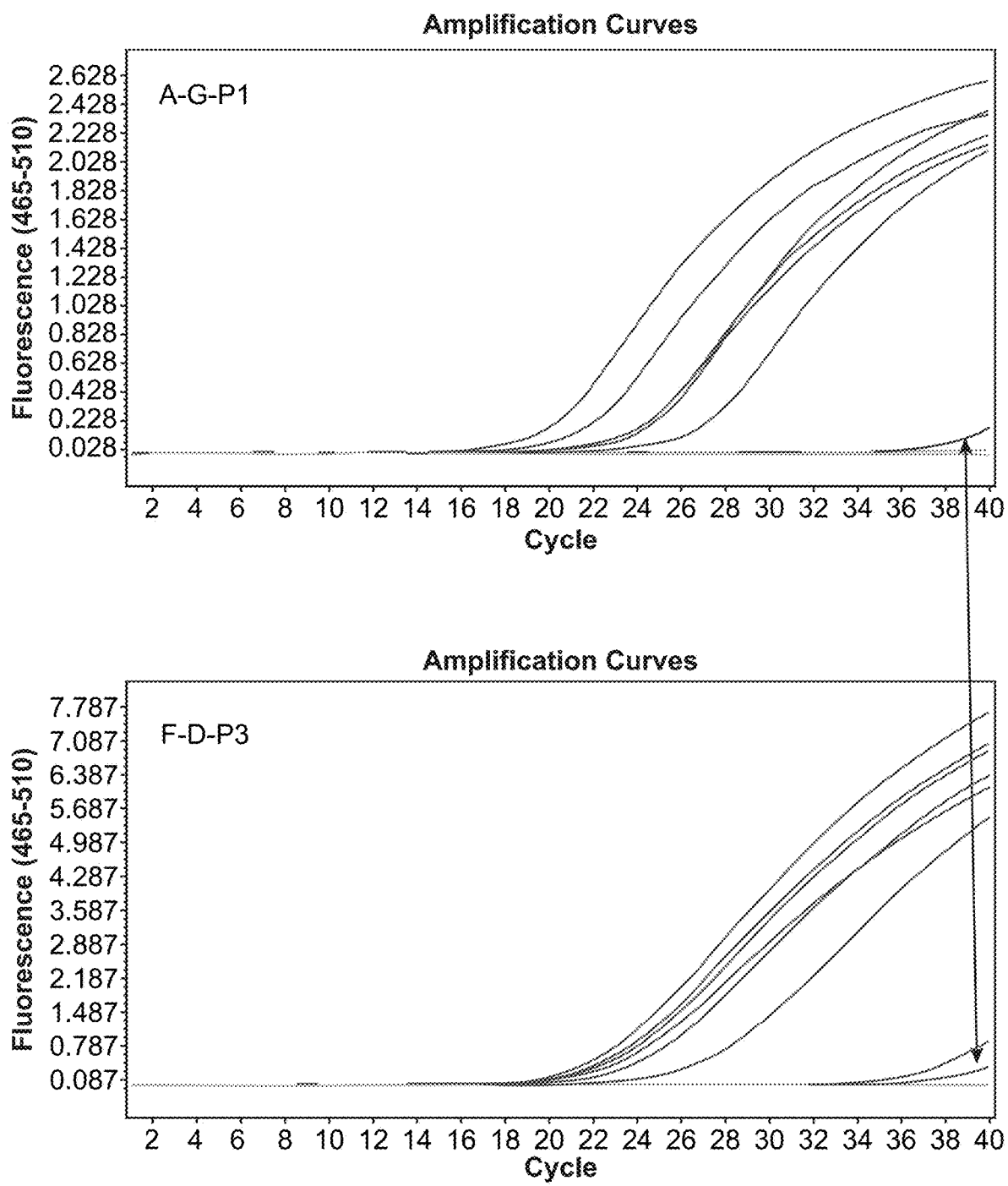
FIG. 5 shows results of an RT-qPCR analysis of the primer pair A-G (A-fwd, G-rev) with probe p1 and primer pair F-D (F-fwd, D-rev) with probe p3 performed on known positive and negative test samples. The arrows point to background and/or late cycle amplification.

A further analysis of the primer pair A-G with probe p1 and primer pair F-D with probe p3 was performed on known positive and negative test samples, and the results are shown in FIG. 5. The reactions were prepared as described above for the experiments shown in FIGS. 2-4. In the HpLVd A-G; p1 test, a robust FAM fluorescent signal was observed as positive for the following known positive samples: Gel CZ1, BS2.1, Gel CZ4, Gel CZ3, and Gel CZ2. Background/late cycle amplification was observed for known negative samples: BBM #4 5.1. No signal was detected in the GSC 5.3 sample, the GG #4 5.1 sample, or the no template control. In the HpLVd A-F; p3 test, a robust FAM fluorescent signal was observed as positive for the following known positive samples: Gel CZ1, BS2.1, Gel CZ4, Gel CZ3, and Gel CZ2. Background/late cycle amplification was observed for known negative samples: BBM #4 5.1 and GSC 5.3. No signal was detected GG #4 5.1 sample or the no template control. To minimize background amplification, DNAase I digestion of RNA template material and/or AMPErase reaction UNG pretreatment may be performed.

Figure 6:
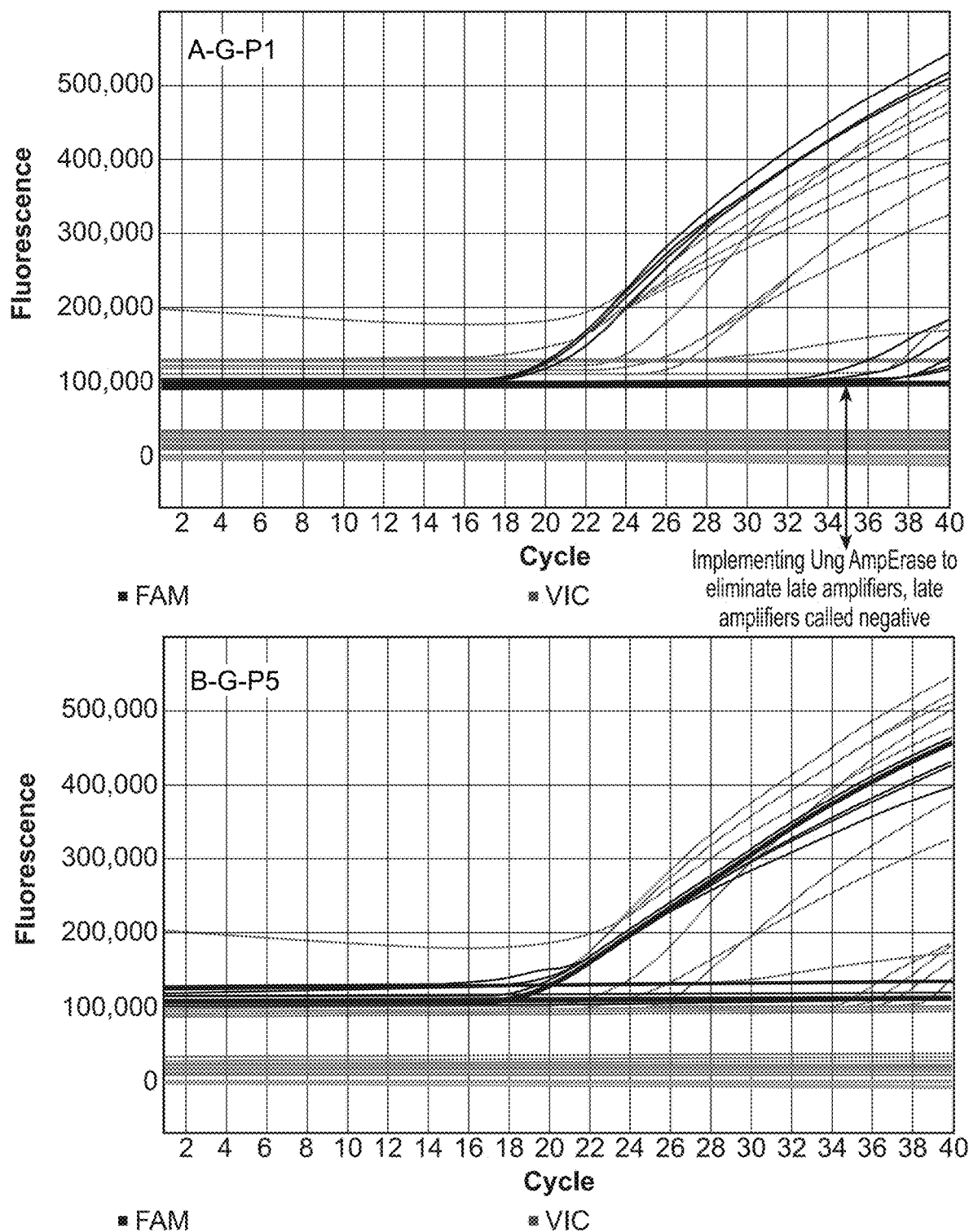
FIG. 6 shows results of an RT-qPCR analysis of unknown test samples performed using primer pair A-G (A-fwd, G-rev) with probe p1, and primer pair B-G (B-fwd, G-rev) with probe p5 using Gel CZ1 as a positive control and no template as a negative control. The arrow points to background and/or late cycle amplification.

An analysis of unknown test samples was performed with the primer pair A-G with probe p1 and primer pair B-G with probe p5 using Gel CZ1 as a positive control and no template as a negative control, and the results are shown in FIG. 6. For this assay, each condition was prepared as described above with duplicate replicates. Data acquisition and analysis was performed on the Applied Biosystems QUANTSTUDIO 5 real time instrument and cloud software. An amplification status flag was applied by software, and if amplification was observed for FAM channel, background or not, it is called an Amp. If no amplification is observed, the Amp status was observed as no Amp. No signal was measured on VIC channel. Positive and negative results were called based on an end point fluorescence threshold. In the HpLVd A-G; p1 test, a robust FAM fluorescent signal was observed in the positive control replicates for Gel CZ1 as well as the following samples: PP1 and SQR2. Background/late cycle amplification with end point fluorescence below threshold was observed for the following samples: GG #4 5.3, RH5.2, RH5.3, SQR3. No fluorescence was detected in the BS2.3 sample, Ven 4.2 sample, and Ven4.3 sample or no template control. In the HpLVd B-G; p5 test, a robust FAM fluorescent signal was observed in the positive control replicates for Gel CZ1 as well as the following samples: PP1 and SQR2. No background/late cycle amplification with end point fluorescence below threshold was observed. No fluorescence was detected in the following samples: GG #4 5.3, RH5.2, RH5.3, SQR3, BS2.3, Ven 4.2, Ven4.3, or no template control.

Figure 7:
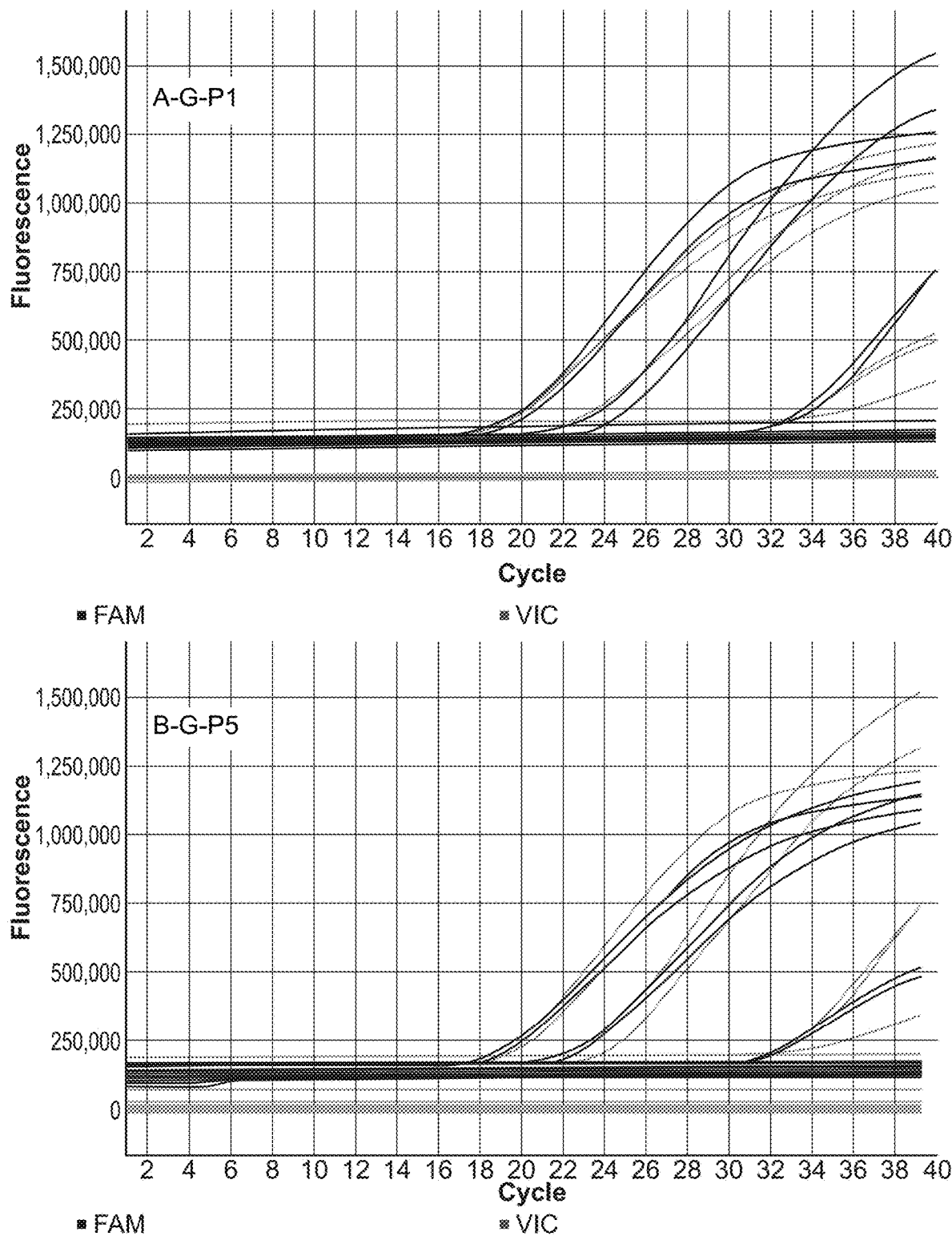
FIG. 7 shows results of an RT-qPCR analysis of genomic DNA and test RNA/cDNA samples was performed using primer pair A-G (A-fwd, G-rev) with probe p1, and primer pair B-G (B-fwd, G-rev) with probe p5 using Gel CZ1 as a positive control and no template as a negative control.

An analysis of genomic DNA and test RNA/cDNA samples was performed with the primer pair A-G with probe p1 and primer pair B-G with probe p5 using Gel CZ1 as a positive control and no template as a negative control, and the results are shown in FIG. 7. This experiment was performed to demonstrate that no off target amplification occurred in genomic DNA template. For this assay, each condition was prepared as described above with duplicate replicates. 1 µL of 5 ng/µL RNA/cDNA/gDNA or water was used as template input. Data acquisition and analysis was performed on the Applied Biosystems QUANTSTUDIO 5 real time instrument and cloud software. An amplification status flag was applied by software, and if amplification was observed for FAM channel, background or not, it is called an Amp. If no amplification is observed, the Amp status was observed as no Amp. No signal was measured on VIC channel. Positive and negative results were called based on an end point fluorescence threshold. In both HpLVd A-G; p1 test and B-G; p5 test, a robust FAM fluorescent signal was observed in the positive control replicates for Gel CZ1 as well as the following samples: Gel 5.1 cDNA, Gel 5.1 Fresh FTA Card RNA, and Gel 5.1 Fresh Leaf RNA. No background/late cycle amplification with end point fluorescence below threshold was observed. No fluorescence or amplification was detected in the following samples: 9.5 Old FTA Card RNA, BK13419 gDNA, BK48007 gDNA, Crag 107-8 Old FTA Card RNA, Crag 108-4 Old FTA Card RNA, Durban Poison gDNA, G17 gDNA, G3 gDNA, OCBG gDNA, or no template control.

Quantitative Real-Time PCR TAQMAN Analysis

A TAQMAN protocol is another method in which the primers described herein may be used. TAQMAN starts from a cDNA library instead of extracted RNA (e.g., used as input for RT-qPCR). qPCR analysis was performed in 10 µL reactions on a LIGHTCYCLER 480 qPCR (Roche Applied Systems) using the following protocol: 1 pre-incubation cycle (95° C. for 20 secs), 45 amplification cycles (95° C. for 1 second, 60° C. for 20 seconds, 72° C. for 20 seconds) with a single acquisition mode setting for each cycle at 60° C. annealing, followed by a final cooling cycle (40° C. for 30 seconds). Each reaction contained: 2.5 µL of 2 ng/µL of the normalized cDNA template used as input, 7.5 µL of TAQMAN Master Mix (prepared per reaction as follows: 5 µL of FASTTQ Advanced Reaction Mix (Applied Biosciences), 0.3 µL 10 µM primer, 0.10 µL-0.25 µL 10 µM probe, 13.6 µL H$_2$O, 0.25 µL TAQ). qPCR data was analyzed using the LIGHTCYCLER 480 software AbsQuant/2nd Derivative Max algorithm for calculating Cp values.

Loop Mediated Isothermal Amplification (LAMP)

Figure 9:
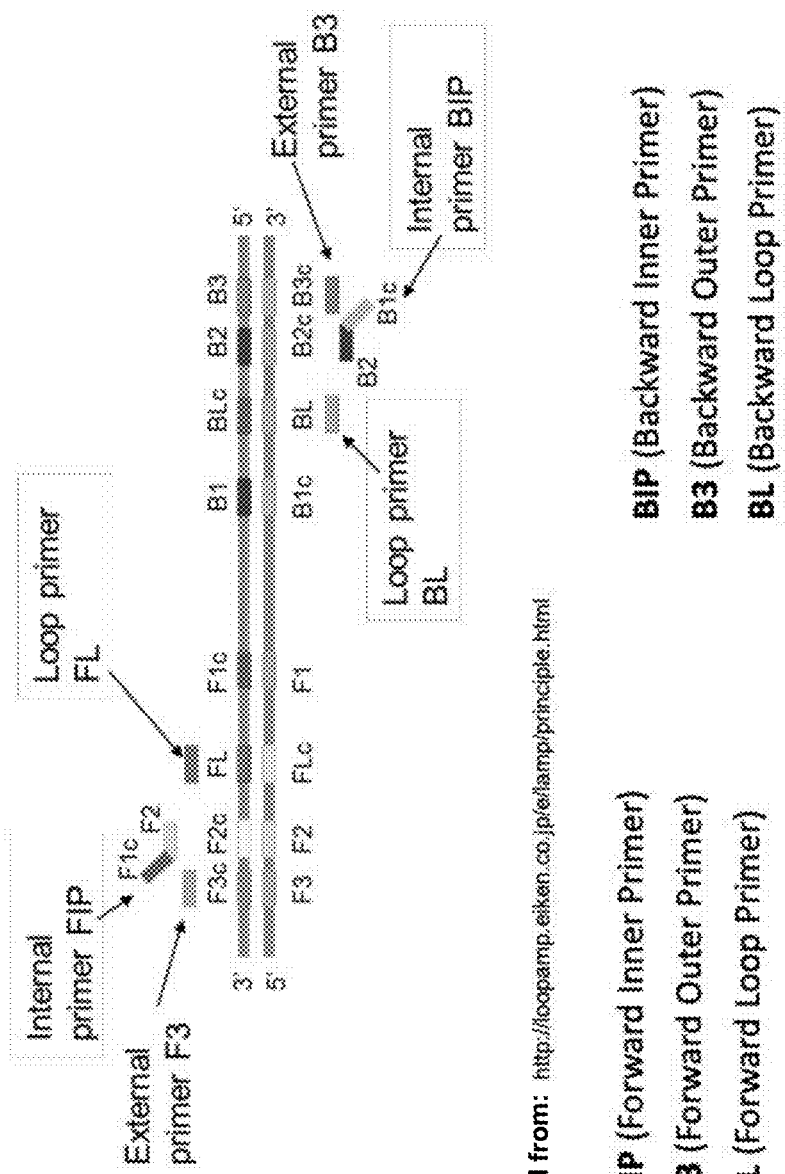
FIG. 9 shows an example illustration of LAMP primers.
Figure 10:
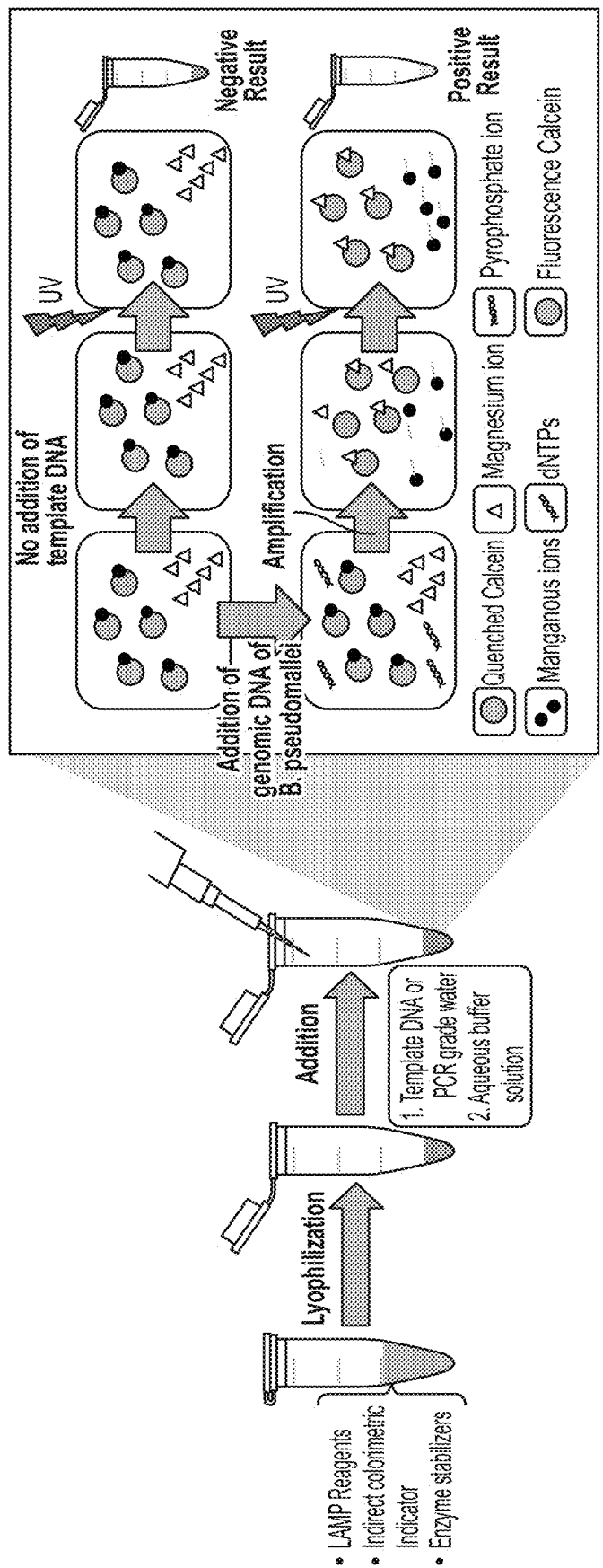
FIG. 10 shows an example illustration of a LAMP assay.
Figure 11B:
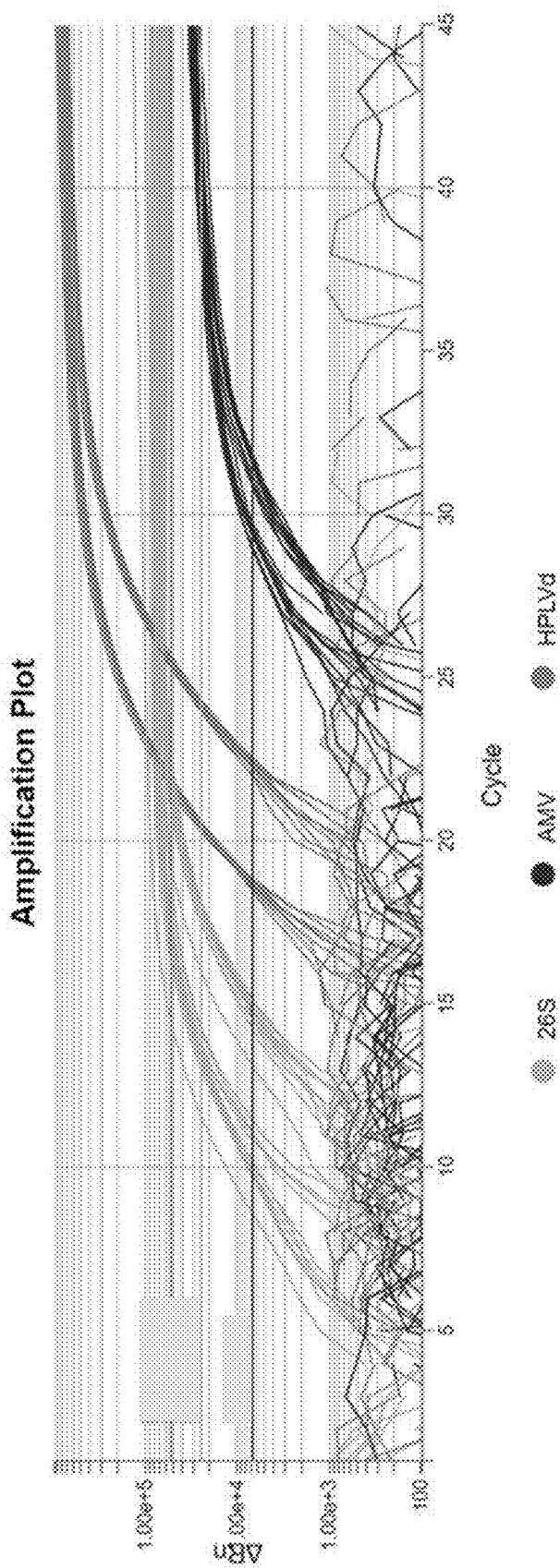

Loop mediated isothermal amplification (LAMP) primers were designed for use as a presence-absence test within a grow or lab environment. These primers provide the user a readily detectable color change if the viroid is present, providing a time-saving and cost-effective solution to identify infected plants within a grow. The primer sets designated in Tables 6 to 9 are used in this methodology under standard reaction conditions following manufacturer instructions for a traditional LAMP assay. Each of the primer sets below were designed for use as a single set. Accordingly four unique assays were created. The FIP (forward inner primer), BIP (backward inner primer), F3 (forward outer primer) and B3 (backward outer primer) primers may be generated with any loop (LB or LF) primers. The BIP and FIP are combinations of the B1c and B2, and F1c & F2 respectively, and may be linked by a polyT stretch that replaces the "-" in the tables below. In a typical LAMP assay, BIP, FIP, F3, B3, and any loop primers (if they exist) are combined with a master mix solution (provided by Eiken, Lucigen or a comparable LAMP master mix provider) and an extracted cDNA solution. If the target sequence is present in cDNA synthesized from extracted RNA, upon incubation, a color change of the solution is observed due to a successful amplification of the target. An example LAMP primer scheme is provided in FIG. 9 and an example LAMP assay is provided in FIG. 10.

The LAMP primers were designed as thermomutant-resistant primers; however, due to their longer size and the number of primers in each set, certain primers bind to thermomutant SNP sites. Generally, these primers were designed such that the known SNP sites are located in the middle of the primed region to allow for amplification of mutant viroids. Four sets of LAMP primers were designed to provide the most robust assay that would be most thermomutant stable.

TABLE 6

LAMP Set 1 (dimer (minimum) dG = −2.18)

| label | 5'pos | 3'pos | len | Tm | 5'dG | 3'dG | GCrate | Sequence | SEQ ID NO |
|---|---|---|---|---|---|---|---|---|---|
| F3 | 39 | 56 | 18 | 59.55 | −6.42 | −5.2 | 0.61 | AGGGCTCGAAGAGGGATC | 21 |
| B3 | 208 | 225 | 18 | 60.31 | −4.32 | −4.27 | 0.56 | TAAGCTCGGCGCTCAAGA | 22 |
| FIP | | | 39 | | | | | CGAAGCAACTTCAGGTCGCCG-CCCGGGGAAACCTACTCG | 23 |
| BIP | | | 41 | | | | | CTTCTCCTTGTTCGCGTCCTGC-CCGGGTAGTTTCCAACTCC | 24 |
| F2 | 57 | 74 | 18 | 60.75 | −7.14 | −4.76 | 0.67 | CCCGGGGAAACCTACTCG | 25 |
| F1c | 107 | 127 | 21 | 65.74 | −6.03 | −7.71 | 0.62 | CGAAGCAACTTCAGGTCGCCG | 26 |
| B2 | 179 | 197 | 19 | 59.09 | −7.12 | −4.85 | 0.58 | CCGGGTAGTTTCCAACTCC | 27 |
| B1c | 129 | 150 | 22 | 65.43 | −4.2 | −6.1 | 0.59 | CTTCTCCTTGTTCGCGTCCTGC | 28 |
| LB | 158 | 178 | 21 | 65.01 | −6.54 | −6.69 | 0.62 | GGCTCCTTCTTCACACCAGCC | 29 |

TABLE 7

LAMP Set 2 (dimer (minimum) dG = −2.18)

| label | 5'pos | 3'pos | len | Tm | 5'dG | 3'dG | GCrate | Sequence | SEQ ID NO |
|---|---|---|---|---|---|---|---|---|---|
| F3 | 39 | 56 | 18 | 59.55 | −6.42 | −5.2 | 0.61 | AGGGCTCGAAGAGGGATC | 30 |
| B3 | 208 | 225 | 18 | 60.31 | −4.32 | −4.27 | 0.56 | TAAGCTCGGCGCTCAAGA | 31 |
| FIP | | | 39 | | | | | CGAAGCAACTTCAGGTCGCCG-CCCGGGGAAACCTACTCG | 32 |
| BIP | | | 42 | | | | | CTTCTCCTTGTTCGCGTCCTGC-ATCCACCGGGTAGTTTCCAA | 33 |
| F2 | 57 | 74 | 18 | 60.75 | −7.14 | −4.76 | 0.67 | CCCGGGGAAACCTACTCG | 34 |
| F1c | 107 | 127 | 21 | 65.74 | −6.03 | −7.71 | 0.62 | CGAAGCAACTTCAGGTCGCCG | 35 |
| B2 | 183 | 202 | 20 | 60.61 | −4.9 | −4.53 | 0.5 | ATCCACCGGGTAGTTTCCAA | 36 |
| B1c | 129 | 150 | 22 | 65.43 | −4.2 | −6.1 | 0.59 | CTTCTCCTTGTTCGCGTCCTGC | 37 |
| LE | 158 | 178 | 21 | 65.01 | −6.54 | −6.69 | 0.62 | GGCTCCTTCTTCACACCAGCC | 38 |

TABLE 8

LAMP Set 3 (dimer (minimum) dG = -2.18)

| label | 5'pos | 3'pos | len | Tm | 5'dG | 3'dG | GCrate | Sequence | SEQ ID NO |
|---|---|---|---|---|---|---|---|---|---|
| F3 | 39 | 56 | 18 | 59.55 | -6.42 | -5.2 | 0.61 | AGGGCTCGAAGAGGGATC | 39 |
| B3 | 209 | 226 | 18 | 59.21 | -4.09 | -4.35 | 0.56 | TTAAGCTCGGCGCTCAAG | 40 |
| FIP | | | 39 | | | | | CGAAGCAACTTCAGGTCGCCG-CCCGGGGAAACCTACTCG | 41 |
| BIP | | | 42 | | | | | CTTCTCCTTGTTCGCGTCCTGC-AGTTGTATCCACCGGGTAGT | 42 |
| F2 | 57 | 74 | 18 | 60.75 | -7.14 | -4.76 | 0.67 | CCCGGGGAAACCTACTCG | 43 |
| F1c | 107 | 127 | 21 | 65.74 | -6.03 | -7.71 | 0.62 | CGAAGCAACTTCAGGTCGCCG | 44 |
| B2 | 189 | 208 | 20 | 59.69 | -4.55 | -4.57 | 0.5 | AGTTGTATCCACCGGGTAGT | 45 |
| B1c | 129 | 150 | 22 | 65.43 | -4.2 | -6.1 | 0.59 | CTTCTCCTTGTTCGCGTCCTGC | 46 |
| LB | 170 | 186 | 17 | 60.91 | -5.56 | -5 | 0.65 | ACACCAGCCGGAGTTGG | 47 |

TABLE 9

LAMP Set 4 (dimer (minimum) dG = -2.18)

| label | 5'pos | 3'pos | len | Tm | 5'dG | 3'dG | GCrate | Sequence | SEQ ID NO |
|---|---|---|---|---|---|---|---|---|---|
| F3 | 39 | 56 | 18 | 59.55 | -6.42 | -5.2 | 0.61 | AGGGCTCGAAGAGGGATC | 48 |
| B3 | 209 | 226 | 18 | 59.21 | -4.09 | -4.35 | 0.56 | TTAAGCTCGGCGCTCAAG | 49 |
| FIP | | | 39 | | | | | CGAAGCAACTTCAGGTCGCCG-CCCGGGGAAACCTACTCG | 50 |
| BIP | | | 41 | | | | | CTTCTCCTTGTTCGCGTCCTGC-CCGGGTAGTTTCCAACTCC | 51 |
| F2 | 57 | 74 | 18 | 60.75 | -7.14 | -4.76 | 0.67 | CCCGGGGAAACCTACTCG | 52 |
| F1c | 107 | 127 | 21 | 65.74 | -6.03 | -7.71 | 0.62 | CGAAGCAACTTCAGGTCGCCG | 53 |
| B2 | 179 | 197 | 19 | 59.09 | -7.12 | -4.85 | 0.58 | CCGGGTAGTTTCCAACTCC | 54 |
| B1c | 129 | 150 | 22 | 65.43 | -4.2 | -6.1 | 0.59 | CTTCTCCTTGTTCGCGTCCTGC | 55 |
| LB | 158 | 178 | 21 | 65.01 | -6.54 | -6.69 | 0.62 | GGCTCCTTCTTCACACCAGCC | 56 |

Reverse Complement Primers and Probes

The reverse complement of the primers provided in Table 1 and the probes provided in Table 5 are provided in Table 10 and Table 11, respectively.

TABLE 10

| Primer Name | Sequence (5' -> 3') | Length | SEQ ID NO |
|---|---|---|---|
| A-fwd - RevComp | GCCACCATACAGGTAAGTCACGTAG | 25 | 57 |
| A-rev - RevComp | CGAGCGCCAGTTCGTGCG | 18 | 58 |
| B-fwd - RevComp | CGCTCGAGTAGGTTTCCCC | 19 | 59 |
| B-rev - RevComp | CGTGCGCGGCGACCTGAAG | 19 | 60 |
| C-fwd - RevComp | CGCCTCGCTCGAGTAGGTTTCC | 22 | 61 |

TABLE 10-continued

| Primer Name | Sequence (5' -> 3') | Length | SEQ ID NO |
|---|---|---|---|
| C-rev - RevComp | TGGAACGGCTCCTTCTTCAC | 20 | 62 |
| D-rev - RevComp | CGGAGTTGGAAACTACCCG | 19 | 63 |
| D-fwd - RevComp | GCGCTCGATCTCCGCCTCG | 19 | 64 |
| E-rev - RevComp | CGGAGTTGGAAACTACCCGG | 20 | 65 |
| E-fwd - RevComp | CGAACTGGCGCTCGATCTC | 19 | 66 |
| F-rev - RevComp | CGGAGTTGGAAACTACCCGGT | 21 | 67 |
| F-fwd - RevComp | CGAACTGGCGCTCGATCT | 18 | 68 |

TABLE 10-continued

| Primer Name | Sequence (5' -> 3') | Length | SEQ ID NO |
|---|---|---|---|
| G-rev - RevComp | GGAAACTACCCGGTGAATACAACTCT | 26 | 69 |
| H-rev - RevComp | GCAGAAGTTCACATAAAAGTGC | 23 | 70 |

TABLE 11

| Probe | Sequence (5' → 3') | SEQ ID NO |
|---|---|---|
| Probe 1 - RevComp | AGGTCGCCGCGCACGA | 71 |
| Probe 2 - RevComp | AACTGGCGCTCGATCTCCG | 72 |
| Probe 3 - RevComp | ACTTCAGGTCGCCGCGCA | 73 |
| Probe 4 - RevComp | TGGCGCTCGATCTCCGCCT | 74 |
| Probe 5 - RevComp | GGAGCCGTTCCACGCAGGA | 75 |

Applications

Figure 12B:
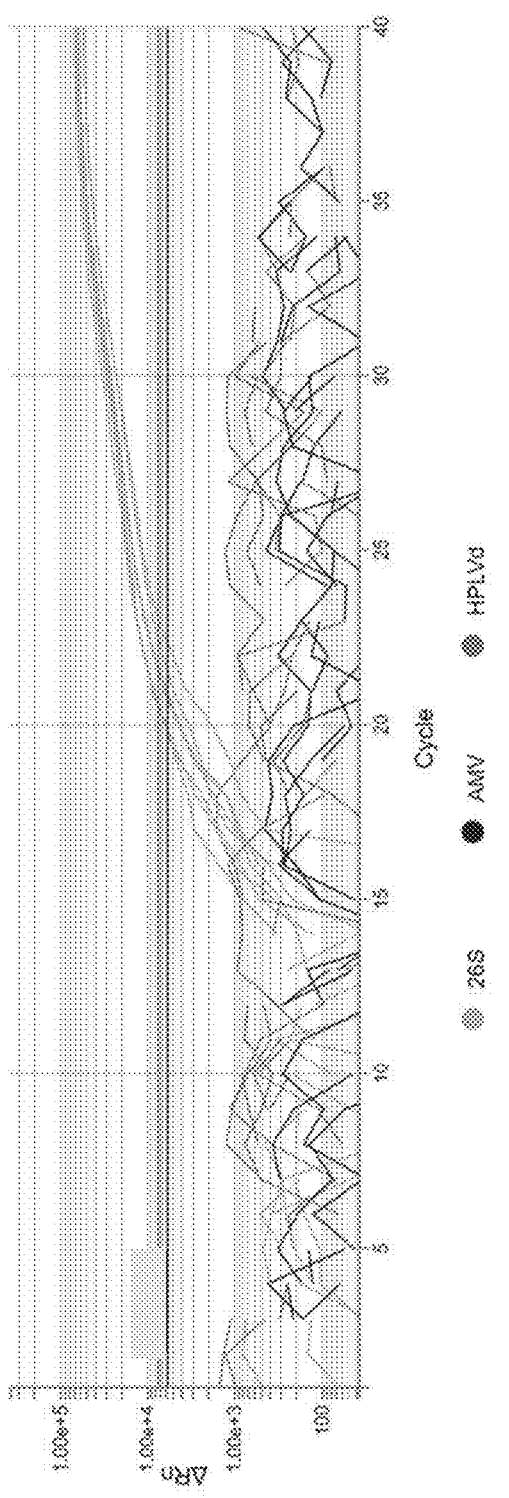
Figure 12B:
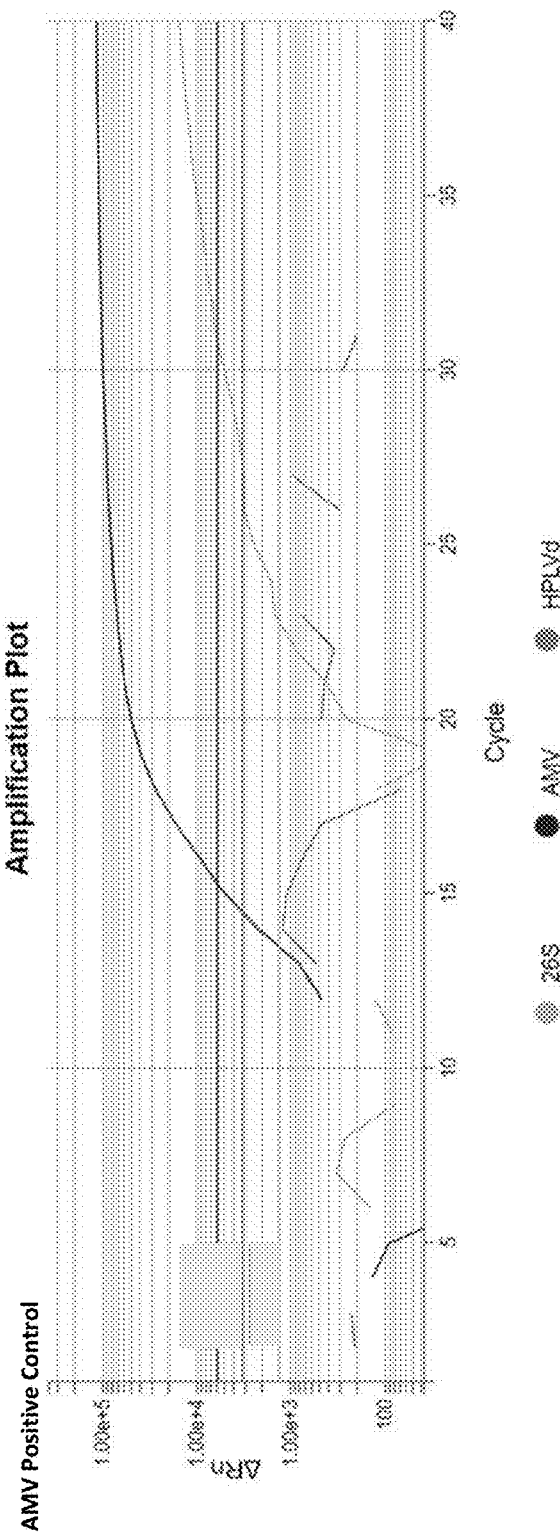

The technology described in this Example may be used in a number of applications, including, for example, in a cultivation facility application setting, in a molecular lab application setting, and/or as part of a kit of pathogen identification markers. Certain applications may identify more or less active variants of the HpLVd genome for transgenic experiments including CRISPR-cas9, Cre-Lox, and other genetic modification applications to inhibit, silence, or interfere with the more or less active variant.

Certain applications may use this technology in a cDNA microassay screening tool to identify presence and/or amount of viroid RNA present in a given *cannabis* cultivar. Such applications may be useful for one or more of 1) relating the amount of viroid in a cell to the presentation or absence of symptoms in infected plants, 2) relating the genotype of viroid in a cell to the presentation or absence of symptoms in infected plants, and 3) relating a given HpLVd genotype to determining the performance, yield, and/or growth characteristics of a given *cannabis* cultivar.

Certain applications may use this technology to verify if in vitro treatments have removed or mutated the HpLVd genome from a given plant. Such applications may be useful for identifying the mutant HpLVd genome to identify detrimental SNPs within the HpLVd genome that inhibit the viroid from affecting the host plants phenotype.

Certain applications may use this technology to identify plant genotypes that are resistant to certain variants of the HpLVd genome. For example, LOX-1 variants that are non-complementary to the HpLVd genome may be identified.

Example 3: Validation of a Multiplexed Method of Determining the Presence, Absence and/or Amount of More than One Pathogen in a Plant Cultivar Total RNA was collected from several *Cannabis* samples and a lyophilized AMV-positive control sample using the kit from Zymo Research as described in Example 1. The total RNA was carried through first strand cDNA synthesis.

To demonstrate broad qualitative sensitivity of high and low input, the following samples were assayed by qPCR:

(1) a pool of cDNA from HpLVd-positive plant material normalized to 1 ng and 0.1 ng and spiked with 1 ng and 0.1 ng AMV Positive Control cDNA in 10 technical replicates, (2) a pool of cDNA from HpLVd and AMV-negative plant material; and (3) a no template control (NTC) of water The samples were assayed using HPLVd, AMV, and 26S ribosomal RNA (rRNA) (internal positive control that is specific for cDNA from the plant genome) in a multiplexed format. Samples assayed were tested across 3 HPLVd primer pairs: HPLVd B-D (SEQ ID NOS: 4 and 8), HPLVd B-E (SEQ ID NOS: 4 and 10), and HPLVd B-F (SEQ ID NOS: 4 and 12) with all 5 HPLVd probes p1-p5 (SEQ ID NOS: 16-20) labeled with 6-FAM in a multiplex with the AMV B-C primer pair (SEQ ID NOS: 82 and 84) with AMV probe B (SEQ ID NO:89) labeled with Cy5, and 1 internal positive control 26S rRNA primer pair (SEQ ID NOS: 107 and 108) with 26S rRNA probe p1 (SEQ ID NO:109) labeled with SUN (or VIC). cDNA, as described above, was used as input into the qPCR assay. The qPCR was formulated using Taqman Fast Advanced Master Mix (Thermo Fisher Scientific, Waltham, Mass.) and optimized primer/probe mix formulations. Cq mean and standard deviation values for HpLVd quantitation were calculated and observed to be relatively consistent across all primer and probe set multiplex combinations and in the presence of various amounts of AMV cDNA spiking, as shown in the validation table in FIG. 11A. HPLVd detection of 1 ng, which is the standard input for the assay, was consistently observed having Cq values between 20-21. The relative uniformity across high (1 ng cDNA) and low (0.1 ng) input Cq values for all HPLVd B-D, B-E, B-F primer sets demonstrates reproducibility and broad sensitivity for detection of the HpLVd pathogen in HpLVd-positive plant samples, using HPLVd probes p1-5, in a multiplex assay in the presence of spiked amounts of cDNA from the AMV pathogen. FIG. 11B shows amplification plots using various primer pair/probe combinations (indicated at the top left) for detecting 26S (positive control; pale gray), HPLVd (medium gray) and AMV (dark gray).

Example 4: Multiplexed RT-qPCR for Determining the Presence, Absence and/or Amount of the HpLVd, AMV and BCTV Pathogens in *Cannabis* Cultivars In this analysis, four *Cannabis* cultivar plant samples from the greenhouse were tested: two mother plants named CW14T520 M001 and CW14T520 M002, and two samplings from a symptomatic Abagail plant. Total RNA was isolated as described in Example 2. For each reaction, 1 ng of quantified and normalized RNA was used as input into an RT-qPCR one step multiplex reaction. The CW14T520 M001 and CW14T520 M002 mother plants and the two samples from the Abagail symptomatic plant (Sample Reps 1 and 2, see FIG. 12) were tested for the HpLVd pathogen using the B-F HPLVd primer pair (SEQ ID NOS: 4 and 12) with HPLVd probe p4 (SEQ ID NO:19) labeled with 6-FAM in a multiplex with the AMV pathogen B-C primer pair (SEQ ID NOS: 82 and 84) with AMV probe B (SEQ ID NO:89) labeled with Cy5, and 1 internal positive control 26S rRNA primer pair (SEQ ID NOS: 107 and 108) with 26S rRNA probe p1 (SEQ ID NO:109) labeled with SUN (or VIC). The two mother plants, CW14T520 M001 and CW14T520 M002 plants had an undetermined Cq value for AMV and HPLVd indicating values below the threshold and therefore indicating the absence of those pathogens in the mother plants. The two samples from the symptomatic Abagail plant tested negative for AMV, with an undetermined Cq value for AMV, and positive for HpLVd, with a Cq value above the threshold and a strong amplification curve observed (FIGS. 12A and 12B; in the amplification plots, 26S is pale gray, HPLVd or BCTV is medium gray; AMV is dark gray). All reactions in this multiplex tested positive for the internal positive control 26S rRNA, with a Cq value crossing the threshold and thereby indicating a successful RT-qPCR reaction.

The two samplings of the symptomatic Abagail plant were also tested for the HpLVd pathogen using the B-F HPLVd primer pair (SEQ ID NOS: 4 and 12) with HPLVd probe p4 (SEQ ID NO:19) labeled with 6-FAM in a multiplex with the BCTV pathogen DRP_MP primer pair (SEQ ID NOS: 93 and 94) with BCTV Probe 1_DRP_MP (SEQ ID NO:95) labeled with Cy5, and 1 internal positive control 26S rRNA primer pair (SEQ ID NOS: 107 and 108) with 26S rRNA probe p1 (SEQ ID NO:109) labeled with SUN (or VIC). The samples from the symptomatic plant again tested positive for HpLVd, with similar Cq values to those observed in the multiplex reaction described above. In addition, the samples from the symptomatic plant tested positive for BCTV, with a Cq value crossing the threshold and a strong amplification curve observed (FIGS. 12A and 12B; in the amplification plots, 26S is pale gray, HPLVd or BCTV is medium gray; AMV is dark gray). 1 ng and 5 ng of a Gelato *Cannabis* sample that was positive for HpLVd was used as a control, along with a AMV positive control sample. Cq values were all observed as expected, and no Cq values for any target was observed (below threshold) in the no template controls (NTC). These results demonstrate selectivity for the individual pathogen targets in symptomatic and test plants from cultivation.

Figure 13B:
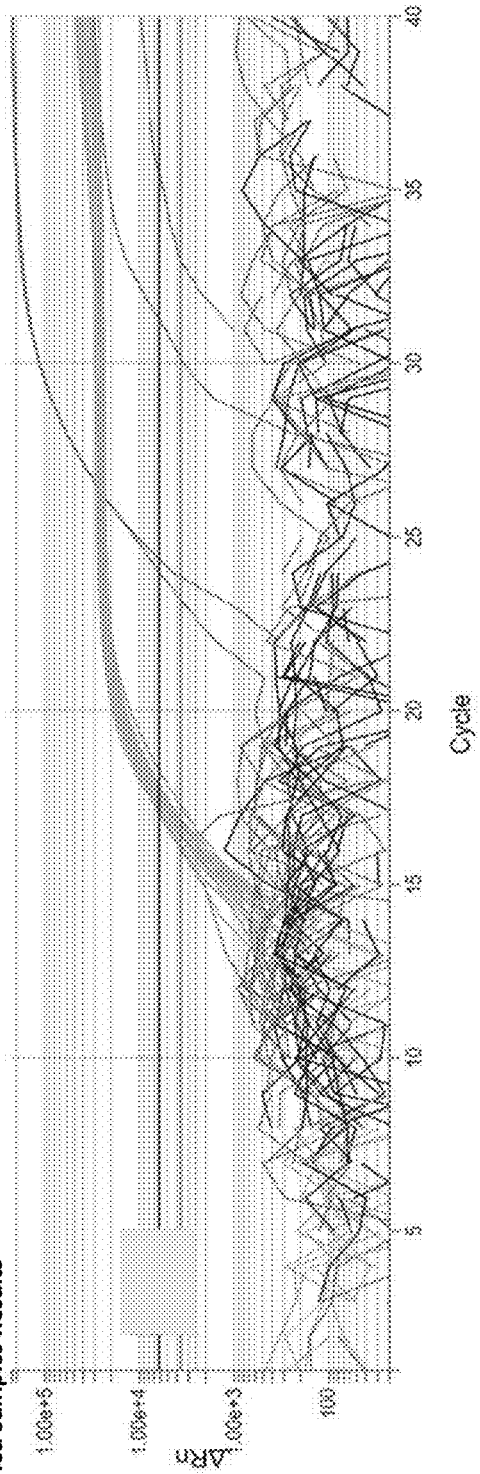
Figure 13B:
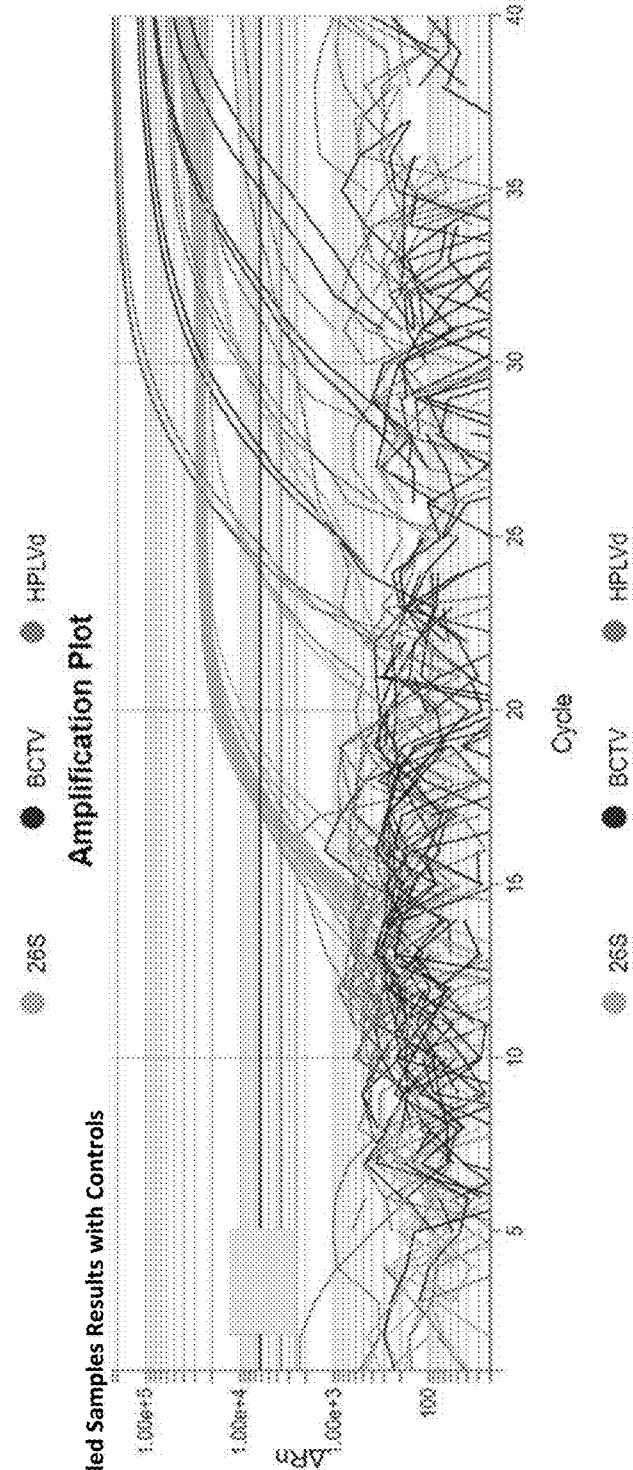

Example 5: Reproducibility of Multiplexed qPCR for Determining the Presence, Absence and/or Amount of the HpLVd, and BCTV Pathogens in Pooled Leaf Samples from *Cannabis* Cultivars In this analysis, ten plants were tested from a *Cannabis* cultivation facility/greenhouse in Salinas, Calif. Total RNA was isolated as described in Example 2. Five pooled leaf samples from ICC mother plants and five pooled leaf samples from BSC mother plants were tested in a total of ten test samples, each with 5 samples per pool (see FIGS. 13A and 13B). For each reaction, 1 ng of quantified and normalized RNA was used as input into an RT-qPCR one step multiplex reaction. The ten pooled samples were tested using the B-F HPLVd primer pair (SEQ ID NOS: 4 and 12) with HPLVd probe p3 (SEQ ID NO:18) labeled with 6-FAM in a multiplex with the BCTV pathogen DRP_MP primer pair (SEQ ID NOS: 93 and 94) with BCTV Probe 1_DRP_MP (SEQ ID NO:95) labeled with Cy5, and 1 internal positive control 26S rRNA primer pair (SEQ ID NOS: 107 and 108) with 26S rRNA probe p1 (SEQ ID NO:109) labeled with SUN (or VIC). 4 out of 5 pools for each of the BSC and ICC samples had an undetermined Cq value for BCTV and HpLVd (below threshold), indicating the absence of those pathogens. One BSC pool (BSC-C) and one ICC pool (ICC-B) tested negative for BCTV, with an undetermined (below threshold) Cq value for BCTV, and positive for HpLVd, with a Cq value that was above the threshold and a strong amplification curve observed (FIGS. 13A and 13B; in the amplification plots, 26S is pale gray, HPLVd is medium gray; BCTV is dark gray). All reactions in this multiplex tested positive for the internal positive control 26S rRNA, with a Cq value crossing the threshold and indicating a successful RT-qPCR reaction.

RNA from the symptomatic Abagail sample (1 ng, 0.1 ng, and 0.01 ng obtained by serial dilution) were used as positive controls and tested for HpLVd using the using the B-F HPLVd primer pair (SEQ ID NOS: 4 and 12) with HPLVd probe p4 (SEQ ID NO:19) labeled with 6-FAM in a multiplex with the BCTV pathogen DRP_MP primer pair (SEQ ID NOS: 93 and 94) with BCTV Probe 1_DRP_MP (SEQ ID NO:95) labeled with Cy5, and 1 internal positive control 26S rRNA primer pair (SEQ ID NOS: 107 and 108) with 26S rRNA probe p1 (SEQ ID NO:109) labeled with SUN (or VIC). The positive control samples all tested positive for HpLVd, with similar Cq values to those observed in the multiplex reaction described above. In addition, the positive control samples tested positive for the BCTV pathogen, with a Cq value crossing the threshold and a strong amplification curve observed. The results demonstrate that the multiplexing method for determining the presence, absence and/or amounts of multiple samples from plant cultivars can reliably be used to analyze multiple samples simultaneously (e.g., amplified using different sets of primers, and/or for detecting more than one pathogen).

Example 6: Sensitivity of Multiplexed RT-qPCR

In this analysis, two *Cannabis* plant samples were tested: one symptomatic Abagail Hemp plant and one *Cannabis* RNA pool from HpLVd positive plants at a concentration of 200 ng/uL that was combined at a 1:1 v/v with the AMV positive control.

Figure 14B:
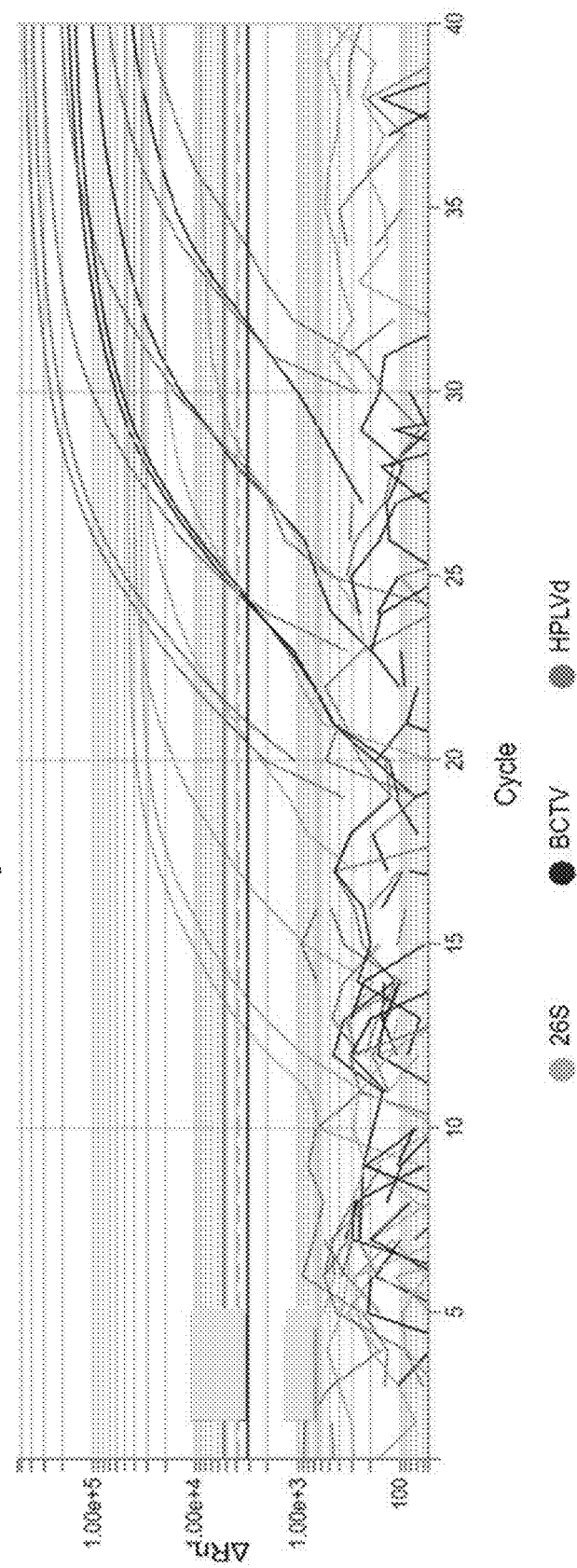
Figure 14C:
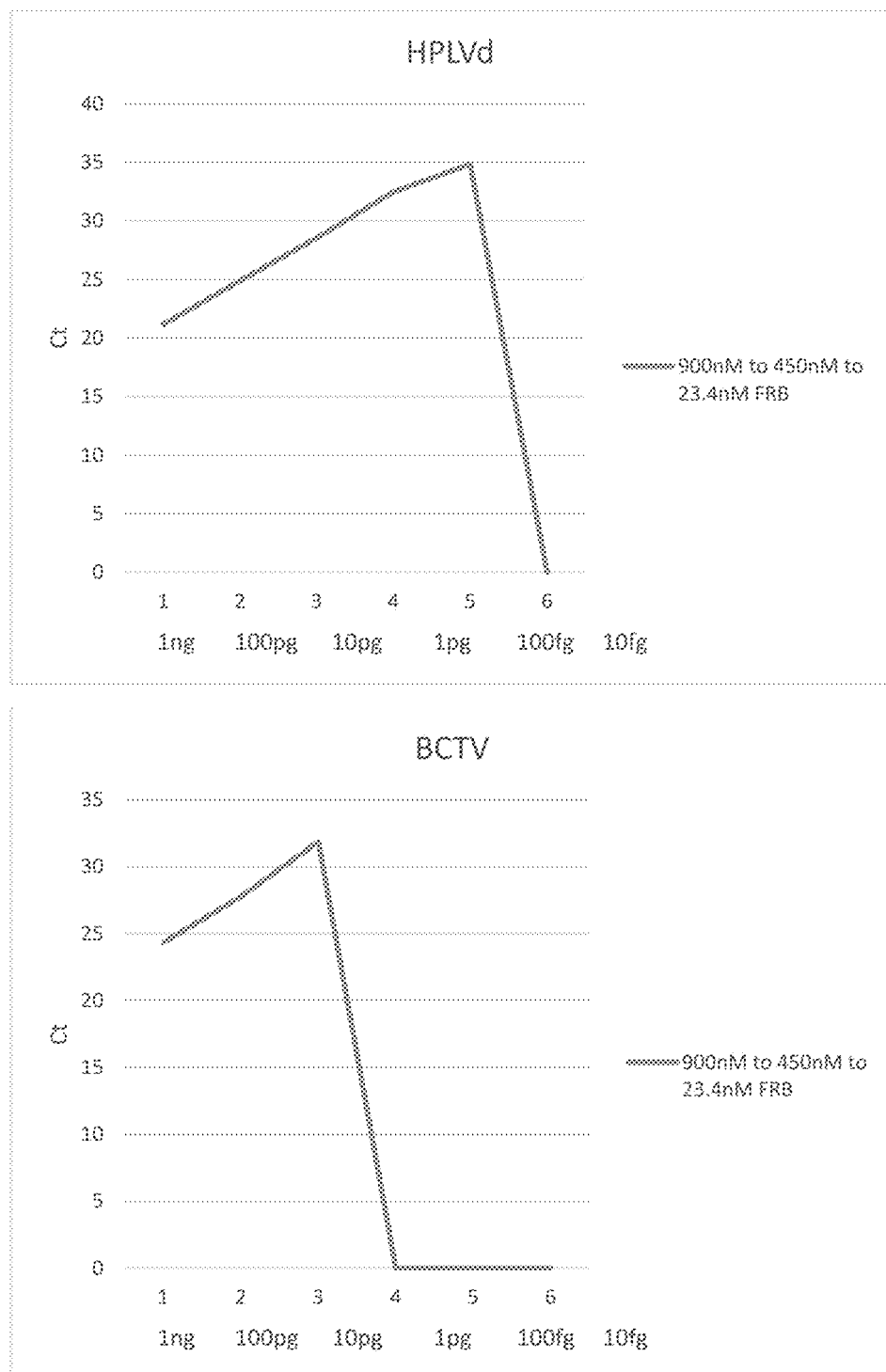

1 ng of quantified and normalized RNA from each sample was serially diluted in a ten-fold dilution series, down to 0.00001 ng, and used as input into RT-qPCR one step multiplex reactions. The Abagail serial dilution standard curve was tested using the B-F HpLVd primer pair (SEQ ID NOS: 4 and 12) with HpLVd probe p3 (SEQ ID NO:18) labeled with 6-FAM in a multiplex with the BCTV pathogen DRP_MP primer pair (SEQ ID NOS: 93 and 94) with BCTV Probe 1_DRP_MP (SEQ ID NO:95) labeled with Cy5, and 1 internal positive control 26S rRNA primer pair (SEQ ID NOS: 107 and 108) with 26S rRNA probe p1 (SEQ ID NO:109) labeled with SUN (or VIC). The Abagail sample showed strong amplification curves down to 100 fg for HPLVd and down to 10 pg for BCTV, with a series of Cq values that crossed the threshold up to the lowest levels of sensitivity for each primer pair under these conditions (FIG. 14A and FIG. 14B; in the amplification plots, 26S is pale gray, HPLVd is medium gray; AMV or BCTV is dark gray). These results indicate sensitivity of the HpLVd and BCTV primers in a multiplex assay. All reactions in this multiplex tested positive for the internal positive control 26S with a Ct value crossing threshold indicating a successful RT-qPCR reaction down to the 100 fg input. No signal was observed below that input level. The 1:1 AMV spiked *cannabis* HpLVd+ pool dilution series were tested for HpLVd using the B-F HpLVd primer pair with the HpLVd probe p4 labeled with 6-FAM in multiplex with AMV B-C primer pair AMV B-C with AMV probe B labeled with Cy5, and 1 internal positive control 26S ribosomal RNA primer pair with 26S probe p1 labeled with SUN. The AMV spiked *Cannabis* HpLVd+ pool had strong amplification curves down to 100 fg for HPpLVd and 10 fg for AMV with a series of Ct values observed crossing threshold until lowest levels of sensitivity for each primer pair under these conditions (FIG. 14A and FIG. 14B; in the amplification plots, 26S is pale gray, HPLVd is medium gray; AMV or BCTV is dark gray). These results indicate high sensitivity of the HpLVd and AMV primers in a multiplex assay. All reactions in this multiplex tested positive for the internal positive control 26S rRNA, with a Cq value crossing the threshold value, thereby indicating a successful RT-qPCR reaction down to the 100 fg amount that was input. No signal for either multiplex was observed in the no template control (NTC). FIG. 14C depicts standard curves for the pathogens in various samples as indicated at the top left of each curve.

Example 7: Robustness, Sensitivity, Specificity and Equivalency of Multiplexed RT-qPCR and LAMP Assays This example demonstrates the robustness, sensitivity, specificity and equivalency of Multiplexed RT-qPCR and LAMP Assays, and further demonstrates that the LAMP colorimetric assay can serve as an accurate, simple, visual alternative to the RT-qPCR method for multiplexed detection of pathogens in a plant.

In this analysis, total RNA was collected from several *Cannabis* samples and an AMV lyophilized positive control using a commercial Plant Quick RNA kit (Zymo Research, Irvine, Calif.). Two sample pools of *Cannabis* RNA were prepared: one from HPLVd, AMV and BCTV negative samples and the other pool prepared and formulated with HPLVd Positive *Cannabis* RNA samples, HPLVd Positive and BCTV Positive *Cannabis* RNA samples and AMV positive RNA samples. All positive and negative RNA pools were prepared at a final concentration of 1 ng/uL. A standard curve was also formulated to assess sensitivity, with serial 10-fold dilutions from 1 ng/uL to 0.00001 ng/uL.

To demonstrate robust qualitative sensitivity and specificity for detection of HPLVd, BCTV, and AMV in a RT-qPCR assay, both positive and negative *Cannabis* RNA pools, an RNA standard curve, and a no template control (NTC) were used as input and assayed as duplicates. 1 uL of input was tested in HPLVd/AMV/26S and HPLVd/BCTV/26S RT-qPCR multiplex assays. A HPLVd/AMV/26S multiplex assay was prepared by formulating iTaq one step RT-qPCR Mastermix (Bio-Rad, Hercules, Calif.) with the B-F HPLVd primer pair and the HPLVd probe p4 labeled with 6-FAM in multiplex and HPLVd probe p2 labeled with ROX NHS, the AMV A-C primer pair with AMV probe B labeled with Cy5 and AMV probe A labeled with TAMRA NHS, and 1 internal positive control 26S ribosomal RNA primer pair with 26S probe p1 labeled with SUN. A second HPLVd/BCTV/26S multiplex was prepared by formulating iTaq one step RT-qPCR mastermix with the B-F HPLVd primer pair with the HPLVd probe p4 labeled with 6-FAM in multiplex and HPLVd probe p2 labeled with ROX NHS, the BCTV DRP MP primer pair with BCTV DRP MP Probe 2 labeled with Cy5 and BCTV DRP MP Probe 1 labeled with TAMRA NHS, and 1 internal positive control 26S ribosomal RNA primer pair with 26S probe p1 labeled with SUN.

Figure 15:
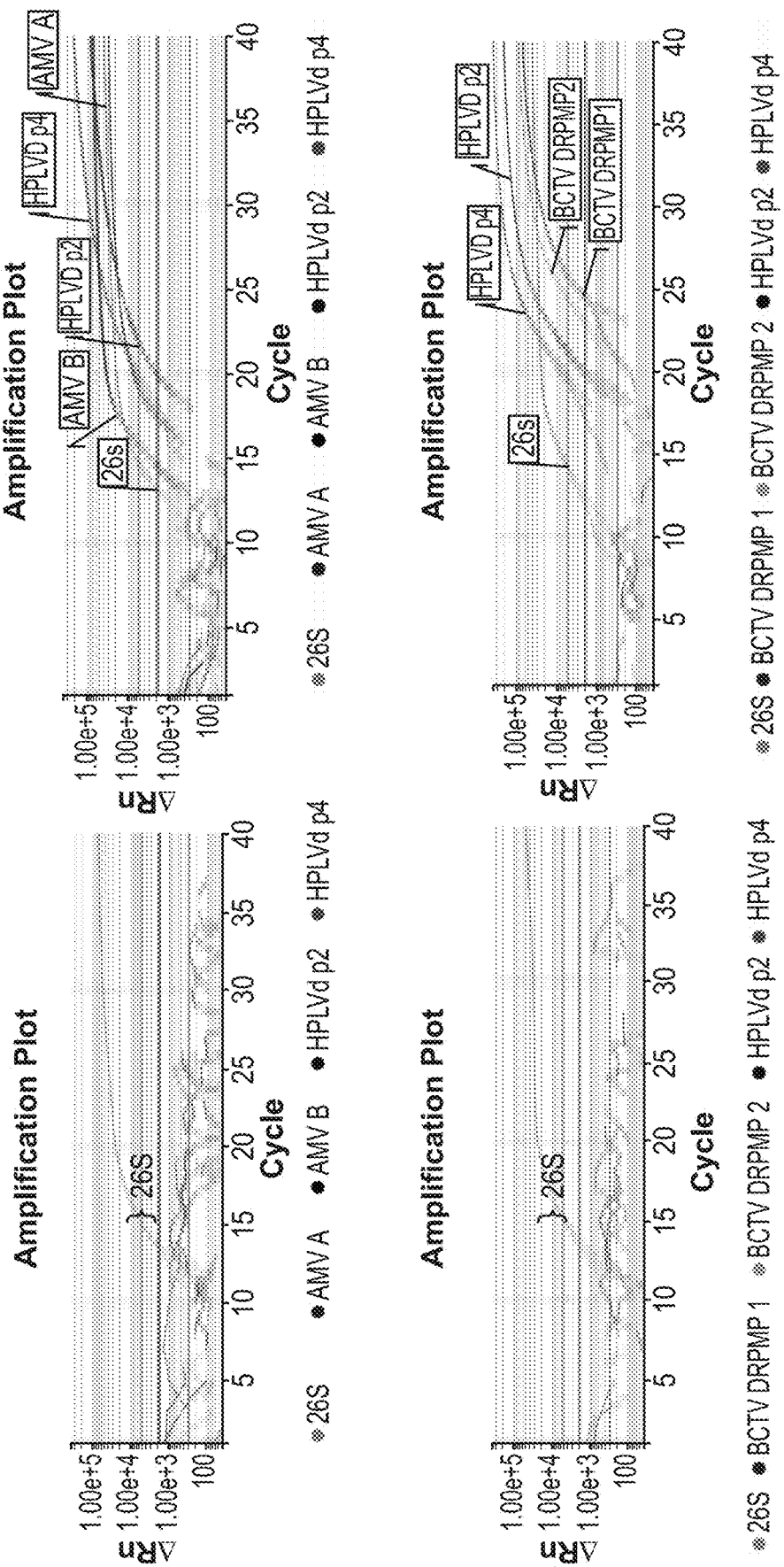
FIG. 15 depicts the sensitivity and specificity for detection of HPLVd, BCTV, and AMV in a RT-qPCR assay.

The results are shown in FIG. 15. FIG. 15 depicts the results for the negative pools (no HPLVd, AMV or BCTV) on the left top and bottom panels, and the results for the positive pools (positive for HPLVd, AMV, BCTV) on the right top and bottom panels. In the HPLVd AMV 5 Target Multiplex, both replicates for the 1 ng *Cannabis* RNA pool that was HPLVd and AMV negative showed a signal for the internal positive control 26S RNA having a Cq value that crossed the threshold, indicating a successful RT-qPCR reaction; no Cq values crossing the threshold were observed for HPLVd or AMV were observed (top left). In both technical replicates of the 1 ng *Cannabis* RNA pool that was HPLVd and AMV positive, a signal for the internal positive control 26S was observed with a Cq value crossing threshold, indicating a successful RT-qPCR reaction as well as Cq values for HPLVd p2 and p4 and AMV A and AMV B were observed indicating duplex target positive detection for HPLVd and AMV in the positive pool (top right). In the standard curve reaction, duplicate positive signals were observed for HPLVd p4 and p2 probes down to 100 fg, AMV A probe sensitivity down to 10 fg, AMV B probe sensitivity down to 100 fg and 26S positive control sensitivity down to 10 fg. No Cq values were obtained for any probe in the no template control.

In the HPLVd BCTV 5 Target Multiplex, both replicates for the 1 ng *Cannabis* RNA pool that were HPLVd and BCTV Negative (negative pool) showed a signal for the internal positive control 26S with a Cq value crossing the threshold, indicating a successful RT-qPCR reaction; no Cq values crossing the threshold were obtained for HPLVd or BCTV (bottom left). In both replicates of the 1 ng *Cannabis* RNA pool that were HPLVd and BCTV positive (positive pool), a signal for the internal positive control 26S was observed, with a Cq value crossing threshold indicating a successful RT-qPCR reaction. In addition, Cq values that crossed the threshold were observed for HPLVd p2 and p4 probes and BCTV DRP MP Probe 1 and Probe 2, indicating duplex target positive detection for HPLVd and BCTV in the positive pool (bottom right). In the standard curve reaction, duplicate positive signals were observed for HPLVd p4 and p2 probes down to 100 fg, BCTV DRP MP Probe 1 and Probe 2 down to 1 pg, and 26S sensitivity down to 10 fg. No Cq value observations were obtained for any probe in the no template control.

To evaluate the equivalency of the LAMP assay and the RT-qPCR assay for multiplexed detection of plant pathogens, crude RNA extract preparation and analysis of 24 different samples were carried out in duplicate for 48 test reactions, along with a positive template control and no template control for RT-qPCR HPLVd detection. High throughput RT-qPCR Method validation was carried out on crude extracts by preparing duplicate FTA Card sampling of leaf material, carrying through 96-well plate preparation and extraction with a nucleic acid extraction buffer. Subsequently, crude extracts underwent one-step cDNA synthesis and pre amplification using iTaq one-step Mastermix (Bio-Rad, Hercules, Calif.) and HPLVd B-F and 26S primers. Standard iTaq RT-PCR protocol conditions were followed with 10 cycles of amplification.

Following the RT-PCR pre-amp protocol, pre-amp reactions were diluted with 100 uL of water and 5 uL was used as input into a qPCR reaction. The qPCR was formulated with Taqman Fast Advanced master mix (Thermo Fisher, Fremond, Calif.) with HPLVd B-F Primers and 26S primers and probes labeled with 6-FAM for HPLVd p4 and NHS Rox for HPLVd p2, and SUN for 26S. Results of the test HPLVd positive and negatives samples were evaluated as HPLVd positive or negative based on detection of a Cq value for HPLVd target probes that crossed the amplification curve Cq threshold. Signals were observed in the HPLVd positive template control (26S) and with the HPLVd p4 and HPLVd p2 probes in both replicates, while no signal was observed in the no template control. Positive test samples showed a Cq value with HPLVd p4, HPLVdp2 and 26S probes, while Negative test samples only showed a Cq value for the positive control 26S probe. The results are shown in FIG. 16.

Results obtained using the qPCR method (see above) were compared to results in a subsequent analysis using the LAMP method and following the LAMP method evaluation for specificity and sensitivity. Total RNA from a commercial kit (Quick Plant RNA Kit, ZymoResearch, Irvine, Calif.) and crude RNA extract (prepared as described previously) was used in the LAMP Method evaluation. 4 LAMP primer sets were initially tested with a couple of concentration levels of purified RNA, to gauge primer set sensitivity and performance. A positive LAMP reaction is observed when a reaction tube changes from pink (seen as gray in grayscale, see FIG. 17) to yellow (seen as pale/transparent in grayscale, see FIG. 17) as target amplicons accumulate. LAMP reactions with purified RNA as input were prepared with NEB WarmStart Colorimetric LAMP Mastermix Mix (New England Biolabs, Ipswich, Mass.) and HPLVd LAMP Primer Sets 1-4. The best sensitivity and performance was observed with HPLVd LAMP Primer Sets 1 and 2, with detection of HPLVd RNA down to 200 fg.

The HPLVd LAMP Primer Set 1 was carried through specificity and sensitivity validation of the high throughput method, and a qPCR equivalency study, using crude extracts. LAMP reactions carried out with crude extracts first underwent one-step cDNA synthesis and pre amplification using iTaq one-step mastermix (Bio-rad, Hercules, Calif.) and HPLVd LAMP Primer Set 1 B3 and F3 primers. Standard iTaq RT-PCR protocol conditions were followed with 10 cycles of amplification. Following RT-PCR preamp protocol, Pre Amp reactions were diluted with 100 uL of water and 1 uL was used as input into a LAMP reaction prepared with NEB WarmStart Colorimetric LAMP Mastermix Mix (New England Biolabs, Ipswich, Mass.) and HPLVd LAMP Primer Set 1 B3, F3 FIP, BIP, and LB. A standard curve was obtained using crude extract diluted in 10-fold series from $10^0$ to $10^{-5}$ ng, along with a no template control (NTC). After 30 minutes at 65° C., a positive signal from the reaction at time 0 (pink) turning to a yellow color could be observed all the way down to $10^{-5}$ ng, while the NTC remained pink.

For evaluation of specificity a small test set of positive and negative samples were prepared for crude extracts, which then underwent RT-PCR preamp reactions followed by LAMP detection. At time 0 after addition of template, the reactions remained pink. After 45 minutes at 65° C., a positive signal from the reaction turning to a yellow color could be observed in the positive test samples and positive template control and a pink reaction color was observed in the negative test samples and in the no template control. Observing a positive reaction color in the positive samples and a negative reaction color in the negative samples demonstrates assay specificity.

To determine equivalency of the RT-qPCR and LAMP assays, follow up analysis of HPLVd RT-qPCR method validation samples was carried out using the LAMP method, and results between RT-qPCR and LAMP detection methods were compared. LAMP reactions were carried out with 24 samples tested in duplicate to yield 48 test crude extracts, as well as positive template control and no template control samples. Samples first underwent one-step cDNA synthesis and pre-amplification using iTaq one-step Mastermix (Bio-Rad, Hercules, Calif.) and HPLVd LAMP Primer Set 1 B3 and F3 primers. Standard RT-PCR protocol conditions were followed with 10 cycles of amplification. Following RT-PCR pre-amp protocol, RT-PCR Pre Amp reactions were diluted with 100 uL of water and 1 uL was used as input into a LAMP detection reaction prepared with NEB WarmStart Colorimetric LAMP Mastermix Mix (New England Biolabs, Ipswich, Mass.) and HPLVd LAMP Primer Set 1 B3, F3 FIP, BIP, and LB. At time 0 after addition of template, samples were pink (the darker the gray shading, the deeper the pink color). Following 45 mins at 65° C., a positive signal from reaction turning to a yellow color (depicted as pale samples in FIG. 17; well numbers are indicated in the Table accompanying the Figure) could be observed in the positive test samples and positive template control (PTC) and a pink reaction color was observed in the negative test samples and in the no template control (NTC) (depicted as gray samples in FIG. 17; well numbers are indicated in the Table accompanying the Figure). Observing a color change in the positive samples and no color change in the negative samples using this LAMP assays matches the RT-qPCR detection results and demonstrates equivalency of the two detection methods.

Example 8: Examples of Embodiments

The examples set forth below illustrate certain embodiments and do not limit the technology.

A1. A method for analyzing nucleic acid from a plant sample, comprising:
  contacting nucleic acid of a plant sample with a plurality of polynucleotide primer pairs under amplification conditions, thereby preparing a mixture; and
  analyzing nucleic acid of the mixture; wherein:
  the majority or all of the polynucleotide primer pairs hybridize to subsequences of SEQ ID NO:1 if present in the nucleic acid of the plant sample under the amplification conditions;
  the subsequences of SEQ ID NO:1 to which the majority or all of the polynucleotide primers hybridize under the amplification conditions contain no variant nucleotide position or one variant nucleotide position; and each subsequence of SEQ ID NO:1 between the subsequences to which the primer pairs hybridize contain two or more variant nucleotide positions.

A1.1 A method for preparing a nucleic acid mixture comprising:
  contacting nucleic acid of a plant sample with a plurality of polynucleotide primer pairs under amplification conditions, thereby preparing a mixture, wherein:
  the majority or all of the polynucleotide primer pairs hybridize to subsequences of SEQ ID NO:1 if present in the nucleic acid of the plant sample under the amplification conditions;
  the subsequences of SEQ ID NO:1 to which the majority or all of the polynucleotide primers hybridize under the amplification conditions contain no variant nucleotide position or one variant nucleotide position; and
  each subsequence of SEQ ID NO:1 between the subsequences to which the primer pairs hybridize contain two or more variant nucleotide positions.

A1.2 The method of embodiment A1.1, comprising analyzing the nucleic acid of the mixture.

A2. A method for analyzing nucleic acid from a plant sample, comprising:
  contacting nucleic acid of a plant sample with one or more polynucleotide primer pairs under amplification conditions, thereby generating one or more amplification products; and
  analyzing the amplification products; wherein:
  the majority or all of the one or more polynucleotide primer pairs hybridize to subsequences of SEQ ID NO:1 if present in the nucleic acid of the plant sample under the amplification conditions;

the subsequences of SEQ ID NO:1 to which the majority or all of the polynucleotide primers hybridize under the amplification conditions contain no variant nucleotide position; and each subsequence of SEQ ID NO:1 between the subsequences to which the one or more primer pairs hybridize contain one or more variant nucleotide positions.

A2.1 A method for generating nucleic acid amplification products from a plant sample, comprising:

contacting nucleic acid of a plant sample with one or more polynucleotide primer pairs under amplification conditions, thereby generating one or more amplification products, wherein:

the majority or all of the one or more polynucleotide primer pairs hybridize to subsequences of SEQ ID NO:1 if present in the nucleic acid of the plant sample under the amplification conditions;

the subsequences of SEQ ID NO:1 to which the majority or all of the polynucleotide primers hybridize under the amplification conditions contain no variant nucleotide position; and each subsequence of SEQ ID NO:1 between the subsequences to which the one or more primer pairs hybridize contain one or more variant nucleotide positions.

A2.2 The method of embodiment A2.1, comprising analyzing the amplification products.

A3. The method of embodiment A2, A2.1, or A2.2, comprising contacting nucleic acid of a plant sample with a plurality of polynucleotide primer pairs under amplification conditions.

A4. The method of any one of embodiments A2 to A3, wherein each subsequence of SEQ ID NO:1 between the subsequences to which the primer pairs hybridize contain two or more variant nucleotide positions.

A5. The method of any one of embodiments A1 to A4, wherein each subsequence of SEQ ID NO:1 between the subsequences to which the primer pairs hybridize contain three or more variant nucleotide positions.

A6. The method of any one of embodiments A1 to A5, wherein each subsequence of SEQ ID NO:1 between the subsequences to which the primer pairs hybridize contain four or more variant nucleotide positions.

A7. The method of any one of embodiments A1, A.1, A1.2, and A3 to A6, wherein the plurality of polynucleotide primer pairs comprises two or more polynucleotide primer pairs.

A8. The method of any one of embodiments A1, A1.1, A1.2, and A3 to A7, wherein the plurality of polynucleotide primer pairs comprises three or more polynucleotide primer pairs.

A9. The method of any one of embodiments A1, A1.1, A1.2, and A3 to A8, wherein the plurality of polynucleotide primer pairs comprises four or more polynucleotide primer pairs.

A10. The method of any one of embodiments A1, A1.1, A1.2, and A3 to A9, wherein the plurality of polynucleotide primer pairs comprises five or more polynucleotide primer pairs.

A11. The method of any one of embodiments A1, A1.1, A1.2, and A3 to A10, wherein the plurality of polynucleotide primer pairs comprises six or more polynucleotide primer pairs.

A12. The method of any one of embodiments A1, A1.1, A1.2, and A3 to A11, wherein the plurality of polynucleotide primer pairs comprises seven or more polynucleotide primer pairs.

A13. The method of any one of embodiments A1, A1.1, A1.2, and A3 to A12, wherein the plurality of polynucleotide primer pairs comprises eight or more polynucleotide primer pairs.

A14. The method of any one of embodiments A1, A1.1, A1.2, and A3 to A13, wherein the plurality of polynucleotide primer pairs comprises nine or more polynucleotide primer pairs.

A15. The method of any one of embodiments A1, A1.1, A1.2, and A3 to A14, wherein the plurality of polynucleotide primer pairs comprises ten or more polynucleotide primer pairs.

A16. The method of any one of embodiments A1 to A15, wherein the plant has been heat treated.

A16.1 The method of any one of embodiments A1 to A15, wherein the plant has not been heat treated.

A16.1.1 The method of any one of embodiments A1 to A16.1, wherein the plant is of the subclass Rosidae.

A16.2 The method of any one of embodiments A1 to A16.1.1, wherein the plant is a *cannabis* plant.

A17. The method of embodiment A16.2, wherein each polynucleotide in each primer pair comprises a sequence that is non-identical to any subsequence, or complement thereof, in a *cannabis* genome.

A18. The method of embodiment A17, wherein each polynucleotide in each primer pair comprises a sequence that is non-identical to any subsequence, or complement thereof, in a CS10 *Cannabis* genome.

A19. The method of embodiment A18, wherein each polynucleotide in each primer pair comprises a sequence comprising at least six mismatches when compared to any subsequence, or complement thereof, in the CS10 *Cannabis* genome.

A20. The method of any one of embodiments A1 to A19, wherein each polynucleotide in each primer pair comprises a sequence that is at least about 90% identical to a subsequence, or complement thereof, of SEQ ID NO:1.

A21. The method of any one of embodiments A1 to A19, wherein each polynucleotide in each primer pair comprises a sequence that is at least about 95% identical to a subsequence, or complement thereof, of SEQ ID NO:1.

A22. The method of any one of embodiments A1 to A19, wherein each polynucleotide in each primer pair comprises a sequence that is 100% identical to a subsequence, or complement thereof, of SEQ ID NO:1.

A23. The method of any one of embodiments A1 to A22, wherein each primer pair comprises a forward primer and a reverse primer.

A24. The method of embodiment A23, wherein each forward primer hybridizes to a subsequence between nucleotide position 60 and nucleotide position 102 of SEQ ID NO:1.

A25. The method of embodiment A23 or A24, wherein each reverse primer hybridizes to a subsequence between nucleotide position 89 and nucleotide position 119 of SEQ ID NO:1, or hybridizes to a subsequence between nucleotide position 178 and nucleotide position 198 of SEQ ID NO:1.

A26. The method of any one of embodiments A23 to A25, wherein one or more forward primers independently are chosen from a polynucleotide comprising a sequence that is at least about 90% identical to GGGGAAACC-TACTCGAGCG (SEQ ID NO:4), GGAAACC-TACTCGAGCGAGGCG (SEQ ID NO:6), CGAGGCG-GAGATCGAGCGC (SEQ ID NO:9), GAGATCGAGCGCCAGTTCG (SEQ ID NO:11), and AGATCGAGCGCCAGTTCG (SEQ ID NO:13).

A27. The method of any one of embodiments A23 to A25, wherein one or more forward primers independently are chosen from a polynucleotide comprising a sequence that is at least about 95% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13).

A28. The method of any one of embodiments A23 to A25, wherein one or more forward primers independently are chosen from a polynucleotide comprising a sequence that is 100% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13).

A29. The method of any one of embodiments A23 to A28, wherein one or more reverse primers independently are chosen from a polynucleotide comprising a sequence that is at least about 90% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

A30. The method of any one of embodiments A23 to A28, wherein one or more reverse primers independently are chosen from a polynucleotide comprising a sequence that is at least about 95% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

A31. The method of any one of embodiments A23 to A28, wherein one or more reverse primers independently are chosen from a polynucleotide comprising a sequence that is 100% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

A32. The method of any one of embodiments A23 to A31, wherein the plurality of polynucleotide primer pairs comprises a plurality of forward primers and a plurality of reverse primers.

A33. The method of embodiment A32, wherein the plurality of forward primers comprises GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13); and the plurality of reverse primers comprises CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), ACCGGGTAGTTTCCAACTCCG (SEQ ID NO:12), and AGAGTTGTATTCACCGGGTAGTTTCC (SEQ ID NO:14).

A34. The method of embodiment A32, wherein the plurality of forward primers consists of GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13); and the plurality of reverse primers consists of CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

A35. The method of any one of embodiments A1 to A34, wherein the analyzing comprises detecting the presence or absence of a hops latent viroid in the plant.

A36. The method of any one of embodiments A1 to A35, wherein the analyzing comprises detecting one or more genetic variations in a hops latent viroid.

A37. The method of embodiment A36, wherein the analyzing comprises detecting two or more genetic variations in a hops latent viroid.

A38. The method of embodiment A36 or A37, wherein detecting the one or more genetic variations in the hops latent viroid comprises contacting the nucleic acid of the plant sample with one or more further polynucleotide primers under amplification conditions, wherein:
the majority or all of the further polynucleotide primers hybridize to subsequences of SEQ ID NO:1 if present in the nucleic acid of the plant sample under the amplification conditions; and
the subsequences of SEQ ID NO:1 to which the majority or all of the further polynucleotide primers hybridize under the amplification conditions contain one or more variant nucleotide positions.

A39. The method of embodiment A38, wherein each further polynucleotide primer comprises a sequence that is non-identical to any subsequence, or complement thereof, in a *cannabis* genome.

A40. The method of embodiment A39, wherein each further polynucleotide primer comprises a sequence that is non-identical to any subsequence, or complement thereof, in a CS10 *Cannabis* genome.

A41. The method of embodiment A40, wherein each further polynucleotide primer comprises a sequence comprising at least six mismatches when compared to any subsequence, or complement thereof, in the CS10 *Cannabis* genome.

A42. The method of any one of embodiments A38 to A41, wherein each further polynucleotide primer comprises a sequence that is at least about 90% identical to a subsequence, or complement thereof, of SEQ ID NO:1.

A43. The method of any one of embodiments A38 to A41, wherein each further polynucleotide primer comprises a sequence that is at least about 95% identical to a subsequence, or complement thereof, of SEQ ID NO:1.

A44. The method of any one of embodiments A38 to A41, wherein each further polynucleotide primer comprises a sequence that is 100% identical to a subsequence, or complement thereof, of SEQ ID NO:1.

A45. The method of any one of embodiments A38 to A44, wherein the one or more further polynucleotide primers independently are chosen from a polynucleotide comprising a sequence that is at least about 90% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

A46. The method of any one of embodiments A38 to A44, wherein the one or more further polynucleotide primers independently are chosen from a polynucleotide comprising a sequence that is at least about 95% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

A47. The method of any one of embodiments A38 to A44, wherein the one or more further polynucleotide primers independently are chosen from a polynucleotide comprising a sequence that is 100% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

A48. The method of any one of embodiments A38 to A44, wherein the one or more further polynucleotide primers comprise CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

A49. The method of any one of embodiments A38 to A44, wherein the one or more further polynucleotide primers consist of CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

A50. The method of any one of embodiments A36 to A49, wherein the one or more genetic variations comprise one or more nucleotide insertions.

A51. The method of any one of embodiments A36 to A50, wherein the one or more genetic variations comprise one or more nucleotide deletions.

A52. The method of embodiment A51, wherein the one or more nucleotide deletions comprise a deletion at nucleotide position 225 of SEQ ID NO:1.

A53. The method of any one of embodiments A36 to A52, wherein the one or more genetic variations comprise one or more single nucleotide variations.

A54. The method of embodiment A53, wherein the one or more single nucleotide variations comprise a variant nucleotide at one or more of nucleotide position 7 of SEQ ID NO:1, nucleotide position 10 of SEQ ID NO:1, nucleotide position 12 of SEQ ID NO:1, nucleotide position 26 of SEQ ID NO:1, nucleotide position 27 of SEQ ID NO:1, nucleotide position 28 of SEQ ID NO:1, nucleotide position 29 of SEQ ID NO:1, nucleotide position 30 of SEQ ID NO:1, nucleotide position 33 of SEQ ID NO:1, nucleotide position 35 of SEQ ID NO:1, nucleotide position 43 of SEQ ID NO:1, nucleotide position 59 of SEQ ID NO:1, nucleotide position 121 of SEQ ID NO:1, nucleotide position 128 of SEQ ID NO:1, nucleotide position 134 of SEQ ID NO:1, nucleotide position 150 of SEQ ID NO:1, nucleotide position 157 of SEQ ID NO:1, nucleotide position 162 of SEQ ID NO:1, nucleotide position 168 of SEQ ID NO:1, nucleotide position 169 of SEQ ID NO:1, nucleotide position 177 of SEQ ID NO:1, nucleotide position 200 of SEQ ID NO:1, nucleotide position 225 of SEQ ID NO:1, nucleotide position 229 of SEQ ID NO:1, nucleotide position 247 of SEQ ID NO:1, nucleotide position 248 of SEQ ID NO:1, and nucleotide position 253 of SEQ ID NO:1

A55. The method of any one of embodiments A36 to A54, wherein the analyzing comprises identifying a hops latent viroid trait according to the one or more genetic variations.

A56. The method of embodiment A36 to A54, wherein the analyzing comprises detecting a genetic variation signature.

A57. The method of embodiment A56, wherein the genetic variation signature comprises genotypes determined at two or more variant nucleotide positions.

A58. The method of embodiment A56, wherein the genetic variation signature comprises genotypes determined at three or more variant nucleotide positions.

A59. The method of embodiment A56, wherein the genetic variation signature comprises genotypes determined at four or more variant nucleotide positions.

A60. The method of embodiment A56, wherein the genetic variation signature comprises genotypes determined at five or more variant nucleotide positions.

A61. The method of embodiment A56, wherein the genetic variation signature comprises genotypes determined at six or more variant nucleotide positions.

A62. The method of embodiment A56, wherein the genetic variation signature comprises genotypes determined at seven or more variant nucleotide positions.

A63. The method of embodiment A56, wherein the genetic variation signature comprises genotypes at determined eight or more variant nucleotide positions.

A64. The method of embodiment A56, wherein the genetic variation signature comprises genotypes determined at nine or more variant nucleotide positions.

A65. The method of embodiment A56, wherein the genetic variation signature comprises genotypes determined at ten or more variant nucleotide positions.

A66. The method of any one of embodiments A56 to A65, wherein the analyzing comprises identifying a hops latent viroid trait according to the genetic variation signature.

A67. The method of any one of embodiments A1 to A66, wherein the method further comprises contacting the nucleic acid of the plant sample with one or more quantitative PCR probes under the amplification conditions.

A68. The method of embodiment A67, wherein the one or more quantitative PCR probes are chosen from one or more of TCGTGCGCGGCGACCT (SEQ ID NO:16), CGGAGATCGAGCGCCAGTT (SEQ ID NO:17), TGCGCGGCGACCTGAAGT (SEQ ID NO:18), AGGCGGAGATCGAGCGCCA (SEQ ID NO:19), and TCCTGCGTGGAACGGCTCC (SEQ ID NO:20).

A69. The method of any one of embodiments A1 to A68, wherein the method comprises contacting the nucleic acid of the plant sample with a set of loop mediated isothermal amplification (LAMP) primers under the amplification conditions.

A70. The method of embodiment A69, wherein the LAMP primer set is chosen from one or more of:
 a) a primer set comprising the polynucleotides of SEQ ID NO:21 to SEQ ID NO:29,
 b) a primer set comprising the polynucleotides of SEQ ID NO:30 to SEQ ID NO:38,
 c) a primer set comprising the polynucleotides of SEQ ID NO:39 to SEQ ID NO:47, and
 d) a primer set comprising the polynucleotides of SEQ ID NO:48 to SEQ ID NO:56.

A71. The method of any one of embodiments A1, A1.1, and A3 to A70, wherein the analyzing comprises performing a high resolution melting (HRM) endpoint assay on the nucleic acid in the mixture.

A72. The method of any one of embodiments A2 to A70, wherein the analyzing comprises performing a high resolution melting (HRM) endpoint assay on the amplification products.

A73. The method of embodiment A72, wherein the analyzing comprises detecting one or more genetic variations in a hops latent viroid according to results obtained from the high resolution melting (HRM) endpoint assay.

A74. The method of embodiment A72, wherein the analyzing comprises detecting two or more genetic variations in a hops latent viroid according to results obtained from the high resolution melting (HRM) endpoint assay.

A75. The method of any one of embodiments A1 to A74, wherein the subsequences of SEQ ID NO:1 to which the majority or all of the polynucleotide primers hybridize under the amplification conditions contain no thermomutant positions.

A76. The method of embodiment A75, wherein the thermomutant positions are chosen from one or more of nucleotide position 7 of SEQ ID NO:1, nucleotide position 10 of SEQ ID NO:1, nucleotide position 12 of SEQ ID NO:1, nucleotide position 26 of SEQ ID NO:1, nucleotide position 27 of SEQ ID NO:1, nucleotide position 28 of SEQ ID NO:1, nucleotide position 29 of SEQ ID NO:1, nucleotide position 30 of SEQ ID NO:1, nucleotide position 33 of SEQ ID NO:1, nucleotide position 35 of SEQ ID NO:1, nucleotide position 43 of SEQ ID NO:1, nucleotide position 59 of SEQ ID NO:1, nucleotide position 121 of SEQ ID NO:1, nucleotide position 128 of SEQ ID NO:1, nucleotide position 134 of SEQ ID NO:1, nucleotide position 150 of SEQ ID NO:1, nucleotide position 157 of SEQ ID NO:1, nucleotide position 162 of SEQ ID NO:1, nucleotide position 168 of SEQ ID NO:1, nucleotide position 169 of SEQ ID NO:1, nucleotide position 177 of SEQ ID NO:1, nucleotide position 200 of SEQ ID NO:1, nucleotide position 225 of SEQ ID NO:1, nucleotide position 229 of SEQ ID NO:1, nucleotide position 247 of SEQ ID NO:1, nucleotide position 248 of SEQ ID NO:1, and nucleotide position 253 of SEQ ID NO:1.

A77. A method for analyzing nucleic acid from a plant sample, comprising:

a) contacting nucleic acid of a plant sample with a first set of polynucleotide primers under amplification conditions, thereby generating a first set of amplification products, wherein:
   i) the majority or all of the primers in the first set of polynucleotide primers hybridize to subsequences of SEQ ID NO:1 if present in the nucleic acid of the plant sample under the amplification conditions,
   ii) the subsequences of SEQ ID NO:1 to which the majority or all of the primers in the first set of polynucleotide primers hybridize under the amplification conditions contain no variant nucleotide position, and
   iii) each subsequence of SEQ ID NO:1 between the subsequences to which the primers in the first set of polynucleotide primers hybridize contain one or more variant nucleotide positions;

b) contacting the nucleic acid of the plant sample with a second set of polynucleotide primers under the amplification conditions, thereby generating a second set of amplification products, wherein:
   i) the majority or all of the primers in the second set of polynucleotide primers hybridize to subsequences of SEQ ID NO:1 if present in the nucleic acid of the plant sample under the amplification conditions, and
   ii) the subsequences of SEQ ID NO:1 to which the majority or all of the primers in the second set of polynucleotide primers hybridize under the amplification conditions contain one or more variant nucleotide positions; and c) analyzing the first and second sets of amplification products.

A78. A method for generating nucleic acid amplification products from a plant sample, comprising:

a) contacting nucleic acid of a plant sample with a first set of polynucleotide primers under amplification conditions, thereby generating a first set of amplification products, wherein:
   i) the majority or all of the primers in the first set of polynucleotide primers hybridize to subsequences of SEQ ID NO:1 if present in the nucleic acid of the plant sample under the amplification conditions,
   ii) the subsequences of SEQ ID NO:1 to which the majority or all of the primers in the first set of polynucleotide primers hybridize under the amplification conditions contain no variant nucleotide position, and
   iii) each subsequence of SEQ ID NO:1 between the subsequences to which the primers in the first set of polynucleotide primers hybridize contain one or more variant nucleotide positions; and b) contacting the nucleic acid of the plant sample with a second set of polynucleotide primers under the amplification conditions, thereby generating a second set of amplification products, wherein:
   i) the majority or all of the primers in the second set of polynucleotide primers hybridize to subsequences of SEQ ID NO:1 if present in the nucleic acid of the plant sample under the amplification conditions, and
   ii) the subsequences of SEQ ID NO:1 to which the majority or all of the primers in the second set of polynucleotide primers hybridize under the amplification conditions contain one or more variant nucleotide positions.

A79. The method of embodiment A78, comprising analyzing the first and second sets of amplification products.

A80. The method of any one of embodiments A77 to A79, comprising one or more features of any one of embodiments A3 to A76.

A81. The method of any one of embodiments A1 to A80 that is performed on a FTA® card.

B1. A composition comprising one or more polynucleotide primer pairs wherein:

each polynucleotide of the one or more primer pairs is identical, or substantially identical, to a subsequence of SEQ ID NO:1, or complement thereof;

each subsequence of SEQ ID NO:1, or complement thereof, to which each polynucleotide is identical, or substantially identical, contains no variant nucleotide position; and each target sequence of SEQ ID NO:1 between the subsequences, or complements thereof, to which the polynucleotides of the one or more primer pairs are identical, or substantially identical, comprises one or more variant nucleotide positions.

B2. Reserved.

B3. The composition of embodiment B1, wherein each target sequence of SEQ ID NO:1 comprises two or more variant nucleotide positions.

B4. The composition of embodiment B1, wherein each target sequence of SEQ ID NO:1 comprises three or more variant nucleotide positions.

B5. The composition of embodiment B1, wherein each target sequence of SEQ ID NO:1 comprises four or more variant nucleotide positions.

B6. The composition of any one of embodiments B1 to B5, wherein the one or more polynucleotide primer pairs comprise two or more polynucleotide primer pairs.

B7. The composition of any one of embodiments B1 to B5, wherein the one or more polynucleotide primer pairs comprise three or more polynucleotide primer pairs.

B8. The composition of any one of embodiments B1 to B5, wherein the one or more polynucleotide primer pairs comprise four or more polynucleotide primer pairs.

B9. The composition of any one of embodiments B1 to B5, wherein the one or more polynucleotide primer pairs comprise five or more polynucleotide primer pairs.

B10. The composition of any one of embodiments B1 to B5, wherein the one or more polynucleotide primer pairs comprise six or more polynucleotide primer pairs.

B11. The composition of any one of embodiments B1 to B5, wherein the one or more polynucleotide primer pairs comprise seven or more polynucleotide primer pairs.

B12. The composition of any one of embodiments B1 to B5, wherein the one or more polynucleotide primer pairs comprise eight or more polynucleotide primer pairs.

B13. The composition of any one of embodiments B1 to B5, wherein the one or more polynucleotide primer pairs comprise nine or more polynucleotide primer pairs.

B14. The composition of any one of embodiments B1 to B5, wherein the one or more polynucleotide primer pairs comprise ten or more polynucleotide primer pairs.

B15. The method of any one of embodiments B1 to B14, wherein each polynucleotide in each primer pair comprises a sequence that is non-identical to any subsequence, or complement thereof, in a *cannabis* genome.

B16. The composition of embodiment B15, wherein each polynucleotide in each primer pair comprises a sequence that is non-identical to any subsequence, or complement thereof, in a CS10 *Cannabis* genome.

B17. The composition of embodiment B16, wherein each polynucleotide in each primer pair comprises a sequence comprising at least six mismatches when compared to any subsequence, or complement thereof, in the CS10 *Cannabis* genome.

B18. The composition of any one of embodiments B1 to B17, wherein each polynucleotide in each primer pair comprises a sequence that is at least about 90% identical to a subsequence, or complement thereof, of SEQ ID NO:1.

B19. The composition of any one of embodiments B1 to B17, wherein each polynucleotide in each primer pair comprises a sequence that is at least about 95% identical to a subsequence, or complement thereof, of SEQ ID NO:1.

B20. The composition of any one of embodiments B1 to B17, wherein each polynucleotide in each primer pair comprises a sequence that is 100% identical to a subsequence, or complement thereof, of SEQ ID NO:1.

B21. The composition of any one of embodiments B1 to B20, wherein each primer pair comprises a forward primer and a reverse primer.

B22. The composition of embodiment B21, wherein each forward primer is identical, or substantially identical, to a subsequence, or complement thereof, between nucleotide position 60 and nucleotide position 102 of SEQ ID NO:1.

B23. The composition of embodiment B21 or B22, wherein each reverse primer is identical, or substantially identical, to a subsequence, or complement thereof, between nucleotide position 89 and nucleotide position 119 of SEQ ID NO:1; or is identical, or substantially identical, to a subsequence, or complement thereof, between nucleotide position 178 and nucleotide position 198 of SEQ ID NO:1

B24. The composition of any one of embodiments B21 to B23, wherein one or more forward primers independently are chosen from a polynucleotide comprising a sequence that is at least about 90% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13).

B25. The composition of any one of embodiments B21 to B23, wherein one or more forward primers independently are chosen from a polynucleotide comprising a sequence that is at least about 95% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13).

B26. The composition of any one of embodiments B21 to B23, wherein one or more forward primers independently are chosen from a polynucleotide comprising a sequence that is 100% identical to GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13).

B27. The composition of any one of embodiments B21 to B26, wherein one or more reverse primers independently are chosen from a polynucleotide comprising a sequence that is at least about 90% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

B28. The composition of any one of embodiments B21 to B26, wherein one or more reverse primers independently are chosen from a polynucleotide comprising a sequence that is at least about 95% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

B29. The composition of any one of embodiments B21 to B26, wherein one or more reverse primers independently are chosen from a polynucleotide comprising a sequence that is 100% identical to CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

B30. The composition of any one of embodiments B21 to B29, comprising a plurality of forward primers and a plurality of reverse primers.

B31. The composition of embodiment B30, wherein the plurality of forward primers comprises GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9). GAGATCGAGCGCCAGTTCG (SEQ ID NO:11), and AGATCGAGCGCCAGTTCG (SEQ ID NO:13); and the plurality of reverse primers comprises CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

B32. The composition of embodiment B30, wherein the plurality of forward primers consists of GGGGAAACCTACTCGAGCG (SEQ ID NO:4), GGAAACCTACTCGAGCGAGGCG (SEQ ID NO:6), CGAGGCGGAGATCGAGCGC (SEQ ID NO:9), GAGATCGAGCGCCAGTTCG (SEQ ID NO:11), and AGATCGAGCGCCAGTTCG (SEQ ID NO:13); and the plurality of reverse primers consists of CGCACGAACTGGCGCTCG (SEQ ID NO:3), CTTCAGGTCGCCGCGCACG (SEQ ID NO:5), CGGGTAGTTTCCAACTCCG (SEQ ID NO:8), CCGGGTAGTTTCCAACTCCG (SEQ ID NO:10), and ACCGGGTAGTTTCCAACTCCG (SEQ ID NO:12).

B33. The composition of any one of embodiments B1 to B32, further comprising one or more quantitative PCR probes.

B34. The composition of embodiment B33, wherein the one or more quantitative PCR probes are chosen from one or more of TCGTGCGCGGCGACCT (SEQ ID NO:16), CGGAGATCGAGCGCCAGTT (SEQ ID NO:17), TGCGCGGCGACCTGAAGT (SEQ ID NO:18), AGGCGGAGATCGAGCGCCA (SEQ ID NO:19), and TCCTGCGTGGAACGGCTCC (SEQ ID NO:20).

B35. The composition of any one of embodiments B1 to B34, comprising a set of loop mediated isothermal amplification (LAMP) primers.

B36. The composition of embodiment B35, wherein the LAMP primer set is chosen from one or more of:
  a) a primer set comprising the polynucleotides of SEQ ID NO:21 to SEQ ID NO:29,
  b) a primer set comprising the polynucleotides of SEQ ID NO:30 to SEQ ID NO:38,
  c) a primer set comprising the polynucleotides of SEQ ID NO:39 to SEQ ID NO:47, and
  d) a primer set comprising the polynucleotides of SEQ ID NO:48 to SEQ ID NO:56.

B37. The composition of any one of embodiments B1 to B36, wherein each subsequence of SEQ ID NO:1, or complement thereof, to which each polynucleotide is identical, or substantially identical, contains no thermomutant positions.

B38. The composition of embodiment B37, wherein the thermomutant positions are chosen from one or more of nucleotide position 7 of SEQ ID NO:1, nucleotide position 10 of SEQ ID NO:1, nucleotide position 12 of SEQ ID NO:1, nucleotide position 26 of SEQ ID NO:1, nucleotide position 27 of SEQ ID NO:1, nucleotide position 28 of SEQ ID NO:1, nucleotide position 29 of SEQ ID NO:1, nucleotide position 30 of SEQ ID NO:1, nucleotide position 33 of SEQ ID NO:1, nucleotide position 35 of SEQ ID NO:1, nucleotide position 43 of SEQ ID NO:1, nucleotide position 59 of SEQ ID NO:1, nucleotide position 121 of SEQ ID NO:1, nucleotide position 128 of SEQ ID NO:1, nucleotide position 134 of SEQ ID NO:1, nucleotide position 150 of SEQ ID NO:1, nucleotide position 157 of SEQ ID NO:1, nucleotide position 162 of SEQ ID NO:1, nucleotide position 168 of SEQ ID NO:1, nucleotide position 169 of SEQ ID NO:1, nucleotide position 177 of SEQ ID NO:1, nucleotide position 200 of SEQ ID NO:1, nucleotide position 225 of SEQ ID NO:1, nucleotide position 229 of SEQ ID NO:1, nucleotide position 247 of SEQ ID NO:1, nucleotide position 248 of SEQ ID NO:1, and nucleotide position 253 of SEQ ID NO:1.

B39. The composition of any one of embodiments B1 to B38, comprising one or more further polynucleotide primers wherein:
  each polynucleotide of the one or more further polynucleotide primers is identical, or substantially identical, to a subsequence of SEQ ID NO:1, or complement thereof;
  each subsequence of SEQ ID NO:1, or complement thereof, to which each polynucleotide is identical, or substantially identical, contains one or more variant nucleotide positions.

B40. The composition of embodiment B39, wherein each further polynucleotide primer comprises a sequence that is non-identical to any subsequence, or complement thereof, in a *cannabis* genome.

B41. The composition of embodiment B40, wherein each further polynucleotide primer comprises a sequence that is non-identical to any subsequence, or complement thereof, in a CS10 *Cannabis* genome.

B42. The composition of embodiment B41, wherein each further polynucleotide primer comprises a sequence comprising at least six mismatches when compared to any subsequence, or complement thereof, in the CS10 *Cannabis* genome.

B43. The composition of any one of embodiments B39 to B42, wherein each further polynucleotide primer comprises a sequence that is at least about 90% identical to a subsequence, or complement thereof, of SEQ ID NO:1.

B44. The composition of any one of embodiments B39 to B42, wherein each further polynucleotide primer comprises a sequence that is at least about 95% identical to a subsequence, or complement thereof, of SEQ ID NO:1.

B45. The composition of any one of embodiments B39 to B42, wherein each further polynucleotide primer comprises a sequence that is 100% identical to a subsequence, or complement thereof, of SEQ ID NO:1.

B46. The composition of any one of embodiments B39 to B45, wherein the one or more further polynucleotide primers independently are chosen from a polynucleotide comprising a sequence that is at least about 90% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

B47. The composition of any one of embodiments B39 to B45, wherein the one or more further polynucleotide primers independently are chosen from a polynucleotide comprising a sequence that is at least about 95% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

B48. The composition of any one of embodiments B39 to B45, wherein the one or more further polynucleotide primers independently are chosen from a polynucleotide comprising a sequence that is 100% identical to CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

B49. The composition of any one of embodiments B39 to B45, wherein the one or more further polynucleotide primers comprise CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

B50. The composition of any one of embodiments B39 to B45, wherein the one or more further polynucleotide primers consist of CTACGTGACTTACCTGTATGGTGGC (SEQ ID NO:2), GTGAAGAAGGAGCCGTTCCA (SEQ ID NO:7), AGAGTTGTATTCACCGGGTAGTTTCC (SEQ ID NO:14), and GCACTTTTTATGTGAACTTCTGC (SEQ ID NO:15).

B51. A composition comprising:
a) a first set of polynucleotide primers wherein:
  i) each polynucleotide of the a first set of polynucleotide primers is identical, or substantially identical, to a subsequence of SEQ ID NO:1, or complement thereof,
  ii) each subsequence of SEQ ID NO:1, or complement thereof, to which each polynucleotide is identical, or substantially identical, contains no variant nucleotide position, and
  iii) each target sequence of SEQ ID NO:1 between the subsequences, or complements thereof, to which the polynucleotides of the first set of polynucleotide primers are identical, or substantially identical, comprises one or more variant nucleotide positions; and
b) a second set of polynucleotide primers wherein:
  i) each polynucleotide of the second set of polynucleotide primers is identical, or substantially identical, to a subsequence of SEQ ID NO:1, or complement thereof, and
  ii) each subsequence of SEQ ID NO:1, or complement thereof, to which each polynucleotide is identical, or substantially identical, contains one or more variant nucleotide positions.

B52. The composition of embodiment B51, comprising one or more features from any one of embodiments B3 to B50.

B53. A kit comprising the composition of any one of embodiments B1 to B52 and instructions for use.

C1. A method for determining the presence, absence and/or amount of a pathogen in a plant cultivar, comprising:
  (a) obtaining a nucleic acid sample from the plant cultivar;
  (b) contacting the nucleic acid sample with at least one polynucleotide primer pair under amplification conditions and amplifying the sample, thereby preparing an amplified nucleic acid mixture, wherein, if the pathogen is present, the polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical to any subsequence of the nucleic acid of the plant genome, or to any complement thereof; and
  (c) determining the presence, absence and/or amount of at least one amplicon that is 300 base pairs or less and is an amplification product of the polynucleotide primer pair in the amplified nucleic acid mixture of (b), thereby determining the presence, absence and/or amount of a pathogen in the plant cultivar.

C1.1. A method of preparing a nucleic acid mixture from a plant cultivar, comprising:
  (b) obtaining a nucleic acid sample from the plant cultivar; and
  (b) preparing an amplified nucleic acid mixture by contacting the nucleic acid sample with at least one polynucleotide primer pair under amplification conditions and amplifying the sample, wherein, if the pathogen is present, the polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical to any subsequence of the nucleic acid of the plant genome, or to any complement thereof.

C1.2. The method of embodiment C1.1, further comprising, determining the presence, absence and/or amount of at least one amplicon that is 300 base pairs or less and is an amplification product of the polynucleotide primer pair in the amplified nucleic acid mixture of (b), thereby determining the presence, absence and/or amount of a pathogen in the plant cultivar.

C1.3. A method for determining the presence, absence and/or amount of at least one pathogen in a plant cultivar, comprising:
  (a) obtaining a nucleic acid sample from the plant cultivar;
  (b) contacting the nucleic acid sample with more than one polynucleotide primer pair under amplification conditions and amplifying the sample, thereby preparing an amplified nucleic acid mixture, wherein, if at least one pathogen is present, at least one polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical to any subsequence of the nucleic acid of the plant genome, or to any complement thereof; and
  (c) determining the presence, absence and/or amount of at least one amplicon that is an amplification product of a polynucleotide primer pair in the amplified nucleic acid mixture of (b), thereby determining the presence, absence and/or amount of a pathogen in the plant cultivar.

C1.4. The method of embodiment C1.3, wherein:
  each of the polynucleotide primer pairs hybridizes to the nucleic acid of the same pathogen;
  each polynucleotide primer pair hybridizes to a subsequence of the nucleic acid of the pathogen that does not overlap with the subsequences to which each of the other primer pairs hybridizes; and
  the presence, absence and/or amount of more than one amplicon of the pathogen that is obtained in (b) is determined in (c).

C1.5. The method of embodiment C1.3, wherein:
  each of the polynucleotide primer pairs hybridizes to the nucleic acid of a pathogen that is different than the pathogens to which each of the other polynucleotide primer pairs hybridize; and
  the presence, absence and/or amount of amplicons obtained from more than one pathogen in (b) is determined in (c).

C1.6. The method of any one of embodiments C1 to C1.5, wherein the determining is by one or more of high-resolution melting (HRM), quantitative PCR (qPCR), RT-PCR, quantitative RT-PCR (RT-qPCR), loop-mediated isothermal amplification (LAMP), restriction endonuclease digestion, gel electrophoresis and sequencing.

C1.7. The method of any one of embodiments C1 to C1.6, wherein the pathogen is a virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

C1.8. A method for determining the presence, absence and/or amount of a pathogen in a plant cultivar, comprising:
 (a) obtaining a nucleic acid sample from the plant cultivar;
 (b) contacting the nucleic acid sample with a polynucleotide primer pair under amplification conditions and amplifying the sample, thereby preparing an amplified nucleic acid mixture, wherein, if the pathogen is present, the polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical to any subsequence of the nucleic acid of the plant genome, or to any complement thereof; and
 (c) determining the presence, absence and/or amount of at least one amplicon that is an amplification product of a polynucleotide primer pair in the amplified nucleic acid mixture of (b) by qPCR or RT-qPCR using more than one polynucleotide probe sequence, thereby determining the presence, absence and/or amount of a pathogen in the plant cultivar.

C1.9. The method of embodiment C1.8, wherein the more than one polynucleotide probe sequences hybridize to non-overlapping regions of the subsequence of the pathogen that is amplified to generate the amplicon.

C1.10. The method of any one of embodiments C1 to C1.9, wherein the pathogen is a virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

C2. The method of any one of embodiments C1 to C1.10, wherein the subsequence of the nucleic acid of the pathogen, or the complement thereof, is in a region of overlap between two genes in the genome of the pathogen.

C3. The method of any one of embodiments C1 to C1.10 and C2, wherein the pathogen is a virus or viroid.

C4. The method of embodiment C3, wherein the virus or viroid comprises nucleic acid that is DNA, or RNA, or DNA and RNA.

C5. The method of embodiment C3 or embodiment C4, wherein the virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

C6. The method of any one of embodiments C1 to C5, wherein the subsequence of the nucleic acid of the pathogen, or the complement thereof, comprises at least exon or at least one portion within an exon.

C7. The method of any one of embodiments C1 to C6, wherein the subsequence comprises more than one exon or more than one portion within an exon of at least two different genes.

C8. The method of any one of embodiments C1 to C7, wherein the subsequence of the nucleic acid of the pathogen, or the complement thereof, comprises more than one exon or more than one portion within an exon of at least two different genes.

C9. The method of any one of embodiments C1 to C8, wherein the method further comprises:
 in (b), contacting the nucleic acid sample with at least one second polynucleotide primer pair under amplification conditions and amplifying the sample, thereby preparing an amplified nucleic acid mixture, wherein the second polynucleotide primer pair is capable of specifically hybridizing to and amplifying a subsequence of the nucleic acid of the plant genome, or to a complement thereof, wherein the subsequence of the nucleic acid of the plant genome, or the complement thereof, is non-identical to any subsequence of the nucleic acid of the pathogen, or to any complement thereof; and
 in (c), determining the presence, absence and/or amount of at least one amplicon that is an amplification product of the second polynucleotide primer pair, thereby determining whether the amplification conditions are effective for generating amplicons.

C9.1. The method of any one of embodiments C1 to C9, wherein the plant is of the subclass Rosidae.

C10. The method of any one of embodiments C1 to C9.1, wherein the plant is a *Cannabis* cultivar.

C11. The method of embodiment C10, wherein the *Cannabis* cultivar is selected from among Jamaican Lion, Purple Kush, CannaTsu, Finola, Valley Fire and Cherry Chem.

C12. The method of embodiment C10, wherein the plant genome is a *Cannabis sativa* eudicots CS10 genome assembly.

C12.1. The method of embodiment C10, wherein the *Cannabis* cultivar is selected from among one or more of Type 1, Type 2, Type 3, Type 4 and Type 5 cultivars.

C13. The method of any one of embodiments C9 to C12.1, wherein the subsequence of the nucleic acid of the plant genome comprises all or a portion of a gene that is conserved among species of the plant.

C14. The method of any one of embodiments C9 to C13, wherein the subsequence of the nucleic acid of the plant genome is of a housekeeping gene or a portion thereof.

C15. The method of embodiment C13 or C14, wherein the conserved gene or housekeeping gene of the plant genome is selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin.

C16. The method of any one of embodiments C1 to C15, wherein the subsequence of the nucleic acid of the pathogen, or the complement thereof, comprises all or a portion of at least one gene that is conserved among species of that pathogen.

C17. The method of embodiment C16, wherein the at least one gene that is conserved among species of the pathogen is selected from among RNA-3 coat protein, SS-ds-DNA Regulator protein, Movement Protein, Pathogenesis Enhancer Protein, Rolling Circle Replication Protein, Cell Cycle Regulator Protein and Replication Enhancer Protein.

C18. The method of any one of embodiments C1 to C17, wherein the determining is by one or more of high-resolution melting (HRM), quantitative PCR (qPCR), RT-PCR, quantitative RT-PCR (RT-qPCR), loop-mediated isothermal amplification (LAMP), restriction endonuclease digestion, gel electrophoresis and sequencing.

C19. The method of embodiment C18, wherein the determining is by qPCR or by RT-qPCR.

C19.1 The method of embodiment C19, wherein the determining comprises quantifying the at least one amplicon generated under amplification conditions wherein the at least one polynucleotide primer pair is substantially hybridized to and amplifies the subsequence of the nucleic acid of the pathogen, or the complement thereof, if present in the sample.

C20. The method of any one of embodiments C1 to C19.1, wherein the pathogen is Alfalfa Mosaic Virus (AMV).

C21. The method of embodiment C20, wherein the subsequence of the nucleic acid of the pathogen to which the polynucleotide primer pair is capable of hybridizing comprises SEQ ID NO:91, or a portion of SEQ ID NO:91, or a complement of SEQ ID NO:91, or a portion of the complement of SEQ ID NO:91.

C22. The method of embodiment C20 or C21, wherein the polynucleotide primer pairs comprise: one primer selected from among those having the sequences set forth in SEQ ID NOS: 80, 82 and 85, or from among sequences that share 90%, 91%, 92%, 93%, 94%, 95%, 96%, 97%, 98%, 99% or more identity with the sequences set forth in SEQ ID NOS: 80, 82 and 85; and one primer selected from among those having the sequences set forth in SEQ ID NOS: 81, 83, 84 and 86; or from among sequences that share 90%, 91%, 92%, 93%, 94%, 95%, 96%, 97%, 98%, 99% or more identity with the sequences set forth in SEQ ID NOS: 81, 83, 84 and 86.

C23. The method of any one of embodiments C20 to C22, wherein the at least one amplicon generated under amplification conditions wherein the at least one polynucleotide primer pair is substantially hybridized to and amplifies the subsequence of the nucleic acid of the pathogen, or the complement thereof, if present in the sample, is quantified using a polynucleotide probe.

C24. The method of embodiment C23, wherein the polynucleotide probe is selected from among the sequences set forth in SEQ ID NOS: 87-90, or from among sequences that share 90%, 91%, 92%, 93%, 94%, 95%, 96%, 97%, 98%, 99% or more identity with the sequences set forth in SEQ ID NOS: 87-90.

C25. The method of any one of embodiments C1 to C19.1, wherein the pathogen is HpLVd.

C26. The method of embodiment C25, wherein the subsequence of the nucleic acid of the pathogen to which the polynucleotide primer pair is capable of hybridizing comprises SEQ ID NO:1, or a portion of SEQ ID NO:1, or a complement of SEQ ID NO:1, or a portion of the complement of SEQ ID NO:1.

C27. The method of embodiment C25 or C26, wherein one or more of the polynucleotide primer pairs comprise:
(i) one thermomutant-specific primer selected from among those having the sequences set forth in SEQ ID NOS: 2 and 77, or from among sequences that share 90%, 91%, 92%, 93%, 94%, 95%, 96%, 97%, 98%, 99% or more identity with the sequences set forth in SEQ ID NOS: 2 and 77; and one thermomutant-specific primer selected from among those having the sequences set forth in SEQ ID NOS: 7, 14, 15 and 78; or from among sequences that share 90%, 91%, 92%, 93%, 94%, 95%, 96%, 97%, 98%, 99% or more identity with the sequences set forth in SEQ ID NOS: 7, 14, 15 and 78; and/or
(ii) one thermomutant-resistant primer selected from among those having the sequences set forth in SEQ ID NOS: 4, 6, 9, 11 and 13, or from among sequences that share 90%, 91%, 92%, 93%, 94%, 95%, 96%, 97%, 98%, 99% or more identity with the sequences set forth in SEQ ID NOS: 4, 6, 9, 11 and 13; and one thermomutant-resistant primer selected from among those having the sequences set forth in SEQ ID NOS: 3, 5, 8, 10 and 12; or from among sequences that share 90%, 91%, 92%, 93%, 94%, 95%, 96%, 97%, 98%, 99% or more identity with the sequences set forth in SEQ ID NOS: 3, 5, 8, 10 and 12.

C28. The method of any one of embodiments C25 to C27, wherein the at least one amplicon generated under amplification conditions wherein the at least one polynucleotide primer pair is substantially hybridized to and amplifies the subsequence of the nucleic acid of the pathogen, or the complement thereof, if present in the sample, is quantified using a polynucleotide probe.

C29. The method of embodiment C23, wherein the polynucleotide probe is selected from among the sequences set forth in SEQ ID NOS: 16-20 and 79, or from among sequences that share 90%, 91%, 92%, 93%, 94%, 95%, 96%, 97%, 98%, 99% or more identity with the sequences set forth in SEQ ID NOS: 16-20 and 79.

C30. The method of any one of embodiments C1 to C19.1, wherein the pathogen is BCTV.

C31. The method of embodiment C30, wherein the subsequence of the nucleic acid of the pathogen to which the polynucleotide primer pair is capable of hybridizing is selected from among SEQ ID NOS:110, 112, 114, 116, 118 or 120, or a portion of SEQ ID NOS:110, 112, 114, 116, 118 or 120, or a complement of SEQ ID NOS:110, 112, 114, 116, 118 or 120, or a portion of the complement of SEQ ID NOS:110, 112, 114, 116, 118 or 120, or to regions of overlap that spans any two of SEQ ID NOS:110, 112, 114, 116, 118 or 120 in the genome of the pathogen.

C32. The method of embodiment C31, wherein the subsequence of the nucleic acid of the pathogen to which the polynucleotide primer pair is capable of hybridizing is in a region of overlap that spans:
(i) the gene encoding the SS-ds-DNA Regulator Protein (SEQ ID NO:110) and the gene encoding Movement Protein (SEQ ID NO:112);
(ii) the gene encoding the Pathogenesis Enhancement Protein (SEQ ID NO:116) and the gene encoding the Rolling Circle Replication Protein (SEQ ID NO:114);

(iii) the gene encoding the Rolling Circle Replication Protein (SEQ ID NO:114) and the gene encoding the Cell Cycle Regulator Protein (SEQ ID NO:118); or (iv) the gene encoding the Pathogenesis Enhancement Protein (SEQ ID NO:116) and the gene encoding the Replication Enhancer Protein (SEQ ID NO:120).

C33. The method of embodiment C32, wherein the polynucleotide primer pairs comprise:

for (i), the primer pair having the sequences set forth in SEQ ID NOS: 93 and 94 or sequences that share 90%, 91%, 92%, 93%, 94%, 95%, 96%, 97%, 98%, 99% or more identity with the sequences set forth in SEQ ID NOS: 93 and 94, or the primer pair having the sequences set forth in SEQ ID NOS: 93 and 105, or sequences that share 90%, 91%, 92%, 93%, 94%, 95%, 96%, 97%, 98%, 99% or more identity with the sequences set forth in SEQ ID NOS: 93 and 105;

for (ii), the primer pair having the sequences set forth in SEQ ID NOS: 96 and 97, or sequences that share 90%, 91%, 92%, 93%, 94%, 95%, 96%, 97%, 98%, 99% or more identity with the sequences set forth in SEQ ID NOS: 96 and 97;

for (iii), the primer pair having the sequences set forth in SEQ ID NOS: 99 and 100, or sequences that share 90%, 91%, 92%, 93%, 94%, 95%, 96%, 97%, 98%, 99% or more identity with the sequences set forth in SEQ ID NOS: 99 and 100; and for (iv), the primer pair having the sequences set forth in SEQ ID NOS: 102 and 103, or sequences that share 90%, 91%, 92%, 93%, 94%, 95%, 96%, 97%, 98%, 99% or more identity with the sequences set forth in SEQ ID NOS: 102 and 103.

C34. The method of any one of embodiments C32 or C33, wherein the at least one amplicon generated under amplification conditions wherein the at least one polynucleotide primer pair is substantially hybridized to and amplifies the subsequence of the nucleic acid of the pathogen, or the complement thereof, if present in the sample, is quantified using a polynucleotide probe.

C35. The method of embodiment C34, wherein the polynucleotide probe comprises:

for (i), the polynucleotide probe having the sequence set forth in SEQ ID NO: 95 or a sequence that shares 90%, 91%, 92%, 93%, 94%, 95%, 96%, 97%, 98%, 99% or more identity with the sequence set forth in SEQ ID NO: 95, and/or the polynucleotide probe having the sequence set forth in SEQ ID NO: 106 or a sequence that shares 90%, 91%, 92%, 93%, 94%, 95%, 96%, 97%, 98%, 99% or more identity with the sequence set forth in SEQ ID NO: 106;

for (ii), the polynucleotide probe having the sequence set forth in SEQ ID NO: 98 or a sequence that shares 90%, 91%, 92%, 93%, 94%, 95%, 96%, 97%, 98%, 99% or more identity with the sequence set forth in SEQ ID NO: 98;

for (iii), the polynucleotide probe having the sequence set forth in SEQ ID NO: 101 or a sequence that shares 90%, 91%, 92%, 93%, 94%, 95%, 96%, 97%, 98%, 99% or more identity with the sequence set forth in SEQ ID NO:101; and for (iv), the polynucleotide probe having the sequence set forth in SEQ ID NO: 104 or a sequence that shares 90%, 91%, 92%, 93%, 94%, 95%, 96%, 97%, 98%, 99% or more identity with the sequence set forth in SEQ ID NO: 104.

C36. The method of any one of embodiments C30 to C35, wherein the nucleic acid sample and/or the amplified nucleic acid mixture comprises genomic DNA of the pathogen, if the pathogen is present in the plant cultivar.

C37. The method of any one of embodiments C30 to C35, wherein the nucleic acid sample and/or the amplified nucleic acid mixture comprises RNA or cDNA of the pathogen, if the pathogen is present in the plant cultivar.

C38. The method of any one of embodiments C1 to C19.1, wherein the pathogen is a DNA virus or viroid and the nucleic acid sample and/or the amplified nucleic acid mixture comprises genomic DNA of the pathogen, if the pathogen is present in the plant cultivar.

C39. The method of any one of embodiments C1 to C19.1, wherein the pathogen is a DNA virus or viroid or an RNA virus or viroid and the nucleic acid sample and/or the amplified nucleic acid mixture comprises RNA or cDNA of the pathogen, if the pathogen is present in the plant cultivar.

C40. The method of any one of embodiments C1 to C39, wherein the presence, absence and/or amount of a plurality of pathogens are determined in the plant cultivar.

C41. The method of embodiment C40, wherein the presence, absence and/or amount of more than one of the plurality of pathogens is determined simultaneously.

C42. The method of embodiment C41, wherein the pathogens are viruses and/or viroids.

C43. The method of embodiment C42, wherein the presence and/or amount of more than one virus and/or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV), is determined simultaneously.

C44. The method of embodiment C43, wherein the presence and/or amount of more than one virus and/or viroid selected from among Hops Latent Viroid (HpLVd), Alfalfa Mosaic Virus (AMV) and Beet Curly Top Virus (BCTV) is determined simultaneously.

C45. The method of any one of embodiments C1 to C44, wherein the determining is by quantitative PCR (qPCR), or quantitative RT-PCR (RT-qPCR), and an amplicon of at least one pathogen is quantified with more than one polynucleotide probe sequence, wherein the polynucleotide probe sequences hybridize to non-overlapping regions of the subsequence of the pathogen that is amplified to generate the amplicon.

C45.1. The method of embodiment C45, further comprising, obtaining the Cq value for each polynucleotide probe sequence.

C46. The method of embodiment C45, wherein, if the Cq value obtained with a first polynucleotide probe sequence is significantly different than the Cq value obtained with any of the other non-overlapping polynucleotide probe sequences, a variant in the genotype of the pathogen is identified where the first polynucleotide probe sequence binds to a subsequence of the pathogen and, if the Cq values obtained with a first polynucleotide probe sequence is similar to the Cq value obtained with any of the other non-overlapping polynucleotide probe sequences, the genotype of the pathogen is identified as not comprising a variant sequence where the first polynucleotide probe sequence binds to a subsequence of the pathogen.

C47. The method of embodiment C46, wherein the presence or absence of a variant in the genotype of the pathogen is correlated to the infectivity of the pathogen.

C48. The method of embodiment C46 or C47, wherein the presence or absence of a variant in the genotype of the pathogen is correlated to resistance or susceptibility of the plant to infection by the pathogen comprising the genotype or a variant thereof.

C48.0. The method of embodiment C48, wherein resistance or susceptibility is measured by determining whether the plant is: (a) infected and symptomatic when exposed to the pathogen or genotypic variant thereof; (b) infected and asymptomatic when exposed to the pathogen or genotypic variant thereof; or (c) resistant to infection when exposed to the pathogen or genotypic variant thereof.

C48.1. The method of embodiment C48, wherein, if the plant is identified as resistant to infection by the pathogen or a genotypic variant thereof, or asymptomatic, the plant is identified as desirable for breeding, or as desirable for cultivating as a crop.

C48.2. The method of embodiment C48.1, further comprising, breeding the plant or cultivating the plant as a crop.

C48.3. The method of any one of embodiments C48, C48.1 or C48.2, wherein the plant is a *Cannabis* plant.

C48.4. The method of any one of embodiments C48 to C48.3, wherein the breeding produces at least one progeny plant that is resistant to infection by a pathogen or genotypic variant thereof, or is asymptomatic when infected by a pathogen or genotypic variant thereof.

C48.5. A method of removing symptomatic, infected plants from a crop, comprising:
(a) identifying a plant as resistant, symptomatic or asymptomatic when exposed to a pathogen by the method of embodiment C48.0;
(b) selecting the plant for breeding one or more progeny plants by the method of embodiment C48.1;
(c) breeding the plant to produce at least one progeny plant by the method of embodiment C48.4; and
(d) replacing at least one symptomatic, infected plant in the crop with at least one progeny plant that is resistant to infection by a pathogen or genotypic variant thereof, or is asymptomatic when infected by a pathogen or genotypic variant thereof.

C48.6. The method of embodiment C48.5, wherein (a), (b), (c) and (d) are repeated until a majority or all of the symptomatic, infected plants in the crop are replaced with progeny plants that are resistant to infection by a pathogen or genotypic variant thereof, or are asymptomatic when infected by a pathogen or genotypic variant thereof.

C49. The method of any one of embodiments C1 to C48.6, comprising:
if the presence, absence and/or amount of one pathogen in the plant cultivar is to be determined, obtaining more than one amplicon by amplifying more than one subsequence of the nucleic acid of the pathogen, or complements thereof, using more than one polynucleotide primer pair, and determining the presence, absence and/or amount of the pathogen by determining the presence, absence and/or amount of at least two amplicons that are 300 base pairs or less and are amplification products of the more than one polynucleotide primer pair in the amplified nucleic acid mixture of (b), thereby determining the presence, absence and/or amount of a pathogen in the plant cultivar; or
if the presence, absence and/or amount of a plurality of pathogens in the plant cultivar is to be determined, obtaining more than one amplicon by amplifying more than one subsequence of the nucleic acid of more than one of the plurality of pathogens, or complements thereof, using more than one polynucleotide primer pair for each of the more than one pathogens, and determining the presence, absence and/or amount of the more than one pathogens by determining the presence, absence and/or amount of at least two amplicons for each pathogen that are 300 base pairs or less and are amplification products of the more than one polynucleotide primer pair in each of the more than one pathogens of the amplified nucleic acid mixture of (b), thereby determining the presence, absence and/or amount of the more than one pathogens in the plant cultivar.

C50. The method of embodiment C49, wherein, based on the presence and/or relative amounts of the more than one amplicon, a variant in the genotype of the pathogen(s) is/are identified or the genotype of the pathogen(s) is/are identified as not comprising a variant sequence.

C51. The method of embodiment C49 or C50, wherein the presence or absence of a variant in the genotype of the pathogen(s) is correlated to resistance or susceptibility of the plant to infection by the pathogen(s) comprising the genotype or a variant thereof.

C51.1. The method of embodiment C51, wherein, if the plant is identified as resistant to infection by the pathogen(s) or a genotypic variant thereof, the plant is identified as desirable for breeding, or as desirable for cultivating as a crop.

C51.2. The method of embodiment C51.1, further comprising, breeding the plant or cultivating the plant as a crop.

C51.3. The method of any one of embodiments C51, C51.1 or C51.2, wherein the plant is a *Cannabis* plant.

C52. The method of any one of embodiments C49 to C51.3, wherein at least one of the pathogens is a virus or a viroid.

C52.1. The method of embodiment C52, wherein the virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), and Tobacco Streak Virus (TSV, *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

C53. The method of embodiment C52 or C52.1, wherein the at least one pathogen is a viroid, and the viroid is HpLVd.

C54. The method of embodiment C53, wherein at least one amplicon is obtained by amplifying a subsequence of the nucleic acid of the pathogen that is thermomutant-resistant, and at least one amplicon is obtained by amplifying a subsequence of the nucleic acid of the pathogen that is thermomutant-specific.

C54.1. The method of embodiment C54, wherein the polynucleotide primer pairs for amplifying subsequence of the nucleic acid of the pathogen that is thermomutant-resistant and the subsequence of the nucleic acid of the pathogen that is thermomutant-specific are selected from among:
- (i) one thermomutant-specific primer selected from among those having the sequences set forth in SEQ ID NOS: 2 and 77, or from among sequences that share 90%, 91%, 92%, 93%, 94%, 95%, 96%, 97%, 98%, 99% or more identity with the sequences set forth in SEQ ID NOS: 2 and 77; and one thermomutant-specific primer selected from among those having the sequences set forth in SEQ ID NOS: 7, 14, 15 and 78; or from among sequences that share 90%, 91%, 92%, 93%, 94%, 95%, 96%, 97%, 98%, 99% or more identity with the sequences set forth in SEQ ID NOS: 7, 14, 15 and 78; and/or
- (ii) one thermomutant-resistant primer selected from among those having the sequences set forth in SEQ ID NOS: 4, 6, 9, 11 and 13, or from among sequences that share 90%, 91%, 92%, 93%, 94%, 95%, 96%, 97%, 98%, 99% or more identity with the sequences set forth in SEQ ID NOS: 4, 6, 9, 11 and 13; and one thermomutant-resistant primer selected from among those having the sequences set forth in SEQ ID NOS: 3, 5, 8, 10 and 12; or from among sequences that share 90%, 91%, 92%, 93%, 94%, 95%, 96%, 97%, 98%, 99% or more identity with the sequences set forth in SEQ ID NOS: 3, 5, 8, 10 and 12.

C55. The method of embodiment C54 or C54.1, wherein, based on the presence and/or relative amounts of the more than one amplicon, a thermomutant variant in the genotype of the at least one pathogen is identified, or the genotype of the at least one pathogen is identified as not comprising a thermomutant variant sequence.

C56. The method of embodiment C54, C54.1 or C55, wherein the presence or absence of a thermomutant variant in the genotype of at least one pathogen is correlated to resistance or susceptibility of the plant to infection by the pathogen comprising the genotype or a variant thereof.

C57. The method of embodiment C52 or C52.1, wherein the at least one pathogen is a virus, and the virus is AMV.

C57.1. The method of embodiment C57, wherein the polynucleotide primer pairs for amplifying the more than one amplicon are selected from among:
- one primer selected from among those having the sequences set forth in SEQ ID NOS: 80, 82 and 85, or from among sequences that share 90%, 91%, 92%, 93%, 94%, 95%, 96%, 97%, 98%, 99% or more identity with the sequences set forth in SEQ ID NOS: 80, 82 and 85; and
- one primer selected from among those having the sequences set forth in SEQ ID NOS: 81, 83, 84 and 86; or from among sequences that share 90%, 91%, 92%, 93%, 94%, 95%, 96%, 97%, 98%, 99% or more identity with the sequences set forth in SEQ ID NOS: 81, 83, 84 and 86.

C58. The method of embodiment C52 or C52.1, wherein the at least one pathogen is a virus, and the virus is BCTV.

C58.1. The method of embodiment C58, wherein the polynucleotide primer pairs for amplifying the more than one amplicon are selected from among polynucleotide primer pairs capable of hybridizing to a subsequence of the nucleic acid of the pathogen that is in a region of overlap that spans:
- (i) the gene encoding the SS-ds-DNA Regulator Protein (SEQ ID NO:110) and the gene encoding Movement Protein (SEQ ID NO:112);
- (ii) the gene encoding the Pathogenesis Enhancement Protein (SEQ ID NO:116) and the gene encoding the Rolling Circle Replication Protein (SEQ ID NO:114);
- (iii) the gene encoding the Rolling Circle Replication Protein (SEQ ID NO:114) and the gene encoding the Cell Cycle Regulator Protein (SEQ ID NO:118); or
- (iv) the gene encoding the Pathogenesis Enhancement Protein (SEQ ID NO:116) and the gene encoding the Replication Enhancer Protein (SEQ ID NO:120).

C58.2. The method of embodiment C58.1, wherein the polynucleotide primer pairs comprise:
- for (i), the primer pair having the sequences set forth in SEQ ID NOS: 93 and 94 or sequences that share 90%, 91%, 92%, 93%, 94%, 95%, 96%, 97%, 98%, 99% or more identity with the sequences set forth in SEQ ID NOS: 93 and 94, or the primer pair having the sequences set forth in SEQ ID NOS: 93 and 105, or sequences that share 90%, 91%, 92%, 93%, 94%, 95%, 96%, 97%, 98%, 99% or more identity with the sequences set forth in SEQ ID NOS: 93 and 105;
- for (ii), the primer pair having the sequences set forth in SEQ ID NOS: 96 and 97, or sequences that share 90%, 91%, 92%, 93%, 94%, 95%, 96%, 97%, 98%, 99% or more identity with the sequences set forth in SEQ ID NOS: 96 and 97;
- for (iii), the primer pair having the sequences set forth in SEQ ID NOS: 99 and 100, or sequences that share 90%, 91%, 92%, 93%, 94%, 95%, 96%, 97%, 98%, 99% or more identity with the sequences set forth in SEQ ID NOS: 99 and 100; and
- for (iv), the primer pair having the sequences set forth in SEQ ID NOS: 102 and 103, or sequences that share 90%, 91%, 92%, 93%, 94%, 95%, 96%, 97%, 98%, 99% or more identity with the sequences set forth in SEQ ID NOS: 102 and 103.

C59. The method of any one of embodiments C1 to C58.2, wherein a plurality of plant cultivars are analyzed for the presence and/or amount of one or more pathogens.

C60. The method of embodiment C59, wherein the plant cultivars are of the same species.

C61. The method of embodiment C59 or C60, wherein one or more plant cultivars is/are a *Cannabis* cultivar.

C62. The method of any one of embodiments C1 to C61, wherein a plurality of *Cannabis* plant cultivars are analyzed.

C63. The method of any one of embodiments C1 to C62, wherein the size of the at least one amplicon that is amplified is 200 base pairs or less.

C64. The method of embodiment C63, wherein the size of the at least one amplicon that is amplified is between about 40 base pairs to about 200 base pairs.

C65. The method of embodiment C64, wherein the size of the at least one amplicon that is amplified is between about 50 base pairs to about 150 base pairs.

C66. The method of any one of embodiments C1 to C65, wherein identification and/or quantitation of the amplicon is by a signal or a label.

C67. The method of embodiment C66, wherein the signal or label is selected from among an electrical signal, an electronic signal, a signal from an optical label or a radiolabel.

C68. The method of embodiment C67, wherein the identification and/or quantitation of the amplicon is by an optical label.

C69. The method of embodiment C68, wherein the optical label is a chromophore, a dye, or a fluorescent label.

C70. The method of any one of embodiments C66 to C69, wherein:
- a plurality of amplicons are analyzed using a plurality of polynucleotide primer pairs, and/or
- a plurality of polynucleotide probes are used to quantitate an amplicon, and
- the plurality of amplicons and/or the plurality of polynucleotide probes are each associated with a unique signal or label for identification and/or quantitation.

C71. The method of any one of embodiments C1 to C70, wherein the nucleic acid sample from the plant cultivar is on a solid support and (b) and (c) are performed on the solid support.

C72. The method of embodiment C71, wherein the presence, absence and/or amount of more than one pathogen in the plant cultivar is determined.

C73. The method of embodiment C71 or C72, wherein the presence, absence and/or amount of one or more pathogens in a plurality of plant cultivars is determined.

C74. The method of any one of embodiments C71 to C73, wherein at least one plant cultivar is *Cannabis*.

C75. The method of embodiment C73, wherein all of the plurality of plant cultivars are *Cannabis* cultivars.

C76. The method of any one of embodiments C1 to C75 that is performed on a FTA® card.

D1. A method of preparing a polynucleotide primer pair for specifically hybridizing to and amplifying nucleic acid of a plant pathogen, comprising:
- (a) Identifying a polynucleotide primer pair that is capable of specifically hybridizing to and amplifying a polynucleotide comprising a subsequence of the nucleic acid of a plant pathogen, or a complement thereof, wherein the plant is capable of being infected by the pathogen and the subsequence of the nucleic acid of the pathogen, or the complement thereof, is non-identical to any subsequence of the nucleic acid of the plant genome, or to any complement thereof;
- (b) identifying whether the subsequence of the nucleic acid of the pathogen is conserved among species of the pathogen; and
- (c) if the subsequence of the nucleic acid of the pathogen is conserved among species of the pathogen, preparing the polynucleotide primer pair.

D1.1. The method of embodiment D1, wherein the subsequence of the nucleic acid of the pathogen, or the complement thereof, comprises at least one exon of at least one gene of the pathogen.

D2. The method of embodiment D1, wherein the size of the product that is amplified by the prepared polynucleotide primer pair is 300 base pairs or less.

D3. The method of embodiment D1 or D2, wherein the size of the product that is amplified by the prepared polynucleotide primer pair is 200 base pairs or less.

D4. The method of any one of embodiments D1 to D3, wherein the size of the product that is amplified by the prepared polynucleotide primer pair is between about 40 base pairs to about 200 base pairs.

D5. The method of any one of embodiments D1 to D4, wherein the size of the product that is amplified by the prepared polynucleotide primer pair is between about 50 base pairs to about 150 base pairs.

D6. The method of any one of embodiments D1 to D5, wherein the melting temperature of each primer hybridized to its target conserved sequence is between about 57° C. to about 63° C.

D7. The method of any one of embodiments D1 to D6, wherein the difference between the melting temperatures of each primer of the primer pair hybridized to its target sequence is 3° C. or less.

D8. The method of any one of embodiments D1 to D7, wherein the subsequence of the nucleic acid of the pathogen, or the complement thereof, comprises more than one exon of at least one gene of the pathogen.

D9. The method of any one of embodiments D1 to D8, wherein the subsequence of the nucleic acid of the pathogen, or the complement thereof, comprises more than one exon spanning more than one gene of the pathogen.

D10. The method of any one of embodiments D1 to D9, further comprising, preparing at least one polynucleotide probe for quantifying the product that is amplified by the prepared polynucleotide pair.

D11. The method of embodiment D10, comprising preparing more than one polynucleotide probe for quantifying the product that is amplified by the prepared polynucleotide pair, wherein each polynucleotide probe binds to a subsequence that does not overlap with the subsequences to which the other polynucleotide probes bind.

D12. The method of any one of embodiments D1 to D11, wherein more than one polynucleotide primer pair is prepared, and each polynucleotide primer pair binds to a subsequence that does not overlap with the subsequences to which the other polynucleotide primer pairs bind.

D13. The method of any one of embodiments D1 to D12, wherein the pathogen is a virus or viroid.

D14. The method of embodiment D13, wherein the virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

D15. The method of embodiment D14, wherein the virus or viroid is selected from among Hops Latent Viroid (HpLVd), Alfalfa Mosaic Virus (AMV) and Beet Curly Top Virus (BCTV).

E1. A composition, comprising one or more polynucleotide primer pairs prepared by the method of any one of embodiments D1 to D15 and, optionally, one or more polynucleotide probes prepared by the method of any one of embodiments D10 to D15.

E1.1. A composition, comprising one or more polynucleotide primer pairs used in the method of any one of embodiments C1 to C70 for specifically hybridizing to and amplifying nucleic acid of a plant pathogen and, optionally, one or more polynucleotide probes for quantifying one or more amplicons generated using the one or more polynucleotide primer pairs.

E1.2. The composition of embodiment E1 or E1.1, wherein the pathogen is a virus or viroid.

E1.3. The composition of embodiment E1.2, wherein the virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn- Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

E2. The composition of any one of embodiments E1 to E1.3, wherein at least one polynucleotide primer pair is capable of specifically hybridizing to and amplifying a subsequence of the nucleic acid of Alfalfa Mosaic Virus (AMV).

E3. The composition of embodiment E2, wherein the subsequence of the nucleic acid of the Alfalfa Mosaic Virus (AMV) to which the polynucleotide primer pair is capable of hybridizing comprises SEQ ID NO:91, or a portion of SEQ ID NO:91, or a complement of SEQ ID NO:91, or a portion of the complement of SEQ ID NO:91.

E4. The composition of embodiment E2 or E3, wherein the at least one polynucleotide primer pair is selected from among: one primer selected from among those having the sequences set forth in SEQ ID NOS: 80, 82 and 85, or from among sequences that share 90%, 91%, 92%, 93%, 94%, 95%, 96%, 97%, 98%, 99% or more identity with the sequences set forth in SEQ ID NOS: 80, 82 and 85; and one primer selected from among those having the sequences set forth in SEQ ID NOS: 81, 83, 84 and 86; or from among sequences that share 90%, 91%, 92%, 93%, 94%, 95%, 96%, 97%, 98%, 99% or more identity with the sequences set forth in SEQ ID NOS: 81, 83, 84 and 86.

E5. The composition of any one of embodiments E1 to E4, further comprising a polynucleotide probe.

E6. The composition of embodiment E5, wherein the polynucleotide probe is selected from among the sequences set forth in SEQ ID NOS: 87-90, or from among sequences that share 90%, 91%, 92%, 93%, 94%, 95%, 96%, 97%, 98%, 99% or more identity with the sequences set forth in SEQ ID NOS: 87-90.

E7. The composition of any one of embodiments E1 to E1.3, wherein at least one polynucleotide primer pair is capable of specifically hybridizing to and amplifying a subsequence of the nucleic acid of HpLVd.

E8. The composition of embodiment E7, wherein the subsequence of the nucleic acid of the pathogen to which the at least one polynucleotide primer pair is capable of hybridizing comprises SEQ ID NO:1, or a portion of SEQ ID NO:1, or a complement of SEQ ID NO:1, or a portion of the complement of SEQ ID NO:1.

E9. The composition of embodiment E7 or E8, wherein the at least one polynucleotide primer pair is selected from among:
(i) one thermomutant-specific primer selected from among those having the sequences set forth in SEQ ID NOS: 2 and 77, or from among sequences that share 90%, 91%, 92%, 93%, 94%, 95%, 96%, 97%, 98%, 99% or more identity with the sequences set forth in SEQ ID NOS: 2 and 77; and one thermomutant-specific primer selected from among those having the sequences set forth in SEQ ID NOS: 7, 14, 15 and 78; or from among sequences that share 90%, 91%, 92%, 93%, 94%, 95%, 96%, 97%, 98%, 99% or more identity with the sequences set forth in SEQ ID NOS: 7, 14, 15 and 78; and/or (ii) one thermomutant-resistant primer selected from among those having the sequences set forth in SEQ ID NOS: 4, 6, 9, 11 and 13, or from among sequences that share 90%, 91%, 92%, 93%, 94%, 95%, 96%, 97%, 98%, 99% or more identity with the sequences set forth in SEQ ID NOS: 4, 6, 9, 11 and 13; and one thermomutant-resistant primer selected from among those having the sequences set forth in SEQ ID NOS: 3, 5, 8, 10 and 12; or from among sequences that share 90%, 91%, 92%, 93%, 94%, 95%, 96%, 97%, 98%, 99% or more identity with the sequences set forth in SEQ ID NOS: 3, 5, 8, 10 and 12.

E10. The composition of any one of embodiments E7 to E9, further comprising a polynucleotide probe.

E11. The composition of embodiment E10, wherein the polynucleotide probe is selected from among the sequences set forth in SEQ ID NOS: 16-20 and 79, or from among sequences that share 90%, 91%, 92%, 93%, 94%, 95%, 96%, 97%, 98%, 99% or more identity with the sequences set forth in SEQ ID NOS: 16-20 and 79.

E12. The composition of any one of embodiments E1 to E1.3, wherein at least one polynucleotide primer pair is capable of specifically hybridizing to and amplifying a subsequence of the nucleic acid of BCTV.

E13. The composition of embodiment E12, wherein the subsequence of the nucleic acid of the pathogen to which the at least one polynucleotide primer pair is capable of hybridizing is selected from among SEQ ID NOS:110, 112, 114, 116, 118 or 120, or a portion of SEQ ID NOS:110, 112, 114, 116, 118 or 120, or a complement of SEQ ID NOS:110, 112, 114, 116, 118 or 120, or a portion of the complement of SEQ ID NOS:110, 112, 114, 116, 118 or 120, or to regions of overlap that spans any two of SEQ ID NOS:110, 112, 114, 116, 118 or 120 in the genome of the pathogen.

E14. The composition of embodiment E12 or E13, wherein the subsequence of the nucleic acid of the pathogen to which the at least one polynucleotide primer pair is capable of hybridizing is in a region of overlap that spans:
(i) the gene encoding the SS-ds-DNA Regulator Protein (SEQ ID NO:110) and the gene encoding Movement Protein (SEQ ID NO:112);
(ii) the gene encoding the Pathogenesis Enhancement Protein (SEQ ID NO:116) and the gene encoding the Rolling Circle Replication Protein (SEQ ID NO:114);
(iii) the gene encoding the Rolling Circle Replication Protein (SEQ ID NO:114) and the gene encoding the Cell Cycle Regulator Protein (SEQ ID NO:118); or
(iv) the gene encoding the Pathogenesis Enhancement Protein (SEQ ID NO:116) and the gene encoding the Replication Enhancer Protein (SEQ ID NO:120).

E15. The composition of embodiment E14, wherein the polynucleotide primer pairs comprise:
for (i), the primer pair having the sequences set forth in SEQ ID NOS: 93 and 94 or sequences that share 90%, 91%, 92%, 93%, 94%, 95%, 96%, 97%, 98%, 99% or more identity with the sequences set forth in SEQ ID NOS: 93 and 94, or the primer pair having the sequences set forth in SEQ ID NOS: 93 and 105, or sequences that share 90%, 91%, 92%, 93%, 94%, 95%, 96%, 97%, 98%, 99% or more identity with the sequences set forth in SEQ ID NOS: 93 and 105;
for (ii), the primers having the sequences set forth in SEQ ID NOS: 96 and 97, or sequences that share 90%, 91%, 92%, 93%, 94%, 95%, 96%, 97%, 98%, 99% or more identity with the sequences set forth in SEQ ID NOS: 96 and 97;

for (iii), the primers having the sequences set forth in SEQ ID NOS: 99 and 100, or sequences that share 90%, 91%, 92%, 93%, 94%, 95%, 96%, 97%, 98%, 99% or more identity with the sequences set forth in SEQ ID NOS: 99 and 100; and for (iv), the primers having the sequences set forth in SEQ ID NOS: 102 and 103, or sequences that share 90%, 91%, 92%, 93%, 94%, 95%, 96%, 97%, 98%, 99% or more identity with the sequences set forth in SEQ ID NOS: 102 and 103.

E16. The composition of any one of embodiments E12 to E15, further comprising a polynucleotide probe.

E17. The composition of embodiment E16, wherein the polynucleotide probe comprises:

for (i), the polynucleotide probe having the sequence set forth in SEQ ID NO: 95 or a sequence that shares 90%, 91%, 92%, 93%, 94%, 95%, 96%, 97%, 98%, 99% or more identity with the sequence set forth in SEQ ID NO: 95, and/or the polynucleotide probe having the sequence set forth in SEQ ID NO: 106 or a sequence that shares 90%, 91%, 92%, 93%, 94%, 95%, 96%, 97%, 98%, 99% or more identity with the sequence set forth in SEQ ID NO: 106;

for (ii), the polynucleotide probe having the sequence set forth in SEQ ID NO: 98 or a sequence that shares 90%, 91%, 92%, 93%, 94%, 95%, 96%, 97%, 98%, 99% or more identity with the sequence set forth in SEQ ID NO: 98;

for (iii), the polynucleotide probe having the sequence set forth in SEQ ID NO: 101 or a sequence that shares 90%, 91%, 92%, 93%, 94%, 95%, 96%, 97%, 98%, 99% or more identity with the sequence set forth in SEQ ID NO:101; and for (iv), the polynucleotide probe having the sequence set forth in SEQ ID NO: 104 or a sequence that shares 90%, 91%, 92%, 93%, 94%, 95%, 96%, 97%, 98%, 99% or more identity with the sequence set forth in SEQ ID NO: 104.

E18. The composition of any one of embodiments E1 to E17, further comprising, a polynucleotide primer pair that is capable of specifically hybridizing to and amplifying a subsequence of the nucleic acid of the plant genome.

E19. The composition of embodiment E18, wherein the subsequence of the nucleic acid of the plant genome comprises all or a portion of a gene that is conserved among species of the plant.

E20. The composition of embodiment E18 or E19, wherein the subsequence of the nucleic acid of the plant genome is of a housekeeping gene or a portion thereof.

E21. The composition of embodiment E19 or E20, wherein the conserved gene or housekeeping gene of the plant genome is selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin.

F1. A kit, comprising one or more of the compositions of any one of embodiments E1 to E21, and instructions for use.

F2. The kit of embodiment F1, further comprising, at least one signal or label.

F3. The kit of embodiment F2, wherein the signal or label is selected from among an electrical signal, an electronic signal, a signal from an optical label or a radiolabel.

F4. The kit of embodiment F3, comprising an optical label.

F5. The kit of embodiment F4, wherein the optical label is a chromophore, a dye, or a fluorescent label.

G1. A solid support, comprising:

single-stranded nucleic acid from a plant cultivar; and one or more polynucleotide primer pairs used in the method of any one of embodiments C1 to C70 or prepared by the method of any one of embodiments D1 to D15 for specifically hybridizing to and amplifying nucleic acid of a plant pathogen.

G2. The solid support of embodiment G1, wherein the single-stranded nucleic acid from the plant cultivar is DNA, RNA or cDNA.

G2.1. The solid support of embodiment G2, wherein the single-stranded nucleic acid from the plant cultivar is DNA that comprises genomic DNA.

G3. The solid support of embodiment G1 or G2, wherein the pathogen is a virus or viroid.

G4. The solid support of embodiment G3, wherein the virus or viroid is selected from among Hops Latent Viroid (HpLVd), Alfalfa Mosaic Virus (AMV), Beet Curly Top Virus (BCTV), Hemp Streak Virus (HSV), Hemp Mosaic Virus (HMV), Tomato spotted wilt virus (TSWV), Sunn-Hemp Mosaic Virus (SHMV), Arabis Mosaic Virus (ArMV), Cucumber Mosaic Virus (CMV), Lettuce Chlorosis Virus (LCV), Tobacco Ringspot Virus (TRSV), Tomato Ringspot Virus (TomRSV), Tobacco Streak Virus (TSV), *Cannabis* Cryptic Virus (CCV), Potato Spindle Tubular Viroid (PSTV), Coconut cadang cadang viroid (CCCV), Apple scar skin viroid (ASSV), Avocado sunblotch viroid (ASBV), Tobacco streak virus (TSV), Tomato mosaic virus (ToMV), Euonymous Ringspot Virus (ERSV), Elm Mosaic Virus (EMV), and Hops Stunting Virus (HpSV).

G5. The solid support of any one of embodiments G1 to G4, comprising more than one polynucleotide primer pair, wherein the polynucleotide primer pairs specifically hybridize to non-overlapping subsequences of the same pathogen, or the polynucleotide primer pairs specifically hybridize to subsequences of different pathogens, or some polynucleotide primer pairs specifically hybridize to non-overlapping subsequences of the same pathogen and some polynucleotide primer pairs specifically hybridize to subsequences of different pathogens.

G6. The solid support of any one of embodiments G1 to G5, wherein at least one polynucleotide primer pair is capable of specifically hybridizing to and amplifying a subsequence of the nucleic acid of Alfalfa Mosaic Virus (AMV).

G7. The solid support of embodiment G6, wherein the subsequence of the nucleic acid of the Alfalfa Mosaic Virus (AMV) to which the polynucleotide primer pair is capable of hybridizing comprises SEQ ID NO:91, or a portion of SEQ ID NO:91, or a complement of SEQ ID NO:91, or a portion of the complement of SEQ ID NO:91.

G8. The solid support of embodiment G6 or G7, wherein the at least one polynucleotide primer pair is selected from among: one primer selected from among those having the sequences set forth in SEQ ID NOS: 80, 82 and 85, or from among sequences that share 90%, 91%, 92%, 93%, 94%, 95%, 96%, 97%, 98%, 99% or more identity with the sequences set forth in SEQ ID NOS: 80, 82 and 85; and one primer selected from among those having the sequences set forth in SEQ ID NOS: 81, 83, 84 and 86; or from among sequences that share 90%, 91%, 92%, 93%, 94%, 95%, 96%, 97%, 98%, 99% or more identity with the sequences set forth in SEQ ID NOS: 81, 83, 84 and 86.

G9. The solid support of any one of embodiments G1 to G8, further comprising a polynucleotide probe.

G10. The solid support of embodiment G9, wherein the polynucleotide probe is selected from among the sequences set forth in SEQ ID NOS: 87-90, or from among sequences that share 90%, 91%, 92%, 93%, 94%, 95%, 96%, 97%, 98%, 99% or more identity with the sequences set forth in SEQ ID NOS: 87-90.

G11. The solid support of any one of embodiments G1 to G5, wherein at least one polynucleotide primer pair is capable of specifically hybridizing to and amplifying a subsequence of the nucleic acid of HpLVd.

G12. The solid support of embodiment G11, wherein the subsequence of the nucleic acid of the pathogen to which the at least one polynucleotide primer pair is capable of hybridizing comprises SEQ ID NO:1, or a portion of SEQ ID NO:1, or a complement of SEQ ID NO:1, or a portion of the complement of SEQ ID NO:1.

G13. The solid support of embodiment G11 or G12, wherein the at least one polynucleotide primer pair is selected from among:
  (i) one thermomutant-specific primer selected from among those having the sequences set forth in SEQ ID NOS: 2 and 77, or from among sequences that share 90%, 91%, 92%, 93%, 94%, 95%, 96%, 97%, 98%, 99% or more identity with the sequences set forth in SEQ ID NOS: 2 and 77; and one thermomutant-specific primer selected from among those having the sequences set forth in SEQ ID NOS: 7, 14, 15 and 78; or from among sequences that share 90%, 91%, 92%, 93%, 94%, 95%, 96%, 97%, 98%, 99% or more identity with the sequences set forth in SEQ ID NOS: 7, 14, 15 and 78; and/or
  (ii) one thermomutant-resistant primer selected from among those having the sequences set forth in SEQ ID NOS: 4, 6, 9, 11 and 13, or from among sequences that share 90%, 91%, 92%, 93%, 94%, 95%, 96%, 97%, 98%, 99% or more identity with the sequences set forth in SEQ ID NOS: 4, 6, 9, 11 and 13; and one thermomutant-resistant primer selected from among those having the sequences set forth in SEQ ID NOS: 3, 5, 8, 10 and 12; or from among sequences that share 90%, 91%, 92%, 93%, 94%, 95%, 96%, 97%, 98%, 99% or more identity with the sequences set forth in SEQ ID NOS: 3, 5, 8, 10 and 12.

G14. The solid support of any one of embodiments G11 to G13, further comprising a polynucleotide probe.

G15. The solid support of embodiment G14, wherein the polynucleotide probe is selected from among the sequences set forth in SEQ ID NOS: 16-20 and 79, or from among sequences that share 90%, 91%, 92%, 93%, 94%, 95%, 96%, 97%, 98%, 99% or more identity with the sequences set forth in SEQ ID NOS: 16-20 and 79.

G16. The solid support of any one of embodiments G1 to G5, wherein at least one polynucleotide primer pair is capable of specifically hybridizing to and amplifying a subsequence of the nucleic acid of BCTV.

G17. The solid support of embodiment G16, wherein the subsequence of the nucleic acid of the pathogen to which the at least one polynucleotide primer pair is capable of hybridizing is selected from among SEQ ID NOS:110, 112, 114, 116, 118 or 120, or a portion of SEQ ID NOS:110, 112, 114, 116, 118 or 120, or a complement of SEQ ID NOS:110, 112, 114, 116, 118 or 120, or a portion of the complement of SEQ ID NOS:110, 112, 114, 116, 118 or 120, or to regions of overlap that spans any two of SEQ ID NOS:110, 112, 114, 116, 118 or 120 in the genome of the pathogen.

G18. The solid support of embodiment G16 or G17, wherein the subsequence of the nucleic acid of the pathogen to which the at least one polynucleotide primer pair is capable of hybridizing is in a region of overlap that spans:
  (i) the gene encoding the SS-ds-DNA Regulator Protein (SEQ ID NO:110) and the gene encoding Movement Protein (SEQ ID NO:112);
  (ii) the gene encoding the Pathogenesis Enhancement Protein (SEQ ID NO:116) and the gene encoding the Rolling Circle Replication Protein (SEQ ID NO:114);
  (iii) the gene encoding the Rolling Circle Replication Protein (SEQ ID NO:114) and the gene encoding the Cell Cycle Regulator Protein (SEQ ID NO:118); or
  (iv) the gene encoding the Pathogenesis Enhancement Protein (SEQ ID NO:116) and the gene encoding the Replication Enhancer Protein (SEQ ID NO:120).

G19. The solid support of embodiment G18, wherein the polynucleotide primer pairs comprise:
  for (i), the primer pair having the sequences set forth in SEQ ID NOS: 93 and 94 or sequences that share 90%, 91%, 92%, 93%, 94%, 95%, 96%, 97%, 98%, 99% or more identity with the sequences set forth in SEQ ID NOS: 93 and 94, or the primer pair having the sequences set forth in SEQ ID NOS: 93 and 105, or sequences that share 90%, 91%, 92%, 93%, 94%, 95%, 96%, 97%, 98%, 99% or more identity with the sequences set forth in SEQ ID NOS: 93 and 105;
  for (ii), the primers having the sequences set forth in SEQ ID NOS: 96 and 97, or sequences that share 90%, 91%, 92%, 93%, 94%, 95%, 96%, 97%, 98%, 99% or more identity with the sequences set forth in SEQ ID NOS: 96 and 97;
  for (iii), the primers having the sequences set forth in SEQ ID NOS: 99 and 100, or sequences that share 90%, 91%, 92%, 93%, 94%, 95%, 96%, 97%, 98%, 99% or more identity with the sequences set forth in SEQ ID NOS: 99 and 100; and
  for (iv), the primers having the sequences set forth in SEQ ID NOS: 102 and 103, or sequences that share 90%, 91%, 92%, 93%, 94%, 95%, 96%, 97%, 98%, 99% or more identity with the sequences set forth in SEQ ID NOS: 102 and 103.

G20. The solid support of any one of embodiments G16 to G19, further comprising a polynucleotide probe.

G21. The solid support of embodiment G20, wherein the polynucleotide probe comprises:
  for (i), the polynucleotide probe having the sequence set forth in SEQ ID NO: 95 or a sequence that shares 90%, 91%, 92%, 93%, 94%, 95%, 96%, 97%, 98%, 99% or more identity with the sequence set forth in SEQ ID NO: 95, and/or the polynucleotide probe having the sequence set forth in SEQ ID NO: 106 or a sequence that shares 90%, 91%, 92%, 93%, 94%, 95%, 96%, 97%, 98%, 99% or more identity with the sequence set forth in SEQ ID NO: 106;
  for (ii), the polynucleotide probe having the sequence set forth in SEQ ID NO: 98 or a sequence that shares 90%, 91%, 92%, 93%, 94%, 95%, 96%, 97%, 98%, 99% or more identity with the sequence set forth in SEQ ID NO: 98;
  for (iii), the polynucleotide probe having the sequence set forth in SEQ ID NO: 101 or a sequence that shares 90%, 91%, 92%, 93%, 94%, 95%, 96%, 97%, 98%, 99% or more identity with the sequence set forth in SEQ ID NO:101; and
  for (iv), the polynucleotide probe having the sequence set forth in SEQ ID NO: 104 or a sequence that shares 90%, 91%, 92%, 93%, 94%, 95%, 96%, 97%, 98%, 99% or more identity with the sequence set forth in SEQ ID NO: 104.

G22. The solid support of any one of embodiments G1 to G21, further comprising, a polynucleotide primer pair that is capable of specifically hybridizing to and amplifying a subsequence of the nucleic acid of the plant genome.

G23. The solid support of embodiment G22, wherein the subsequence of the nucleic acid of the plant genome comprises all or a portion of a gene that is conserved among species of the plant.

G24. The solid support of embodiment G22 or G23, wherein the subsequence of the nucleic acid of the plant genome is of a housekeeping gene or a portion thereof.

G25. The solid support of embodiment G23 or G24, wherein the conserved gene or housekeeping gene of the plant genome is selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin.

G26. The solid support of any one of embodiments G1 to G25 that comprises a bead, column, capillary, disk, filter, dipstick, membrane, wafer, comb, pin or a chip.

G27. The solid support of any one of embodiments G1 to G26 that comprises a material selected from among silicon, silica, glass, controlled-pore glass (CPG), nylon, Wang resin, Merrifield resin, Sephadex, Sepharose, cellulose, magnetic beads, Dynabeads, a metal, a metal surface, a plastic or polymer or combinations thereof.

G28. The solid support of any one of embodiments G1 to G27, comprising a plurality of plant cultivars.

G29. A collection of solid supports comprising two or more solid supports of any one of embodiments G1 to G27, wherein each solid support in the collection comprises nucleic acid from a different plant cultivar.

C29.1. The solid support of embodiment G28 or the collection of embodiment G29, wherein at least one of the plant cultivars is of the subclass Rosidae.

G30. The solid support of embodiment G28 or the collection of embodiment G29 or

G29.1, wherein at least one of the plant cultivars is a *Cannabis* cultivar.

G31. The solid support of embodiment G28 or the collection of embodiment G29, wherein more than one of the plant cultivars is a *Cannabis* cultivar.

G32. The solid support of embodiment G28 or the collection of embodiment G29, wherein the plurality of plant cultivars are *Cannabis* cultivars.

The entirety of each patent, patent application, publication and document referenced herein is incorporated by reference. Citation of patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

The technology has been described with reference to specific implementations. The terms and expressions that have been utilized herein to describe the technology are descriptive and not necessarily limiting. Certain modifications made to the disclosed implementations can be considered within the scope of the technology. Certain aspects of the disclosed implementations suitably may be practiced in the presence or absence of certain elements not specifically disclosed herein.

Each of the terms "comprising," "consisting essentially of," and "consisting of" may be replaced with either of the other two terms. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%; e.g., a weight of "about 100 grams" can include a weight between 90 grams and 110 grams). Use of the term "about" at the beginning of a listing of values modifies each of the values (e.g., "about 1, 2 and 3" refers to "about 1, about 2 and about 3"). When a listing of values is described, the listing includes all intermediate values and all fractional values thereof (e.g., the listing of values "80%, 85% or 90%" includes the intermediate value 86% and the fractional value 86.4%). When a listing of values is followed by the term "or more," the term "or more" applies to each of the values listed (e.g., the listing of "80%, 90%, 95%, or more" or "80%, 90%, 95% or more" or "80%, 90%, or 95% or more" refers to "80% or more, 90% or more, or 95% or more"). When a listing of values is described, the listing includes all ranges between any two of the values listed (e.g., the listing of "80%, 90% or 95%" includes ranges of "80% to 90%," "80% to 95%" and "90% to 95%").

Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for determining the presence, absence or amount of at least one pathogen in a plant cultivar, comprising:
   (a) obtaining a nucleic acid sample from the plant cultivar, wherein the plant cultivar is a *Cannabis* plant cultivar;
   (b) contacting the nucleic acid sample with more than one polynucleotide primer pair under amplification conditions and amplifying the sample, thereby preparing an amplified nucleic acid mixture, wherein, if at least one pathogen is present, at least one polynucleotide primer pair is capable of specifically hybridizing to and amplifying a subsequence of the nucleic acid of the pathogen, or to a complement thereof, wherein the subsequence of the nucleic acid of the pathogen, or the complement thereof, is non-identical to any subsequence of the nucleic acid of the plant genome, or to any complement thereof; and
   (c) determining the presence, absence or amount of at least one amplicon that is an amplification product of a polynucleotide primer pair in the amplified nucleic acid mixture of (b) by quantitative PCR (qPCR) using more than one polynucleotide probe sequence, thereby determining the presence, absence or amount of a pathogen in the plant cultivar, wherein:
      the pathogen is a virus or viroid that is selected from among one or both of Hops Latent Viroid (HpLVd) and Beet Curly Top Virus (BCTV) and the presence, absence or amount of the at least one amplicon is determined from a Cq value for each polynucleotide probe sequence, wherein if the Cq value obtained with a first polynucleotide probe sequence is significantly different than the Cq value obtained with another non-overlapping polynucleotide probe sequence, a variant in the genotype of the pathogen is identified; and
      if the Cq value obtained with a first polynucleotide probe sequence is similar to the Cq value obtained with another non-overlapping polynucleotide probe sequence, the genotype of the pathogen is identified as not comprising a variant sequence.

2. The method of claim 1, wherein:
more than one polynucleotide primer pair hybridizes to the nucleic acid of the same pathogen;
each polynucleotide primer pair hybridizes to a subsequence of the nucleic acid of the pathogen that does not overlap with the subsequences to which each of the other primer pairs hybridizes; and
the presence, absence or amount of more than one amplicon of the pathogen that is obtained in (b) is determined in (c).

3. The method of claim 1, wherein:
each of the polynucleotide primer pairs hybridizes to the nucleic acid of a pathogen that is different than the pathogen to which each of the other polynucleotide primer pairs hybridizes; and
the presence, absence or amount of amplicons obtained from more than one pathogen in (b) is determined in (c).

4. The method of claim 1, wherein at least one amplicon is 300 base pairs or less.

5. The method of claim 1, wherein the more than one polynucleotide probe sequences hybridize to non-overlapping regions of the subsequence of the pathogen that is amplified to generate the amplicon.

6. The method of claim 1, wherein:
the pathogen is Beet Curly Top Virus (BCTV), and
the subsequence of the nucleic acid of the pathogen, or the complement thereof, is in a region of overlap between two genes in the genome of the pathogen.

7. The method of claim 1, wherein:
the pathogen is Beet Curly Top Virus (BCTV), and
the subsequence of the nucleic acid of the pathogen, or the complement thereof, comprises at least an exon or at least one portion within an exon.

8. The method of claim 1, wherein the method further comprises:
   in (b), contacting the nucleic acid sample with at least one second polynucleotide primer pair under amplification conditions and amplifying the sample, thereby preparing an amplified nucleic acid mixture, wherein the second polynucleotide primer pair is capable of specifically hybridizing to and amplifying a subsequence of the nucleic acid of the plant genome, or a complement thereof, wherein the subsequence of the nucleic acid of the plant genome, or the complement thereof, is non-identical to any subsequence of the nucleic acid of the pathogen, or to any complement thereof; and in (c), determining the presence, absence or amount of at least one amplicon that is an amplification product of the second polynucleotide primer pair, thereby determining whether the amplification conditions are effective for generating amplicons.

9. The method of claim 8, wherein the subsequence of the nucleic acid of the plant genome comprises all or a portion of a gene that is conserved among species of the plant or is a housekeeping gene.

10. The method of claim 9, wherein the conserved gene or housekeeping gene of the plant genome is selected from among 26S rRNA, beta-tubulin, ATP Synthase, an rRNA subunit, glyceraldehyde-3-phosphate dehydrogenase, Ubiquitin-conjugating enzyme E2, eukaryotic transcription factors, eukaryotic initiation factor 1 and beta-actin.

11. The method of claim 1, wherein:
the pathogen is Beet Curly Top Virus (BCTV), and
the subsequence of the nucleic acid of the pathogen, or the complement thereof, comprises all or a portion of at least one gene that is conserved among species of that pathogen.

12. The method of claim 11, wherein the at least one gene that is conserved among species of the pathogen is selected from among RNA-3 coat protein, SS-ds-DNA Regulator protein, Movement Protein, Pathogenesis Enhancer Protein, Rolling Circle Replication Protein, Cell Cycle Regulator Protein and Replication Enhancer Protein.

13. The method of claim 1, wherein:
(1) when the pathogen is the viroid Hops Latent Viroid (HpLVd),
  (i) the subsequence of the nucleic acid of the viroid to which the polynucleotide primer pair is capable of hybridizing comprises SEQ ID NO:1, or a complement of SEQ ID NO:1, and/or
  (ii) one or more of the polynucleotide primer pairs comprise:
    one thermomutant-specific primer selected from among those having the sequences set forth in SEQ ID NOS: 2 and 77, or from among sequences that share 90%, 91%, 92%, 93%, 94%, 95%, 96%, 97%, 98%, 99% or more identity with the sequences set forth in SEQ ID NOS: 2 and 77, and one thermomutant-specific primer selected from among those having the sequences set forth in SEQ ID NOS: 7, 14, 15 and 78, or from among sequences that share 90%, 91%, 92%, 93%, 94%, 95%, 96%, 97%, 98%, 99% or more identity with the sequences set forth in SEQ ID NOS: 7, 14, 15 and 78, and/or
    one thermomutant-resistant primer selected from among those having the sequences set forth in SEQ ID NOS: 4, 6, 9, 11 and 13, or from among sequences that share 90%, 91%, 92%, 93%, 94%, 95%, 96%, 97%, 98%, 99% or more identity with the sequences set forth in SEQ ID NOS: 4, 6, 9, 11 and 13, and one thermomutant-resistant primer selected from among those having the sequences set forth in SEQ ID NOS: 3, 5, 8, 10 and 12, or from among sequences that share 90%, 91%, 92%, 93%, 94%, 95%, 96%, 97%, 98%, 99% or more identity with the sequences set forth in SEQ ID NOS: 3, 5, 8, 10 and 12, and/or
  (iii) each polynucleotide probe sequence selected from among the sequences set forth in SEQ ID NOS: 16-20 and 79, or from among sequences that share 90%, 91%, 92%, 93%, 94%, 95%, 96%, 97%, 98%, 99% or more identity with the sequences set forth in SEQ ID NOS: 16-20 and 79; and
(2) when the pathogen is the virus Beet Curly Top Virus (BCTV),
  (i) the subsequence of the nucleic acid of the virus to which the polynucleotide primer pair is capable of hybridizing is selected from among SEQ ID NOS: 110, 112, 114, 116, 118 or 120, or a portion of SEQ ID NOS:110, 112, 114, 116, 118 or 120, or a complement of SEQ ID NOS:110, 112, 114, 116, 118 or 120, or one or more regions of overlap that span any two of SEQ ID NOS:110, 112, 114, 116, 118 or 120 in the genome of the virus, and
  (ii) the subsequence of the nucleic acid of the virus to which the polynucleotide primer pair is capable of hybridizing is in a region of overlap that spans:
    (w) the gene encoding the SS-ds-DNA Regulator Protein (SEQ ID NO:110) and the gene encoding Movement Protein (SEQ ID NO:112), (x) the gene encoding the Pathogenesis Enhancement Protein (SEQ ID NO:116) and the gene encoding the Rolling Circle Replication Protein (SEQ ID NO:114),
    (y) the gene encoding the Rolling Circle Replication Protein (SEQ ID NO:114) and the gene encoding the Cell Cycle Regulator Protein (SEQ ID NO:118), or
    (z) the gene encoding the Pathogenesis Enhancement Protein (SEQ ID NO:116) and the gene encoding the Replication Enhancer Protein (SEQ ID NO:120).

14. The method of claim 13, wherein, when the pathogen is Beet Curly Top Virus (BCTV), the polynucleotide primer pairs comprise:
for subsequence (w), the primer pair having the sequences set forth in SEQ ID NOS: 93 and 94 or sequences that share 90%, 91%, 92%, 93%, 94%, 95%, 96%, 97%, 98%, 99% or more identity with the sequences set forth in SEQ ID NOS: 93 and 94, or the primer pair having the sequences set forth in SEQ ID NOS: 93 and 105, or sequences that share 90%, 91%, 92%, 93%, 94%, 95%, 96%, 97%, 98%, 99% or more identity with the sequences set forth in SEQ ID NOS: 93 and 105;
for subsequence (x), the primer pair having the sequences set forth in SEQ ID NOS: 96 and 97, or sequences that share 90%, 91%, 92%, 93%, 94%, 95%, 96%, 97%, 98%, 99% or more identity with the sequences set forth in SEQ ID NOS: 96 and 97;
for subsequence (y), the primer pair having the sequences set forth in SEQ ID NOS: 99 and 100, or sequences that share 90%, 91%, 92%, 93%, 94%, 95%, 96%, 97%, 98%, 99% or more identity with the sequences set forth in SEQ ID NOS: 99 and 100; and
for subsequence (z), the primer pair having the sequences set forth in SEQ ID NOS: 102 and 103, or sequences that share 90%, 91%, 92%, 93%, 94%, 95%, 96%, 97%, 98%, 99% or more identity with the sequences set forth in SEQ ID NOS: 102 and 103.

15. The method of claim 13, wherein, when the pathogen is Beet Curly Top Virus (BCTV), each polynucleotide probe sequence comprises:
for subsequence (w), the polynucleotide probe sequence having the sequence set forth in SEQ ID NO: 95 or a sequence that shares 90%, 91%, 92%, 93%, 94%, 95%, 96%, 97%, 98%, 99% or more identity with the sequence set forth in SEQ ID NO: 95, and/or the polynucleotide probe sequence having the sequence set forth in SEQ ID NO: 106 or a sequence that shares 90%, 91%, 92%, 93%, 94%, 95%, 96%, 97%, 98%, 99% or more identity with the sequence set forth in SEQ ID NO: 106;

for subsequence (x), the polynucleotide probe sequence having the sequence set forth in SEQ ID NO: 98 or a sequence that shares 90%, 91%, 92%, 93%, 94%, 95%, 96%, 97%, 98%, 99% or more identity with the sequence set forth in SEQ ID NO: 98;

for subsequence (y), the polynucleotide probe sequence having the sequence set forth in SEQ ID NO: 101 or a sequence that shares 90%, 91%, 92%, 93%, 94%, 95%, 96%, 97%, 98%, 99% or more identity with the sequence set forth in SEQ ID NO:101; and for subsequence (z), the polynucleotide probe sequence having the sequence set forth in SEQ ID NO: 104 or a sequence that shares 90%, 91%, 92%, 93%, 94%, 95%, 96%, 97%, 98%, 99% or more identity with the sequence set forth in SEQ ID NO: 104.

16. The method of claim 1, wherein the presence or absence of a variant in the genotype of the pathogen is correlated to resistance or susceptibility of the plant to infection by the pathogen comprising the genotype or variant thereof.

17. The method of claim 16, wherein, if the plant is identified as resistant to infection by the pathogen or a genotypic variant thereof, or asymptomatic, the plant is identified as desirable for breeding, or as desirable for cultivating as a crop.

18. The method of claim 17, further comprising, breeding the plant or cultivating the plant as a crop.

19. The method of claim 1, wherein the presence, absence or amount of at least one pathogen is determined in a plurality of *Cannabis* plant cultivars.

* * * * *